United States Patent
Marson et al.

(10) Patent No.: US 12,359,179 B2
(45) Date of Patent: Jul. 15, 2025

(54) COMPOSITIONS AND METHODS FOR MODIFYING A TARGET NUCLEIC ACID

(71) Applicant: The Regents of the University of California, Oakland, CA (US)

(72) Inventors: Alexander Marson, Oakland, CA (US); Theodore Lee Roth, Oakland, CA (US); Daniel Goodman, Oakland, CA (US); David-Huy Nhu Nguyen, Oakland, CA (US); Francis C. Szoka, Jr., Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 976 days.

(21) Appl. No.: 17/312,191

(22) PCT Filed: Dec. 12, 2019

(86) PCT No.: PCT/US2019/066079
§ 371 (c)(1),
(2) Date: Jun. 9, 2021

(87) PCT Pub. No.: WO2020/123871
PCT Pub. Date: Jun. 18, 2020

(65) Prior Publication Data
US 2022/0017882 A1    Jan. 20, 2022

Related U.S. Application Data

(60) Provisional application No. 62/935,568, filed on Nov. 14, 2019, provisional application No. 62/813,577, filed on Mar. 4, 2019, provisional application No. 62/778,814, filed on Dec. 12, 2018.

(51) Int. Cl.
*C12N 9/22* (2006.01)
*C12N 15/11* (2006.01)
*C12N 15/90* (2006.01)

(52) U.S. Cl.
CPC ............ *C12N 9/22* (2013.01); *C12N 15/11* (2013.01); *C12N 15/907* (2013.01); *C07K 2319/09* (2013.01); *C07K 2319/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2013/0326645 A1    12/2013    Cost et al.
2018/0110877 A1    4/2018    Wilson et al.

FOREIGN PATENT DOCUMENTS

WO    2018/140220 A1    8/2018

OTHER PUBLICATIONS

Ribeiro LF, Ribeiro LFC, Barreto MQ, Ward RJ. Protein Engineering Strategies to Expand CRISPR-Cas9 Applications. Int J Genomics. Aug. 2, 2018;2018:1652567. doi: 10.1155/2018/1652567. PMID: 30155473; PMCID: PMC6098869. (Year: 2018).*
Miyaoka, Y., Berman, J., Cooper, S. et al. Systematic quantification of HDR and NHEJ reveals effects of locus, nuclease, and cell type on genome-editing. Sci Rep 6, 23549 (2016). https://doi.org/10.1038/srep23549 (Year: 2016).*
Liang X, Potter J, Kumar S, Ravinder N, Chesnut JD. Enhanced CRISPR/Cas9-mediated precise genome editing by improved design and delivery of gRNA, Cas9 nuclease, and donor DNA. J Biotechnol. Jan. 10, 2017;241:136-146. doi: 10.1016/j.jbiotec.2016.11.011. Epub Nov. 11, 2016. PMID: 27845164. (Year: 2016).*
Goeckel ME, Basgall EM, Lewis IC, Goetting SC, Yan Y, Halloran M, Finnigan GC. Modulating CRISPR gene drive activity through nucleocytoplasmic localization of Cas9 in S. cerevisiae. BioRxiv Sep. 4, 2018 https://doi.org/10.1101/408369 (Year: 2018).*
International Search Report in PCT/US2019/066079, mailed May 19, 2020, 6 pages.
Kurosaki, et al., Ternary complexes of pDNA, polyethylenimine, and γ-polyglutamic acid for gene delivery systems. Biomaterials. May 1, 2009;30(14):2846-53.
Roth et al., Tobin V. Reprogramming human T cell function and specificity with non-viral genome targeting. Nature. Jul. 2018;559(7714):405-9.

* cited by examiner

*Primary Examiner* — Allison M Fox
*Assistant Examiner* — Qinhua Gu
(74) *Attorney, Agent, or Firm* — Kilpatrick Townsend & Stockton LLP

(57) ABSTRACT

The disclosure provides compositions and methods for modifying a target nucleic acid. In some embodiments, a composition can include a targetable nuclease, a DNA-binding protein, and a donor template comprising a homology directed repair (HDR) template and one or more DNA-binding protein target sequences. In some embodiments, a composition can include a Cas protein, one or more single guide RNAs (sgRNAs), and an anionic polymer.

16 Claims, 58 Drawing Sheets

Specification includes a Sequence Listing.

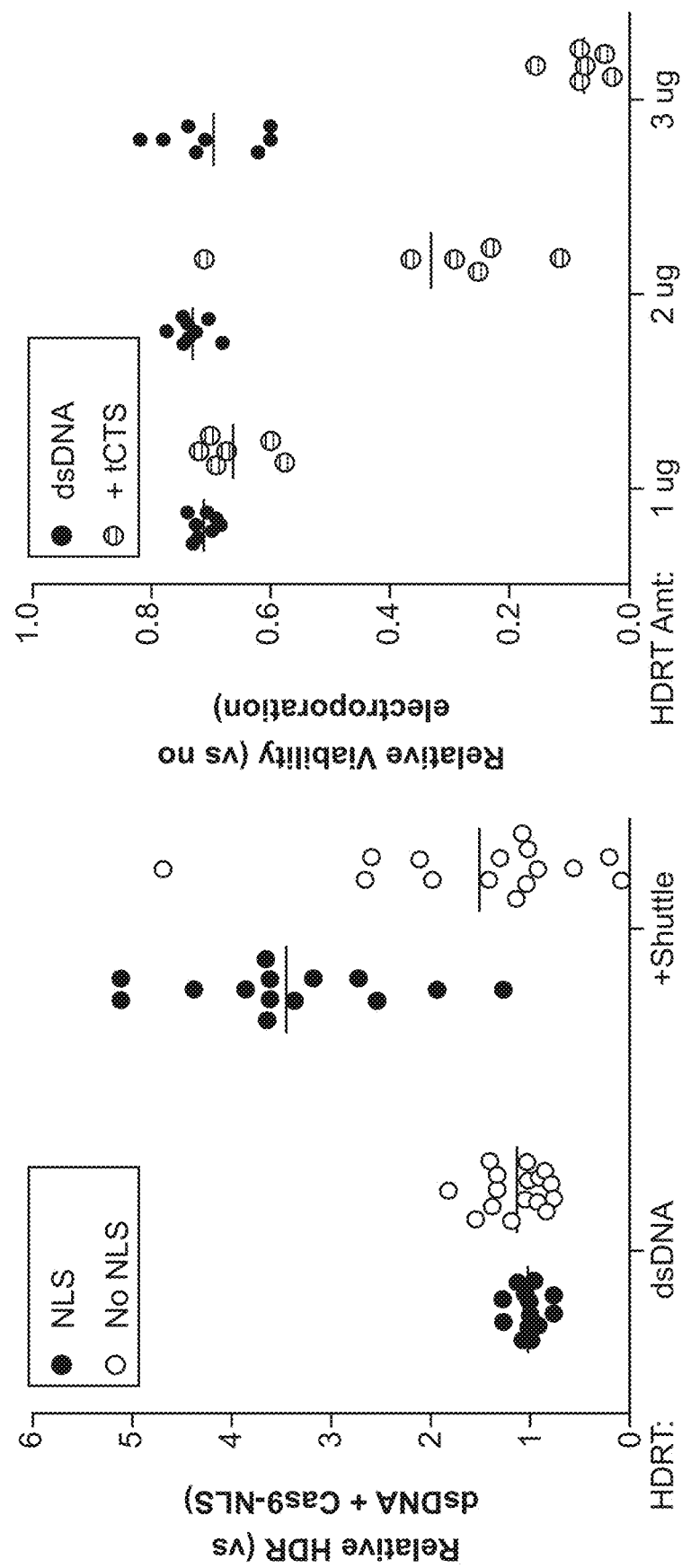

% mCherry+ Day 3 mCherry+ Day 3

| Sample | Z-avg (nm) | PDI | peak 1 (nm) | peak 1 (volume %) | peak 2 (nm) | peak 2 (volume %) |
|---|---|---|---|---|---|---|
| Cas9 + gRNA 1 | 177.50 | 0.343 | 217.90 | 68.10 | 62.80 | 31.90 |
| Cas9 + gRNA 2 | 195.90 | 0.277 | 173.20 | 80.80 | 46.76 | 19.20 |
| Cas9 + gRNA + ssODNenh 1 | 90.76 | 0.357 | 115.30 | 85.90 | 21.14 | 14.10 |
| Cas9 + gRNA + ssODNenh 2 | 115.00 | 0.183 | 87.88 | 89.50 | 17.04 | 10.50 |
| Cas9 + gRNA + PGA 1 | 77.87 | 0.317 | 116.40 | 87.10 | 23.21 | 12.90 |
| Cas9 + gRNA + PGA 2 | 81.31 | 0.317 | 127.00 | 85.90 | 25.89 | 14.10 |
| Cas9 alone 1 | 25.21 | 0.633 | 10.66 | 99.80 | 309.40 | 0.10 |
| Cas9 alone 2 | 31.83 | 0.44 | 15.80 | 99.50 | 131.00 | 0.50 |

FIG. 24 (Cont.)

COMPOSITIONS AND METHODS FOR MODIFYING A TARGET NUCLEIC ACID

CROSS-REFERENCE TO RELATED APPLICATIONS

This application claims priority to U.S. Provisional Application No. 62/778,814, filed Dec. 12, 2018, U.S. Provisional Application No. 62/813,577, filed Mar. 4, 2019, and U.S. Provisional Application No. 62/935,568, filed Nov. 14, 2019, the disclosures of which are hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. DK111914, P50 GM082250, and R01 DK119979 awarded by The National Institutes of Health. The Government has certain rights in the invention.

REFERENCE TO SUBMISSION OF A SEQUENCE LISTING AS A TEXT FILE

The Sequence Listing written in file 1254975_SL.txt created on Jun. 4, 2021, 33,528 bytes, machine format IBM-PC, MS-Windows operating system, is hereby incorporated by reference in its entirety for all purposes.

BACKGROUND OF THE DISCLOSURE

The application of clustered regularly interspaced short palindromic repeats (CRISPR) and CRISPR-associated (Cas) proteins has revolutionized molecular biology by making genome editing possible. CRISPR-mediated gene editing is a powerful and practical tool with potential for creating new scientific tools, correcting clinically relevant mutations, and engineering new cell-based immunotherapies. Viral delivery vectors and electroporation have emerged as two strategies for CRISPR-based editing in immune cells. However, the field of gene therapy has been fraught with complications of viral delivery vectors.

The ability to manipulate T cells, hematopoietic stem cells, and induced pluripotent stems cells provides both a scientific tool and a potentially therapeutic avenue to immune-engineering. Until the discovery of CRISPR-Cas gene editing in human cells, gene therapy directed towards the immune system relied almost exclusively upon viral vectors such as retroviruses and lentiviruses to insert a transgene by a (semi)random genomic integration. However, clinical trials have had unintended consequences, such as leukemia, due to insertion into proto-oncogenes and fatal systemic immune responses to the viral vector. Despite improvements in viral vectors to minimize genetic damage and immune responses, viral insertions (such as lentivirus used clinically to generate CAR-T cells) can result in gene over-expression, e.g., overexpression of genes that are not under endogenous regulation, restricting the clinical utility of this method.

BRIEF SUMMARY OF THE DISCLOSURE

In one aspect, the disclosure features a composition for modifying a target nucleic acid, comprising: (a) a targetable nuclease; (b) a DNA-binding protein; (c) a donor template comprising a homology directed repair (HDR) template and one or more DNA-binding protein target sequences.

In some embodiments of this aspect, (a) the targetable nuclease and DNA-binding protein comprise an RNA-guided nuclease, wherein the RNA-guided nuclease comprises CRISPR-CAS; (b) the composition comprises a target guide RNA (gRNA) and a donor gRNA; (c) the donor template comprises one or more protospacer adjacent motifs (PAMs); (d) the target gRNA is complementary to the target nucleic acid; (e) the DNA-binding protein target sequence hybridizes to the donor gRNA or a portion thereof; and (f) the composition comprises an anionic polymer.

In some embodiments, the donor template comprises at least two DNA-binding protein target sequences and at least two PAMs, and the anionic polymer comprises a polyglutamic acid (PGA), a polyaspartic acid, or a polycarboxyglutamic acid.

In some embodiments of this aspect, each of the targetable nuclease and the DNA-binding protein is an RNA-guided nuclease. The composition can further comprise a target guide RNA (gRNA) and a donor gRNA. The donor template can further comprise one or more protospacer adjacent motifs (PAMs). The target gRNA can be complementary to the target nucleic acid and the DNA-binding protein target sequence can hybridize to the donor gRNA or a portion thereof.

In some embodiments of this aspect, the donor template has one DNA-binding protein target sequence and one PAM. In some embodiments, the DNA-binding protein target sequence and the PAM are located at the 5' terminus of the HDR template. Particularly, in some embodiments, the PAM can be located at the 5' terminus of the DNA-binding protein target sequence. In other embodiments, the PAM can be located at the 3' terminus of the DNA-binding protein target sequence.

In some embodiments, the DNA-binding protein target sequence and the PAM are located at the 3' terminus of the HDR template. Particularly, in some embodiments, the PAM can be located at the 5' terminus of the DNA-binding protein target sequence. In other embodiments, the PAM is located at the 3' terminus of the DNA-binding protein target sequence.

In some embodiments of this aspect, the donor template has two DNA-binding protein target sequences and two PAMs. Particularly, in some embodiments, a first DNA-binding protein target sequence and a first PAM are located at the 5' terminus of the HDR template and a second DNA-binding protein target sequence and a second PAM are located at the 3' terminus of the HDR template. In some embodiments, the first PAM is located at the 5' terminus of the first DNA-binding protein target sequence and the second PAM is located at the 5' of the second DNA-binding protein target sequence. In other embodiments, the first PAM is located at the 5' terminus of the first DNA-binding protein target sequence and the second PAM is located at the 3' of the second DNA-binding protein target sequence. In yet other embodiments, the first PAM is located at the 3' terminus of the first DNA-binding protein target sequence and the second PAM is located at the 5' of the second DNA-binding protein target sequence. In yet other embodiments, the first PAM is located at the 3' terminus of the first DNA-binding protein target sequence and the second PAM is located at the 3' of the second DNA-binding protein target sequence.

In some embodiments of this aspect, the DNA-binding protein target sequence is complementary to an equal length portion of the sequence of the donor gRNA.

In some embodiments, the target gRNA and the donor gRNA have the same sequence. In other embodiments, the target gRNA and the donor gRNA have the different sequences.

In some embodiments of this aspect, the targetable nuclease and the target gRNA are in a molar ratio of between 1:10 and 2:1, respectively. In some embodiments, the DNA-binding protein and the donor template are in a molar ratio of between 10:1 and 1000:1, respectively. In some embodiments, the DNA-binding protein and the donor gRNA are in a molar ratio of between 1:10 and 2:1, respectively.

In some embodiments of this aspect, the DNA-binding protein comprises a transcription activator-like (TAL) effector DNA-binding protein or a zinc finger DNA-binding protein.

In some embodiments, the targetable nuclease comprises a transcription activator-like (TAL) effector DNA-binding protein and a nuclease.

In some embodiments, the targetable nuclease comprises a zinc finger DNA-binding protein and a nuclease.

In some embodiments, the targetable nuclease is fused to a nuclear localization signal (NLS) sequence. In some embodiments, the DNA-binding protein is fused to an NLS sequence.

In some embodiments of this aspect, the targetable nuclease has nuclease activity. In other embodiments, the targetable nuclease does not have nuclease activity.

In some embodiments of this aspect, the composition further comprises an anionic polymer. The anionic polymer can be an anionic polypeptide or an anionic polysaccharide. In some embodiments, the anionic polymer is an anionic polypeptide, such as a polyglutamic acid (PGA) (e.g., a poly-gamma-glutamic acid), a polyaspartic acid, or polycarboxyglutamic acid.

In another aspect, the disclosure features a method for modifying a target nucleic acid in a cell, comprising introducing into the cell a composition described herein, wherein the HDR template is integrated into the target nucleic acid. In some embodiments, the introducing comprises electroporation.

In some embodiments of this aspect, the cell is a primary cell (e.g., a primary T cell).

In one aspect, the disclosure features a composition for modifying a target nucleic acid, comprising: (a) a Cas protein; and (b) an anionic polymer. In some embodiments, the composition further comprises one or more single guide RNAs (sgRNAs).

In some embodiments of this aspect, the anionic polymer is an anionic polypeptide or an anionic polysaccharide. In some embodiments, the anionic polymer is an anionic polypeptide (e.g., a polyglutamic acid (PGA), a polyaspartic acid, or polycarboxyglutamic acid). In some embodiments, the anionic polymer is an anionic polysaccharide (e.g., hyaluronic acid (HA), heparin, heparin sulfate, or glycosaminoglycan). In some embodiments, the anionic polymer is poly(acrylic acid) (PAA), poly(methacrylic acid) (PMAA), poly(styrene sulfonate), or polyphosphate.

In some embodiments, the anionic polymer has a molecular weight of at least 15 kDa (e.g., between 15 kDa and 50 kDa (e.g., between 15 kDa and 45 kDa, between 15 kDa and 40 kDa, between 15 kDa and 35 kDa, between 15 kDa and 30 kDa, between 15 kDa and 25 kDa, between 15 kDa and 20 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa).

In some embodiments, the anionic polymer and the Cas protein are in a molar ratio of between 10:1 and 120:1, respectively (e.g., 10:1, 20:1, 30:1, 40:1, 50:1, 60:1, 70:1, 80:1, 90:1, 100:1, 110:1, or, 120:1; between 10:1 and 110:1, between 10:1 and 100:1, between 10:1 and 90:1, between 10:1 and 80:1, between 10:1 and 70:1, between 10:1 and 60:1, between 10:1 and 50:1, between 10:1 and 40:1, between 10:1 and 30:1, between 10:1 and 20:1, between 20:1 and 120:1, between 30:1 and 120:1, between 40:1 and 120:1, between 50:1 and 120:1, between 60:1 and 120:1, between 70:1 and 120:1, between 80:1 and 120:1, between 90:1 and 120:1, between 100:1 and 120:1, or between 110:1 and 120:1). In some embodiments, the anionic polymer and the Cas protein are in a molar ratio of between 1:1 and 10:1, respectively (e.g., between 1:1 and 9:1, between 1:1 and 8:1, between 1:1 and 7:1, between 1:1 and 6:1, between 1:1 and 5:1, between 1:1 and 4:1, between 1:1 and 3:1, between 1:1 and 2:1, between 2:1 and 10:1, between 3:1 and 10:1, between 4:1 and 10:1, between 5:1 and 10:1, between 6:1 and 10:1, between 7:1 and 10:1, between 8:1 and 10:1, or between 9:1 and 10:1).

In some embodiments of this aspect, the Cas protein is a Cas9 protein. In some embodiments, the Cas protein has nuclease activity. In other embodiments, the Cas protein does not have nuclease activity.

In some embodiments of this aspect, the composition is an aqueous composition.

In some embodiments, the Cas protein is active for at least one week in liquid form at room temperature, 4° C., or 37° C.

In some embodiments of this aspect, the composition is a lyophilized composition. In some embodiments, the composition is a dry composition. In some embodiments, the Cas protein is active for at least one week at room temperature, 4° C., or 37° C. after reconstitution of the composition into liquid form.

In another aspect, the disclosure provides a ribonucleoprotein (RNP) complex for modifying a target nucleic acid, comprising a composition described herein.

In another aspect, the disclosure features a method for modifying a target nucleic acid in a cell, comprising introducing into the cell a composition described herein. In some embodiments, the introducing comprises electroporation.

In another aspect, the disclosure features a method for modifying a target nucleic acid in a cell, comprising introducing into the cell: (a) a Cas protein; (b) an anionic polymer; and (c) a viral vector comprising an sgRNA. In some embodiments, (a) and (b) are introduced into the cell in the same composition via electroporation. In some embodiments, (a) and (b) are introduced into the cell before (c). In some embodiments, (c) is introduced into the cell before (a) and (b).

In some embodiments, the cell is a primary cell (e.g., a primary T cell).

In some embodiments, an exogenous nucleotide sequence is introduced into the cell and the modifying comprises inserting the exogenous nucleotide sequence into the target nucleic acid.

In some embodiments, the modifying comprises excising the target nucleic acid. In some embodiments, the modifying comprises targeting an exogenous protein to the target nucleic acid. In some embodiments, the exogenous protein is a transcription activator or repressor.

In some embodiments of this aspect, the method is performed in vivo, in vitro, or ex vivo.

In another aspect, the disclosure features a method of forming a ribonucleoprotein (RNP) complex, comprising incubating a Cas protein, an sgRNA, and an anionic polymer in a mixture. In some embodiments, the Cas protein and the sgRNA are incubated together first, followed by the addition of the anionic polymer. In some embodiments, the Cas protein and the sgRNA are incubated together at 37° C. for at least 15 minutes (e.g., 20, 25, 30, 35, 40, 45, 50, 55, 60, 65, 70, 75, 80, 85, 90, 95, 100, 110, or 120 minutes). In some embodiments, the Cas protein, the sgRNA, and the anionic polymer are incubated together at 37° C. for at least 15 minutes (e.g., 20, 25, 30, 35, 40, 45, 50, 55, 60, 65, 70, 75, 80, 85, 90, 95, 100, 110, or 120 minutes).

In some embodiments of this aspect, the molar ratio of sgRNA:Cas protein is between 0.25:1 and 4:1 (e.g., 0.25:1, 0.5:1, 1:1, 1.2:1, 1.4:1, 1.6:1, 1.8:1, 2:1, 2.2:1, 2.4:1, 2.6:1, 2.8:1, 3:1, 3.2:1, 3.4:1, 3.6:1, 3.8:1, or 4:1). The molar ratio of sgRNA:Cas protein can range from 12:1 to 2:1, for example, 10:1, 11:1, or 12:1. In some embodiments, the molar ratio of anionic polymer:Cas protein is between 10:1 and 120:1 (e.g., 10:1, 20:1, 30:1, 40:1, 50:1, 60:1, 70:1, 80:1, 90:1, 100:1, 110:1, or, 120:1; between 10:1 and 110:1, between 10:1 and 100:1, between 10:1 and 90:1, between 10:1 and 80:1, between 10:1 and 70:1, between 10:1 and 60:1, between 10:1 and 50:1, between 10:1 and 40:1, between 10:1 and 30:1, between 10:1 and 20:1, between 20:1 and 120:1, between 30:1 and 120:1, between 40:1 and 120:1, between 50:1 and 120:1, between 60:1 and 120:1, between 70:1 and 120:1, between 80:1 and 120:1, between 90:1 and 120:1, between 100:1 and 120:1, or between 110:1 and 120:1). In some embodiments, the molar ratio of anionic polymer:Cas protein is 500:1 to 20:1, e.g., 100:1. In some embodiments, the molar ratio of RNP (nuclease and gRNA) to template can be 10:1 to 20:1, e.g., 10:1, 11:1, 12:1, 13:1, 14:1, 15:1, 16:1, 17:1, 18:1, 19:1, or 20:1.

In some embodiments of this aspect, the RNP complex has a size that is less than 100 nm (e.g., between 20 nm and 90 nm; 20, 25, 30, 35, 40, 45, 50, 55, 60, 65, 70, 75, 80, 85, or 90 nm).

In another aspect, the disclosure features a composition comprising a donor template comprising a homology directed repair (HDR) template and one or more DNA-binding protein target sequences.

In some embodiments of this aspect, the donor template further comprises one or more protospacer adjacent motifs (PAMs). In some embodiments, the donor template has one DNA-binding protein target sequence and one PAM. In certain embodiments, the DNA-binding protein target sequence and the PAM are located at the 5' terminus of the HDR template. In particular embodiments, the PAM is located at the 5' terminus of the DNA-binding protein target sequence. In particular embodiments, the PAM is located at the 3' terminus of the DNA-binding protein target sequence.

In certain embodiments, the DNA-binding protein target sequence and the PAM are located at the 3' terminus of the HDR template. In particular embodiments, the PAM is located at the 5' terminus of the DNA-binding protein target sequence. In particular embodiments, the PAM is located at the 3' terminus of the DNA-binding protein target sequence.

In some embodiments of this aspect, the donor template has two DNA-binding protein target sequences and two PAMs. In certain embodiments, a first DNA-binding protein target sequence and a first PAM are located at the 5' terminus of the HDR template and a second DNA-binding protein target sequence and a second PAM are located at the 3' terminus of the HDR template. In certain embodiments, the first PAM is located at the 5' terminus of the first DNA-binding protein target sequence and the second PAM is located at the 5' of the second DNA-binding protein target sequence. In certain embodiments, the first PAM is located at the 5' terminus of the first DNA-binding protein target sequence and the second PAM is located at the 3' of the second DNA-binding protein target sequence. In certain embodiments, the first PAM is located at the 3' terminus of the first DNA-binding protein target sequence and the second PAM is located at the 5' of the second DNA-binding protein target sequence. In certain embodiments, the first PAM is located at the 3' terminus of the first DNA-binding protein target sequence and the second PAM is located at the 3' of the second DNA-binding protein target sequence.

In some embodiments of this aspect, the donor template comprises from 5' to 3' the sequence: $E1_a$-$P1_b$-D1-$P2_c$-H-$P3_d$-D2-$P4_e$-$E2_f$, and wherein: (1) E1 and E2 are edge sequences; (2) P1, P2, P3, and P4 are PAM sequences; (3) D1 and D2 are the one or more DNA-binding protein target sequences and one or both of D1 and D2 are present; (4) H is the HDR template; (5) a is 0 or 1; (6) b is 0 or 1; (7) c is 0 or 1; (8) d is 0 or 1; (9) e is 0 or 1; and (10) f is 0 or 1.

In some embodiments, the composition further comprises (a) a targetable nuclease; and (b) a DNA-binding protein. In certain embodiments, the targetable nuclease and the DNA-binding protein is an RNA-guided nuclease, optionally CRISPR-Cas (e.g., a Cas9 protein).

In some embodiments, the composition further comprises a target guide RNA (gRNA) and a donor gRNA, wherein the target gRNA is complementary to a target nucleic acid and wherein the DNA-binding protein target sequence hybridizes to the donor gRNA or a portion thereof. In some embodiments, the DNA-binding protein target sequence is complementary to an equal length portion of the sequence of the donor gRNA. In certain embodiments, the target gRNA and the donor gRNA have the same sequence. In certain embodiments, the target gRNA and the donor gRNA have the different sequences.

In some embodiments of this aspect, the targetable nuclease and the target gRNA are in a molar ratio of between 1:10 and 2:1, respectively. In some embodiments, the DNA-binding protein and the donor template are in a molar ratio of between 10:1 and 1000:1, respectively. In some embodiments, the DNA-binding protein and the donor gRNA are in a molar ratio of between 1:10 and 2:1, respectively.

In some embodiments of this aspect, the DNA-binding protein comprises a transcription activator-like (TAL) effector DNA-binding protein or a zinc finger DNA-binding protein. In some embodiments, the targetable nuclease comprises a transcription activator-like (TAL) effector DNA-binding protein and a nuclease. In some embodiments, the targetable nuclease comprises a zinc finger DNA-binding protein and a nuclease. In certain embodiments, the targetable nuclease is fused to a nuclear localization signal (NLS) sequence. In certain embodiments, the DNA-binding protein is fused to an NLS sequence.

In some embodiments of this aspect, the composition further comprises an anionic polymer, e.g., an anionic polypeptide or an anionic polysaccharide. In certain embodiments, the anionic polymer is an anionic polypeptide, e.g., a polyglutamic acid (PGA), a polyaspartic acid, or polycarboxyglutamic acid.

In certain embodiments, the targetable nuclease and the DNA-binding protein is CRISPR-Cas and the anionic polymer is PGA.

In certain embodiments, the donor template is a plasmid.

In some embodiments, the targetable nuclease and the DNA-binding protein comprises CRISPR-Cas (e.g., a Cas9 protein) and the anionic polymer is water soluble and biologically inert. In certain embodiments, the anionic polymer has a molecular weight of 15,000 to 50,000 kDa, and optionally wherein the anionic polymer comprises polyglutamic acid (PGA).

Definitions

As used in this specification and the appended claims, the singular forms "a," "an," and "the" include plural reference unless the context clearly dictates otherwise.

As used herein, the "CRISPR-Cas" system refers to a class of bacterial systems for defense against foreign nucleic acid. CRISPR-Cas systems are found in a wide range of eubacterial and archaeal organisms. CRISPR-Cas systems include type I, II, and III sub-types. Wild-type type II CRISPR-Cas systems utilize an RNA-mediated nuclease, for example, Cas9 protein, in complex with guide and activating RNA (e.g., single-guide RNA or sgRNA) to recognize and cleave foreign nucleic acids, i.e., foreign nucleic acids including natural or modified nucleotides.

As used herein, the term "targetable nuclease" refers to a protein that can recognize a sequence of a target nucleic acid (e.g., a target gene within a genome) and bind to the target nucleic acid. In some embodiments, the targetable nuclease can modify the target nucleic acid. In some embodiments, a targetable nuclease can be an RNA-guided nuclease, e.g., a Cas protein. In other embodiments, a targetable nuclease can be a fusion protein that includes a protein that can bind to the target nucleic acid (e.g., a transcription activator-like (TAL) effector DNA-binding protein or a zinc finger DNA-binding protein) and a protein that can modify the target nucleic acid (e.g., a nuclease, a transcription activator or repressor). In some embodiments, the targetable nuclease has nuclease activity. In other embodiments, the targetable nuclease does not have nuclease activity. In some embodiments, the targetable nuclease can modify the target nucleic acid by cleaving the target nucleic acid. The cleaved target nucleic acid can then undergo homologous recombination with a nearby a homology directed repair (HDR) template. In other embodiments, the targetable nuclease (e.g., a targetable nuclease without any nuclease activity) can regulate the expression of the target nucleic acid. For example, a targetable nuclease can be a fusion protein containing a TAL effector DNA-binding protein and a transcription activator.

As used herein, the term "DNA-binding protein" refers to a protein that can directly or indirectly bind to a DNA-binding protein target sequence within a donor template (which includes an HDR template). Without being bound by any theory, the DNA-binding protein serves to transport or shuttle the donor template to a cellular location close to the target nucleic acid. Thus, the DNA-binding protein can improve the delivery of the HDR template into target cells, especially to the cell nucleus, and increase knock-in efficiencies. In some embodiments, the DNA-binding protein can be a transcription activator-like (TAL) effector DNA-binding protein or a zinc finger DNA-binding protein. Each of the transcription activator-like (TAL) effector DNA-binding protein and zinc finger DNA-binding protein can directly bind to a DNA-binding protein target sequence within a donor template. In some embodiments, the DNA-binding protein can be an RNA-guided nuclease, e.g., a Cas protein, which can indirectly bind to a DNA-binding protein target sequence within a donor template via a donor gRNA.

As used herein, the term "donor template" refers a polynucleotide that includes a homology directed repair (HDR) template and one or more DNA-binding protein target sequences. An HDR template can include a 5' homology arm, a nucleotide insert (e.g., an exogenous sequence and/or a sequence that encodes a heterologous protein or fragment thereof), and a 3' homology arm (for example, see FIGS. 1A, 1B, and 2A). In some embodiments, the donor template can also include one or more edge sequences at one or both termini of the donor template. As described further herein, pre-incubation of the RNP complex containing the DNA-binding protein (e.g., a Cas protein) and donor gRNA and the donor template prior to electroporation improves in knock-in efficiency.

As used herein, the term "DNA-binding protein target sequence" refers to a nucleotide sequence that is recognized and bound by a DNA-binding protein. In some embodiments, the DNA-binding protein, e.g., a transcription activator-like (TAL) effector DNA-binding protein or zinc finger DNA-binding protein, can directly recognize and bind a DNA-binding protein target sequence. In other embodiments, a DNA-binding protein, e.g., an RNA-guided nuclease, can indirectly recognize and bind a DNA-binding protein target sequence via a donor gRNA. The DNA-binding protein, e.g., the RNA-guided nuclease, binds to the donor gRNA, which hybridizes to the DNA-binding protein target sequence. In some embodiments, the DNA-binding protein target sequence is a portion of the target nucleic acid.

As used herein, the "RNA-guided nuclease" refers to a nuclease that binds to a guide RNA (gRNA) and utilizes the gRNA to search for regions within a DNA polynucleotide that it can target. In general, an RNA-guided nuclease can target nearly any sequence within the DNA polynucleotide that is complementary to the gRNA. In some embodiments, the RNA-guided nuclease has nuclease activity and can cleave the linkage (e.g., phosphodiester bonds) between nucleotides in the DNA polynucleotide. In other embodiments, the RNA-guided nuclease does not have nuclease activity and can be used to target or localize other proteins (e.g., transcritional activator or repressors) that are fused to the RNA-guided nuclease to the region of interest within the DNA polynucleotide.

As used herein, the term "guide RNA" or "gRNA" refers to a DNA-targeting RNA that can guide an RNA-guided nuclease (e.g., a Cas protein) to a target nucleic acid by hybridizing to the target nucleic acid. In some embodiments, a guide RNA can be a single-guide RNA (sgRNA), which contains a guide sequence (i.e., crRNA equivalent portion of the single-guide RNA) that targets the RNA-guided nuclease to the target nucleic acid and a scaffold sequence (i.e., tracrRNA equivalent portion of the single-guide RNA) that interacts with the RNA-guided nuclease. In other embodiments, a guide RNA can contain two components, a guide sequence (i.e., crRNA equivalent portion of the single-guide RNA) that targets the RNA-guided nuclease to the target nucleic acid and a scaffold sequence (i.e., tracrRNA equivalent portion of the single-guide RNA) that interacts with the RNA-guided nuclease. A portion of the guide sequence can hybridize to a portion of the scaffold sequence to form the two-component guide RNA.

As used herein, the term "target guide RNA" or "target gRNA" refers to a gRNA that can hybridize to the target nucleic acid, e.g., at a location in the target nucleic acid where integration of the HDR template happens.

As used herein, the term "donor guide RNA" or "donor gRNA" refers to a gRNA that can hybridize a DNA-binding protein target sequence within a donor template. In some embodiments, a DNA-binding protein target sequence can be complementary (e.g., partially complementary or completely complementary) to an equal length portion of the sequence of a donor gRNA.

As used herein, the term "single-guide RNA" or "sgRNA" refers to a DNA-targeting RNA containing a guide sequence (i.e., crRNA equivalent portion of the single-guide RNA) that targets the Cas protein to the target DNA and a scaffold sequence (i.e., tracrRNA equivalent portion of the single-guide RNA) that interacts with the Cas protein.

As used herein, the term "complementary" or "complementarity" refers to the capacity for base pairing between nucleobases, nucleosides, or nucleotides, as well as the capacity for base pairing between one polynucleotide to another polynucleotide. In some embodiments, one polynucleotide can have "complete complementarity," or be "completely complementary," to another polynucleotide, which means that when the two polynucleotides are optionally aligned, each nucleotide in one polynucleotide can engage in Watson-Crick base pairing with its corresponding nucleotide in the other polynucleotide. In other embodiments, one polynucleotide can have "partial complementarity," or be "partially complementary," to another polynucleotide, which means that when the two polynucleotides are optionally aligned, at least 60% (e.g., 65%, 70%, 75%, 80%, 85%, 90%, 95%, or 97%) but less than 100% of the nucleotides in one polynucleotide can engage in Watson-Crick base pairing with their corresponding nucleotides in the other polynucleotide. In other words, there is at least one (e.g., one, two, three, four, five, six, seven, eight, nine, or ten) mismatched nucleotide base pair when the two polynucleotides are hybridized. Pairs of nucleotides that engage in Watson-Crick base pairing includes, e.g., adenine and thymine, cytosine and guanine, and adenine and uracil, which all pair through the formation of hydrogen bonds. Examples of mismatched bases include a guanine and uracil, guanine and thymine, and adenine and cytosine pairing.

As used herein, the term "Cas protein" refers to a Clustered Regularly Interspaced Short Palindromic Repeats-associated protein or nuclease. A Cas protein can be a wild-type Cas protein or a Cas protein variant. Cas9 protein is an example of a Cas protein that belongs in the type II CRISPR-Cas system (e.g., Rath et al., *Biochimie* 117:119, 2015). Other examples of Cas proteins are described in detail further herein. A naturally-occurring Cas protein requires both a crRNA and a tracrRNA for site-specific DNA recognition and cleavage. The crRNA associates, through a region of partial complementarity, with the tracrRNA to guide the Cas protein to a region homologous to the crRNA in the target DNA called a "protospacer". A naturally-occurring Cas protein cleaves DNA to generate blunt ends at the double-strand break at sites specified by a guide sequence contained within a crRNA transcript. In some embodiments of the compositions and methods described herein, a Cas protein associates with a target gRNA or a donor gRNA to form a ribonucleoprotein (RNP) complex. In some embodiments of the compositions and methods described herein, the Cas protein has nuclease activity. In other embodiments, the Cas protein does not have nuclease activity.

As used herein, the term "Cas protein variant" refers to a Cas protein that has at least one amino acid substitution (e.g., one, two, three, four, five, six, seven, eight, nine, ten, or more amino acid substitutions) relative to the sequence of a wild-type Cas protein and/or is a truncated version or fragment of a wild-type Cas protein. In some embodiments, a Cas protein variant has at least 75% sequence identity (e.g., at least 75%, 80%, 85%, 90%, 91%, 92%, 93%, 94% 95%, 96%, 97%, 98%, 99%, or 100% sequence identity) to the sequence of a wild-type Cas protein. In some embodiments, a Cas protein variant is a fragment of a wild-type Cas protein and has at least one amino acid substitution relative to the sequence of the wild-type Cas protein. A Cas protein variant can be a Cas9 protein variant. In some embodiments, a Cas protein variant has nuclease activity. In other embodiments, a Cas protein variant does not have nuclease activity.

As used herein, the term "ribonucleoprotein complex" or "RNP complex" refers to a complex comprising a Cas protein or variant (e.g., a Cas9 protein or variant) and a gRNA.

As used herein, the term "modifying" in the context of modifying a target nucleic acid in the genome of a cell refers to inducing a change (e.g., cleavage) in the target nucleic acid. In some embodiments, the change can be a structural change in the sequence of the target nucleic acid. For example, the modifying can take the form of inserting a nucleotide sequence into the target nucleic acid. For example, an exogenous nucleotide sequence can be inserted into the target nucleic acid. The target nucleic acid can also be excised and replaced with an exogenous nucleotide sequence. In another example, the modifying can take the form of cleaving the target nucleic acid without inserting a nucleotide sequence into the target nucleic acid. For example, the target nucleic acid can be cleaved and excised. Such modifying can be performed, for example, by inducing a double stranded break within the target nucleic acid, or a pair of single stranded nicks on opposite strands and flanking the target nucleic acid. Methods for inducing single or double stranded breaks at or within a target nucleic acid include the use of a targetable nuclease (e.g., a Cas protein) as described herein directed to the target nucleic acid. In other embodiments, modifying a target nucleic acid includes targeting another protein to the target nucleic acid and does not include cleaving the target nucleic acid.

As used herein, the term "anionic polymer" refers to a molecule composed of multiple subunits or monomers that has an overall negative charge. Each subunit or monomer in a polymer can, independently, be an amino acid, a small organic molecule (e.g., an organic acid), a sugar molecule (e.g., a monosaccharide or a disaccharide), or a nucleotide. An anionic polymer can contain multiple amino acids, small organic molecules (e.g., organic acids), nucleotides (e.g., natural or non-natural nucleotides, or analogues thereof), or a combination thereof. An anionic polymer can be an anionic homopolymer where all subunits or monomers in the polymer are the same. An anionic polymer can be an anionic heteropolymer where the subunits and monomers in the polymer are different. An anionic polymer does not refer to a nucleic acid, such as a deoxyribonucleic acid (DNA), ribonucleic acid (RNA), that is composed entirely of nucleotides. However, an anionic polymer can include one or more nucleobases (e.g., guanosine, cytidine, adenosine, thymidine, and uridine) together with other subunits or monomers, such as amino acids and/or small organic molecules (e.g., an organic acid). In some embodiments, at least 50% (e.g., 55%, 60%, 65%, 70%, 75%, 80%, 85%, 90%, 95%, or 100%) of the subunits or monomers in the polymer are not nucleotides or do not contain nucleobases. An anionic polymer can be an anionic polypeptide or an anionic polysaccharide. An anionic polymer can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "anionic polypeptide" refers to an anionic polymer that has at least 50% (e.g., 55%, 60%, 65%, 70%, 75%, 80%, 85%, 90%, 95%, or 100%) of its subunits or monomers being amino acids, such as acidic amino acids (e.g., glutamic acids and aspartic acids), or derivatives thereof. Aside from amino acids, an anionic polypeptide can also contain small organic molecules (e.g., organic acids), sugar molecules (e.g., monosaccharides or disaccharides), or nucleotides. In some embodiments, an anionic polypeptide can be a homopolymer where all of its subunits are the same. In other embodiments, an anionic polypeptide can be a heteropolymer that contains two or more different subunits. For example, an anionic polypeptide can be polyglutamic acid (PGA) (e.g., poly-gamma-glutamic acid), polyaspartic acid, and polycarboxyglutamic acid. In another example, an anionic polypeptide can contain a mixture of glutamic acids and aspartic acids. In some embodiments, at least 50% (e.g., 55%, 60%, 65%, 70%, 75%, 80%, 85%, 90%, 95%, or 100%) of the subunits or monomers in an anionic polypeptide can be glutamic acids and/or aspartic acids. An anionic polypeptide can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "anionic polysaccharide" refers to an anionic polymer that has at least 50% (e.g., 55%, 60%, 65%, 70%, 75%, 80%, 85%, 90%, 95%, or 100%) of its subunits or monomers being sugar molecules, such as monosaccharides (e.g., fructose, galactose, and glucose) and disaccharides (e.g., hyaluronic acid, lactose, maltose, and sucrose), or derivatives thereof. Aside from sugar molecules, an anionic polysaccharide can also contain small organic molecules (e.g., organic acids), amino acids (e.g., glutamic acids or aspartic acids), or nucleotides. In some embodiments, an anionic polysaccharide can be a homopolymer where all of its subunits are the same. In other embodiments, an anionic polysaccharide can be a heteropolymer that contains two or more different subunits. For example, an anionic polysaccharide can be hyaluronic acid (HA), heparin, heparin sulfate, or glycosaminoglycan. In some embodiments, at least 50% (e.g., 55%, 60%, 65%, 70%, 75%, 80%, 85%, 90%, 95%, or 100%) of the subunits or monomers in an anionic polysaccharide can be HA. An anionic polysaccharide can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers).

As used herein, the term "active for at least one week" refers to a Cas protein in the presence of an anionic polymer, or a Cas protein and sgRNA RNP complex formed in the presence of an anionic polymer that has activity (e.g., nuclease activity) for at least one week (e.g., at least 2, 3, 4, 5, 6, 7, 8, 9, 10, 11, 12, 13, 14, 15, 16, 17, 18, 19, 20, 21, 22, 23, or 24 weeks) in liquid form at room temperature, 4° C., or 37° C. In the case where the composition comprising the Cas protein and the anionic polymer or the composition comprising the Cas protein, the anionic polymer, and the sgRNA is a lyophilized composition, the term "active for at least one week" also refers to that the Cas protein is active for at least one week at room temperature, 4° C., or 37° C. after reconstituting the lyophilized composition into liquid form. In other words, in some embodiments, if the composition containing the Cas protein and the anionic polymer or the composition containing the Cas protein and sgRNA RNP complexes and the anionic polymer (e.g., a PGA) is lyophilized and later reconstituted, the Cas protein has activity for at least one week (e.g., at least 2, 3, 4, 5, 6, 7, 8, 9, 10, 11, 12, 13, 14, 15, 16, 17, 18, 19, 20, 21, 22, 23, or 24 weeks) at room temperature, 4° C., or 37° C. after reconstitution.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A: Initial testing of a dCas9 shuttle. A full 20 bp DNA-binding protein target sequence (referred to as "Cas9 Target Sequence (CTS)") was added to the edge of a dsDNA HDR template that inserts a new TCR specificity (1G4 TCR clone, specific for the NY-ESO1 cancer antigen) at the endogenous TCR locus5. A dCas9 RNP was formed with a gRNA specific for the CTS attached to the ends of the HDR template, incubated with the dsDNA HDR template for 5 min at room temperature, and then electroporated into primary human T cells along with a separate Cas9 RNP with a gRNA specific for the target locus, in this case the TCR alpha constant region exon 1. HDR template with an "In" facing orientation (PAM sequence towards the center of the insert) on both the 5' and 3' homology arms showed the greatest improvement in knock-in efficiency. FIG. 1B: The dCas9 shuttle RNP could be complexed with the same gRNA sequence as the on-target cutting Cas9 RNP by appending the Cas9 Target Sequence as the on-target genomic locus to the ends of the HDR template. Similarly, an "In" facing orientation of the sequence on both edges of the homology arm showed improved knock-in efficiency. The relative rates of HDR four days post electroporation when including the dCas9 shuttle RNP compared to electroporation of the HDR template and Cas9 without the dCas9 shuttle for n=2 donors are displayed (FIGS. 1A and 1B).

FIGS. 2A-2H: Cas9 complexing to dsDNA HDR templates increases large non-viral knock-in efficiency. FIG. 2A: Enzymatically active Cas9-NLS RNPs can bind truncated DNA-binding protein target sequence (referred to as "truncated Cas9 Target Sequence (tCTS)") added to the ends of a HDR template. FIG. 2B: An "in" facing orientation of the tCTS (PAM facing in towards the center of the inserted sequence vs "out" away from the insert) on the edges of both the 5' and 3' homology arms showed improved knock-in efficiency of a new TCRα-TCRβ specificity at the endogenous TRAC locus. FIG. 2C: Representative flow cytometry plots show improved targeting efficiency across target genomic loci with the HDRTs containing tCTS compared to an unmodified dsDNA HDR template. FIG. 2D: tCTS modified HDRTs improved targeting efficiencies of large knock-ins across eight genomic loci tested in both $CD4^+$ and $CD8^+$ T cells. Note CD4-GFP expression was not observed at significant levels in $CD8^+$ T cells. FIG. 2E: Multiplexed electroporation of GFP and RFP knock-in templates to the RAB11A locus where neither, one, or both templates had a tCTS modification revealed improved knock-in efficiency selectively of the "shuttle" system compared to unmodified dsDNA template in the same cell. FIG. 2F: Cas9 "shuttle" improved multiplexed dual knock-in at different genomic loci as well as bi-allelic knock-in at a single target locus. FIG. 2G: Improved knock-in efficiencies with the Cas9 "shuttle" were aided by Cas9 possessing an NLS peptide. FIG. 2H: Decreased viability was seen with the Cas9 "shuttle" at lower DNA concentrations compared to unmodified dsDNA HDR template. The relative rates of HDR (FIGS. 2B, 2D, 2E, and 2G), multiplexed HDR (FIG. 2F), or viability (FIG. 2H) with the Cas9-NLS shuttle is displayed compared to unmodified dsDNA HDR template (FIGS. 2B and 2D-2G) or to no electroporation controls (FIG. 2H) in n=4 donors (FIGS. 2B, 2C, and 2D) or multiple technical replicates from n=2 donors (FIGS. 2E-2H). HDR efficiency was measured 4 days post electroporation and viability (total number of live cells relative to no electroporation control) at 2 days post electroporation. * $P<0.05$ (Mann-Whitney test).

FIG. 3A: DNA sequence design for the Cas9 "shuttle" system. A short DNA sequence can be easily added to the edges of a dsDNA HDR template by PCR. To mediate binding of a Cas9-NLS RNP to the HDR template but prevent cutting, a 16 bp truncated Cas9 Target Sequence (tCTS) is added to either or both of the 5' and 3' homology arms, along with a 3 bp PAM sequence (NGG for spCas9) and 4 bp of gRNA mismatches. An additional 16 bps of random DNA edge sequence is added outside of the gRNA binding site. The gRNA site can have two orientations, one "In" facing with the PAM directed towards the center of the HDR template, and another "Out" facing with the PAM directed towards the edge of the HDR template. The sequence of the donor template is shown as SEQ ID NO: 6. FIG. 3B: Optimization of the orientation and multiplicity of the truncated Cas9 Target Sequence. Single or multiple 16 bp gRNA binding sites with PAMs were added to the 5' homology arm, 3' homology arm, or both homology arms of an HDR template that replaces the endogenous T cell receptor with a new specificity (insertion size ~1.5 kb). Inwards facing orientations on both edges of the HDR template showed the greatest improvements in HDR efficiency, either with a single copy of the tCTS ("In") or two copies in parallel ("In-In"). For simplicity a single copy was used in all subsequent experiments. FIG. 3C: Optimization of the length of the truncated Cas9 Target Sequence. Note that a 20-nucleotide length gRNA was used in all experiments, while the length of the gRNAs DNA target site varied. A DNA sequence with 16 bps matching the gRNA sequence proved optimal, corresponding to previously demonstrated gRNA target site lengths that mediate Cas9 binding but not cutting (Doudna and Charpentier, Science 346: 1258096, 2014). Again, presence of the truncated Cas9 target sequence on both homology arms increased HDR efficiency. FIG. 3D: Optimization of the edge sequence length showed that a 16 bp random DNA sequence outside to the truncated Cas9 target sequence-binding site yielded the greatest improvements in HDR efficiency. Maximal gains in HDR were aided by the presence of the Cas9 shuttle sequence on both homology arms. The relative rates of HDR (1.5 kb knock-in) at the TCR locus with the indicated shuttle sequence modifications compared to unmodified dsDNA HDR template for n=2 donors are displayed (FIGS. 3A and 3B).

FIG. 4A: Percentage of primary human CD4 or CD8 T cells expressing a knocked in GFP or tNGFR after non-viral genome targeting of eight different genomic sites with and without Cas9 'shuttle' tCTS-modifications to the dsDNA HDR template. Across all eight tested loci the Cas9 shuttle improved knock-in percentages in both cell types. Note that knock-in of a GFP to the CD4 locus does not show GFP expression in $CD8^+$ T cells. FIG. 4B: Aggregation of data across donors and target sites shows that the Cas9 shuttle shows large increases in the % of cells with an observed large knock-in of GFP or tNGFR across initial knock-in efficiencies with an unmodified dsDNA HDR template. FIG. 4C: Relative improvement in HDR efficiency with tCTS modifications is dependent on the initial knock-in efficiency with an unmodified dsDNA HDR template. At lower initial knock-in efficiencies, the relative gain in HDR with the Cas9 shuttle was higher than at target sites where the unmodified template efficiency was higher. Linear regression with a goodness of fit R2 value of 0.20 is overlaid. FIG. 4D: In a cohort of 12 healthy primary T cell donors, all donors showed an improved knock-in efficiency with the Cas9 "shuttle" compared to unmodified dsDNA HDR template for knock-in of a GFP fusion at the RAB11A locus. Lines connect individual donor values. FIG. 4E: Relative improvement in HDR efficiency at the RAB11A locus with a Cas9 shuttle across 12 donors. Knock-ins were assayed 4 days after electroporation in n=4 (FIGS. 4A-4C) or n=12 (FIGS. 4D-4E) donors.

FIG. 5A: Diagram of multiplexing experiments with two HDR templates, encoding either a GFP or RFP integration, simultaneously electroporated into the same cells. Neither, one, or both HDR templates have a truncated Cas9 Target Sequence added to the ends of the homology arms, and the percentage of single and dual knock-in positive cells were assayed by flow cytometry.

FIG. 5B: Representative flow cytometric plots for bi-allelic knock-in of GFP and RFP to the RAB11A housekeeping gene. When one HDR template possessed tCTS "shuttle" modifications, the knock-in rates for that fluorescent protein (either GFP or RFP) increased, whereas the knock-in rates for the other fluorescent protein remained largely unaffected. Knock-ins with both templates possessing Cas9 shuttle sequences increased the percentage of bi-allelic targeting. Note that the percentage of GFP+RFP+ cells is only approximately half of the true bi-allelic knock-in percentage, as knock-ins of either GFP or RFP at both alleles still yields a single positive at the protein level (Roth et al., Nature 559:405-409, 2018). FIG. 5C: Quantification of percent knock-in efficiency across bi-allelic knock-in experiments. FIG. 5D: Representative flow cytometric plots for multiplexed knock-in experiments at two genomic loci, the CLTA locus encoding Clathrin and the RAB11A housekeeping gene. Again, the greatest improvements in multiplexed knock-in efficiency were observed when both templates possess truncated Cas9 Target Sequences. FIG. 5E: Quantification of percent knock-in efficiency across multiplexed knock-in experiments. Knock-ins were assayed 4 days after electroporation in n=2 (FIGS. 5B-5E) donors.

FIGS. 7A and 7B: Cas9 RNPs were prepared at a 2:1 ratio gRNA:protein with or without PGA polymer and mixed with high doses (2-4 µg) of regular dsDNA or tCTS-modified HDR template targeting knock-in at multiple genomic loci: transgenic NY-ESO 1 tumor antigen T cell receptor into the TRAC locus, or GFP fusion at the N- or C- of RAB11A, CD4, TUBA1B, ACTB, FBL, or CLTA genes. The combination of PGA-stabilized Cas9 RNP nanoparticles and "shuttle" tCTS-modified-HDR template both improved relative frequency of HDR measured as percent positive cells compared to standard RNP with unmodified dsDNA HDR template (FIG. 7A) and resulted in higher yield of successfully edited cells (FIG. 7B). Error bars indicate standard deviation; (*) indicates significant difference compared to control dsDNA (p<0.05) (ANOVA with Bonferroni's multiple comparisons test correction). FIGS. 7C-7D: Cas9 RNPs were prepared at 2:1 ratio gRNA:protein with or without PGA polymer and mixed with low doses (0.5-1 µg) of unmodified dsDNA or "shuttle" tCTS-modified HDR templates targeting knock-in of GFP or mCherry to the N-terminus of Clathrin. The PGA-stabilized Cas9 RNP nanoparticles and tCTS-modified HDR templates markedly improved editing efficiency in a variety of primary human immune cell types as visualized in representative flow cytometry plots (after gating for live cells and respective cell type-specific surface markers) (FIG. 7C) or expressed as relative frequency of GFP or mCherry positive cells compared to standard RNP with unmodified dsDNA HDR template (FIG. 7D), and result in higher yield of number of successfully edited cells (FIG. 7E). Error bars indicate standard deviation; (*) indicates significant difference compared to control dsDNA (p<0.05) (ANOVA with Bonferroni's multiple comparisons test correction).

(FIG. 8A) GFP-expressing cells and (FIG. 8B) quantity recovered GFP cells were quantified at day 3 by flow cytometry. Data shown from two different blood donors with lines connecting means for each condition.

DETAILED DESCRIPTION OF THE DISCLOSURE

Figure 1A:
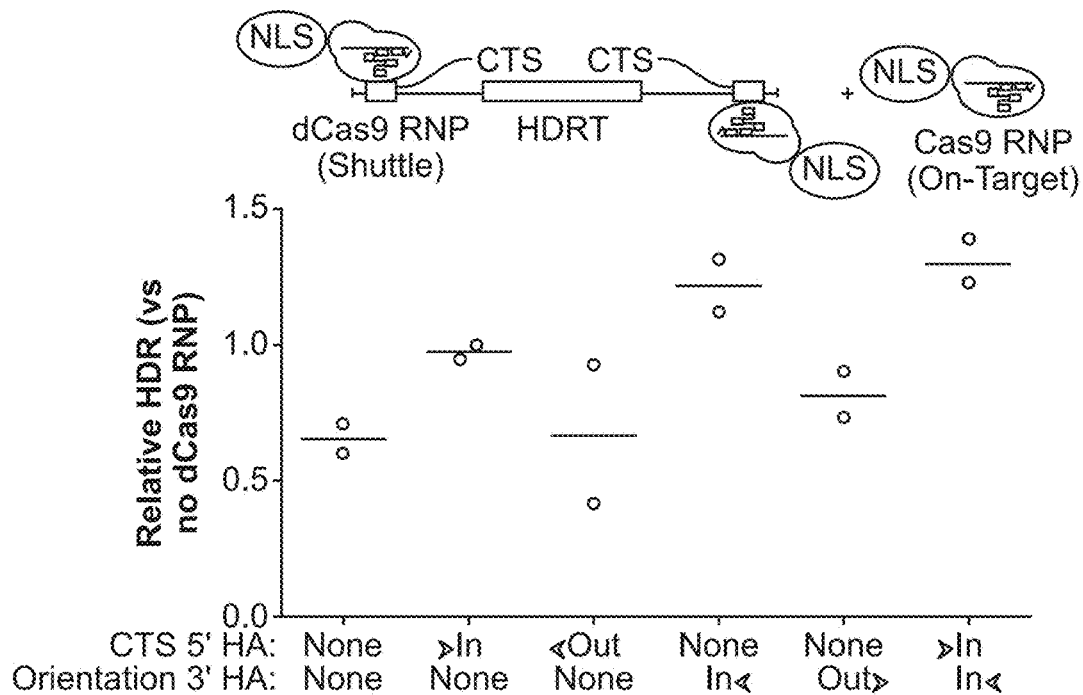
FIGS. 1A and 1B: dCas9 complexing to DNA HDR templates moderately improves knock-in efficiencies.

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

I. Introduction

Virus-modified T cells are approved for cancer immunotherapy, but more versatile and precise genome modifications are needed for a wider range of adoptive cellular therapies (Yin et al., *Nat Rev Clin Oncol*, 16(5):281-295, 2019; Dunbar et al., *Science* 359:6372, 2018; Cornu et al., *Nat Med* 23:415-423, 2017; and David and Doherty, *Toxicol Sci* 155:315-325, 2017). The CRISPR (Clustered Regularly Interspaced Short Palindromic Repeats)-Cas (CRISPR-associated protein) nuclease system is an engineered nuclease system based on a bacterial system that can be used for genome engineering. It is based on part of the adaptive immune response of many bacteria and archaea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide the Cas (e.g., Cas9) nuclease to a region homologous to the crRNA in the target DNA called a "protospacer." The Cas (e.g., Cas9) nuclease cleaves the DNA to generate blunt ends at the double-strand break at sites specified by a 20-nucleotide guide sequence contained within the crRNA transcript. The Cas (e.g., Cas9) nuclease can require both the crRNA and the tracrRNA for site-specific DNA recognition and cleavage. This system has now been engineered such that the crRNA and tracrRNA can be combined into one molecule (the "single-guide RNA" or "sgRNA"), and the crRNA equivalent portion of the sgRNA can be engineered to guide the Cas (e.g., Cas9) nuclease to target any desired sequence (see, e.g., Jinek et al. (2012) *Science* 337:816-821; Jinek et al. (2013) *eLife* 2:e00471; Segal (2013) *eLife* 2:e00563). Thus, the CRISPR-Cas system can be engineered to create a double-strand break at a desired target in a genome of a cell, and harness the cell's endogenous mechanisms to repair the induced break by homology-directed repair (HDR) or nonhomologous end-joining (NHEJ).

As described herein, the inventors discovered that one or more DNA-binding protein target sequences, when added at the ends of the homology directed repair (HDR) template, can interact with DNA-binding proteins to "shuttle" the template to the desired cellular location (e.g., a cellular location in proximity to the target nucleic acid (e.g., the nucleus)) and enhance target nucleic acid modification efficiency.

Further, the disclosure also provides compositions and methods for modifying a target nucleic acid that include a Cas protein (e.g., a Cas9 protein), one or more single guide RNAs (sgRNAs), and an anionic polymer. Without being bound by any theory, the addition of an anionic polymer to the Cas protein and sgRNA ribonucleoprotein (RNP) complex stabilizes complex and prevents aggregation. The compositions and methods described herein may be used for genetic modifications that improve cell viability, achieve therapeutically-relevant large transgene insertion levels, and minimize dependence upon foreign DNA, thus reducing potential for off-target genotoxicity. The disclosure provides a strategy for improving Cas protein and sgRNA RNP complex editing outcomes that in conjunction improve primary human T cell editing and cell survival and enable high efficiency large transgene knock-in in both iPS-derived and primary human hematopoietic stem cells.

Non-viral strategies, such as electroporation, to deliver the CRISPR-Cas system into the cell for genetic modification avoid many complications associated with viral delivery, such as fatal systemic immune responses to viral vectors, viral delivery inefficiency, and viral insertion-related gene overexpression. However, in some cases, poor stability, RNP complex aggregation into micron-sized particles, the need for large amounts of HDR template, and dose-dependent cytotoxicity can occur when non-viral strategies for CRISPR-Cas system delivery are employed. For example, Cas9 proteins can be unstable when complexed with the single-guide RNA (sgRNA), forming cloudy precipitates immediately or over a few hours of time, which correlate with reduced editing efficiency.

It was observed that anionic polymers, such as the ones described herein, markedly improved the stability and editing efficiency of Cas9 protein and single-guide RNA (sgRNA) ribonucleoprotein complex (RNP). Without being bound by any theory, the anionic polymer may interact favorably with the very positively-charged (at physiological pH) Cas9 protein, stabilize the RNP complex into dispersed particles, prevent aggregation, and improve nuclease editing activity and efficiency. The addition of anionic polymers to a solution containing a Cas protein or a solution containing a Cas protein and sgRNA RNP complex also allow the solution to be lyophilized and reconstituted for use, thus providing an affordable and robust benchtop platform for editing multiple genes simultaneously in a variety of clinically-relevant cell types.

II. Compositions

The disclosure provides compositions and methods for modifying a target nucleic acid that include: (a) a targetable nuclease; (b) a DNA-binding protein; and (c) a donor template comprising a homology directed repair (HDR) template and one or more DNA-binding protein target sequences. The DNA-binding protein can directly or indirectly bind to the DNA-binding protein target sequence within the donor template. As described in detail further herein, in some embodiments, when the DNA-binding protein is a transcription activator-like (TAL) effector DNA-binding protein, the TAL effector DNA-binding protein can directly recognize and bind to the DNA-binding target sequence. In some embodiments, when the DNA-binding protein is a zinc finger DNA-binding protein, the zinc finger DNA-binding protein can directly recognize and bind to the DNA-binding target sequence. In other embodiments, when the DNA-binding protein is an RNA-guided nuclease (e.g., a Cas protein), the RNA-guided nuclease can indirectly bind to a DNA-binding protein target sequence via a donor gRNA, which can hybridize to the DNA-binding protein target sequence. Without being bound by any theory, the DNA-binding protein serves to transport or shuttle the donor template to a cellular location close to the target nucleic acid. Thus, the DNA-binding protein can improve the delivery of the HDR template into target cells, especially to the cell nucleus, and increase knock-in efficiencies.

The disclosure provides compositions and methods for modifying a target nucleic acid that include a Cas protein (e.g., a Cas9 protein), one or more single guide RNAs (sgRNAs), and an anionic polymer. Without being bound by any theory, the addition of an anionic polymer to the Cas protein and sgRNA ribonucleoprotein (RNP) complex stabilizes complex and prevents aggregation.

III. CRISPR/Cas

In some embodiments of the compositions and methods described herein, the targetable nuclease is a first RNA-guided nuclease, the DNA-binding protein is a second RNA-guided nuclease, and the donor template further comprises one or more protospacer adjacent motifs (PAMs). The composition also further comprises a target guide RNA (gRNA) that is complementary to the target nucleic acid and a donor gRNA that hybridizes to the DNA-binding protein target sequence. The target gRNA can form a first RNP complex with the first RNA-guided nuclease and guide the first RNA-guided nuclease (e.g., Cas protein) to the target nucleic acid. In some embodiments, a portion of the target gRNA (e.g., a portion of the target gRNA that is at least 15 nucleotides (e.g., 15, 16, 17, 18, 19, 20, 21, 22, 23, 24, or 25 nucleotides) is complementary to the target nucleic acid. The donor gRNA can form a second RNP with the second RNA-guided nuclease. The DNA-binding protein target sequence in the donor template can hybridize to the donor gRNA or a portion thereof. Therefore, the complex containing the second RNA-guided nuclease, the donor gRNA, and the donor template can bring the donor template into the desired intracellular location (e.g., the nucleus) for homologous recombination to occur at the integration site in the target nucleic acid. In some embodiments, the sequences of the target gRNA and the donor gRNA are the same. In some embodiments, the sequences of the target gRNA and the donor gRNA are different. In some embodiments, the first and second RNA-guided nucleases are the same. In other embodiments, the first and second RNA-guided nucleases are different. In other embodiments, a composition described herein can also be used for integrating the donor template through non-homology directed repair mediated methods, such as homology independent targeted integration (HITI).

The composition can contain the targetable nuclease and the target gRNA in a molar ratio of between 1:10 and 2:1 (e.g., between 1:5 and 2:1, between 2:5 and 2:1, between 3:5 and 2:1, between 4:5 and 2:1, between 1:1 and 2:1, between 1:10 and 1:1, between 1:10 and 4:5, between 1:10 and 3:5, between 1:10 and 2:5, or between 1:10 and 1:5), respectively. In some embodiments, the composition can contain the DNA-binding protein and the donor template in a molar ratio of between 10:1 and 1000:1 (e.g., between 50:1 and 1000:1, between 100:1 and 1000:1, between 200:1 and 1000:1, between 300:1 and 1000:1, between 400:1 and 1000:1, between 500:1 and 1000:1, between 600:1 and 1000:1, between 700:1 and 1000:1, between 800:1 and 1000:1, between 900:1 and 1000:1, between 10:1 and 900:1, between 10:1 and 800:1, between 10:1 and 700:1, between 10:1 and 600:1, between 10:1 and 500:1, between 10:1 and 400:1, between 10:1 and 300:1, between 10:1 and 200:1, between 10:1 and 100:1, or between 10:1 and 50:1), respectively. In some embodiments, the DNA-binding protein and the donor gRNA are in a molar ratio of between 1:10 and 2:1 (e.g., between 1:5 and 2:1, between 2:5 and 2:1, between 3:5 and 2:1, between 4:5 and 2:1, between 1:1 and 2:1, between 1:10 and 1:1, between 1:10 and 4:5, between 1:10 and 3:5, between 1:10 and 2:5, or between 1:10 and 1:5), respectively.

The RNA-guided nuclease can also be fused with a localization peptide or protein. For example, the RNA-guided nuclease can be fused with one or more nuclear localization signal (NLS) sequences, which can direct the nuclease and the RNP complexes it forms to the nucleus to modify the target nucleic acid. Examples of NLS sequences are known in the art, e.g., as described in Lange et al., *J Biol Chem.* 282(8):5101-5, 2007, and also include, but are not limited to, AVKRPAATKKAGQAKKKKLD (SEQ ID NO: 1), MSRRRKANPTKLSENAKKLAKEVEN (SEQ ID NO: 2), PAAKRVKLD (SEQ ID NO: 3), KLKIKRPVK (SEQ ID NO: 4), and PKKKRKV (SEQ ID NO: 5). Examples of other peptide or proteins that can be used to a RNA-guided nuclease, such as cell-penetrating peptides and cell-targeting peptides are available in the art and described, e.g., Vivés et al., *Biochim Biophys Acta.* 1786(2):126-38, 2008.

IV. Single-Guide RNAs

A Cas protein may be guided to its target DNA by a single-guide RNA (sgRNA). An sgRNA is a version of the naturally occurring two-piece guide RNA (crRNA and tracrRNA) engineered into a single, continuous sequence. An sgRNA may contain a guide sequence (e.g., the crRNA equivalent portion of the sgRNA) that targets the Cas protein to the target DNA and a scaffold sequence that interacts with the Cas protein (e.g., the tracrRNAs equivalent portion of the sgRNA). An sgRNA may be selected using a software. As a non-limiting example, considerations for selecting an sgRNA can include, e.g., the PAM sequence for the Cas9 protein to be used, and strategies for minimizing off-target modifications. Tools, such as NUPACK® and the CRISPR Design Tool, can provide sequences for preparing the sgRNA, for assessing target modification efficiency, and/or assessing cleavage at off-target sites.

Guide Sequence

The guide sequence in the sgRNA may be complementary to a specific sequence within a target DNA. The 3' end of the target DNA sequence can be followed by a PAM sequence. Approximately 20 nucleotides upstream of the PAM sequence is the target DNA. In general, a Cas9 protein or a variant thereof cleaves about three nucleotides upstream of the PAM sequence. The guide sequence in the sgRNA can be complementary to either strand of the target DNA.

In some embodiments, the guide sequence of an sgRNA may comprise about 10 to about 2000 nucleic acids, for example, about 10 to about 100 nucleic acids, about 10 to about 500 nucleic acids, about 10 to about 1000 nucleic acids, about 10 to about 1500 nucleic acids, about 10 to about 2000 nucleic acids, about 50 to about 100 nucleic acids, about 50 to about 500 nucleic acids, about 50 to about 1000 nucleic acids, about 50 to about 1500 nucleic acids, about 50 to about 2000 nucleic acids, about 100 to about 500 nucleic acids, about 100 to about 1000 nucleic acids, about 100 to about 1500 nucleic acids, about 100 to about 2000 nucleic acids, about 500 to about 1000 nucleic acids, about 500 to about 1500 nucleic acids, about 500 to about 2000 nucleic acids, about 1000 to about 1500 nucleic acids, about 1000 to about 2000 nucleic acids, or about 1500 to about 2000 nucleic acids at the 5' end of the sgRNA that can direct the Cas protein to the target DNA site using RNA-DNA complementarity base pairing. In some embodiments, the guide sequence of an sgRNA comprises about 100 nucleic acids at the 5' end of the sgRNA that can direct the Cas protein to the target DNA site using RNA-DNA complementarity base pairing. In some embodiments, the guide sequence comprises 20 nucleic acids at the 5' end of the sgRNA that can direct the Cas protein to the target DNA site using RNA-DNA complementarity base pairing. In other embodiments, the guide sequence comprises less than 20, e.g., 19, 18, 17, 16, 15 or less, nucleic acids that are complementary to the target DNA site. In some instances, the guide sequence in the sgRNA contains at least one nucleic acid mismatch in the complementarity region of the target DNA site. In some instances, the guide sequence contains about 1 to about 10 nucleic acid mismatches in the complementarity region of the target DNA site.

Scaffold Sequence

The scaffold sequence in the sgRNA may serve as a protein-binding sequence that interacts with the Cas protein or a variant thereof. In some embodiments, the scaffold sequence in the sgRNA can comprise two complementary stretches of nucleotides that hybridize to one another to form a double-stranded RNA duplex (dsRNA duplex). The scaffold sequence may have structures such as lower stem, bulge, upper stem, nexus, and/or hairpin. In some embodiments, the scaffold sequence in the sgRNA can be between about 90 nucleic acids to about 120 nucleic acids, e.g., about 90 nucleic acids to about 115 nucleic acids, about 90 nucleic acids to about 110 nucleic acids, about 90 nucleic acids to about 105 nucleic acids, about 90 nucleic acids to about 100 nucleic acids, about 90 nucleic acids to about 95 nucleic acids, about 95 nucleic acids to about 120 nucleic acids, about 100 nucleic acids to about 120 nucleic acids, about 105 nucleic acids to about 120 nucleic acids, about 110 nucleic acids to about 120 nucleic acids, or about 115 nucleic acids to about 120 nucleic acids.

V. Target gRNA and Donor gRNA

Guide RNAs (gRNAs) in general refer to a DNA-targeting RNA containing (1) a guide sequence that is complementary to a target nucleic acid and guides the RNA-guided nuclease to the target nucleic acid and (2) a scaffold sequence that interacts and binds with the RNA-guided nuclease. In some embodiments of the disclosure, the target gRNA and the donor gRNA have the same sequence. In other embodiments of the disclosure, the target gRNA and the donor gRNA have different sequences. In the compositions and methods described herein, a target gRNA comprises a portion that is complementary to the target nucleic acid. Once the target gRNA forms an RNP complex with the targetable nuclease (e.g., a first RNA-guided nuclease), the RNP complex can be guided to the target nucleic acid by the complementarity between the target gRNA and the target nucleic acid. In some embodiments, the targetable nuclease is a Cas9 protein. The Cas9 protein identifies the target nucleic acid by first identifying a 3-base pair protospacer adjacent motif (PAM) located 3' of the target nucleic acid. Once the PAM is identified, the target gRNA in the RNP complex hybridizes to the target nucleic acid upstream of the PAM. In some embodiments, a target gRNA includes a portion of nucleotides that are complementary to a portion in the target nucleic acid that is approximately 20 nucleotides upstream of the PAM sequence. In general, a Cas9 protein or a variant thereof cleaves about three nucleotides upstream of the PAM sequence. A gRNA can be selected using a software. As a non-limiting example, considerations for selecting a gRNA can include, e.g., the PAM sequence for the RNA-guided nuclease to be used, and strategies for minimizing off-target modifications. Tools, such as NUPACK® and the CRISPR Design Tool, can provide sequences for preparing the gRNA, for assessing target modification efficiency, and/or assessing cleavage at off-target sites.

In some embodiments, the target gRNA comprises a portion of at least 15 nucleotides (e.g., 15, 16, 17, 18, 19, 20, 21, 22, 23, 24, or 25 nucleotides) that are complementary to the target nucleic acid. In some embodiments, the target gRNA can be completely complementary or partially complementary to the target nuclei acid. In some embodiments, at least 60% (e.g., 65%, 70%, 75%, 80%, 85%, 90%, 95%, or 97%) of the nucleotides in the target nucleic acid can engage in Watson-Crick base pairing with their corresponding nucleotides in the target gRNA.

Similar to the target gRNA, the donor gRNA forms a complex with the DNA-binding protein (e.g., a RNA-guided nuclease). In the compositions and methods described herein, a donor gRNA comprises a portion that is complementary to the DNA-binding protein target sequence, which is at one or both termini of the HDR template in the donor template. Once the donor gRNA forms an RNP complex with the DNA-binding protein (e.g., a RNA-guided nuclease), the RNP complex can be guided to the donor template by the complementarity between the donor gRNA and the DNA-binding protein target sequence. In some embodiments, the DNA-binding protein target sequence is complementary to an equal length portion of the sequence of the donor gRNA. In some embodiments, the donor gRNA comprises a portion of at least 15 nucleotides (e.g., 15, 16, 17, 18, 19, 20, 21, 22, 23, 24, or 25 nucleotides) that can hybridize to the DNA-binding protein target sequence. The donor gRNA can be completely complementary or partially complementary to the DNA-binding protein target sequence. In some embodiments, at least 60% (e.g., 65%, 70%, 75%, 80%, 85%, 90%, 95%, or 97%) of the nucleotides in the DNA-binding protein target sequence can engage in Watson-Crick base pairing with their corresponding nucleotides in the donor gRNA. In some embodiments, the DNA-binding protein target sequence can have at least one (e.g., one, two, three, four, five, six, seven, eight, nine, or ten) mismatched nucleotide to its corresponding nucleotide in the donor gRNA when the DNA-binding protein target sequence and the donor gRNA are hybridized. Examples of mismatched bases include a guanine and uracil, guanine and thymine, and adenine and cytosine pairing.

As described in detail further herein, the DNA-binding protein target sequence and the PAM on one or both termini of the HDR template can be designed with different configurations. The complex containing the DNA-binding protein (e.g., a RNA-guided nuclease), the donor gRNA, and the donor template can shuttle the donor template, without cleavage of the DNA-binding protein target sequence, to the desired intracellular location (e.g., the nucleus) such that the HDR template can integrate into the cleaved target nucleic acid.

In some embodiments of the disclosure, the target gRNA and the donor gRNA have the same sequence and each of the targetable nuclease and the DNA-binding protein is an RNA-guided nuclease (e.g., a Cas protein). In this case, the gRNA can form a first RNP complex with the RNA-guided nuclease. The first RNP complex can bind to the target nucleic acid via the hybridization between the gRNA and the target nucleic acid. The gRNA can also form a second RNP complex with the RNA-guided nuclease and the donor template. In this second RNP complex, the gRNA can bind to the DNA-binding protein target sequence in the donor template to bring the donor template to the desired intracellular location (e.g., the nucleus) for homologous recombination to occur at the cleaved target nucleic acid. In some embodiments, the gRNA and the DNA-binding protein target sequence only have partial complementarity.

VI. Donor Template

The HDR template, one or more (e.g., one, two, three, four, or five) DNA-binding protein target sequences, and one or more (e.g., one, two, three, four, or five) PAMs (when present) can have several different configurations in the donor template to enhance homology directed repair between the HDR template and the target nucleic acid. The donor template can also contain one or more edge sequences to facilitate the binding of the DNA-binding protein. In one example, the donor template contains one DNA-binding protein target sequence and one PAM. In some embodiments of this example, the DNA-binding protein target sequence and the PAM are located at the 5' terminus of the HDR template. In particular, when both the DNA-binding protein target sequence and the PAM are located at the 5' terminus of the HDR template, the PAM can be located at the 5' terminus or the 3' terminus of the DNA-binding protein target sequence. In other embodiments of this example, the DNA-binding protein target sequence and the PAM are located at the 3' terminus of the HDR template. In particular, when both the DNA-binding protein target sequence and the PAM are located at the 3' terminus of the HDR template, the PAM can be located at the 5' terminus or the 3' terminus of the DNA-binding protein target sequence.

In some embodiments, the size or length of the donor template is greater than about 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1 kb, 1.1 kb, 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.1 kb, 9.2 kb, 9.3 kb, 9.4 kb, 9.5 kb, 9.6 kb, 9.7 kb, 9.8 kb, 9.9 kb, 10.0 kb, any size of template in between these sizes, or greater than 10 kb. For example, the size of the template can be about 200 bp to about 500 bp, about 200 bp to about 750 bp, about 200 bp to about 1 kb, about 200 bp to about 1.5 kb, about 200 bp to about 2.0 kb, about 200 bp to about 2.5 kb, about 200 bp to about 3.0 kb, about 200 bp to about 3.5 kb, about 200 bp to about 4.0 kb, about 200 bp to about 4.5 kb, about 200 bp to about 5.0 kb. In some cases, the size of the template is large enough and in sufficient quantity to be lethal as naked DNA.

In some embodiments, the donor template encodes a heterologous protein or a fragment thereof. In some embodiments, the template includes regulatory sequences, for example, a promoter sequence and/or an enhancer sequence to regulate expression of the heterologous protein or fragment thereof, e.g., after insertion into the genome of a cell. A heterologous protein can include a chimeric antigen receptor (CAR). A heterologous protein can include a T cell receptor (TCR).

In some embodiments, the donor template includes an exogenous sequence such as an exogenous nucleotide sequence. An exogenous sequence can include an encoded heterologous protein or a fragment thereof. An exogenous sequence can include a gene or portion thereof. An exogenous nucleotide sequence can be a short sequence, e.g., of 3-100 nucleotides in length. An exogenous nucleotide sequence of interest can be a single nucleotide. In addition, an exogenous nucleotide sequence of interest can be a long sequence, e.g., of 500-3000 nucleotides in length. An exogenous nucleotide sequence of interest can be coding or non-coding for a polypeptide sequence. In addition, an exogenous nucleotide sequence of interest can be inserted in a cell such that it forms a chimeric gene upon insertion. For example, an exogenous receptor portion can be inserted in frame in an endogenous receptor coding sequence to produce a chimeric receptor coding sequence that, post-editing, includes the exogenous receptor portion operably linked to an endogenous intracellular portion (e.g., for signal transduction).

In some examples, a gene or portion thereof can be a protein-coding nucleotide sequence (i.e., a nucleotide sequence encoding a polypeptide sequence). In general, any protein coding nucleotide can be used. In some examples, a protein coding nucleotide sequence encodes a protein useful in autologous cell therapies (e.g., autologous T cell therapies). In some examples, a protein coding nucleotide sequence can include, but is not limited to, a factor that modulates the immune system, a cytokine, a factor that modulates T cell function, a factor that promotes T-cell survival, a factor that promotes T-cell function, or an immune checkpoint inhibitor. A protein coding nucleotide sequence, particularly a secreted protein or membrane-bound proteins, can include a nucleotide sequence encoding a signal peptide. The signal peptide can be endogenous to the protein encoded by the protein coding nucleotide sequence. The signal peptide can be exogenous to the protein encoded by the protein coding nucleotide sequence.

In some examples, a gene or portion thereof can be a non-protein coding nucleotide sequence. In general, any non-protein coding nucleotide can be used. In some cases, a non-protein coding nucleotide sequence can be a nucleotide sequence useful in autologous cell therapies (e.g., autologous T cell therapies). In some cases, a non-protein coding nucleotide sequence can include, but is not limited to, an shRNA, an siRNA, an miRNA, and an lncRNA.

Although a nucleotide sequence encoding at least a portion of a gene (e.g., an exogenous gene of interest) can, in general, be any size, practical considerations, such as the impact of gene size on overall template size and on subsequent overall editing efficiency, can be taken into account. Thus, in a particular aspect, provided herein are modified cells that are genomically edited, or are capable of being genomically edited, to express an exogenous gene greater than or equal to 100 bases in length at HR efficiency rates greater than those previously described (e.g., a greater percentage of a population having an integrated polynucleotide sequence), particularly when using non-viral delivery methods. The improved HR efficiency rates similarly apply to genes greater than 100 bases in length, such as introducing exogenous sequences greater than or equal to 200 bases in length, greater than or equal to 400 bases in length, greater than or equal to 500 bases in length, greater than or equal to 600 bases in length, greater than or equal to 750 bases in length, greater than or equal to 1000 bases in length greater than or equal to 1500 bases in length, greater than or equal to 2000 bases in length, greater than or equal to 3000 bases in length, or greater than or equal to 4000 bases in length. The at least a portion of a gene can be greater than or equal to 800 bases in length. The at least a portion of a gene can be greater than or equal to 1600 bases in length.

Exogenous sequences can be between 100-200 bases in length, between 100-300 bases in length, between 100-400 bases in length, between 100-500 bases in length, between 100-600 bases in length, between 100-700 bases in length, between 100-800 bases in length, between 100-900 bases in length, or between 100-1000 bases in length. Exogenous sequences can be between 100-2000 bases in length, between 100-3000 bases in length, between 100-4000 bases in length, between 100-5000 bases in length, between 100-6000 bases in length, between 100-7000 bases in length, between 100-8000 bases in length, between 100-9000 bases in length, or between 100-10,000 bases in length. Exogenous sequences can be between 1000-2000 bases in length, between 1000-3000 bases in length, between 1000-4000 bases in length, between 1000-5000 bases in length, between 1000-6000 bases in length, between 1000-7000 bases in length, between 1000-8000 bases in length, between 1000-9000 bases in length, or between 1000-10,000 bases in length.

Exogenous sequences can be greater than or equal to 10 bases in length, greater than or equal to 20 bases in length, greater than or equal to 30 bases in length, greater than or equal to 40 bases in length, greater than or equal to 50 bases in length, greater than or equal to 60 bases in length, greater than or equal to 70 bases in length, greater than or equal to 80 bases in length greater than or equal to 90 bases in length, or greater than or equal to 95 bases in length. Exogenous sequences can be between 1-100 bases in length, between 1-90 bases in length, between 1-80 bases in length, between 1-70 bases in length, between 1-60 bases in length, between 1-50 bases in length, between 1-40 bases in length, or between 1-30 bases in length. Exogenous sequences can be between 1-20 bases in length, between 2-20 bases in length, between 3-20 bases in length, between 5-20 bases in length, between 10-20 bases in length, or between 15-20 bases in length. Exogenous sequences can be between 1-10 bases in length, between 2-10 bases in length, between 3-10 bases in length, between 5-10 bases in length, between 1-5 bases in length, or between 1-15 bases in length. Exogenous sequences can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 150, 175, 200, 225, or 250 bases in length. Exogenous sequences can be 1, 2, 3, 4, 5, 6, 7, 8, 9, 10, 11, 12, 13, or 14 bases in length. Exogenous sequences can be greater than about 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1 kb, 1.1 kb, 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb or any size of template in between these sizes.

In examples where multiple exogenous sequences are introduced, the multiple exogenous sequences can be different sizes, e.g., a first exogenous sequence can be greater than or equal to 100 bases and a second exogenous sequence can be greater than or equal to 100 bases, or a first exogenous sequence can be greater than or equal to 100 bases and a second exogenous sequence can be less than 100 bases (e.g., between 1-100 bases in length).

In some cases, the donor template is a linear DNA template. In some cases, the template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA. In some cases, the donor template is a double-stranded plasmid. In some cases the donor template is a single-stranded plasmid. In some cases the donor template is a mini-circle.

A donor template can be non-viral. A template can be a plasmid. A template can be a minicircle. A template can be a nanoplasmid. A template can be circular.

Figure 1B:
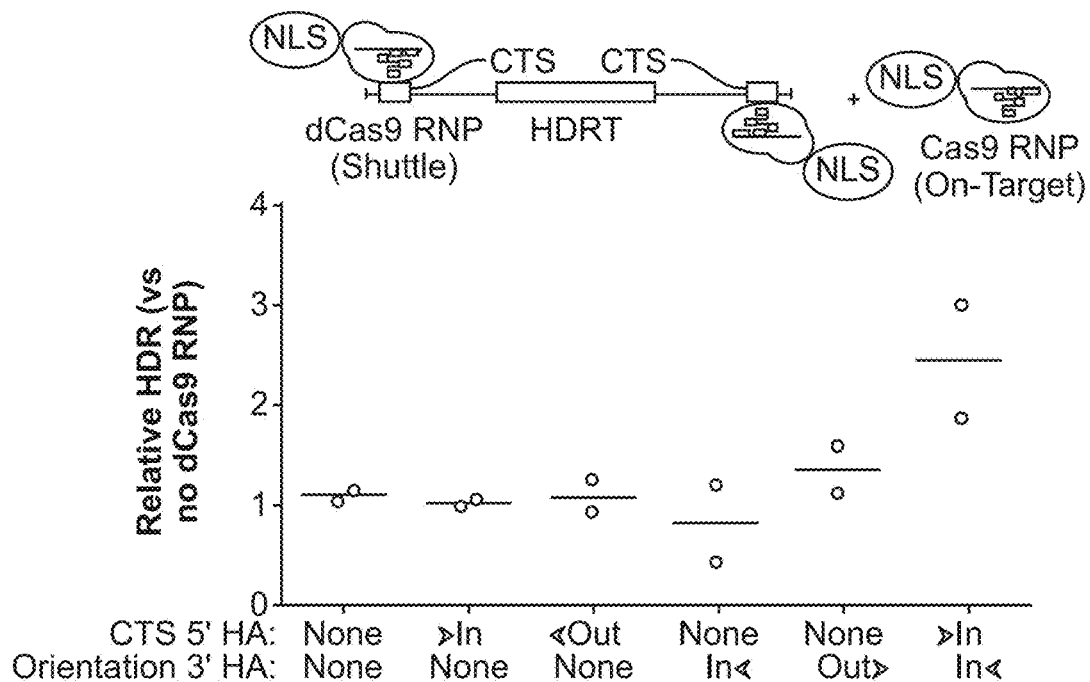
Figure 2A:
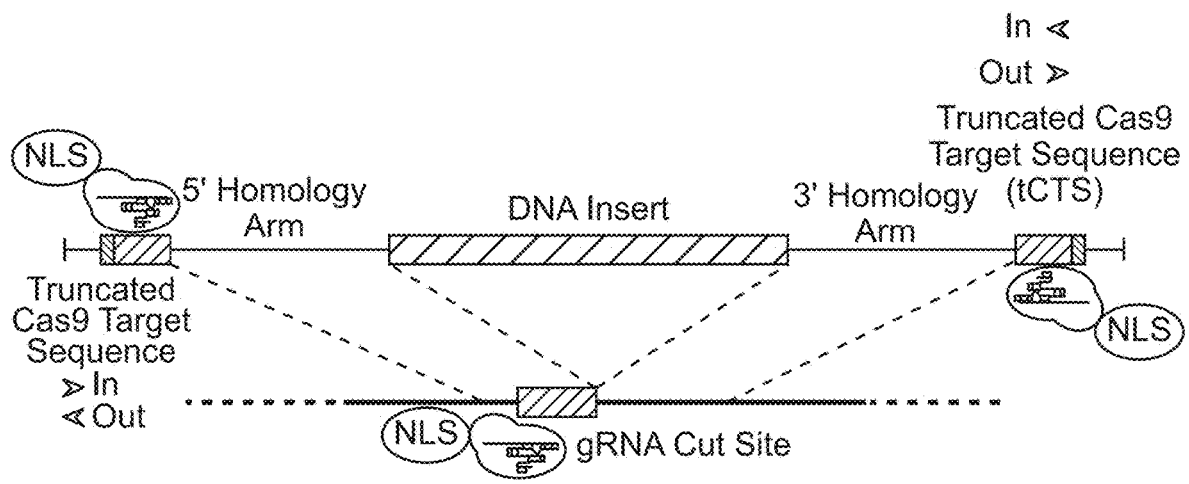
Figure 2B:
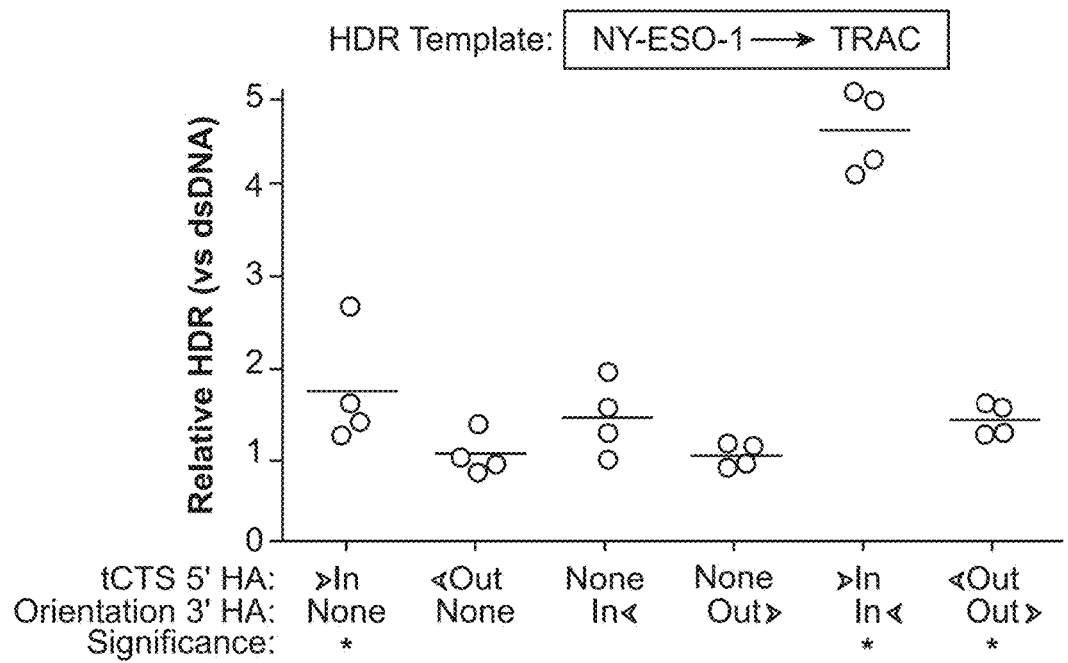
Figure 2C:
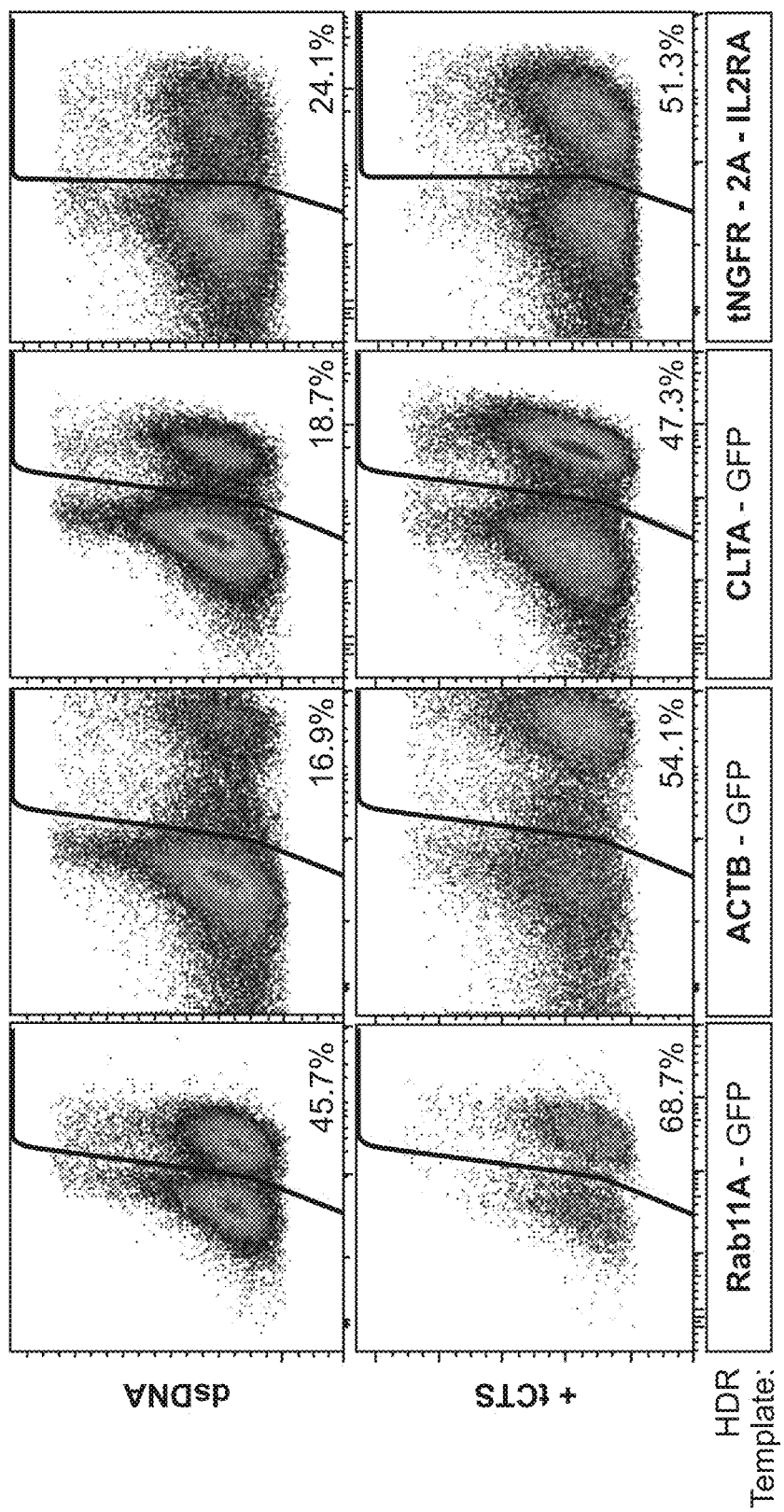
Figure 2D:
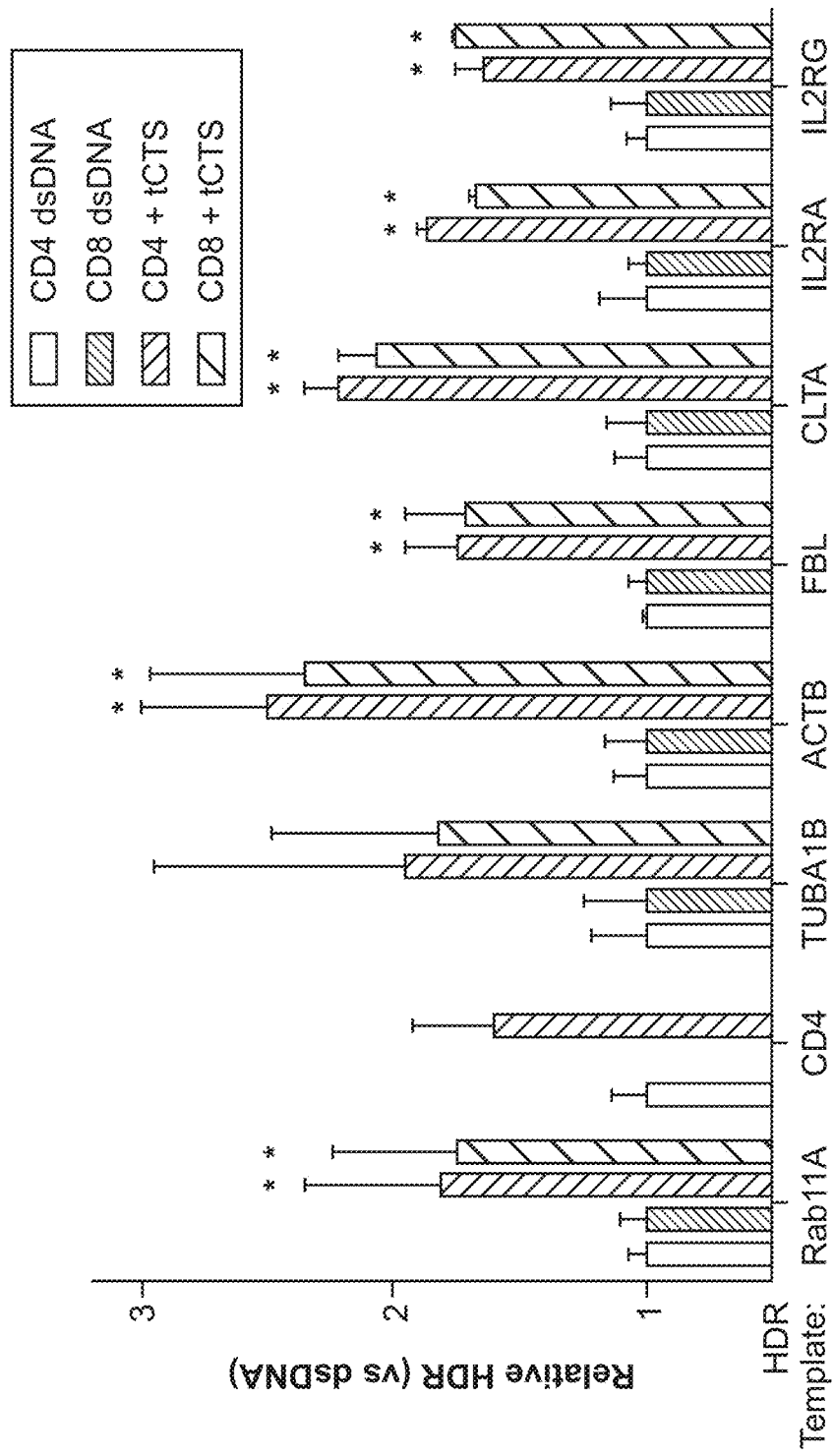
Figure 2F:
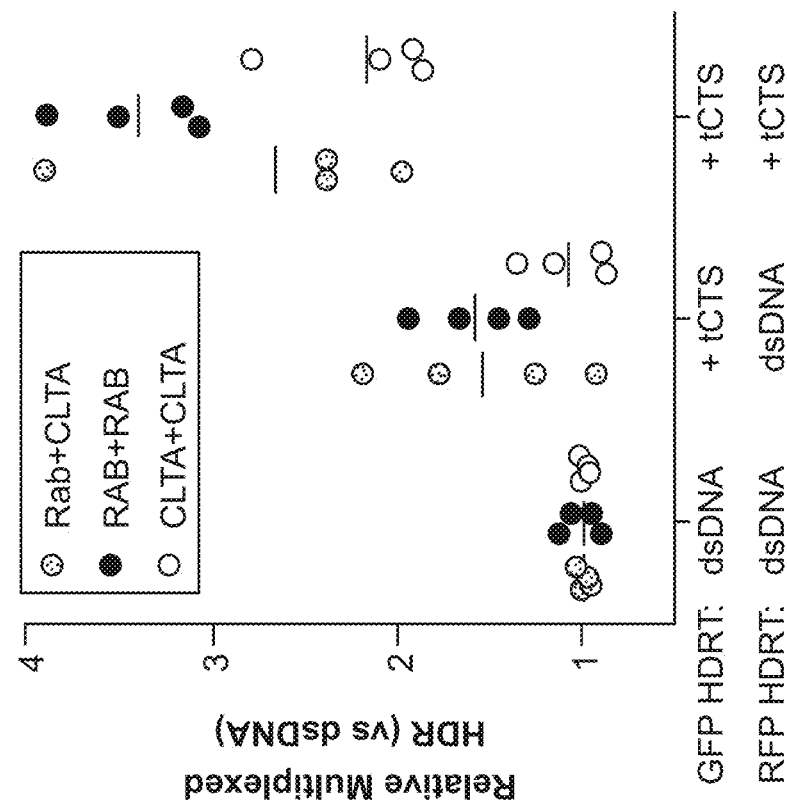
Figure 2E:
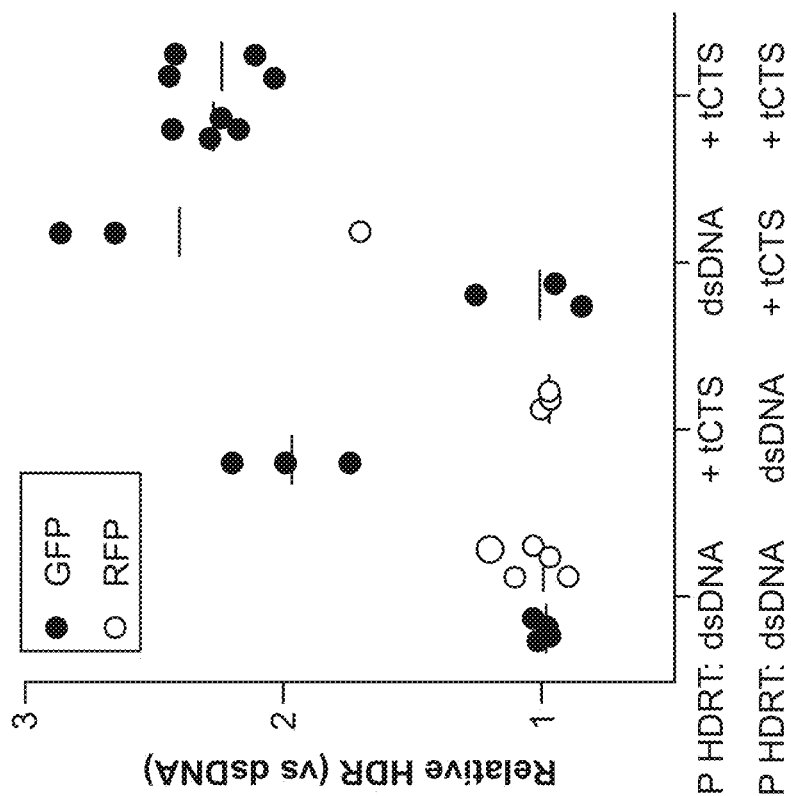
Figure 3A:
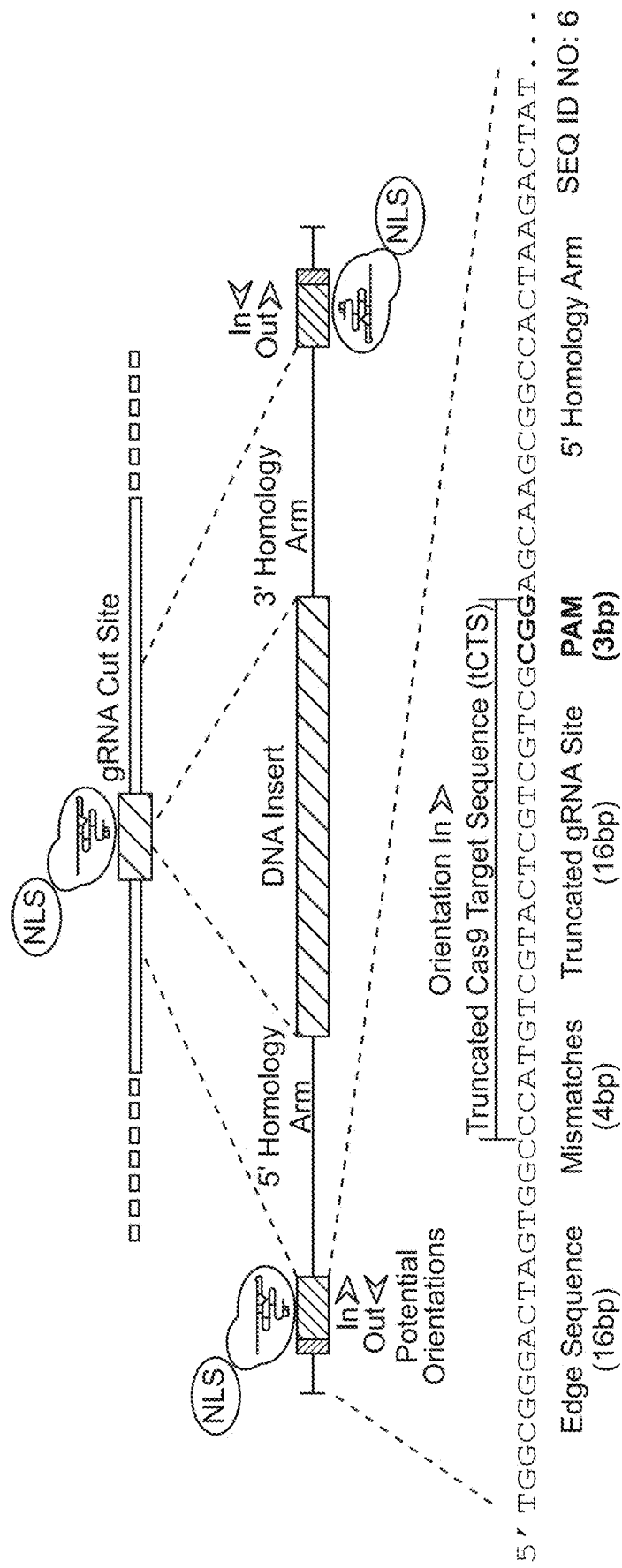
FIGS. 3A-3D: Optimization of Cas9 "shuttle" system through varying DNA-binding protein target sequence (referred to as "Cas9 Target Sequence (CTS)") parameters on HDR templates.
Figures 3B, 3C, 3D:
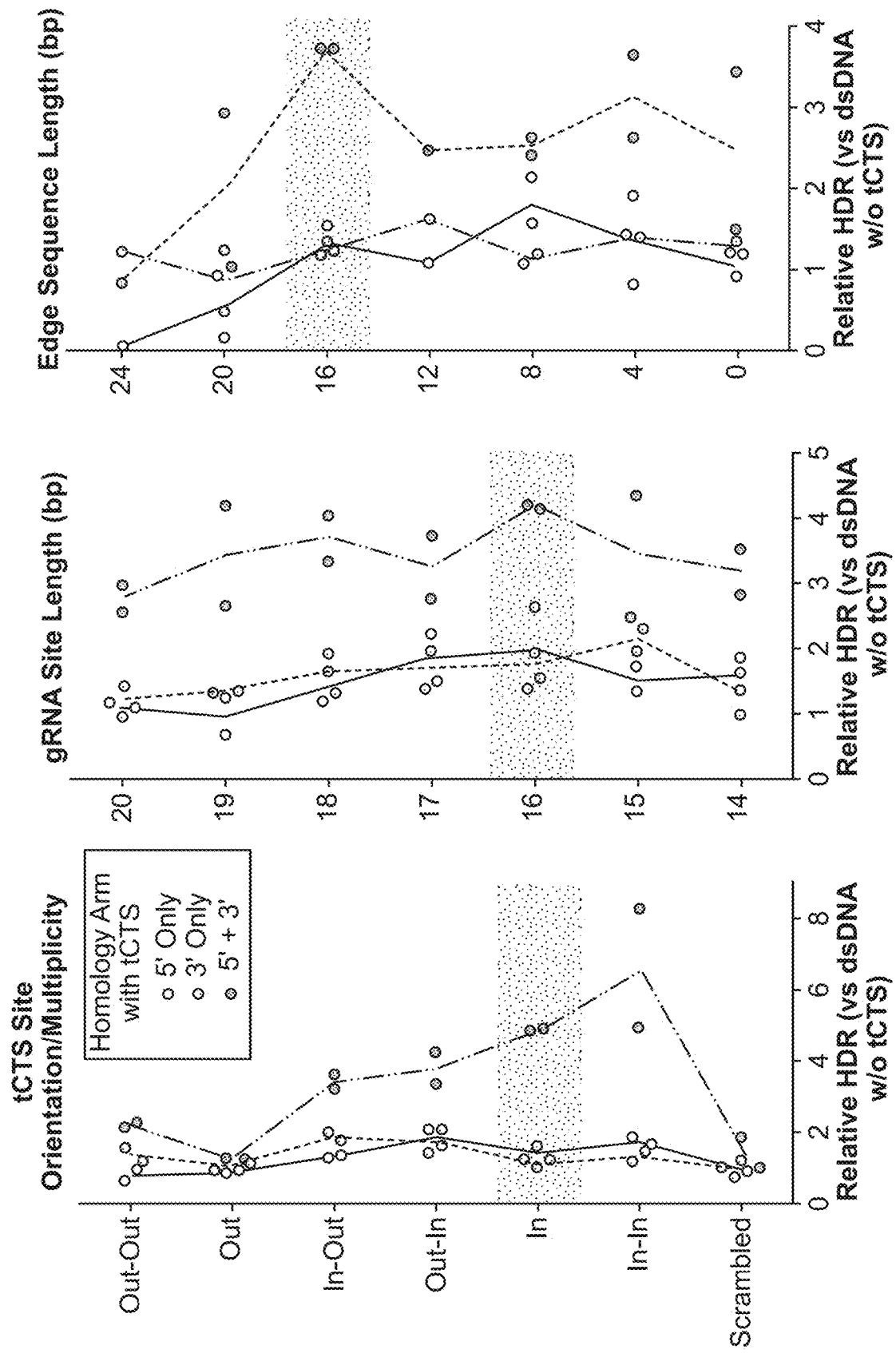
Figure 4A:
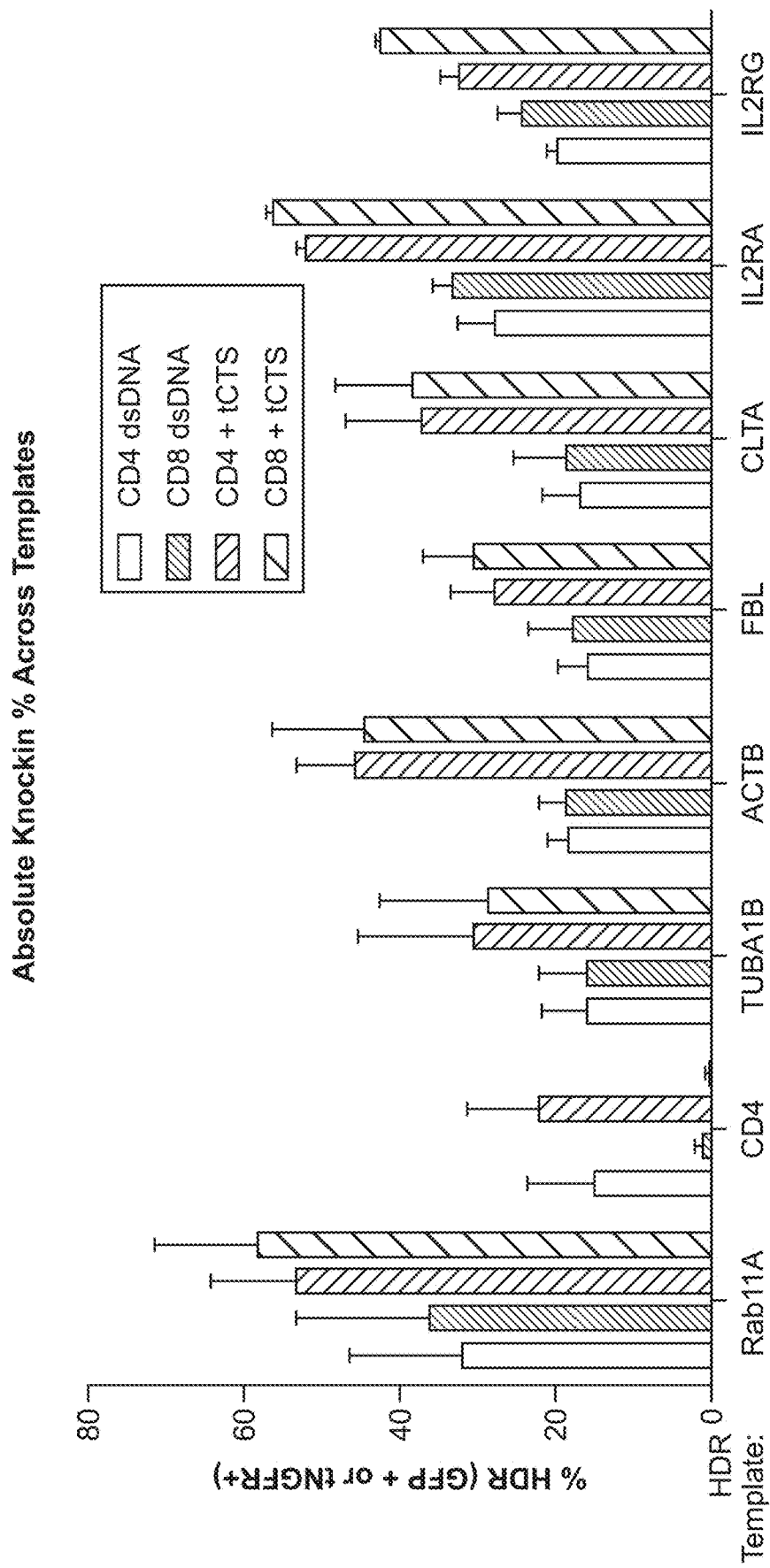
FIGS. 4A-4E: Cas9 "shuttle" tCTS HDR template modifications improved large knock-in efficiency across donors and genomic target loci.
Figure 4B:
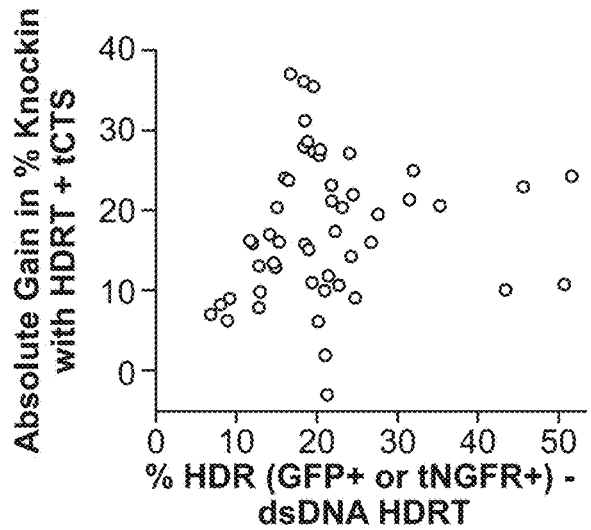
Figure 4C:
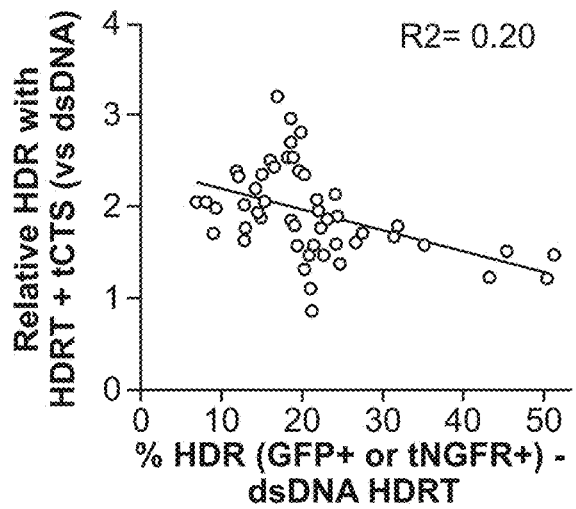
Figure 4D:
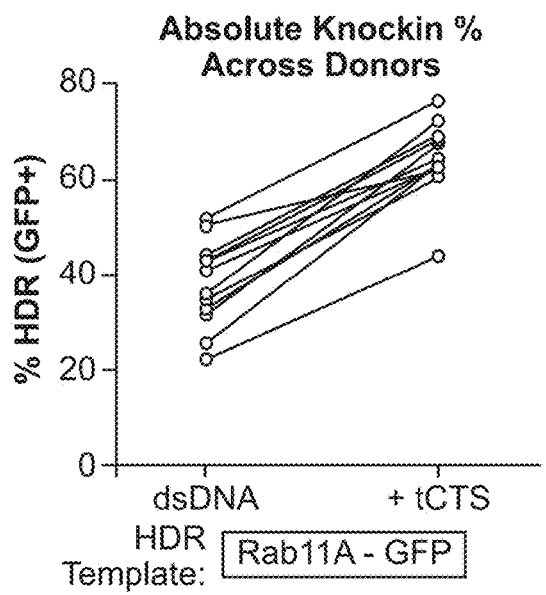
Figure 4E:
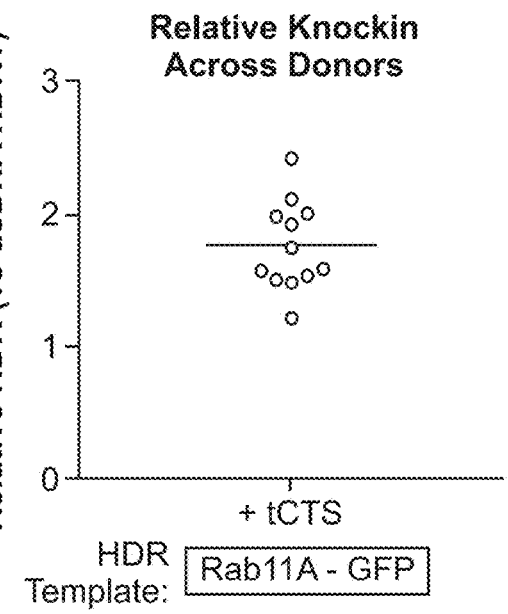
Figure 5A:
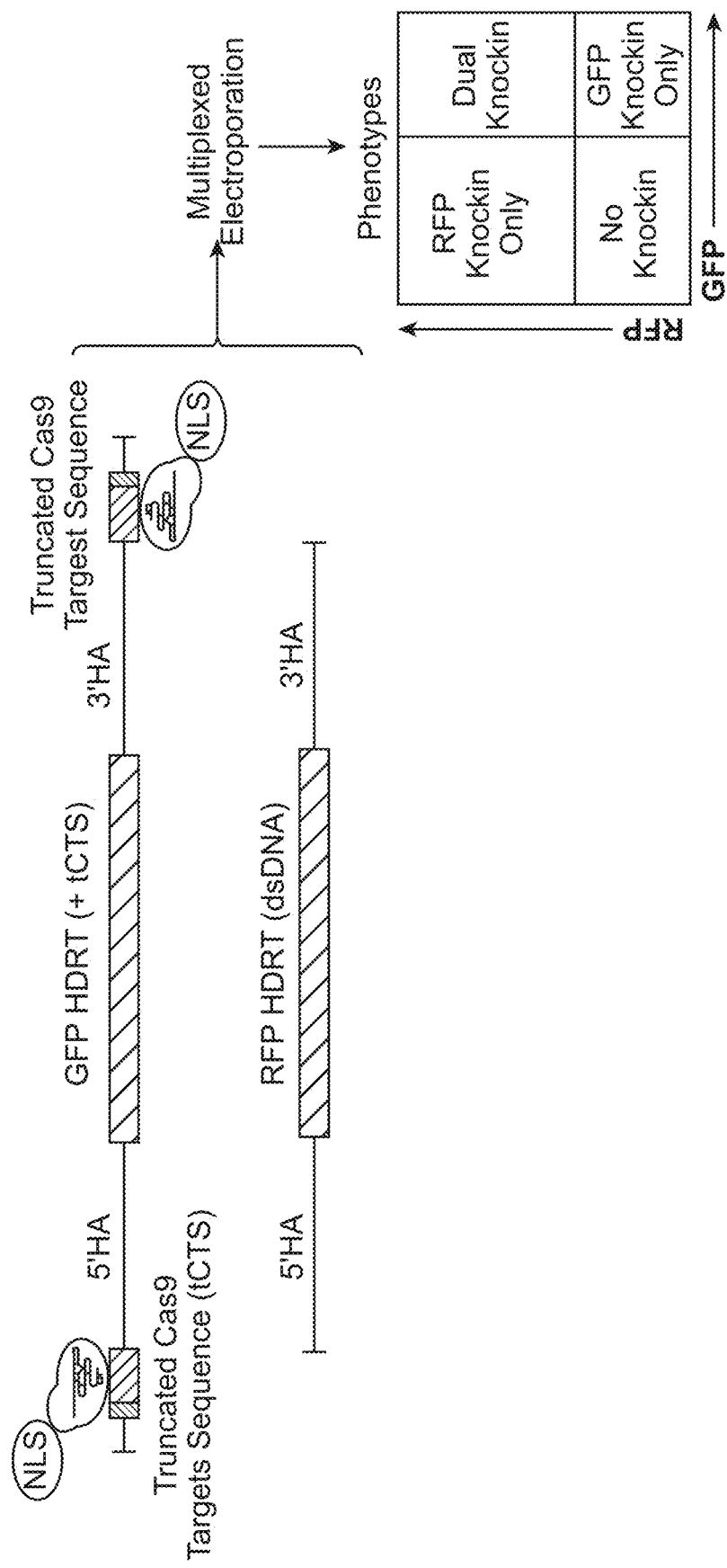
FIGS. 5A-5E: Improved bi-allelic and multiplexed knock-in efficiency with Cas9 shuttle.
Figure 5B:
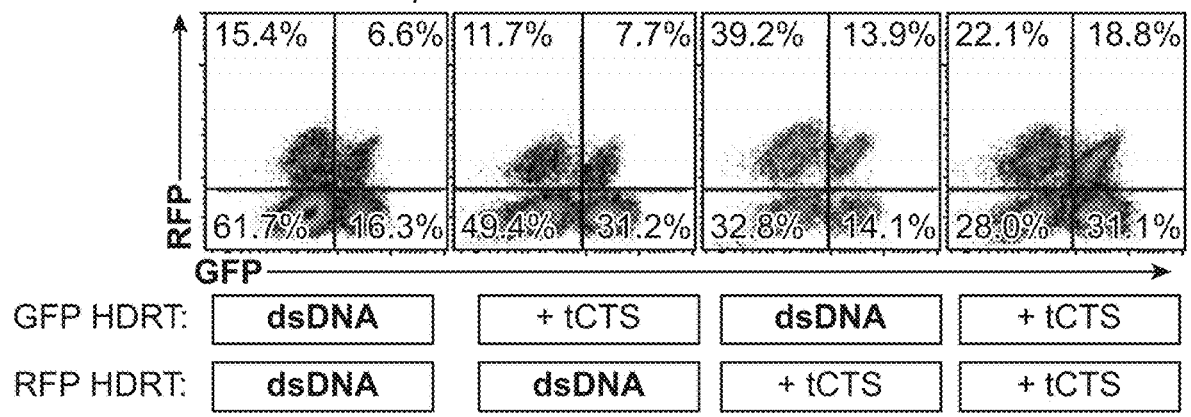
Figure 5C:
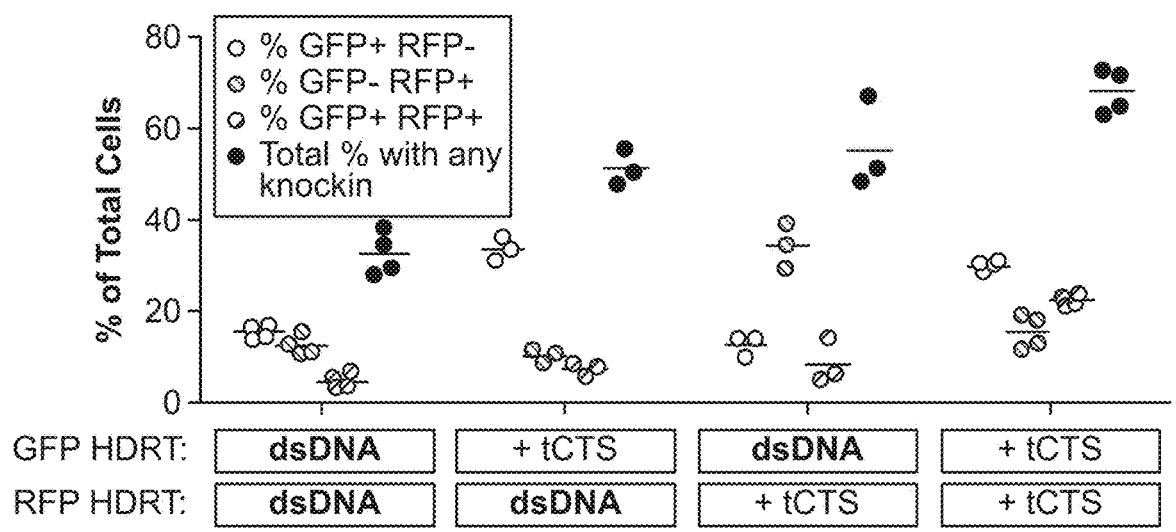
Figure 5D:
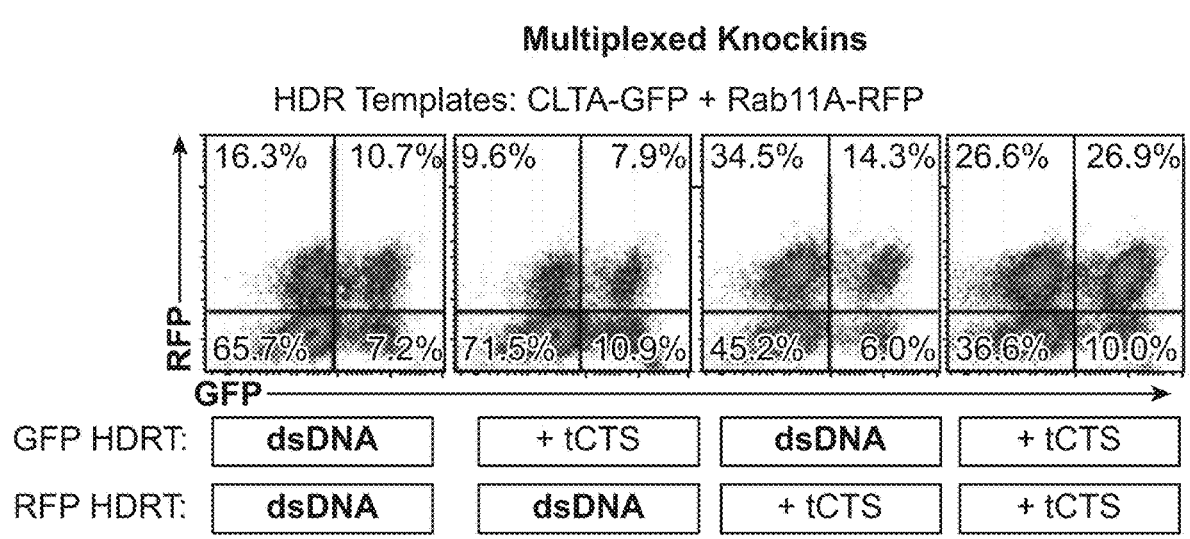
Figure 5E:
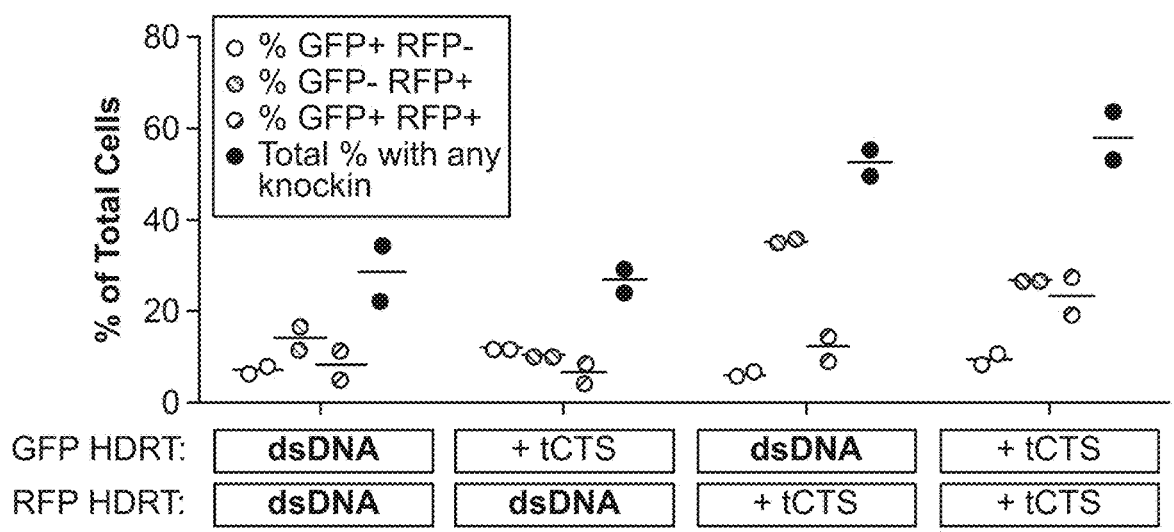
Figure 6A:
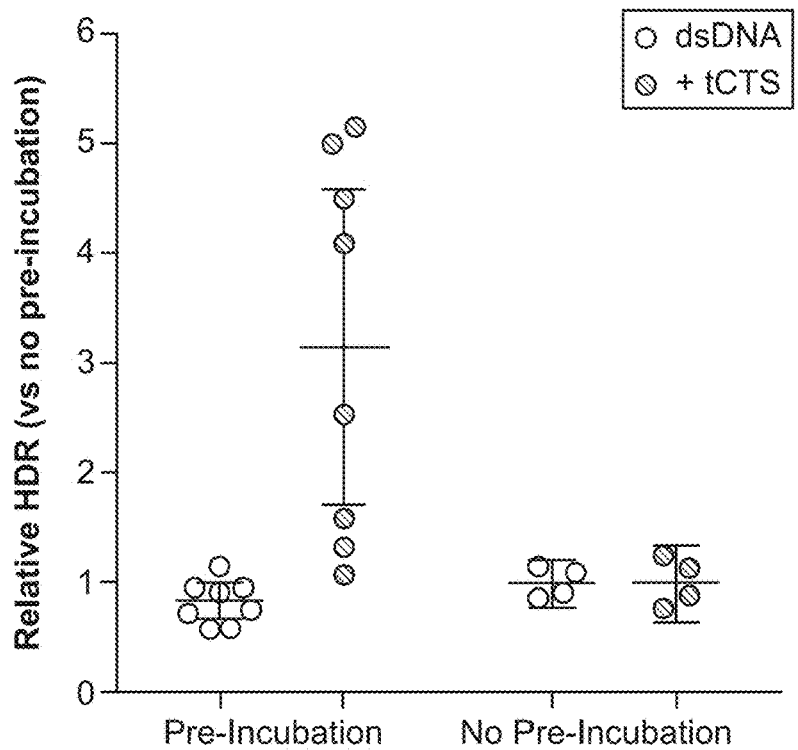
FIG. 6A: Pre-incubation of the Cas9 RNP along with dsDNA HDR template containing tCTS on the ends of its homology arms was useful for the improvement in knock-in efficiency. Pre-incubation was performed for a minimum of 30 seconds at room temperature. In no pre-incubation conditions, the dsDNA HDR template was first mixed with cells, followed by mixing with Cas9 RNP immediately prior to electroporation.
Figure 6B:
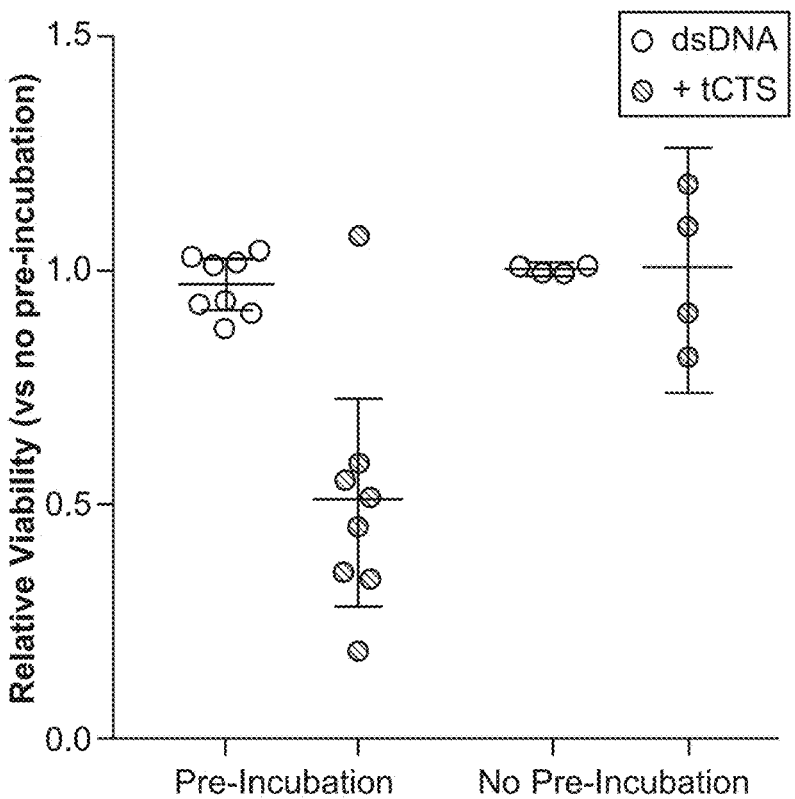
FIG. 6B: Pre-incubation was also useful for the observed drop in viability when comparing Cas9 shuttle DNA HDR template to unmodified dsDNA.
Figure 6C:
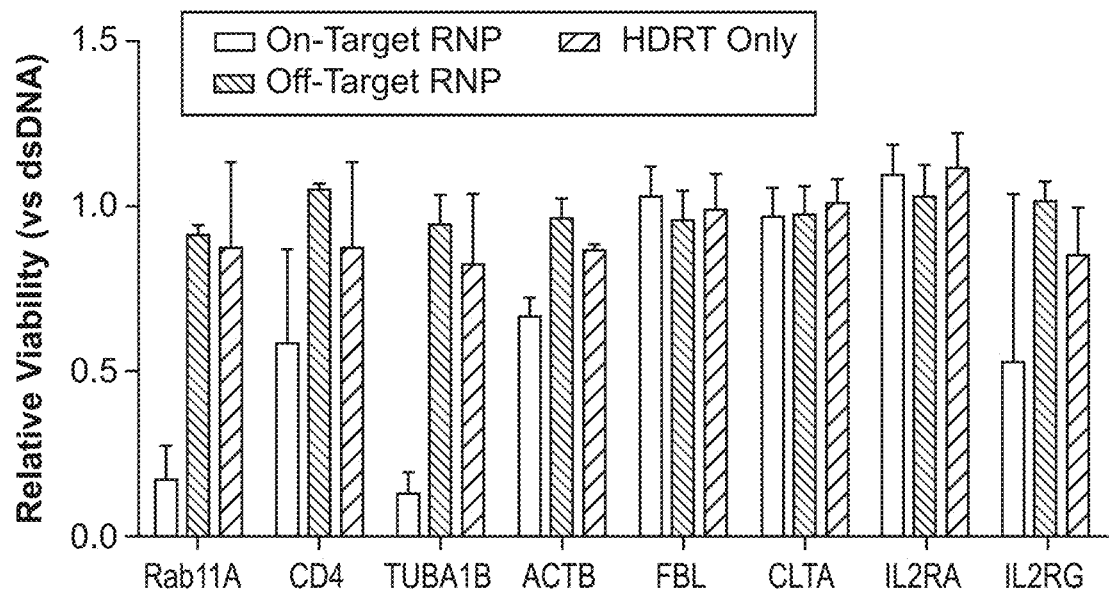
FIG. 6C: Use of an on-target gRNA in the Cas9 RNP (specific for both cutting at the desired genomic locus and for binding to the truncated Cas9 Target Sequence introduced on the edges of the HDR template homology arms) was useful for the observed drop in viability with the Cas9 shuttle at certain genomic sites. Note that there was no drop in viability compared to unmodified dsDNA HDR template when electroporating the Cas9 shuttle HDR template by itself or with an off-target scrambled RNP, indicating the decreased viability was not an inherent property of the tCTS containing DNA template, but rather due to the specific interaction with the on-target Cas9 RNP. This reduced viability was not observed at all genomic loci tested.
Figure 6D:
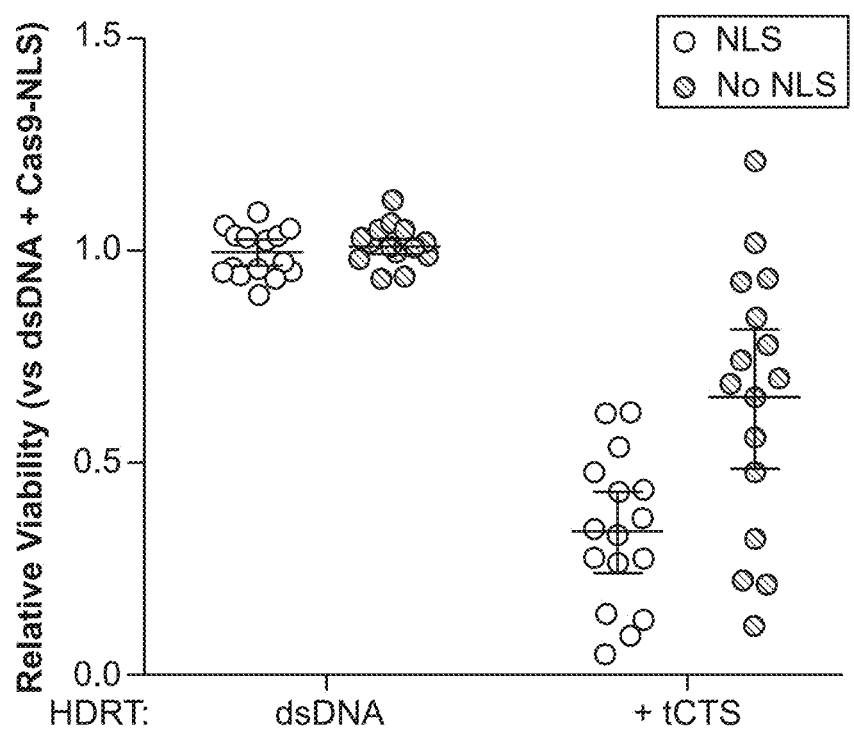
FIG. 6D: Use of a Cas9 RNP for the Cas9 shuttle that did not possess an NLS sequence still showed a drop in viability when compared to unmodified dsDNA HDR template. The relative rates of knock-in (FIG. 6A) or viability (FIGS. 6B-6D) with the Cas9-NLS shuttle is displayed compared to unmodified dsDNA HDR template (FIGS. 6A-6D) for TCR replacement at the TRAC locus (1.5 kb knock-in, FIGS. 6A, 6B, and 6D) or GFP or tNGFR knock-in at the indicated locus (FIG. 6C) in multiple technical replicates from n=2 donors (FIGS. 6A-6D). Knock-in was measured 4 days post electroporation and viability (total number of live cells relative to no electroporation control) at 2 days post electroporation.

The shuttle sequence(s) can be introduced into dsDNA templates of any format, including linear dsDNA sequences produced by PCR, restriction enzyme digestions, or any other linearization method, as well as circular dsDNA sequences such as plasmids. In the case of a plasmid, the shuttle sequence(s) can be cloned into the plasmid outside of the homology arms and DNA insert regions, including but not limited to adjacent to the edge(s) of the homology arm(s). Similar to linear dsDNA templates, the DNA binding protein complex (e.g., RNP made from Cas9 and gRNA) can be incubated briefly with plasmid DNA template to allow for binding of the DNA plasmid by the RNP prior to introduction into the cell (e.g., via electroporation). See, e.g., FIGS. 1, 2, and 10B of International Patent Publication No. WO2018232356 and paragraph [0100] of International Patent Publication No. WO2019084552. Plasmid templates with shuttle sequence(s) can also be used with one or more anionic polymers, e.g., as described herein.

In another example, the donor template contains two DNA-binding protein target sequences and two PAMs. In some embodiments of this example, a first DNA-binding protein target sequence and a first PAM are located at the 5' terminus of the HDR template and a second DNA-binding protein target sequence and a second PAM are located at the 3' terminus of the HDR template. Further, in some embodiments, the first PAM can be located at the 5' terminus of the first DNA-binding protein target sequence and the second PAM can be located at the 5' of the second DNA-binding protein target sequence. In some embodiments, the first PAM can be located at the 5' terminus of the first DNA-binding protein target sequence and the second PAM can be located at the 3' of the second DNA-binding protein target sequence. In some embodiments, the first PAM can be located at the 3' terminus of the first DNA-binding protein target sequence and the second PAM can be located at the 5' of the second DNA-binding protein target sequence. In some embodiments, the first PAM can be located at the 3' terminus of the first DNA-binding protein target sequence and the second PAM can be located at the 3' of the second DNA-binding protein target sequence.

In other examples, one or more DNA-binding protein target sequences and one or more PAMs can be located within the HDR template as long as they do not interfere with the homology directed repair between the HDR template and the target nucleic acid.

The donor template can further contain one or more edge sequences at either or both of the 5' and 3' termini of the donor template. An edge sequence in the donor template can facilitate binding between the donor template and the DNA-binding protein (e.g., an RNA-guided nuclease). In some embodiments, an edge sequence can have at least 2 nucleotides, e.g., between 2 and 24 nucleotides (e.g., between 2 and 22, between 2 and 20, between 2 and 18, between 2 and 16, between 2 and 14, between 2 and 12, between 2 and 10, between 2 and 8, between 2 and 6, between 2 and 4, between 4 and 24, between 6 and 24, between 8 and 24, between 10 and 24, between 12 and 24, between 14 and 24, between 16 and 24, between 18 and 24, between 20 and 24, or between 22 and 24 nucleotides; 2, 3, 4, 5, 6, 7, 8, 9, 10, 11, 12, 13, 14, 15, 16, 17, 18, 19, 20, 21, 22, 23, or 24 nucleotides).

VII. Targetable Nuclease

As described above, in some embodiments of the compositions and methods described herein, the targetable nuclease is an RNA-guided nuclease (e.g., a Cas protein). The targetable nuclease can recognize a sequence of a target nucleic acid (e.g., a target gene within a genome), bind to the target nucleic acid, and modify the target nucleic acid. In other embodiments, the targetable nuclease can be a fusion protein that includes a protein that can bind to the target nucleic acid and a protein that can modify the target nucleic acid (e.g., a nuclease, a transcription activator or repressor).

In some embodiments, the targetable nuclease has nuclease activity. For example, the targetable nuclease can modify the target nucleic acid by cleaving the target nucleic acid. The cleaved target nucleic acid can then undergo homologous recombination with a nearby a homology directed repair (HDR) template. For example, the Cas nuclease can direct cleavage of one or both strands at a location in a target nucleic acid. Non-limiting examples of Cas nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc 1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, variants thereof, mutants thereof, and derivatives thereof. There are three main types of Cas nucleases (type I, type II, and type III), and 10 subtypes including 5 type I, 3 type II, and 2 type III proteins (see, e.g., Hochstrasser and Doudna, *Trends Biochem Sci*, 2015:40(1):

58-66). Type II Cas nucleases include Cas 1, Cas2, Csn2, Cas9, and Cfp 1. These Cas nucleases are known to those skilled in the art. For example, the amino acid sequence of the *Streptococcus pyogenes* wild-type Cas9 polypeptide is set forth, e.g., in NBCI Ref. Seq. No. NP_269215, and the amino acid sequence of *Streptococcus thermophilus* wild-type Cas9 polypeptide is set forth, e.g., in NBCI Ref. Seq. No. WP_011681470.

Cas nucleases, e.g., Cas9 nucleases, can be derived from a variety of bacterial species including, but not limited to, *Veillonella atypical, Fusobacterium nucleatum, Filifactor alocis, Solobacterium moorei, Coprococcus catus, Treponema denticola, Peptoniphilus duerdenii, Catenibacterium mitsuokai, Streptococcus mutans, Listeria innocua, Staphylococcus pseudintermedius, Acidaminococcus intestine, Olsenella uli, Oenococcus kitaharae, Bifidobacterium bifidum, Lactobacillus rhamnosus, Lactobacillus gasseri, Finegoldia magna, Mycoplasma mobile, Mycoplasma gallisepticum, Mycoplasma ovipneumoniae, Mycoplasma canis, Mycoplasma synoviae, Eubacterium rectale, Streptococcus thermophilus, Eubacterium dolichum, Lactobacillus corynniformis* subsp. *Torquens, Ilyobacter polytropus, Ruminococcus albus, Akkermansia muciniphila, Acidothermus cellulolyticus, Bifidobacterium longum, Bifidobacterium dentium, Corynebacterium diphtheria, Elusimicrobium minutum, Nitratifractor salsuginis, Sphaerochaeta globus, Fibrobacter succinogenes* subsp. *Succinogenes, Bacteroides fragilis, Capnocytophaga ochracea, Rhodopseudomonas palustris, Prevotella micans, Prevotella ruminicola, Flavobacterium columnare, Aminomonas paucivorans, Rhodospirillum rubrum, Candidatus Puniceispirillum marinum, Verminephrobacter eiseniae, Ralstonia syzygii, Dinoroseobacter shibae, Azospirillum, Nitrobacter hamburgensis, Bradyrhizobium, Wolinella succinogenes, Campylobacter jejuni* subsp. *Jejuni, Helicobacter mustelae, Bacillus cereus, Acidovorax ebreus, Clostridium perfringens, Parvibaculum lavamentivorans, Roseburia intestinalis, Neisseria meningitidis, Pasteurella multocida* subsp. *Multocida, Sutterella wadsworthensis, proteobacterium, Legionella pneumophila, Parasutterella excrementihominis, Wolinella succinogenes,* and *Francisella novicida.*

Cas9 protein refers to an RNA-guided double-stranded DNA-binding nuclease protein or nickase protein. Wild-type Cas9 nuclease has two functional domains, e.g., RuvC and HNH, that cut different DNA strands. Cas9 can induce double-strand breaks in genomic DNA (target DNA) when both functional domains are active. The Cas9 enzyme can comprise one or more catalytic domains of a Cas9 protein derived from bacteria belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor,* and *Campylobacter*. In some embodiments, the Cas9 can be a fusion protein, e.g., the two catalytic domains are derived from different bacteria species.

In some embodiments, a Cas protein can be a Cas protein variant. For example, useful variants of the Cas9 nuclease can include a single inactive catalytic domain, such as a RuvC⁻ or HNH⁻ enzyme or a nickase. A Cas9 nickase has only one active functional domain and can cut only one strand of the target DNA, thereby creating a single strand break or nick. In some embodiments, the Cas9 nuclease can be a mutant Cas9 nuclease having one or more amino acid mutations. For example, the mutant Cas9 having at least a D10A mutation is a Cas9 nickase. In other embodiments, the mutant Cas9 nuclease having at least a H840A mutation is a Cas9 nickase. Other examples of mutations present in a Cas9 nickase include, without limitation, N854A and N863A. A double-strand break can be introduced using a Cas9 nickase if at least two DNA-targeting RNAs that target opposite DNA strands are used. A double-nicked induced double-strand break can be repaired by NHEJ or HDR (Ran et al., 2013, Cell, 154:1380-1389). Non-limiting examples of Cas9 nucleases or nickases are described in, for example, U.S. Pat. Nos. 8,895,308; 8,889,418; and 8,865,406 and U.S. Application Publication Nos. 2014/0356959, 2014/0273226 and 2014/0186919. The Cas9 nuclease or nickase can be codon-optimized for the target cell or target organism.

In some embodiments, a Cas protein variant that lacks cleavage (e.g., nickase) activity. A Cas protein variant may contain one or more point mutations that eliminates the protein's nickase activity. In some embodiments, such Cas protein variants can be fused to other proteins and serve as targeting domains to direct the other proteins to the target nucleic acid. For example, Cas protein variants without nickase activity may be fused to transcriptional activation or repression domains to control gene expression (Ma et al., *Protein and Cell*, 2(11):879-888, 2011; Maeder et al., *Nature Methods*, 10:977-979, 2013; and Konermann et al., *Nature*, 517:583-588, 2014). A Cas protein variant that lacks nickase activity may be used to target genomic regions, resulting in RNA-directed transcriptional control. In some embodiments, a Cas protein variant without any cleavage (e.g., nickase) activity may be used to target an exogenous protein to the target nucleic acid. An exogenous protein may be fused to the Cas protein variant and the fusion protein may be enhanced by the addition of the anionic polymer. An exogenous protein may be an effector protein domain. An exogenous protein may be a transcription activator or repressor. Other examples of exogenous proteins include, but are not limited to, VP64-p65-Rta (VPR), VP64, P65, Krab, Ten-eleven translocation methylcytosine dioxygenase (TET), and DNA methyltransferase (DNMT). Specific Cas protein variants that lack cleavage (e.g., nickase) activity are also described below.

In some embodiments, the Cas nuclease can be a high-fidelity or enhanced specificity Cas9 polypeptide variant with reduced off-target effects and robust on-target cleavage. Non-limiting examples of Cas9 polypeptide variants with improved on-target specificity include the SpCas9 (K855A), SpCas9 (K810A/K1003A/R1060A) (also referred to as eSpCas9(1.0)), and SpCas9 (K848A/K1003A/R1060A) (also referred to as eSpCas9(1.1)) variants described in Slaymaker et al., *Science*, 351(6268):84-8 (2016), and the SpCas9 variants described in Kleinstiver et al., *Nature*, 529(7587): 490-5 (2016) containing one, two, three, or four of the following mutations: N497A, R661A, Q695A, and Q926A (e.g., SpCas9-HF1 contains all four mutations). As demonstrated in Example 21 and FIGS. 27A-27D, the improved editing efficiency provided by anionic polymers was observed with a variety of Cas9 RNPs, e.g., HiFi Cas9 and D10a 'nickase' variant Cas9.

In some embodiments, a targetable nuclease can also be can be a fusion protein that contains a protein that can bind to the target nucleic acid and a protein that can cleave the target nucleic acid. For example, a protein that can recognize and bind to the target nucleic acid can be a Cas protein variant without any cleavage activity. A Cas protein variant without any cleavage activity can be a Cas9 polypeptide that contains two silencing mutations of the RuvC1 and HNH nuclease domains (D10A and H840A), which is referred to as dCas9 (Jinek et al., *Science*, 2012, 337:816-821; Qi et al., Cell, 152(5):1173-1183). In one embodiment, the dCas9 polypeptide from *Streptococcus pyogenes* comprises at least one mutation at position D10, G12, G17, E762, H840, N854, N863, H982, D983, A984, D986, A987 or any combination thereof. Descriptions of such dCas9 polypeptides and variants thereof are provided in, for example, International Patent Publication No. WO 2013/176772. The dCas9 enzyme can contain a mutation at D10, E762, H983, or D986, as well as a mutation at H840 or N863. In some instances, the dCas9 enzyme can contain a D10A or D10N mutation. Also, the dCas9 enzyme can contain a H840A, H840Y, or H840N. In some embodiments, the dCas9 enzyme can contain D10A and H840A; D10A and H840Y; D10A and H840N; $D_{10}N$ and H840A; D10N and H840Y; or D10N and H840N substitutions. The substitutions can be conservative or non-conservative substitutions to render the Cas9 polypeptide catalytically inactive and able to bind to target DNA.

In other embodiments, a protein that can recognize and bind to the target nucleic acid can be a transcription activator-like (TAL) effector DNA-binding protein or a zinc finger DNA-binding protein. The TAL effector DNA-binding protein has a central domain of DNA-binding tandem repeats usually containing 33-35 amino acids in length and two hypervariable amino acid residues at positions 12 and 13 that can recognize one or more specific DNA base pairs. The zinc finger DNA-binding protein has a DNA-binding motif that is often characterized by the absence or presence one or more zinc ions in order to coordinate and stabilize the motif fold. The zinc finger DNA-binding protein contains multiple finger-like protrusions that make tandem contacts with their target molecule. Some zinc finger DNA-binding proteins also form salt bridges to stabilize the finger-like folds. They were first identified as a DNA-binding motif in transcription factor TFIIIA from *Xenopus laevis* (African clawed frog), however they are now recognized to bind DNA, RNA, protein, and/or lipid substrates.

In some embodiments, a targetable nuclease in the compositions and methods described herein can be a fusion protein containing a TAL effector DNA-binding protein and a protein that can cleave the target nucleic acid (also referred to as "Transcription activator-like effector nucleases (TALEN)"). In other embodiments, a targetable nuclease in the compositions and methods described herein can be a fusion protein containing a zinc finger DNA-binding protein and a protein that can cleave the target nucleic acid. For example, a protein that can cleave the target nucleic acid can be a wild-type or mutated FokI endonuclease or the catalytic domain of FokI. Detailed descriptions of TALENs and their uses for gene editing are found, e.g., in U.S. Pat. Nos. 8,440,431; 8,440,432; 8,450,471; 8,586,363; and 8,697,853; Scharenberg et al., *Curr Gene Ther,* 2013, 13(4):291-303; Gaj et al., *Nat Methods,* 2012, 9(8):805-7; Beurdeley et al., *Nat Commun,* 2013, 4:1762; and Joung and Sander, *Nat Rev Mol Cell Biol,* 2013, 14(1):49-55. Examples of a zinc finger DNA-binding protein fused to a protein that can cleave the target nucleic acid are described in the art and include, but are not limited to, those described in Urnov et al., *Nature Reviews Genetics,* 2010, 11:636-646; Gaj et al., *Nat Methods,* 2012, 9(8):805-7; U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140.

In some embodiments, the targetable nuclease does not have nuclease activity. For example, the targetable nuclease (e.g., a targetable nuclease without any nuclease activity) can regulate the expression of the target nucleic acid. In some embodiments, the targetable nuclease can be a fusion protein that includes a protein that can bind to the target nucleic acid, such as a Cas protein variant without any cleavage activity (e.g., a dCas9), a TAL effector DNA-binding protein, and a zinc finger DNA-binding protein as described above, and a protein that can modify the target nucleic acid, such as a transcription activator or repressor.

The targetable nuclease can also be fused with a localization peptide or protein. For example, the targetable nuclease can be fused with one or more nuclear localization signal (NLS) sequences, which can direct the targetable nuclease and the RNP complexes it forms to the nucleus to modify the target nucleic acid. Examples of NLS sequences are known in the art, e.g., as described in Lange et al., *J Biol Chem.* 282(8):5101-5, 2007, and also include, but are not limited to, AVKRPAATKKAGQAKKKKLD (SEQ ID NO: 1), MSRRRKANPTKLSENAKKLAKEVEN (SEQ ID NO: 2), PAAKRVKLD (SEQ ID NO: 3), KLKIKRPVK (SEQ ID NO: 4), and PKKKRKV (SEQ ID NO: 5). Examples of other peptide or proteins that can be used to a targetable nuclease, such as cell-penetrating peptides and cell-targeting peptides are available in the art and described, e.g., Vives et al., *Biochim Biophys Acta.* 1786(2):126-38, 2008.

VIII. DNA-Binding Protein

A DNA-binding protein is a protein that can directly or indirectly bind to a DNA-binding protein target sequence within a donor template (which includes an HDR template). In some embodiments, a DNA-binding protein can be an RNA-guided nuclease (e.g., a Cas protein) that can recognize and bind the DNA-binding protein target sequence, but not cleave the DNA-binding protein target sequence. The RNA-guided nuclease can bind to the DNA-binding protein target sequence via the donor gRNA as described above. In some embodiments, the donor gRNA and the DNA-binding protein target sequence can have partial complementarity which allows the RNA-guided nuclease to bind to the DNA-binding protein target sequence via the donor gRNA but not cleave the DNA-binding protein target sequence. In other embodiments, a DNA-binding protein can be a Cas protein variant without any cleavage activity (e.g., a dCas9), a TAL effector DNA-binding protein, or a zinc finger DNA-binding protein as described above. Each of the TAL effector DNA-binding protein and zinc finger DNA-binding protein can directly bind to a DNA-binding protein target sequence within a donor template. Without being bound by any theory, the DNA-binding protein serves to transport or shuttle the donor template to a cellular location close to the target nucleic acid (e.g., the nucleus).

The DNA-binding protein can also be fused with a localization peptide or protein. For example, the DNA-binding protein can be fused with one or more nuclear localization signal (NLS) sequences, which can direct the DNA-binding protein and the RNP complexes it forms to the nucleus to modify the target nucleic acid. Examples of NLS sequences are known in the art, e.g., as described in Lange et al., *J Biol Chem.* 282(8):5101-5, 2007, and also include, but are not limited to, AVKRPAATKKAGQAKKKKLD (SEQ ID NO: 1), MSRRRKANPTKLSENAKKLAKEVEN (SEQ ID NO: 2), PAAKRVKLD (SEQ ID NO: 3), KLKIKRPVK (SEQ ID NO: 4), and PKKKRKV (SEQ ID NO: 5). Examples of other peptide or proteins that can be used to a DNA-binding protein, such as cell-penetrating peptides and cell-targeting peptides are available in the art and described, e.g., Vives et al., *Biochim Biophys Acta.* 1786(2):126-38, 2008.

IX. DNA-Binding Protein Target Sequence

A DNA-binding protein target sequence is a nucleotide sequence that is recognized and bound by a DNA-binding protein. In the compositions and methods described herein, one or more DNA-binding protein target sequences are added to an HDR template, such that the HDR template can be brought or "shuttled" into the desired intracellular location (e.g., the nucleus) to be near the target nucleic acid. Thus, the DNA-binding protein target sequence can help to improve homology directed repair efficiency and target nucleic acid modification efficiency.

In some embodiments, a DNA-binding protein target sequence can be directly recognized and bound by a DNA-binding protein, e.g., a TAL effector DNA-binding protein or zinc finger DNA-binding protein. In other embodiments, a DNA-binding protein target sequence can be indirectly recognized and bound by a DNA-binding protein, e.g., an RNA-guided nuclease, via a donor gRNA. In some embodiments, at least 60% (e.g., 65%, 70%, 75%, 80%, 85%, 90%, 95%, or 97%) of the nucleotides in the DNA-binding protein target sequence can engage in Watson-Crick base pairing with their corresponding nucleotides in the donor gRNA. In some embodiments, the DNA-binding protein target sequence can have at least one (e.g., one, two, three, four, five, six, seven, eight, nine, or ten) mismatched nucleotide to its corresponding nucleotide in the donor gRNA when the DNA-binding protein target sequence and the donor gRNA are hybridized. Examples of mismatched bases include a guanine and uracil, guanine and thymine, and adenine and cytosine pairing. In some embodiments, the DNA-binding protein target sequence is a portion of the target nucleic acid.

One or more DNA-binding protein target sequences can be present on one or both termini of the HDR template in the donor template as described above. The DNA-binding protein target sequence and the PAM in a donor template can have different configurations as described above. The DNA-binding protein target sequence is only recognized and bound, but not cut, by the DNA-binding protein (e.g., an RNA-guided nuclease). In some embodiments, the DNA-binding protein target sequence is complementary to an equal length portion of the sequence of the donor gRNA. In some embodiments, the DNA-binding protein target sequence has at least 14 nucleotides, e.g., between 14 and 20 nucleotides (e.g., between 14 and 19, between 14 and 18, between 14 and 17, between 14 and 16, or between 14 and 15 nucleotides; 14, 15, 16, 17, 18, 19, or 20 nucleotides). A DNA-binding protein target sequence can include 12-20, 14-20, 14-19, 16-18, 15-17, 12, 13, 14, 15, 16, 17, 18, 19, or 20 nucleotides. In some embodiments, the DNA-binding protein target sequence is partially complementarity, i.e., comprises nucleotide mismatches, compared to an equal length portion of the sequence of the donor gRNA. For example, the DNA-binding protein target sequence having 20 nucleotides can have between 1 and 6 nucleotide mismatches (e.g., between 1 and 5, between 1 and 4, between 1 and 3, between 1 and 2 nucleotide mismatches; 1, 2, 3, 4, 5, or 6 nucleotide mismatches) compared to a 20-nucleotide portion of the sequence of the donor gRNA.

X. Anionic Polymers

In some embodiments of the compositions described herein, an anionic polymer can be added to a composition, e.g., to improve the stability and editing efficiency of Cas9 protein and sgRNA ribonucleoprotein complex (RNP). The inventors have discovered that the addition of anionic polymers to a composition containing a Cas protein (e.g., a Cas9 protein) or a composition containing a Cas protein (e.g., a Cas9 protein) and sgRNA RNP complex is able to stabilize the Cas protein or the RNP complex and prevent aggregation, leading to high nuclease activity and editing efficiency. Without being bound by any theory, the anionic polymer (e.g., PGA) may interact favorably with the Cas protein, i.e., the anionic polymer (e.g., PGA) may interact favorably with the positively-charged (at physiological pH) Cas9 protein, stabilize the RNP complex into dispersed particles, prevent aggregation, and improve nuclease editing activity and efficiency. An anionic polymer can be water soluble. An anionic polymer can be biologically inert. An anionic polymer can have no or minimal effects on cell state. In some aspects an anionic polymer is not a DNA sequence. An anionic polymer can be capable of being undergoing freeze/thaw cycling while retaining functionality (all or substantially all). An anionic polymer can be lyophilized while retaining functionality (all or substantially all). An anionic polymer can have a molecular weight of 15,000 to 50,000 kDa. An anionic polymer can be polyglutamic acid (PGA).

An anionic polymer described herein can be added to a composition to stabilize the composition, improve editing, reduce toxicity, and enable lyophilization of the composition without loss of activity. In some embodiments, a composition containing the Cas protein and the anionic polymer is an aqueous composition that appears homogenous, has a clear visual appearance, and is free of cloudy precipitates or aggregates. In some embodiments, a composition containing the Cas protein and sgRNA RNP complex and the anionic polymer is an aqueous composition that appears homogenous, has a clear visual appearance, and is free of cloudy precipitates or aggregates. In some embodiments, a composition comprising a targetable nuclease, a DNA-binding protein, a donor template, and an anionic polymer is an aqueous composition that appears homogenous, has a clear visual appearance, and is free of cloudy precipitates or aggregates. Having a stable composition allows efficiency gene knock-outs and large transgene knock-ins with high cell survival rate. Further, the composition can also be lyophilized for long-term storage and reconstituted for later use. A composition comprising an anionic polymer can also be used in methods of modifying a target nucleic acid, where the target nucleic acid can be removed, replaced by an exogenous nucleic acid sequence, or an exogenous nucleic acid sequence can be inserted within the target nucleic acid. Compositions comprising an anionic polymer are also described in U.S. Application Nos. 62/778,814 and 62/935,568, which are incorporated herein by reference in their entirety.

An anionic polymer that can be added to a composition described herein is a molecule composed of subunits or monomers that has an overall negative charge. An anionic polymer can be an anionic polypeptide or an anionic polysaccharide. An anionic polypeptide is an anionic polymer that has at least 50% (e.g., 55%, 60%, 65%, 70%, 75%, 80%, 85%, 90%, 95%, or 100%) of its subunits or monomers being amino acids, such as acidic amino acids (e.g., glutamic acids and aspartic acids), or derivatives thereof. Examples of anionic polypeptides include, but are not limited to, polyglutamic acid (PGA) (e.g., poly-gamma-glutamic acid), polyaspartic acid, and polycarboxyglutamic acid. In some embodiments, an anionic polypeptide is a PGA (e.g., poly-gamma-glutamic acid), such as a poly(L-glutamic) acid or a poly(D-glutamic) acid. An anionic polypeptide can contain a mixture of glutamic acids and aspartic acids. In some embodiments, at least 50% (e.g., 55%, 60%, 65%, 70%, 75%, 80%, 85%, 90%, 95%, or 100%) of the subunits or monomers in an anionic polypeptide can be glutamic acids and/or aspartic acids. An anionic polysaccharide is an anionic polymer that has at least 50% (e.g., 55%, 60%, 65%, 70%, 75%, 80%, 85%, 90%, 95%, or 100%) of its subunits or monomers being sugar molecules, such as monosaccharides (e.g., fructose, galactose, and glucose) and disaccharides (e.g., hyaluronic acid, lactose, maltose, and sucrose), or derivatives thereof. Examples of anionic polysaccharides include, but are not limited to, hyaluronic acid (HA), heparin, heparin sulfate, and glycosaminoglycan. In some embodiments, at least 50% (e.g., 55%, 60%, 65%, 70%, 75%, 80%, 85%, 90%, 95%, or 100%) of the subunits or monomers in an anionic polysaccharide can be HA. Other examples of anionic polymers include, but are not limited to, poly(acrylic acid) (PAA), poly(methacrylic acid) (PMAA), poly(styrene sulfonate), and polyphosphate.

An anionic polymer herein does not refer to a nucleic acid, such as a deoxyribonucleic acid (DNA), ribonucleic acid (RNA), that is composed entirely of nucleotides. In some embodiments, an anionic polymer can include one or more nucleobases (e.g., guanosine, cytidine, adenosine, thymidine, and uridine) together with other subunits or monomers, such as amino acids and/or small organic molecules (e.g., an organic acid). In some embodiments, at least 50% (e.g., 55%, 60%, 65%, 70%, 75%, 80%, 85%, 90%, 95%, or 100%) of the subunits or monomers in the anionic polymer are not nucleotides or do not contain nucleobases. An anionic polymer can contain at least two subunits or monomers (e.g., at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 subunits or monomers; between 100 and 400, between 120 and 400, between 140 and 400, between 160 and 400, between 180 and 400, between 200 and 400, between 220 and 400, between 240 and 400, between 260 and 400, between 280 and 400, between 300 and 400, between 320 and 400, between 340 and 400, between 360 and 400, between 380 and 400, between 100 and 380, between 100 and 360, between 100 and 340, between 100 and 320, between 100 and 300, between 100 and 280, between 100 and 260, between 100 and 240, between 100 and 220, between 100 and 200, between 100 and 180, between 100 and 160, between 100 and 140, or between 100 and 120 subunits or monomers). In some embodiments, the anionic polymer has a molecular weight of at least 3 kDa (e.g., 5, 10, 15, 20, 25, 30, 35, 40, 45, or 50 kDa). In some embodiments, the anionic polymer has a molecular weight of between 3 kDa and 50 kDa (e.g., between 3 kDa and 45 kDa, between 3 kDa and 40 kDa, between 3 kDa and 35 kDa, between 3 kDa and 30 kDa, between 3 kDa and 25 kDa, between 3 kDa and 20 kDa, between 3 kDa and 15 kDa, between 3 kDa and 10 kDa, between 3 kDa and 5 kDa, between 5 kDa and 50 kDa, between 10 kDa and 50 kDa, between 15 kDa and 50 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa). In some embodiments, the anionic polymer has a molecular weight of between 50 kDa and 150 kDa (e.g., between 50 kDa and 140 kDa, between 50 kDa and 130 kDa, between 50 kDa and 120 kDa, between 50 kDa and 110 kDa, between 50 kDa and 100 kDa, between 50 kDa and 90 kDa, between 50 kDa and 80 kDa, between 50 kDa and 70 kDa, between 50 kDa and 60 kDa, between 60 kDa and 150 kDa, between 70 kDa and 150 kDa, between 80 kDa and 150 kDa, between 90 kDa and 150 kDa, between 100 kDa and 150 kDa, between 110 kDa and 150 kDa, between 120 kDa and 150 kDa, between 130 kDa and 150 kDa, or between 140 kDa and 150 kDa). In some embodiments, the anionic polymer has a molecular weight of between 15 kDa and 50 kDa (e.g., between 15 kDa and 45 kDa, between 15 kDa and 40 kDa, between 15 kDa and 35 kDa, between 15 kDa and 30 kDa, between 15 kDa and 25 kDa, between 15 kDa and 20 kDa, between 20 kDa and 50 kDa, between 25 kDa and 50 kDa, between 30 kDa and 50 kDa, between 35 kDa and 50 kDa, between 40 kDa and 50 kDa, or between 45 kDa and 50 kDa). As shown in Example 17 and FIGS. 23A and 23B, PGA enhanced editing at various molecular weights from 3 kD to 120 kD. In some embodiments, a composition described herein has a molar ratio of anionic polymer:targetable nuclease at between 10:1 and 120:1, e.g., 10:1, 20:1, 30:1, 40:1, 50:1, 60:1, 70:1, 80:1, 90:1, 100:1, 110:1, or, 120:1; between 10:1 and 110:1, between 10:1 and 100:1, between 10:1 and 90:1, between 10:1 and 80:1, between 10:1 and 70:1, between 10:1 and 60:1, between 10:1 and 50:1, between 10:1 and 40:1, between 10:1 and 30:1, between 10:1 and 20:1, between 20:1 and 120:1, between 30:1 and 120:1, between 40:1 and 120:1, between 50:1 and 120:1, between 60:1 and 120:1, between 70:1 and 120:1, between 80:1 and 120:1, between 90:1 and 120:1, between 100:1 and 120:1, or between 110:1 and 120:1.

XI. Lyophilized Composition

An anionic polymer can be used to stabilize a composition described herein during lyophilization and preserve protein activity after the lyophilized composition was reconstituted. Lyophilization of preformed RNP complexes would allow for improved stability, but lyophilization had previously been observed to destroy RNP complex activity. As shown in FIG. 10J and Example 7, the anionic polymer PGA was able to stabilize the RNP complex during lyophilization and preserve RNP complex activity after the lyophilized composition was reconstituted. In some embodiments, if the composition containing the Cas protein (e.g., Cas9 protein) and the anionic polymer or the composition containing the Cas protein (e.g., Cas9 protein) and sgRNA RNP complexes and the anionic polymer is lyophilized and later reconstituted, the Cas protein has activity for at least one week (e.g., at least 2, 3, 4, 5, 6, 7, 8, 9, 10, 11, 12, 13, 14, 15, 16, 17, 18, 19, 20, 21, 22, 23, or 24 weeks) at room temperature, 4° C., or 37° C. after reconstitution. In some embodiments, if a composition is lyophilized and later reconstituted, the targetable nuclease and/or the DNA-binding protein in the composition has activity for at least one week (e.g., at least 2, 3, 4, 5, 6, 7, 8, 9, 10, 11, 12, 13, 14, 15, 16, 17, 18, 19, 20, 21, 22, 23, or 24 weeks) at room temperature, 4° C., or 37° C. after reconstitution.

In some embodiments, a cryoprotectant can be added to a composition described herein before the composition is lyophilized. Examples of cryoprotectants include, but are not limited to, dimethyl sulfoxide (DMSO), glycerol, ethylene glycol, propylene glycol, 2-Methyl-2,4-pentanediol (MPD), sucrose, lactose, trehalose, raffinose, mannitol, and combinations thereof. Cryoprotectants added to the composition described herein to form a lyophilized composition does not affect the activity of the RNP complexes.

As demonstrated in Examples 16 and 23, PGA-stabilized Cas9 nanoparticles retained high editing efficiency when reconstituted for use after lyophilization. The Cas9 RNPs worked well even when no cryoprotectant was used.

XII. RNP Complex Formation in the Presence of Anionic Polymers

In some embodiments, an RNP complex may be formed by annealing an sgRNA to a Cas protein, as described in, e.g., Schumann et al. PNAS 112: 10437-10442, 2015 and Hultquist et al. *Cell Rep.* 17: 1438-1452, 2016, in the presence of an anionic polymer. In other embodiments, an anionic polymer may be added to a composition comprising an sgRNA and a Cas protein. In other words, to form an RNP complex, in some embodiments, a Cas protein and an sgRNA may be incubated together first, i.e., incubated at between 25° C. and 37° C. (e.g., at 25° C., 27° C., 29° C., 31° C., 33° C., or 35° C.; at 25° C. or at 37° C.) for at least 15 minutes (e.g., 20, 25, 30, 35, 40, 45, 50, 55, 60, 65, 70, 75, 80, 85, 90, 95, 100, 110, or 120 minutes), followed by the addition of an anionic polymer. Once the anionic polymer is added, the mixture containing all three components (the Cas protein, the sgRNA, and the anionic polymer) may be further incubated at between 25° C. and 37° C. (e.g., at 25° C., 27° C., 29° C., 31° C., 33° C., or 35° C.; at 25° C. or at 37° C.) for at least 15 minutes (e.g., 20, 25, 30, 35, 40, 45, 50, 55, 60, 65, 70, 75, 80, 85, 90, 95, 100, 110, or 120 minutes). In other embodiments, all three components (the Cas protein, the sgRNA, and the anionic polymer) may be added together in a mixture at approximately the same time and incubated together at between 25° C. and 37° C. (e.g., at 25° C., 27° C., 29° C., 31° C., 33° C., or 35° C.; at 25° C. or at 37° C.) for at least 15 minutes (e.g., 20, 25, 30, 35, 40, 45, 50, 55, 60, 65, 70, 75, 80, 85, 90, 95, 100, 110, or 120 minutes). In yet other embodiments, an sgRNA may be added to a composition containing a Cas protein and an anionic polymer. All three components (the Cas protein, the sgRNA, and the anionic polymer) may be incubated together at between 25° C. and 37° C. (e.g., at 25° C., 27° C., 29° C., 31° C., 33° C., or 35° C.; at 25° C. or at 37° C.) for at least 15 minutes (e.g., 20, 25, 30, 35, 40, 45, 50, 55, 60, 65, 70, 75, 80, 85, 90, 95, 100, 110, or 120 minutes).

In some embodiments, in a mixture comprising the three components (the Cas protein, the sgRNA, and the anionic polymer), the molar ratio of sgRNA:Cas protein may be between 0.25:1 and 4:1, e.g., 0.25:1, 0.5:1, 1:1, 1.2:1, 1.4:1, 1.6:1, 1.8:1, 2:1, 2.2:1, 2.4:1, 2.6:1, 2.8:1, 3:1, 3.2:1, 3.4:1, 3.6:1, 3.8:1, or 4:1. In some embodiments, in a mixture comprising the three components (the Cas protein, the sgRNA, and the anionic polymer) or a mixture comprising the Cas protein and the anionic polymer, the molar ratio of anionic polymer:Cas protein may be, e.g., between 10:1 and 120:1, e.g., 10:1, 20:1, 30:1, 40:1, 50:1, 60:1, 70:1, 80:1, 90:1, 100:1, 110:1, or, 120:1; between 10:1 and 110:1, between 10:1 and 100:1, between 10:1 and 90:1, between 10:1 and 80:1, between 10:1 and 70:1, between 10:1 and 60:1, between 10:1 and 50:1, between 10:1 and 40:1, between 10:1 and 30:1, between 10:1 and 20:1, between 20:1 and 120:1, between 30:1 and 120:1, between 40:1 and 120:1, between 50:1 and 120:1, between 60:1 and 120:1, between 70:1 and 120:1, between 80:1 and 120:1, between 90:1 and 120:1, between 100:1 and 120:1, or between 110:1 and 120:1. In some embodiments, the RNP complexes are electroporated into cells immediately after formation. In other embodiments, a Cas protein and an anionic polymer may be electroporated into cells and an sgRNA may be introduced into cells via viral delivery. Methods of forming RNP complexes are also described in, e.g., International Patent Application No. PCT/US2018/037919 and U.S. Patent Application Nos. 62/676,650 and 62/578,153.

In some embodiments, an RNP complex containing a Cas protein (e.g., a Cas9 protein) and an sgRNA that is formed in the presence of an anionic polymer has a size that is less than 100 nm (e.g., 95, 90, 85, 80, 75, 70, 65, 60, 55, 50, 45, 40, 35, 30, 25, or 20 nm). A Cas protein and sgRNA RNP complex may have a size that is between 20 nm and 90 nm (e.g., 20, 25, 30, 35, 40, 45, 50, 55, 60, 65, 70, 75, 80, 85, or 90 nm), as determined by known techniques in the art, e.g., dynamic light scattering. As shown in FIG. 10I and Example 7, the addition of an anionic polymer (e.g., a PGA) improved the size of RNP complex, which exhibited stable peaks in the 20 nm and 90 nm range. In some embodiments, a composition containing a Cas protein and sgRNA RNP complex and an anionic polymer includes at least 50% (e.g., 55%, 60%, 65%, 70%, 75%, 80%, 85%, 90%, 95%, or 100%) of the RNP complexes that have a size that is between 20 nm and 90 nm (e.g., 20, 25, 30, 35, 40, 45, 50, 55, 60, 65, 70, 75, 80, 85, or 90 nm).

XIII. Gene Targeting Nucleic Acids in Cells

The compositions described herein can be used in methods of modifying a target nucleic acid in a cell, e.g., an eukaryotic cells, prokaryotic cell, animal cell, plant cell, fungal cell, and the like. Optionally, the cell is a mammalian cell, for example, a human cell. The cell can be in vitro, ex vivo, or in vivo. The cell can also be a primary cell, a germ cell, a stem cell, or a precursor cell. The precursor cell can be, for example, a pluripotent stem cell, or a hematopoietic stem cell. In some embodiments, the cell is a primary hematopoietic cell, a primary hematopoietic stem cell, or a primary T cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a CD4$^+$ T cell. In some embodiments, the T cell is a CD8$^+$ T cell. In some embodiments, the T cell is a CD4$^+$CD8$^+$ T cell. In some embodiments, the T cell is a CD4$^-$CD8$^-$T cell. In some embodiments the T cell is an αβ T cell, in some embodiments the T cell is a γδ T cell. Populations of any of the cells modified by any of the methods described herein are also provided. In some embodiments, the methods further comprise expanding the population of modified cells.

In a particular aspect, a population of cells (e.g., a population of T cells), is provided. The population of cells can comprise any of the modified cells described herein. The modified cell can be within a heterogeneous population of cells and/or a heterogeneous population of different cell types. The population of cells can be heterogeneous with respect to the percentage of cells that are genomically edited. A population of cells can have greater than 10%, greater than 20%, greater than 30%, greater than 40%, greater than 50%, greater than 60%), greater than 70%, greater than 80%, or greater than 90% of the population comprise an integrated nucleotide sequence. In a certain aspect, a populations of cells comprises an integrated nucleotide sequence, wherein the integrated nucleotide sequence comprises at least a portion of a gene, the integrated nucleotide sequence is integrated at an endogenous genomic target locus, and the integrated nucleotide sequence is orientated such that the at least a portion of the gene is capable of being expressed, wherein the population of cells is substantially free of viral-mediated delivery components, and wherein greater than 10%), greater than 20%, greater than 30%, greater than 40%, greater than 50%, greater than 60%), greater than 70%, greater than 80%, or greater than 90% of the cells in the population comprise the integrated nucleotide sequence.

A population of cells can have greater than 91%, greater than 92%, greater than 93%), greater than 94%, greater than 95%, greater than 96%, or greater than 97%, greater than 98%), greater than 99%, greater than 99.5%, or greater than 99.9% of the population comprise an integrated nucleotide sequence. A population of cells can have greater than 20% of the population comprise an integrated nucleotide sequence. A population of cells can have greater than 30% of the population comprise an integrated nucleotide sequence. A population of cells can have greater than 60% of the population comprise an integrated nucleotide sequence. A population of cells can have greater than 70% of the population comprise an integrated nucleotide sequence.

A cell can include a cell comprising a non-virally inserted sequence such as an exogenous sequence. A cell can be virus-free. A cell can be substantially free of virus. A cell can include at least one nucleic acid sequence (e.g., comprising at least one heterologous gene) non-virally inserted into at least one target region. In certain aspects, a cell does not comprise a viral vector, e.g., for introducing at least one nucleic acid sequence such as a donor template.

A cell can include one or more primary cells that include a non-virally inserted exogenous sequence that is at least 200 base pairs in size. The primary cells can be primary hematopoietic cells or primary hematopoietic stem cells. The primary cells can be primary hematopoietic cells and the primary hematopoietic cells can be immune cells. The immune cells can be T cells. The primary cells can be human cells. In some aspects, the primary cells do not comprise a viral vector. The size of the exogenous sequence can be greater than a length selected from the group consisting of: 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1 kb, 1.1 kb, 1.2 kb, 1.3 kb, 1.4 kb, 1.5 kb, 1.6 kb, 1.7 kb, 1.8 kb, 1.9 kb, 2.0 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb, and 5.0 kb. The size of the exogenous sequence can be greater than 1.5 kb. The size of the exogenous sequence can be about 200 bp to about 500 bp, about 200 bp to about 750 bp, about 200 bp to about 1 kb, about 200 bp to about 1.5 kb, about 200 bp to about 2.0 kb, about 200 bp to about 2.5 kb, about 200 bp to about 3.0 kb, about 200 bp to about 3.5 kb, about 200 bp to about 4.0 kb, about 200 bp to about 4.5 kb, about 200 bp to about 5.0 kb. The size of the exogenous sequence can be greater than about 1 kb. The exogenous sequence can include a regulatory sequence, optionally wherein the regulatory sequence comprises a promoter sequence and/or an enhancer sequence.

The exogenous sequence can encode a heterologous protein or a fragment thereof. The exogenous sequence can encode a chimeric antigen receptor (CAR). The exogenous sequence can encode a T cell receptor (TCR).

A cell can include a primary human T cell comprising a non-virally inserted DNA template having a size of greater than 1 kb.

A cell can include a primary human T cell comprising: at least one nucleic acid sequence comprising at least one heterologous gene non-virally inserted into at least one target region of one or both of: endogenous T cell receptor alpha subunit constant gene (TRAC), and endogenous T cell receptor beta subunit constant gene (TRBC), the at least one heterologous gene comprises at least one of: (1) a variable region of a heterologous T cell receptor alpha (TCR-α) chain gene and (2) a variable region of a heterologous T cell receptor beta (TCR-β) chain gene. In some aspects, the T cell does not comprise a viral vector for introducing the at least one nucleic acid sequence to the T cell. In some aspects, the at least one nucleic acid sequence is at least 1.5 kb in size. In some aspects, the at least one nucleic acid sequence is at least 500 bp in size. In some aspects, the target region is in exon 1, 2, or 3 of TRAC. In some aspects, the target region is in exon 1, 2, or 3 of TRBC. In some aspects, the T cell is a CD8+ T cell or a CD4+ T cell. In some aspects, the at least one heterologous gene comprises at least one of: (1) a) variable region or b) variable region and constant region of the heterologous T cell receptor alpha (TCR-α) chain gene and (2) a) variable region or b) variable region and constant region of the heterologous T cell receptor beta (TCR-β) chain gene. In some aspects, the at least one heterologous gene comprises each of: (1) the a) variable region or b) variable region and constant region of the heterologous T cell receptor alpha (TCR-α) chain gene and (2) the a) variable region or b) variable region and constant region of the heterologous T cell receptor beta (TCR-β) chain gene. In some aspects, the T cell comprises each of (1) the a) variable region or b) variable region and constant region of the heterologous TCR-α chain gene and (2) the a) variable region or b) variable region and constant region of the heterologous TCR-β chain gene. In some aspects, the heterologous genes form an antigen-specific T cell receptor (TCR) upon expression. In some aspects, the heterologous TCR-α chain gene and the heterologous TCR-α chain gene are operably linked by a linker sequence, optionally the linker sequence is a cleavable linker sequence or a multi-cistronic element. In some aspects, the heterologous TCR-α chain gene and the heterologous TCR-β chain gene are inserted into TRAC. In some aspects, expression of the at least one heterologous gene is driven by an endogenous promoter. In some aspects, expression of one or both of TRAC and TRBC is reduced in the cell relative to a control T cell, wherein the control T cell is a primary human T cell that lacks the non-viral insertion.

A cell can include a primary human T cell comprising: at least one nucleic acid sequence comprising at least one heterologous gene inserted into at least one target region of one or both of: endogenous T cell receptor alpha subunit constant gene (TRAC), and endogenous T cell receptor beta subunit constant gene (TRBC), the at least one heterologous gene comprises at least one of: (1) a variable region of a heterologous T cell receptor alpha (TCR-α) chain gene and (2) a variable region of a heterologous T cell receptor beta (TCR-β) chain gene, and wherein the T cell does not comprise a viral vector for introducing the at least one nucleic acid sequence to the T cell.

A cell can include a primary cell comprising: at least one nucleic acid sequence comprising at least one heterologous gene non-virally inserted into at least one target region of the cell's genome. In some aspects the at least one heterologous gene encodes a CAR or other chimeric receptor. In some aspects the at least one heterologous gene comprises at least one or both of: (1) a variable region of a heterologous T cell receptor alpha (TCR-α) chain gene and (2) a variable region of a heterologous T cell receptor beta (TCR-β) chain gene. In some aspects the primary cell is a T cell. In some aspects, the cell does not comprise a viral vector for introducing the at least one nucleic acid sequence to the cell. In some aspects, the at least one nucleic acid sequence is at least 1.5 kb in size. In some aspects, the at least one nucleic acid sequence is at least 500 bp in size. In some aspects, the target region is in TRAC, e.g., exon 1, 2, or 3 of TRAC. In some aspects, the target region is in TRBC, e.g., exon 1, 2, or 3 of TRBC. In some aspects, the T cell is a CD8+ T cell or a CD4+ T cell. In some aspects, expression of the at least one heterologous gene is driven by an endogenous promoter. In some aspects, expression of one or both of TRAC and TRBC is reduced in the T cell relative to a control T cell, wherein the control T cell is a primary human T cell that lacks the non-viral insertion.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors. In some embodiments, the chimeric antigen receptor includes an extracellular portion containing an antibody or fragment described herein. In some aspects, the chimeric antigen receptor includes an extracellular portion containing an antibody or fragment described herein and an intracellular signaling domain. In some embodiments, an antibody or fragment includes an scFv or a single-domain VH antibody and the intracellular domain contains an ITAM. In some aspects, the intracellular signaling domain includes a signaling domain of a ζ chain of a CD3 (CD3ζ chain) In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB. In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g., an IgG4 hinge, such as a hinge-only spacer. In some embodiments, the transmembrane domain of the receptor, e.g., the CAR, is a transmembrane domain of human CD28 or variant thereof, e.g., a 27-amino acid transmembrane domain of a human CD28 (Accession No.: P10747.1). In some embodiments, the chimeric antigen receptor contains an intracellular domain of a T cell costimulatory molecule. In some aspects, the T cell costimulatory molecule is CD28 or 41BB. In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof. In some embodiments, the intracellular signaling domain comprises a human CD3 zeta stimulatory signaling domain or functional variant thereof, such as an 112 AA cytoplasmic domain of isoform 3 of human CD3ζ (Accession No.: P20963.2) or a CD3ζ signaling domain as described in U.S. Pat. No. 7,446,190 or 8,911,993.

Methods for modifying a target nucleic acid in a cell described herein comprise introducing into the cell a composition described herein, wherein the HDR template is integrated into the target nucleic acid. As demonstrated in the Examples, pre-incubation of the DNA-binding protein (e.g., an RNA guided nuclease) and donor gRNA RNP complex with the donor template (comprising DNA-binding protein target sequence-modified HDR template) before introducing the composition into the cell enhances genome targeting efficiency. In some embodiments, a composition described herein is introduced into the cell via electroporation.

In some cases, the cells are removed from a subject, modified using any of the methods described herein and administered to the subject. In other cases, a composition described herein can be delivered to the subject in vivo. See, for example, U.S. Pat. No. 9,737,604 and Zhang et al. "Lipid nanoparticle-mediated efficient delivery of CRISPR/Cas9 for tumor therapy," *NPG Asia Materials* Volume 9, page e441 (2017).

In particular embodiments, the compositions described herein can be used in methods of modifying a target nucleic acid in a primary cell. The compositions described herein can be used in methods for inducing a stable gene modification of a target nucleic acid in a primary cell. In some embodiments, the method includes introducing into the primary cell a composition comprising a Cas protein (e.g., a Cas9 protein), one or more single guide RNAs (sgRNAs), and an anionic polymer. The sgRNA may comprise a first nucleotide sequence that is complementary to the target nucleic acid and a second nucleotide sequence that interacts with the Cas protein (e.g., Cas9 protein). In some embodiments, a Cas protein (e.g., a Cas9 protein), an sgRNA, and an anionic polymer may be incubated together to form a RNP complex prior to introducing into the primary cell. A composition comprising a Cas protein (e.g., a Cas9 protein), one or more single guide RNAs (sgRNAs), and an anionic polymer may be electroporated into the primary cell. In other embodiments, a composition comprising a Cas protein and an anionic polymer may be electroporated into the primary cell and an sgRNA may be introduced into the primary cell via viral delivery. In some embodiments, the primary cell is selected from the group consisting of an immune cell (e.g., a primary T cell), a blood cell, a progenitor or stem cell thereof, a mesenchymal cell, and a combination thereof. In some instances, the immune cell is selected from the group consisting of a T cell, a B cell, a dendritic cell, a natural killer cell, a macrophage, a neutrophil, an eosinophil, a basophil, a mast cell, a precursor thereof, and a combination thereof. The progenitor or stem cell can be selected from the group consisting of a hematopoietic progenitor cell, a hematopoietic stem cell, and a combination thereof. In some cases, the blood cell is a blood stem cell. In some instances, the mesenchymal cell is selected from the group consisting of a mesenchymal stem cell, a mesenchymal progenitor cell, a mesenchymal precursor cell, a differentiated mesenchymal cell, and a combination thereof. The differentiated mesenchymal cell can be selected from the group consisting of a bone cell, a cartilage cell, a muscle cell, an adipose cell, a stromal cell, a fibroblast, a dermal cell, and a combination thereof. In some embodiments, the primary cell can comprise a population of primary cells. In some cases, the population of primary cells comprises a heterogeneous population of primary cells. In other cases, the population of primary cells comprises a homogeneous population of primary cells.

In some embodiments, the primary cell is isolated from a mammal prior to introducing a composition described herein into the primary cell. For instance, the primary cell can be harvested from a human subject. In some instances, the primary cell or a progeny thereof is returned to the mammal after introducing the composition described herein into the primary cell. In other words, the genetically modified primary cell undergoes autologous transplantation. In other instances, the genetically modified primary cell undergoes allogeneic transplantation. For example, a primary cell that has not undergone stable gene modification is isolated from a donor subject, and then the genetically modified primary cell is transplanted into a recipient subject who is different than the donor subject.

A composition described herein can be introduced into a cell (e.g., a primary cell) using available methods and techniques in the art. Non-limiting examples of suitable methods include electroporation, particle gun technology, and direct microinjection. In some embodiments, the step of introducing the composition described herein into the cell comprises electroporating the composition into the cell.

In other embodiments, a composition comprising a Cas protein and an anionic polymer may be electroporated into the cell and an sgRNA may be introduced into the cell via viral delivery using a viral vector. For example, viral vectors can be based on vaccinia virus, poliovirus, adenovirus, adeno-associated virus, SV40, herpes simplex virus, human immunodeficiency virus, and the like. A retroviral vector can be based on Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, mammary tumor virus, and the like. An sgRNA may also be introduced into the cell using other expression vectors. Useful expression vectors are known to those of skill in the art, and many are commercially available. The following vectors are provided by way of example for eukaryotic host cells: pXT1, pSG5, pSVK3, pBPV, pMSG, and pSVLSV40. Examples of techniques that may be used to introduce an sgRNA in an expression vector (e.g., a viral vector) into a cell include, but not limited to, viral or bacteriophage infection, transfection, protoplast fusion, lipofection, calcium phosphate precipitation, polyethyleneimine (PEI)-mediated transfection, DEAE-dextran mediated transfection, liposome-mediated transfection, calcium phosphate precipitation, nanoparticle-mediated nucleic acid delivery, and the like.

In some embodiments, the stable gene modification of the target nucleic acid is induced in greater than about 5% of the population of cells (e.g., the population of primary cells), e.g., about 6%, about 7%, about 8%, about 9%, about 10%, about 12%, about 14%, about 16%, about 18%, about 20%, about 22%, about 24%, about 26%, about 28%, or about 30% of the population of cells. In some embodiments, the stable gene modification of the target nucleic acid is induced in greater than about 50% of the population of cells (e.g., the population of primary cells), e.g., about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the population of cells. In other embodiments, the stable gene modification of the target nucleic acid is induced in greater than about 70% of the population of cells, e.g., about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the population of cells. In yet other embodiments, the stable gene modification of the target nucleic acid is induced in greater than about 90% of the population of cells, e.g., about 90%, about 91%, about 92%, about 93%, about 94%, about 95%, about 96%, about 97%, about 98%, about 99%, or about 100% of the population of cells.

In other embodiments, the stable gene modification of the target nucleic acid comprises the replacement of a genetic mutation in the target nucleic acid (e.g., to correct a point mutation or a single nucleotide polymorphism (SNP) in the target nucleic acid that is associated with a disease) or the insertion of an open reading frame (ORF) comprising a normal copy of the target nucleic acid (e.g., to knock in a wild-type cDNA of the target nucleic acid that is associated with a disease).

In some embodiments, any of the methods described herein can also include purifying the cell (e.g., a primary cell) having the stable gene modification of the target nucleic acid. In some cases, the composition isolated by the purifying step includes at least about 80% cells having the stable gene modification of the target nucleic acid, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more cells having the stable gene modification of the target nucleic acid.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following examples are provided by way of illustration only and not by way of limitation. Those of skill in the art will readily recognize a variety of non-critical parameters that could be changed or modified to yield essentially the same or similar results.

Example 1—Experimental Methods

Cell Culture

Primary adult cells were obtained from healthy human donors from leukoreduction chamber residuals after Trima Apheresis (Blood Centers of the Pacific) or from freshly drawn whole blood under a protocol approved by the UCSF IRB (BU101283). Peripheral blood mononuclear cells (PBMCs) were isolated by Ficoll-Paque (GE Healthcare) centrifugation using SepMate tubes (STEMCELL, per manufacturer's instructions). Specific lymphocytes were then further isolated by magnetic negative selection using an EasySep Human B Cell, CD4$^+$ T Cell, CD3$^+$ (Pan) T Cell, CD8$^+$ T cell, CD4$^+$ CD127$^{low}$ CD25$^-$ Regulatory T Cell, Gamma/Delta T Cell, or NK Cell Isolation kit (STEMCELL, per manufacturer's instructions).

Isolated CD4$^+$, CD8$^+$, CD3$^+$ (Bulk T Cells), Regulatory (CD25$^{hi}$CD127$^{low}$), or Gamma/Delta T cells were activated and cultured for 2 days at 0.5 to 1.0 million cells/mL in XVivo 15 medium (Lonza) with 5% Fetal Bovine Serum, 50 mM 2-mercaptoethanol, 10 mM N-Acetyl L-Cystine, anti-human CD3/CD28 magnetic Dynabeads (ThermoFisher) at a beads to cells concentration of 1:1, and a cytokine cocktail of IL-2 at 200 U/mL (UCSF Pharmacy), IL-7 at 5 ng/mL (ThermoFisher), and IL-15 at 5 ng/mL (ThermoFischer). Activated T cells were harvested from their culture vessels and Dynabeads were removed by placing cells on an Easy-Sep cell separation magnet (STEMCELL) for 5 minutes. Isolated B cells were cultured in IMDM (ThermoFischer) with 5% Fetal Bovine Serum, 100 ng/mL MEGACD40L (Enzo), 1000 ng/mL CpG (InvivoGen), 500 U/mL IL-2 (UCSF Pharmacy), 50 ng/mL IL-10 (ThermoFischer), and 10 ng/mL IL-15 (ThermoFischer). Freshly isolated NK cells were cultured in Xvivo15 medium (Lonza) with 5% Fetal Bovine Serum, 50 mM 2-mercaptoethanol, 10 mM N-Acetyl L-Cystine, together with IL-2 (at 1000 U/mL) and MACSi-Bead Particles pre-loaded with anti-human CD335 (NKp46) and anti-human CD2 antibodies (Miltenyi Biotech). Primary peripheral blood G-CSF-mobilized CD34$^+$ hematopoietic stem cells were purchased from StemExpress Inc and cultured at 0.5e6 cells/mL in SFEM II media supplemented with CC110 cytokine cocktail (STEMCELL) for two days prior to electroporation. Induced pluripotent stem-cells were generated and differentiated into CD34$^+$ HSPCs as previously described (Vo et al., *Nature* 553:506-510, 2018) then cultured in SFEM media (STEMCELL) supplemented with IL-2 at 10 ng/mL, IL-6 at 50 ng/mL, SCF at 50 ng/mL, FLT-3L at 50 ng/mL, and TPO at 50 ng/mL (Peprotech).

RNP Formulation with Polymers

Cas9 RNPs were formulated immediately prior to electroporation, except when frozen for lyophilization. Synthetic crRNA (with guide sequence listed in Table 1) and tracrRNA were chemically synthesized (Edit-R, Dharmacon Horizon or Integrated DNA Technologies (IDT)), resuspended in 10 mM Tris-HCL (7.4 pH) with 150 mM KCl or IDT duplex buffer at a concentration of 160 μM, and stored in aliquots at −80° C. To make gRNA, crRNA and tracrRNA aliquots were thawed, mixed 1:1 by volume, and annealed by incubation at 37° C. for 30 min to form an 80 μM gRNA solution. For comparison, chemically modified gRNA was purchased from Synthego and resuspended according to manufacturer's protocol. Cas9-NLS, dCas9-NLS, or Cas9 without NLS was purchased from the UC Berkeley QB3 MAcrolab; HiFiCas9 was purchased from IDT. To make RNPs, gRNA was then further diluted in buffer first, or directly mixed 1:1 by volume with 40 μM Cas9-NLS protein to achieve the desired molar ratio of gRNA:Cas9 (2:1 ratio unless otherwise stated). Unless otherwise stated, final dose of RNP per nucleofection was 50 pmol on a Cas9 protein basis.

TABLE 1

| HDR Template | Insertion Location | 5' HA Size | Insertion Size | 3' HA Size | HDR Total Size | HDR Template Seq | Fwd Primer Sequence (To amplify HDR template and add DNA-binding protein target sequence) | Rev Primer Sequence (To amplify HDR template and add DNA-binding protein target sequence) | gRNA Sequence |
|---|---|---|---|---|---|---|---|---|---|
| RAB11A-GFP | N Term. | 306 | 732 | 312 | 12 | SEQ ID NO: 8 | GGGACTAGTGGCCC ATGTCGTACTCGTC GTCGCGGAGCAAGC GGCCACTAAGACTA T (SEQ ID NO: 30) | ACTTCCAGCACCCC ATGTCGTACTCGTC GTCGCGGCGTAGAA CCCGGGGAAAGGAA T (SEQ ID NO: 39) | GGTAGTCGTACTCG TCGTCG (SEQ ID NO. 19) |
| RAB11A-mCherry | N Term. | 306 | 750 | 312 | 12 | SEQ ID NO: 9 | GGGACTAGTGGCCC ATGTCGTACTCGTC GTCGCGGAGCAAGC GGCCACTAAGACTA T (SEQ ID NO: 30) | ACTTCCAGCACCCC ATGTCGTACTCGTC GTCGCGGCGTAGAA CCCGGGGAAAGGAA T (SEQ ID NO: 39) | GGTAGTCGTACTCG TCGTCG (SEQ ID NO: 19) |

TABLE 1-continued

| HDR Template | Insertion Location | 5' HA Size | Insertion Size | 3' HA Size | HDR Total Template Size | Template Seq | Fwd Primer Sequence (To amplify HDR template and add DNA-binding protein target sequence) | Rev Primer Sequence (To amplify HDR template and add DNA-binding protein target sequence) | gRNA Sequence |
|---|---|---|---|---|---|---|---|---|---|
| CLTA-GFP | N Term. | 351 | 729 | 303 | 13 | SEQ ID NO: 10 | GGGACTAGTGGCCTTGGGATCCAGCTCAGCCACGGCTCCCTATCAGGCAGCACTTCC (SEQ ID NO: 31) | ACTTCCAGCACCCTTGGGATCCAGCTCAGCCACGGCAAGGAGCACGAGTCACACAGA | GAACGGATCCAGCTCAGCCA (SEQ ID NO: 20) |
| CLTA-mCherry | N Term. | 351 | 1401 | 303 | 13 | SEQ ID NO: 11 | GGGACTAGTGGCCTTGGGATCCAGCTCAGCCACGGCTCCCTATCAGGCAGCACTTCC (SEQ ID NO: 31) | ACTTCCAGCACCCTTGGGATCCAGCTCAGCCACGGCAAGGAGCACGAGTCACACAGA | GAACGGATCCAGCTCAGCCA (SEQ ID NO: 20) |
| mEGFP-TUBA1B (Microtubules) | N Term. | 404 | 743 | 343 | 13 | SEQ ID NO: 12 | GGGACTAGTGGCACCTGATGCACTCACGCTGCCGGCCCGGTTTAGGATGGGAAGGTA (SEQ ID NO: 32) | ACTTCCAGCACCACCTGATGCACTCACGCTGCCGGAGTGCGAACTTCATCTGGAGGA | TGGAGATGCACTCACGCTGC (SEQ ID NO: 21) |
| ACTB-mEGFP (Actin) | N Term. | 439 | 754 | 330 | 13 | SEQ ID NO: 13 | GGGACTAGTGGCGCGCGCGATATCATCATCCACGGCTGGGACTCAAGGCGCTAACT (SEQ ID NO: 33) | ACTTCCAGCACCGCGCGCGATATCATCATCCACGGCGATGGGGTACTTCAGGGTGAG (SEQ ID NO: 42) | CGCGGCGATATCATCATCCA (SEQ ID NO: 22) |
| FBL-mEGFP (Nucleus) | C Term. | 308 | 790 | 380 | 13 | SEQ ID NO: 14 | GGGACTAGTGGCTGAACAGTTCTTCACCTTGGCGGGAAAAACAGCCCAAAGCCCTGT (SEQ ID NO: 34) | ACTTCCAGCACCTGAACAGTTCTTCACCTTGGCGGAGCAAAATGGCGACCACAACAA | ACTTCAGTTCTTCACCCTTGG (SEQ ID NO: 23) |
| CD4-C-GFP | C Term. | 260 | 729 | 357 | 13 | SEQ ID NO: 15 | GGGACTAGTGGCGACCCCTCGTGCCTCAAATGCGGCTAAAGGGGTGTGGTGAGAGG (SEQ ID NO: 35) | ACTTCCAGCACCGACCCCTCGTGCCTCAAATGCGGGGAAAAGGAAATGGCGTGGAGG (SEQ ID NO: 44) | CTGGCCTCGTGCCTCAAATG (SEQ ID NO: 24) |
| IL2RA-N-2A-tNGFR | N Term. | 228 | 912 | 368 | 13 | SEQ ID NO: 16 | GGGACTAGTGGCACTCCAGTCCCCACATCAGCCGGAGAGTGCTAGGCAGTTTCCTGG (SEQ ID NO: 36) | ACTTCCAGCACCACTCCAGTCCCCACATCAGCCGGCTGCTCATCGGGACCCTGTTAA (SEQ ID NO: 45) | TGAGCAGTCCCCACATCAGC (SEQ ID NO: 25) |
| IL2RG-N-2A-tNGFR | N Term. | 491 | 912 | 516 | 13 | SEQ ID NO: 17 | GGGACTAGTGGCTCCCATGTGAATGGTAATGACGGGTATATGTGCCCACAGGAGCCA (SEQ ID NO: 37) | ACTTCCAGCACCTCCCATGTGAATGGTAATGACGGCAGTGGGCATAGTGGTCAGGAA (SEQ ID NO: 46) | TGGTAATGATGGCTTCAACA (SEQ ID NO: 26) |
| NYESO β/α into TRAC | TRAC Exon 1 | 302 | 1503 | 304 | 13 | SEQ ID NO: 18 | TGGCGGACTAGTGGCTCTCTCTCTCAGCTGGTACACGGTTTCAGGTTTCCTTGAGTGGCA (SEQ ID NO: 38) | CACCACTTCCAGCACCTCTCTCTCTCAGCTGGTACACGGTGGCCATTCCTGAAGCAAGGAA (SEQ ID NO: 47) | AGAGTCTCTCAGCTGGTACA (SEQ ID NO: 27) |

Scrambled gRNA Sequence: GGTTCTTGACTACCGTAATT (SEQ ID NO: 28);
Off-Target gRNA Sequence Targeting CXCR4: GAAGCGTGATGACAAAGAGG (SEQ ID NO: 29)

SEQ ID NO: 8:
GGTAGCTAGGAGTTCCAGGACTCAGTTTCCCCTTTGAGCCTCCTTTAGCGACTAAAGCTTGAAGCC

CCACGCATCTCGACTCTCGCGCACACCGCCCTTGTTGGGCTCAGGGGCGGGGCGCCGCCCCCGGAA

```
GTACTTCCCCTTAAAGGCTGGGGCCTGCCGGAAATGGCGCAGCGGCAGGGAGGGGCTCTTCACCC

AGTCCGGCAGTTGAAGCTCGGCGCTCGGGTTACCCCTGCAGCGACGCCCCTGGTCCCACAGATAC

CACTGCTGCTCCCGCCCTTTCGCTCCTCGGCCGCGCAATGGGCGGATCGGGTGGGACTAGTGGCAG

CAAGGGCGAGGAGCTGTTCACCGGGGTGGTGCCCATCCTGGTCGAGCTGGACGGCGACGTAAACG

GCCACAAGTTCAGCGTGCGCGGCGAGGGCGAGGGCGATGCCACCAACGGCAAGCTGACCCTGAA

GTTCATCTGCACCACCGGCAAGCTGCCCGTGCCCTGGCCCACCCTCGTGACCACCCTGACCTACGG

CGTGCAGTGCTTCAGCCGCTACCCCGACCACATGAAGCGCCACGACTTCTTCAAGTCCGCCATGCC

CGAAGGCTACGTCCAGGAGCGCACCATCAGCTTCAAGGACGACGGCACCTACAAGACCCGCGCCG

AGGTGAAGTTCGAGGGCGACACCCTGGTGAACCGCATCGAGCTGAAGGGCATCGACTTCAAGGAG

GACGGCAACATCCTGGGGCACAAGCTGGAGTACAACTTCAACAGCCACAACGTCTATATCACCGC

CGACAAGCAGAAGAACGGCATCAAGGCCAACTTCAAGATCCGCCACAACGTGGAGGACGGCAGC

GTGCAGCTCGCCGACCACTACCAGCAGAACACCCCCATCGGCGACGGCCCCGTGCTGCTGCCCGA

CAACCACTACCTGAGCACCCAGTCCGTGCTGAGCAAAGACCCCAACGAGAAGCGCGATCACATGG

TCCTGCTGGAGTTCGTGACCGCCGCCGGGATCACTGGAACCGGTGCTGGAAGTGGTACACGCGAC

GACGAGTACGACTACCTCTTTAAAGGTGAGGCCATGGGCTCTCGCACTCTACACAGTCCTCGTTCG

GGGACCCGGGCCACTCCCGGTGGACCCTCGTGCCGGCCACCCCTGCACTGATATAGGCCTCCCTCA

GCCCTTCCTTTTTGTGCGGTTCCGTCTCCTACCCAGCTCAGCCTCTTCTCCCCCGCTCAGACAGGGG

TCCCCATCACATGCCGCTCTCTGAGCGACCTCTCCATAGGCCTTCGCTGGCCTCAGAGCCCCTCCCT

GCGTGTCCTTCCCCTGGCGGACTGCCTTCTCCCACATCGT

SEQ ID NO: 9:
GGTAGCTAGGAGTTCCAGGACTCAGTTTCCCCTTTGAGCCTCCTTTAGCGACTAAAGCTTGAAGCC

CCACGCATCTCGACTCTCGCGCACACCGCCCTTGTTGGGCTCAGGGGCGGGGCGCCGCCCCCGGAA

GTACTTCCCCTTAAAGGCTGGGGCCTGCCGGAAATGGCGCAGCGGCAGGGAGGGGCTCTTCACCC

AGTCCGGCAGTTGAAGCTCGGCGCTCGGGTTACCCCTGCAGCGACGCCCCTGGTCCCACAGATAC

CACTGCTGCTCCCGCCCTTTCGCTCCTCGGCCGCGCAATGGGCGGATCGGGTGGGACTAGTGGCGT

GAGCAAGGGCGAGGAGGATAACATGGCCATCATCAAGGAGTTCATGCGCTTCAAGGTGCACATGG

AGGGCTCCGTGAACGGCCACGAGTTCGAGATCGAGGGCGAGGGCGAGGGCCGCCCCTACGAGGG

CACCCAGACCGCCAAGCTGAAGGTGACCAAGGGTGGCCCCCTGCCCTTCGCCTGGGACATCCTGTC

CCCTCAGTTCATGTACGGCTCCAAGGCCTACGTGAAGCACCCCGCCGACATCCCCGACTACTTGAA

GCTGTCCTTCCCCGAGGGCTTCAAGTGGGAGCGCGTGATGAACTTCGAGGACGGCGGCGTGGTGA

CCGTGACCCAGGACTCCTCCCTGCAGGACGGCGAGTTCATCTACAAGGTGAAGCTGCGCGGCACC

AACTTCCCCTCCGACGGCCCCGTAATGCAGAAGAAGACCATGGGCTGGGAGGCCTCCTCCGAGCG

GATGTACCCCGAGGACGGCGCCCTGAAGGGCGAGATCAAGCAGAGGCTGAAGCTGAAGGACGGC

GGCCACTACGACGCTGAGGTCAAGACCACCTACAAGGCCAAGAAGCCCGTGCAGCTGCCCGGCGC

CTACAACGTCAACATCAAGTTGGACATCACCTCCCACAACGAGGACTACACCATCGTGGAACAGT

ACGAACGCGCCGAGGGCCGCCACTCCACCGGCGGCATGGACGAGCTGTACAAGGGAACCGGTGCT

GGAAGTGGTACACGCGACGACGAGTACGACTACCTCTTTAAAGGTGAGGCCATGGGCTCTCGCAC

TCTACACAGTCCTCGTTCGGGGACCCGGGCCACTCCCGGTGGACCCTCGTGCCGGCCACCCCTGCA

CTGATATAGGCCTCCCTCAGCCCTTCCTTTTTGTGCGGTTCCGTCTCCTACCCAGCTCAGCCTCTTCT

CCCCCGCTCAGACAGGGGTCCCCATCACATGCCGCTCTCTGAGCGACCTCTCCATAGGCCTTCGCT

GGCCTCAGAGCCCCTCCCTGCGTGTCCTTCCCCTGGCGGACTGCCTTCTCCCACATCGT
```

SEQ ID NO: 10:
CTCCCTATCAGGCAGCACTTCCGCCTCCCGGGGCCCGCGCAGCTCACCTCCCTCACCTCCCGCCCT
ACCCCAGTCACGAGTTGTTTTAGGGGACCGCCCCTCCACTTGCTGATTGGGTAGCTCCTGAACCA
TTGTTGTCCTCTGATTGGTTGTTCCCTTTTCGGCTCTGCAACACCGCCTAGACCGACCGGATACACG
GGTAGGGCTTCCGCTTTACCCGTCTCCCTCCTGGCGCTTGTCCTCCTCTCCCAGTCGGCACCACAGC
GGTGGCTGCCGGGCGTGGTGTCGGTGGTCGGTTGGTTTTTGTCTCACCGTTGGTGTCCGTGCCGTT
CAGTTGCCCGCCATGGCTGGATCGGGTGGGACTAGTGGCAGCAAGGGCGAGGAGCTGTTCACCGG
GGTGGTGCCCATCCTGGTCGAGCTGGACGGCGACGTAAACGGCCACAAGTTCAGCGTGCGCGGCG
AGGGCGAGGGCGATGCCACCAACGGCAAGCTGACCCTGAAGTTCATCTGCACCACCGGCAAGCTG
CCCGTGCCCTGGCCCACCCTCGTGACCACCCTGACCTACGGCGTGCAGTGCTTCAGCCGCTACCCC
GACCACATGAAGCGCCACGACTTCTTCAAGTCCGCCATGCCCGAAGGCTACGTCCAGGAGCGCAC
CATCAGCTTCAAGGACGACGGCACCTACAAGACCCGCGCCGAGGTGAAGTTCGAGGGCGACACCC
TGGTGAACCGCATCGAGCTGAAGGGCATCGACTTCAAGGAGGACGGCAACATCCTGGGGCACAAG
CTGGAGTACAACTTCAACAGCCACAACGTCTATATCACCGCCGACAAGCAGAAGAACGGCATCAA
GGCCAACTTCAAGATCCGCCACAACGTGGAGGACGGCAGCGTGCAGCTCGCCGACCACTACCAGC
AGAACACCCCCATCGGCGACGGCCCCGTGCTGCTGCCCGACAACCACTACCTGAGCACCCAGTCC
GTGCTGAGCAAAGACCCCAACGAGAAGCGCGATCACATGGTCCTGCTGGAGTTCGTGACCGCCGC
CGGGATCACTGGAACCGGTGCTGGAAGTGGTGAGCTGGATCCGTTCGGCGCCCCTGCCGGCGCCC
CTGGCGGTCCCGCGCTGGGGAACGGAGTGGCCGGCGCCGGCGAAGAAGACCCGGCTGCGGCCTTC
TTGGCGCAGCAAGAGAGCGAGATTGCGGGCATCGAGAACGACGAGGCCTTCGCCATCCTGGACGG
CGGCGCCCCGGGCCCCAGCCGCACGGCGAGCCGCCGGGGGGTCCGGGTGAGAGTGCGGGCGCGT
TTGGGGCGAGAGGACTTGTCTGGAAACTCGGTCCACAGTGGGTCCGAGAGCTTCTGTGTGACTCGT
GCTCCTTG
SEQ ID NO: 11:
CTCCCTATCAGGCAGCACTTCCGCCTCCCGGGGCCCGCGCAGCTCACCTCCCTCACCTCCCGCCCT
ACCCCAGTCACGAGTTGTTTTAGGGGACCGCCCCTCCACTTGCTGATTGGGTAGCTCCTGAACCA
TTGTTGTCCTCTGATTGGTTGTTCCCTTTTCGGCTCTGCAACACCGCCTAGACCGACCGGATACACG
GGTAGGGCTTCCGCTTTACCCGTCTCCCTCCTGGCGCTTGTCCTCCTCTCCCAGTCGGCACCACAGC
GGTGGCTGCCGGGCGTGGTGTCGGTGGGTCGGTTGGTTTTTGTCTCACCGTTGGTGTCCGTGCCGTT
CAGTTGCCCGCCATGGCTGGATCGGGTGGGACTAGTGGCGTGAGCAAGGGCGAGGAGGATAACAT
GGCCATCATCAAGGAGTTCATGCGCTTCAAGGTGCACATGGAGGGCTCCGTGAACGGCCACGAGT
TCGAGATCGAGGGCGAGGGCGAGGGCCGCCCCTACGAGGGCACCCAGACCGCCAAGCTGAAGGT
GACCAAGGGTGGCCCCCTGCCCTTCGCCTGGGACATCCTGTCCCCTCAGTTCATGTACGGCTCCAA
GGCCTACGTGAAGCACCCCGCCGACATCCCCGACTACTTGAAGCTGTCCTTCCCCGAGGGCTTCAA
GTGGGAGCGCGTGATGAACTTCGAGGACGGCGGCGTGGTGACCGTGACCCAGGACTCCTCCCTGC
AGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCT
GAAGGGCGAGATCAAGCAGAGGCTGAAGCTGAAGGACGGCGGCCACTACGACGCTGAGGTCAAG
ACCACCTACAAGGCCAAGAAGCCCGTGCAGCTGCCCGGCGCCTACAACGTCAACATCAAGTTGGA
CATCACCTCCCACAACGAGGACTACACCATCGTGGAACAGTACGAACGCGCCGAGGGCCGCCACT
CCACCGGCGGCATGGACGAGCTGTACAAGGGAACCGGTGCTGGAAGTGGTGAGCTGGATCCGTTC

```
GGCGCCCCTGCCGGCGCCCCTGGCGGTCCCGCGCTGGGGAACGGAGTGGCCGGCGCCGGCGAAGA

AGACCCGGCTGCGGCCTTCTTGGCGCAGCAAGAGAGCGAGATTGCGGGCATCGAGAACGACGAGG

CCTTCGCCATCCTGGACGGCGGCGCCCCCGGGCCCCAGCCGCACGGCGAGCCGCCGGGGGGTCCG

GGTGAGAGTGCGGGCGCGTTTGGGGCGAGAGGACTTGTCTGGAAACTCGGTCCACAGTGGGTCCG

AGAGCTTCTGTGTGACTCGTGCTCCTTG

SEQ ID NO: 12:
CCCGGTTTAGGATGGGAAGGTAACATTCATTAAAAGCAACGTAGACTATAGTGTAGCTGTTCTCAA

AAGTAGTACATCTTAGAAAAGGATCTTTAGAAAAGATCGCTTTAGAAAAGGAAATTCGTTTTCAG

ATTACGTGAGTAGCCTAGGTAACACAGCCAGACCTCATCTCCACAAAAAAAATGAAAAAATTAGC

CAGCTTGGTGGTCTGTGCCTGTGGTCCCAGCTGCTCCAGAGGCTGAGGTGGGGGATGACTGGAG

CCTAGGCTGCAGTGAGCCTAGATGGCATCACTGCACTCAAGCCTGGGCGACAGACCTTATCTCTAA

AAAAATAAAGATTGCATGAGTATTTTGTTCCACTTGACAGTCATCAATAGATTGGTTTAAATTGTG

ATATCTTTTTTACTTACCGCAGGTGAGCAAGGGCGAGGAGCTGTTCACCGGGGTGGTGCCCATCCT

GGTCGAGCTGGACGGCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCTGCCCGTGCCCTGGCCC

ACCCTCGTGACCACCCTGACCTACGGCGTGCAGTGCTTCAGCCGCTACCCCGACCACATGAAGCAG

CACGACTTCTTCAAGTCCGCCATGCCCGAAGGCTACGTCCAGGAGCGCACCATCTTCTTCAAGGAC

GACGGCAACTACAAGACCCGCGCCGAGGTGAAGTTCGAGGGCGACACCCTGGTGAACCGCATCGA

GCTGAAGGGCATCGACTTCAAGGAGGACGGCAACATCCTGGGGCACAAGCTGGAGTACAACTACA

ACAGCCACAACGTCTATATCATGGCCGACAAGCAGAAGAACGGCATCAAGGTGAACTTCAAGATC

CGCCACAACATCGAGGACGGCAGCGTGCAGCTCGCCGACCACTACCAGCAGAACACCCCCATCGG

CGACGGCCCCGTGCTGCTGCCCGACAACCACTACCTGAGCACCCAGTCCAAGCTGAGCAAAGACC

CCAACGAGAAGCGCGATCACATGGTCCTGCTGGAGTTCGTGACCGCCGCCGGGATCACTCTCGGC

ATGGACGAGCTGTACAAGGGAGGTTCAGGAGGCAGCGAGTGCATCTCCATCCACGTTGGCCAGGC

TGGTGTCCAGATTGGCAATGCCTGCTGGGAGCTCTACTGCCTGGAACACGGCATCCAGCCCGATGG

CCAGATGCCAAGTGACAAGACCATTGGGGGAGGAGATGACTCCTTCAACACCTTCTTCAGTGAGA

CGGGCGCTGGCAAGCACGTGCCCCGGGCTGTGTTTGTAGACTTGGAACCCACAGTCATTGGTGAGT

TGACCTCAGTAACCTGAGATCCCAGGATGCTGGGACAGGAGGTCTGTCCAGGGGCTTCTCTTGTCA

CTCACTCACTCCCTCCGTCCTTCTCTCCCTCCTCCAGATGAAGTTCGCACT

SEQ ID NO: 13:
CTGGGACTCAAGGCGCTAACTGCGCGTGCGTTCTGGGGCCCGGGGTGCCGCGGCCTGGGCTGGGG

CGAAGGCGGGCTCGGCCGGAAGGGGTGGGGTCGCCGCGGCTCCCGGGCGCTTGCGCGCACTTCCT

GCCCGAGCCGCTGGCCGCCCGAGGGTGTGGCCGCTGCGTGCGCGCGCCGACCCGGCGCTGTTT

GAACCGGGCGGAGGCGGGGCTGGCGCCCGGTTGGGAGGGGGTTGGGGCCTGGCTTCCTGCCGCGC

GCCGCGGGACGCCTCCGACCAGTGTTTGCCTTTTATGGTAATAACGCGGCCGGCCCGGCTTCCTT

TGTCCCCAATCTGGGCGCGCGCCGGCGCCCCCTGGCGGCCTAAGGACTCGGCGCGCCGGAAGTGG

CCAGGGCGGGGGCGACCTCGGCTCACAGCGCGCCCGGCTATTCTCGCAACTGACAATGGTGAGCA

AGGGCGAGGAGCTGTTCACCGGGGTGGTGCCCATCCTGGTCGAGCTGGACGGCGACGTAAACGGC

CACAAGTTCAGCGTGTCCGGCGAGGGCGAGGGCGATGCCACCTACGGCAAGCTGACCCTGAAGTT

CATCTGCACCACCGGCAAGCTGCCCGTGCCCTGGCCCACCCTCGTGACCACCCTGACCTACGGCGT

GCAGTGCTTCAGCCGCTACCCCGACCACATGAAGCAGCACGACTTCTTCAAGTCCGCCATGCCCGA

AGGCTACGTCCAGGAGCGCACCATCTTCTTCAAGGACGACGGCAACTACAAGACCCGCGCCGAGG
```

-continued

```
TGAAGTTCGAGGGCGACACCCTGGTGAACCGCATCGAGCTGAAGGGCATCGACTTCAAGGAGGAC

GGCAACATCCTGGGGCACAAGCTGGAGTACAACTACAACAGCCACAACGTCTATATCATGGCCGA

CAAGCAGAAGAACGGCATCAAGGTGAACTTCAAGATCCGCCACAACATCGAGGACGGCAGCGTG

CAGCTCGCCGACCACTACCAGCAGAACACCCCCATCGGCGACGGCCCCGTGCTGCTGCCCGACAA

CCACTACCTGAGCACCCAGTCCAAGCTGAGCAAAGACCCCAACGAGAAGCGCGATCACATGGTCC

TGCTGGAGTTCGTGACCGCCGCCGGGATCACTCTCGGCATGGACGAGCTGTACAAGGCCGGCTCC

GGTACCGATGATGATATCGCAGCGCTCGTCGTCGACAACGGCTCCGGCATGTGCAAGGCCGGCTTC

GCGGGCGACGATGCCCCCCGGGCCGTCTTCCCCTCCATCGTGGGGCGCCCCAGGCACCAGGTAGG

GGAGCTGGCTGGGTGGGGCAGCCCCGGGAGCGGGCGGGAGGCAAGGGCGCTTTCTCTGCACAGG

AGCCTCCCGGTTTCCGGGGTGGGGGCTGCGCCCGTGCTCAGGGCTTCTTGTCCTTTCCTTCCCAGGG

CGTGATGGTGGGCATGGGTCAGAAGGATTCCTATGTGGGCGACGAGGCCCAGAGCAAGAGAGGC

ATCCTCACCCTGAAGTACCCCATCG

SEQ ID NO: 14:
GAAAAACAGCCCAAAGCCCTGTTGTAGACATTAGTCCTTTCTCCTCTTTAGGCCAACTGCATTGAC

TCCACAGCCTCAGCCGAGGCCGTGTTTGCCTCCGAAGTGAAAAAGATGCAACAGGAGAACATGAA

GCCGCAGGAGCAGTTGACCCTTGAGCCATATGAAAGAGACCATGCCGTGGTCGTGGGAGTGTACA

GGTGAGCAGGGCCCAGCAATACACCAAGACAGACATCTCTGTCCCTTGCACCCCGAGTGCCATG

ATCCTGGGGACCCTCCTTCATCACCTATCTTCCTCTCACAGGCCACCTCCTAAAGTGAAGAACAAG

CCCAACAGCGCCGTGGACGGCACCGCCGGCCCCGGCGTGAGCAAGGGCGAGGAGCTGTTCACCGG

GGTGGTGCCCATCCTGGTCGAGCTGGACGGCGACGTAAACGGCCACAAGTTCAGCGTGTCCGGCG

AGGGCGAGGGCGATGCCACCTACGGCAAGCTGACCCTGAAGTTCATCTGCACCACCGGCAAGCTG

CCCGTGCCCTGGCCCACCCTCGTGACCACCCTGACCTACGGCGTGCAGTGCTTCAGCCGCTACCCC

GACCACATGAAGCAGCACGACTTCTTCAAGTCCGCCATGCCCGAAGGCTACGTCCAGGAGCGCAC

CATCTTCTTCAAGGACGACGGCAACTACAAGACCCGCGCCGAGGTGAAGTTCGAGGGCGACACCC

TGGTGAACCGCATCGAGCTGAAGGGCATCGACTTCAAGGAGGACGGCAACATCCTGGGGCACAAG

CTGGAGTACAACTACAACAGCCACAACGTCTATATCATGGCCGACAAGCAGAAGAACGGCATCAA

GGTGAACTTCAAGATCCGCCACAACATCGAGGACGGCAGCGTGCAGCTCGCCGACCACTACCAGC

AGAACACCCCCATCGGCGACGGCCCCGTGCTGCTGCCCGACAACCACTACCTGAGCACCCAGTCC

AAGCTGAGCAAAGACCCCAACGAGAAGCGCGATCACATGGTCCTGCTGGAGTTCGTGACCGCCGC

CGGGATCACTCTCGGCATGGACGAGCTGTACAAGTAATGAAGTTCAGCCCTGAGCGGATTGCGAG

AGATGTGTGTTGATACTGTTGCACGTGTGTTTTTCTATTAAAAGACTCATCCGTCTCCCATGTCTGC

TGCTCATTCCTCCCCTTGACCTGCTGACACAGGGAGCACGCACCCTTGGTCAATTTTGCGGGGTTG

GGTAAATTCTCACTCGGTCACAGAGCGCATGCTCCGTTTCTAGCTGCCTTTGCGCAGCGGCAGCCT

GGATTTCGGTTCTTGGGTGGGATTGGTAGCTCGCTGCGCATGCGTGCAGGTAAGCGGCCATCTCGC

GCAGGCGGAGTGTCAGTGTGGGTCACGTGAGGGGAGCGGAGAGGGAGGGATGGGGGCGGAGTCC

AGGGCGTGGGGGGGCCGGTTTGTTGTGGTCGCCATTTTGCT

SEQ ID NO: 15:
GGAGATGGGGGCTAAAGGGGTGTGGTGGAGAGGATAGAGGGGTGGGAAAAGATGGCCAGGAGCT

AGAAGGAGGCAGAAGTGGGAGGATGGAGCTGAAGGAGCAGCAGGCCAGGAAAGGCCCTGCTGGA

AAGCCACTGGAGCTGTGCTGCGCTGGAAAGGCCATTGGAGGTGCTAGAACGCAAAGGGGTTGCAG

TGGGGACAGACCTGCTCCCCTTCTTCTTTGTTCCTGCAGCCGGTTTCAGAAGACATGTAGCCCCATT
```

-continued

```
GGATCGGGTGGGACTAGTGGCAGCAAGGGCGAGGAGCTGTTCACCGGGGTGGTGCCCATCCTGGT

CGAGCTGGACGGCGACGTAAACGGCCACAAGTTCAGCGTGCGCGGCGAGGGCGAGGGCGATGCC

ACCAACGGCAAGCTGACCCTGAAGTTCATCTGCACCACCGGCAAGCTGCCCGTGCCCTGGCCCACC

CTCGTGACCACCCTGACCTACGGCGTGCAGTGCTTCAGCCGCTACCCCGACCACATGAAGCGCCAC

GACTTCTTCAAGTCCGCCATGCCCGAAGGCTACGTCCAGGAGCGCACCATCAGCTTCAAGGACGA

CGGCACCTACAAGACCCGCGCCGAGGTGAAGTTCGAGGGCGACACCCTGGTGAACCGCATCGAGC

TGAAGGGCATCGACTTCAAGGAGGACGGCAACATCCTGGGGCACAAGCTGGAGTACAACTTCAAC

AGCCACAACGTCTATATCACCGCCGACAAGCAGAAGAACGGCATCAAGGCCAACTTCAAGATCCG

CCACAACGTGGAGGACGGCAGCGTGCAGCTCGCCGACCACTACCAGCAGAACACCCCCATCGGCG

ACGGCCCCGTGCTGCTGCCCGACAACCACTACCTGAGCACCCAGTCCGTGCTGAGCAAAGACCCC

AACGAGAAGCGCGATCACATGGTCCTGCTGGAGTTCGTGACCGCCGCCGGGATCACTGGAACCGG

TGCTGGAAGTGGTTGAGGCACGAGGCCAGGCAGATCCCACTTGCAGCCTCCCCAGGTGTCTGCCCC

GCGTTTCCTGCCTGCGGACCAGATGAATGTAGCAGATCCCCAGCCTCTGGCCTCCTGTTCGCCTCCT

CTACAATTTGCCATTGTTTCTCCTGGGTTAGGCCCCGGCTTCACTGGTTGAGTGTTGCTCTCTAGTT

TCCAGAGGCTTAATCACACCGTCCTCCACGCCATTTCCTTTTCCTTCAAGCCTAGCCCTTCTCTCAT

TATTTCTCTCTGACCCTCTCCCCACTGCTCATTTGGATCCCAGGGGAGTGTTCAGGGCCAGCCCTGG

CTGGCATGGAGGGTGAGGCTGGGTGTCTGGAAGCAT

SEQ ID NO: 16:
AGAGTGCTAGGCAGTTTCCTGGCTGAACACGCCAGCCCAATACTTAAAGAGAGCAACTCCTGACT

CCGATAGAGACTGGATGGACCCACAAGGGTGACAGCCCAGGCGGACCGATCTTCCCATCCCACAT

CCTCCGGCGCGATGCCAAAAAGAGGCTGACGGCAACTGGGCCTTCTGCAGAGAAAGACCTCCGCT

TCACTGCCCCGGCTGGTCCCAAGGGTCAGGAAGATGGGGGCAGGTGCCACTGGCCGCGCCATGGA

CGGGCCGCGCCTGCTGCTGTTGCTGCTTCTGGGGGTGTCCCTTGGAGGTGCCAAGGAGGCATGCCC

CACAGGCCTGTACACACACAGCGGTGAGTGCTGCAAAGCCTGCAACCTGGGCGAGGGTGTGGCCC

AGCCTTGTGGAGCCAACCAGACCGTGTGTGAGCCCTGCCTGGACAGCGTGACGTTCTCCGACGTGG

TGAGCGCGACCGAGCCGTGCAAGCCGTGCACCGAGTGCGTGGGGCTCCAGAGCATGTCGGCGCCA

TGCGTGGAGGCCGACGACGCCGTGTGCCGCTGCGCCTACGGCTACTACCAGGATGAGACGACTGG

GCGCTGCGAGGCGTGCCGCGTGTGCGAGGCGGGCTCGGGCCTCGTGTTCTCCTGCCAGGACAAGC

AGAACACCGTGTGCGAGGAGTGCCCCGACGGCACGTATTCCGACGAGGCCAACCACGTGGACCCG

TGCCTGCCCTGCACCGTGTGCGAGGACACCGAGCGCCAGCTCCGCGAGTGCACACGCTGGGCCGA

CGCCGAGTGCGAGGAGATCCCTGGCCGTTGGATTACACGGTCCACACCCCCAGAGGGCTCGGACA

GCACAGCCCCCAGCACCCAGGAGCCTGAGGCACCTCCAGAACAAGACCTCATAGCCAGCACGGTG

GCAGGTGTGGTGACCACAGTGATGGGCAGCTCCCAGCCCGTGGTGACCCGAGGCACCACCGACAA

CCTCATCCCTGTCTATTGCTCCATCCTGGCTGCTGTGGTTGTGGGTCTTGTGGCCTACATAGCCTTC

AAGAGGTGGAACAGCCGCGCCAAGCGCTCGGGTTCGGGTGCCACCAACTTCAGCCTGCTGAAGCA

GGCCGGCGACGTGGAGGAGAACCCCGGCCCCATGGATTCATATCTGCTGATGTGGGACTGCTCA

CGTTCATCATGGTGCCTGGCTGCCAGGCAGGTAAGGGCCTGTGGGTGCCCCCGGAATTCCGGGAA

GGCTGATGGGCATCCCTCTTCCCAGCCACAGAACCAGAGGGAGTCCCCAGGTAGATGGTTCCAAG

AAGGGAGTTGAATCTTGGGTTCCACCTCTTGCCTGTGACCCACGGGGACCCCAGTTTATGCCTCAC
```

```
TGTTCCTTGGTCTGTCAAGAGAGCCTGAAATAGCATTAGGTTCTCCTGTCCTTCTCAGTCCTTGACA

ATTAATTCTGGGAAGAATAGTGTGGCATGATATTTGGGATATTTGGATGTTAACAGGGTCCCGATG

AGCAG

SEQ ID NO: 17:
GTATATGTGCCCACAGGAGCCAAGACGGTATTTTCCATCCTCCCAAAACAGTAGAGCTTTGACAGA

GATTTAAGGGTGACCAAGTCAAGGAAGAGGCATGGCATAGAACGGTGATGTCGGGGGTGGGGGTT

CAGAACTTCCATTATAGAAGGTAATGATTTAGAGGAGAAGGTGGTTGAGAATGGTGCTAGTGGTA

GTGAACAGATCCTTCCCAGGATCTAGGTGGGCTGAGGATTTTTGAGTCTGTGACACTATTGTATAT

CCAGCTTTAGTTTCTGTTTACCACCTTACAGCAGCACCTAATCTCCTAGAGGACTTAGCCCGTGTCA

CACAGCACATATTTGCCACACCCTCTGTAAAGCCCTGGTTTATAAGGTTCTTTCCACCGGAAGCTA

TGACAGAGGAAACGTGTGGGTGGGGAGGGGTAGTGGGTGAGGGACCCAGGTTCCTGACACAGAC

AGACTACACCCAGGGAATGAAGAGCAAGCGCCATGGGGGCAGGTGCCACTGGCCGCGCCATGGA

CGGGCCGCGCCTGCTGCTGTTGCTGCTTCTGGGGGTGTCCCTTGGAGGTGCCAAGGAGGCATGCCC

CACAGGCCTGTACACACACAGCGGTGAGTGCTGCAAAGCCTGCAACCTGGGCGAGGGTGTGGCCC

AGCCTTGTGGAGCCAACCAGACCGTGTGTGAGCCCTGCCTGGACAGCGTGACGTTCTCCGACGTGG

TGAGCGCGACCGAGCCGTGCAAGCCGTGCACCGAGTGCGTGGGGCTCCAGAGCATGTCGGCGCCA

TGCGTGGAGGCCGACGACGCCGTGTGCCGCTGCGCCTACGGCTACTACCAGGATGAGACGACTGG

GCGCTGCGAGGCGTGCCGCGTGTGCGAGGCGGGCTCGGGCCTCGTGTTCTCCTGCCAGGACAAGC

AGAACACCGTGTGCGAGGAGTGCCCCGACGGCACGTATTCCGACGAGGCCAACCACGTGGACCCG

TGCCTGCCCTGCACCGTGTGCGAGGACACCGAGCGCCAGCTCCGCGAGTGCACACGCTGGGCCGA

CGCCGAGTGCGAGGAGATCCCTGGCCGTTGGATTACACGGTCCACACCCCCAGAGGGCTCGGACA

GCACAGCCCCAGCACCCAGGAGCCTGAGGCACCTCCAGAACAAGACCTCATAGCCAGCACGGTG

GCAGGTGTGGTGACCACAGTGATGGGCAGCTCCCAGCCCGTGGTGACCCGAGGCACCACCGACAA

CCTCATCCCTGTCTATTGCTCCATCCTGGCTGCTGTGGTTGTGGGTCTTGTGGCCTACATAGCCTTC

AAGAGGTGGAACAGCCGCGCCAAGCGCTCGGGTTCGGGTGCCACCAACTTCAGCCTGCTGAAGCA

GGCCGGCGACGTGGAGGAGAACCCCGGCCCCATGTTGAAGCCATCGTTGCCGTTTACCTCCCTCTT

ATTCCTGCAGCTGCCCCTGCTGGGAGTGGGGCTGAACACGACAATTCTGACGCCCAATGGGAATG

AAGACACCACAGCTGGTGGGAAATCTGGGACTGGAGGGGGCTGGTGAGAAGGGTGGCTGTGGGA

AGGGGCCGTACAGAGATCTGGTGCCTGCCACTGGCCATTACAATCATGTGGGCAGAATTGAAAAG

TGGAGTGGGAAGGGCAAGGGGGAGGGTTCCCTGCCTCACGCTACTTCTTCTTTCTTTCTTGTTTGTT

TGTTTCTTTCTTTCTTTTGAGGCAGGGTCTCACTATGTTGCCTAGGCTGGTCTCAAACTCCTGGCCTC

TAGTGATCCTCCTGCCTCAGCCTTTCAAAGCACCAGGATTACAGACATGAGCCACCGTGCTTGGCC

TCCTCCTTCTGACCATCATTTCTCTTTCCCTCCCTGCCTTCATTTTCTCCCCAATCTAGATTTCTTCCT

GACCACTATGCCCACTG

SEQ ID NO: 18:
TTTCAGGTTTCCTTGAGTGGCAGGCCAGGCCTGGCCGTGAACGTTCACTGAAATCATGGCCTCTTG

GCCAAGATTGATAGCTTGTGCCTGTCCCTGAGTCCCAGTCCATCACGAGCAGCTGGTTTCTAAGAT

GCTATTTCCCGTATAAAGCATGAGACCGTGACTTGCCAGCCCCACAGAGCCCCGCCCTTGTCCATC

ACTGGCATCTGGACTCCAGCCTGGGTTGGGCAAAGAGGGAAATGAGATCATGTCCTAACCCTGA

TCCTCTTGTCCCACAGATATCCAGAACCCTGACCCTGCCTCCGGATCCGGAGAGGGCAGGGGATCT

CTCCTTACTTGTGGCGACGTGGAGGAGAACCCCGGCCCCATGAGCATCGGCCTCCTGTGCTGTGCA
```

-continued
```
GCCTTGTCTCTCCTGTGGGCAGGTCCAGTGAATGCTGGTGTCACTCAGACCCCAAAATTCCAGGTC

CTGAAGACAGGACAGAGCATGACACTGCAGTGTGCCCAGGATATGAACCATGAATACATGTCCTG

GTATCGACAAGACCCAGGCATGGGGCTGAGGCTGATTCATTACTCAGTTGGTGCTGGTATCACTGA

CCAAGGAGAAGTCCCCAATGGCTACAATGTCTCCAGATCAACCACAGAGGATTTCCCGCTCAGGC

TGCTGTCGGCTGCTCCCTCCCAGACATCTGTGTACTTCTGTGCCAGCAGTTACGTCGGGAACACCG

GGGAGCTGTTTTTTGGAGAAGGCTCTAGGCTGACCGTACTGGAGGACCTGAAAAACGTGTTCCCAC

CCGAGGTCGCTGTGTTTGAGCCATCAGAAGCAGAGATCTCCCACACCCAAAAGGCCACACTGGTA

TGCCTGGCCACAGGCTTCTACCCCGACCACGTGGAGCTGAGCTGGTGGGTGAATGGGAAGGAGGT

GCACAGTGGGGTCAGCACAGACCCGCAGCCCCTCAAGGAGCAGCCCGCCCTCAATGACTCCAGAT

ACTGCCTGAGCAGCCGCCTGAGGGTCTCGGCCACCTTCTGGCAGAACCCCGCAACCACTTCCGCT

GTCAAGTCCAGTTCTACGGGCTCTCGGAGAATGACGAGTGGACCCAGGATAGGGCCAAACCCGTC

ACCCAGATCGTCAGCGCCGAGGCCTGGGGTAGAGCAGACTGTGGCTTCACCTCCGAGTCTTACCA

GCAAGGGGTCCTGTCTGCCACCATCCTCTATGAGATCTTGCTAGGGAAGGCCACCTTGTATGCCGT

GCTGGTCAGTGCCCTCGTGCTGATGGCTATGGTCAAGAGAAAGGATTCCAGAGGCCGGGCCAAGC

GGTCCGGATCCGGAGCCACCAACTTCAGCCTGCTGAAGCAGGCCGGCGACGTGGAGGAGAACCCC

GGCCCCATGGAGACCCTCTTGGGCCTGCTTATCCTTTGGCTGCAGCTGCAATGGGTGAGCAGCAAA

CAGGAGGTGACGCAGATTCCTGCAGCTCTGAGTGTCCCAGAAGGAGAAAACTTGGTTCTCAACTG

CAGTTTCACTGATAGCGCTATTTACAACCTCCAGTGGTTTAGGCAGGACCCTGGGAAAGGTCTCAC

ATCTCTGTTGCTTATTCAGTCAAGTCAGAGAGAGCAAACAAGTGGAAGACTTAATGCCTCGCTGGA

TAAATCATCAGGACGTAGTACTTTATACATTGCAGCTTCTCAGCCTGGTGACTCAGCCACCTACCT

CTGTGCTGTGAGGCCCCTGTACGGAGGAAGCTACATACCTACATTTGGAAGAGGAACCAGCCTTAT

TGTTCATCCGTATATCCAGAACCCTGACCCTGCGGTGTACCAGCTGAGAGACTCTAAATCCAGTGA

CAAGTCTGTCTGCCTATTCACCGATTTTGATTCTCAAACAAATGTGTCACAAAGTAAGGATTCTGA

TGTGTATATCACAGACAAAACTGTGCTAGACATGAGGTCTATGGACTTCAAGAGCAACAGTGCTGT

GGCCTGGAGCAACAAATCTGACTTTGCATGTGCAAACGCCTTCAACAACAGCATTATTCCAGAAG

ACACCTTCTTCCCCAGCCCAGGTAAGGGCAGCTTTGGTGCCTTCGCAGGCTGTTTCCTTGCTTCAGG

AATGGCCA
```

For initial screening, polymers were purchased dry (see Table 2) and resuspended to 100 mg/mL in water except as noted, passed through a 0.2 μm syringe filter, and stored at −80° C. prior to use. The ssODNenh electroporation enhancer (SEQ ID NO: 7) was synthesized (IDT) and resuspended to 100 μM in water. Serial dilutions of polymers or ssODNenh were made in water, then mixed 1:1 volume with preformed RNPs. For subsequent knock-in experiments, 15-50 kDa poly(L-glutamic acid) (Sigma) was resuspended to 100 mg/mL in water, sterile filtered, and mixed with freshly-prepared gRNA at 0.8:1 volume ratio prior to complexing with Cas9 protein for final volume ratio gRNA:PGA:Cas9 of 2:1.6:1.

Long double-strand HDR templates encoding various gene insertions (see Table 1) and 300-350 bp homology arms were synthesized as GeneBlocks (IDT) and cloned into a pUC19 plasmid, which then served as a template for generating a PCR amplicon. Specific PCR primers targeting the left and right homology arms and with additional described Cas9 Target Sequences (CTS) (see FIGS. 3A-3D) were synthesized (IDT) without chemical modifications. Amplicons were generated as previously described (Roth et al., Nature 559:405-409, 2018) with KapaHiFi polymerase (Kapa Biosystems), purified by SPRI bead cleanup, and resuspended in water to 0.5 to 2 μg/μL measured by light absorbance on a NanoDrop spectrophotometer (ThermoFisher). HDR templates were mixed and incubated with RNPs for at least 5 minutes prior to mixing with and electroporating into cells.

RNP particle size was measured by dynamic light scattering dispersed in PBS on a Zetasizer Nano ZS (Malvern Panalytical). For RNP lyophilization, freshly prepared RNPs premixed with PGA or ssODNenh and HDR templates were diluted 1:1 v:v in 50 mM trehalose, flash frozen in a liquid nitrogen bath then immediately dried on a Labconco Freeze Dry System-Freezone 4.5 lyophilizer for 24 hours, and finally stored at −80° C. until use. Dry RNP was resuspended in water to achieve the original concentration, incubated for 5 minutes at 37° C., then mixed with cells for electroporation.

Immediately prior to electroporation in a Lonza 4D 96-well format Nucleofector (Lonza), cells were centrifuged for 10 minutes at 90g, media aspirated, and resuspended in the electroporation buffer P3 (Lonza) using 17-20 μL buffer per 0.5 to 1.0e6 cells. T cells, NK cells, and B cells were electroporated with pulse code EH-115; primary HSPCs with pulse code ER-100, and iPS-derived CD34 HSPCs with pulse code EY-100. Immediately after electroporation, cells were rescued with addition of 80 μL of growth media directly into the electroporation well, incubated for 10-20 minutes, then removed and diluted to 0.5-1e6 cells/mL in growth media. Additional fresh growth media and cytokines were added every 48 hours.

At days 3-5 post electroporation, cells were collected for staining and flow cytometry analysis. Briefly, cells were stained for cell type-specific surface markers and live-dead discrimination (see list of antibodies in Table 3) then analyzed on an Attune NxT Flow Cytometer with automated 96-well sampler (ThermoFisher) sampling a defined volume (between 50-150 μL per well) to obtain quantitative cell counts. Cytometry data was processed and analyzed using FlowJo software (BD Biosciences).

TABLE 2

Polymers Tested

| Polymer | Abbreviation | MW (kDa) | Concentration (mg/mL) | Manufacturer |
|---|---|---|---|---|
| polyethylenimine (branched) | bPEI | 2 | 5 | Sigma |
| poly(L-arginine) HCL | PLA | 15-70 | 100 | Sigma |
| poly(L-lysine) HBr | PLL | 15-30 | 100 | Sigma |
| poly(L-ornithine) HBr | PLO | 30-70 | 100 | Sigma |
| Protamine Sulfate | PS | >100 U/mg | 10 | Fresenius Kabi |
| Poly(ethylene glycol) | PEG-35 | 35 | 44 | Sigma |
| Poly(L-glutamic acid) | PGA | 15-50 | 100 | Sigma |
| Poly(L-glutamic acid) | PLE20 | 3 | 100 | Alamanda Polymers |
| Poly(L-glutamic acid) | PLE50 | 7.5 | 100 | Alamanda Polymers |
| Poly(L-glutamic acid) | PLE100 | 15 | 100 | Alamanda Polymers |
| Poly(L-glutamic acid) | PLE200 | 30 | 100 | Alamanda Polymers |
| Poly(L-glutamic acid) | PLE800 | 120 | 100 | Alamanda Polymers |
| Heparin | Hep | >180 U/mg | 60 | Sigma |
| Hyaluronic acid | HA-150 | 100-150 | 75 | Lifecore Biomedical |
| Poly(acrylic acid) | PAA-5 | 5 | 180 | Sigma |
| Poly(acrylic acid) | PAA-25 | 25 | 100 | Sigma |
| Poly(acrylic acid) | PAA-250 | 250 | 72 | Sigma |
| poly(L-aspartic acid) | PLD | 27 | 13.3 | Alamanda Polymers |
| ssODNenh electroporation enhancer* | ssODNenh | 31 | 3.1 | IDT Technologies |

*ssODNenh sequence: TTAGCTCTGTTTACGTCCCAGCGGGCATGAGAGTAACAAGAGGGTGTGGTAATAT-TACGGTACCGAGCACTATCGATACAATATGTGTCATACGGACACG (SEQ ID NO: 7)

TABLE 3

Flow Cytometry Stains

| Target | Fluor | Vendor | Clone | Catalog Number |
|---|---|---|---|---|
| Fc Receptor | — | Biolegend | Human TruStain FcX | 422302 |
| GhostDye Red 780 | — | Tonbo | — | 13-0865-T500 |
| GhostDye Violet 510 | — | Tonbo | — | 13-0870-T500 |
| LIVE/DEAD ® Fixable Aqua Dead Cell Stain | — | ThermoFisher Scientific | — | L34966 |
| CD19 | PacBlue | Biolegend | HIB19 | 302223 |
| CD271 (tNGFR) | APC | Biolegend | ME20.4 | 345108 |
| CD3 | AlexaFluor 700 | Becton-Dickson | UCHT1 | 557943 |
| CD3 | PE | Biolegend | UCHT1 | 300408 |
| CD34 | PE-Cy7 | Becton-Dickson | 8G12 | 348791 |
| CD4 | PE-Cy7 | Biolegend | OKT4 | 317414 |
| CD4 | FITC | Biolegend | SK3 | 344604 |
| CD4 | PerCP | Tonbo | SK3 | 67-0047-T500 |
| CD56 | PerCP | Biolegend | HCD56 | 318342 |
| CD8 | APC | Tonbo | OKT8 | 20-0086-T100 |
| CD8 | PE-Cy7 | Becton-Dickson | SKI | 335787 |
| TCR- 1G4 | PE | Immudex | HLA-A*0201/SLLMWITQV | WB3247-PE |
| TCR-gd | PE-Cy7 | Biolegend | B1 | 331221 |
| TCR-αβ | BV-421 | Biolegend | IP26 | 306722 |

Example 2—Addition of a DNA-Binding Protein Target Sequence to the HDR Template

An approach to reprogram human T cells with CRISPR-based genome targeting without the need for viral vectors (Roth et al., Nature 559:405-409, 2018) was previously reported. However many research and clinical applications still depend upon improved efficiency, cell viability, and generalizability of non-viral genome targeting across cell types (Yin et al., Nat Rev Clin Oncol, 16(5):281-295, 2019; Dunbar et al., Science 359:6372, 2018; Cornu et al., Nat Med 23:415-423, 2017; and David and Doherty, Toxicol Sci 155:315-325, 2017). It was previously found that varying the relative concentrations of both Cas9 RNP and HDR template had significant effects on targeting efficiency and toxicity (Roth et al., Nature 559:405-409, 2018). Here, an initial experiment was conducted to optimize the interactions between the HDR template and stabilized RNPs to see if further improvements could be made independent of cell type.

The experiment included a new approach to promote nuclear entry of the template. It was attempted to recruit Cas9 with nuclear location sequences (NLS) to the HDR template by enhancing binding between the RNP and HDR template without complex covalent linkages (Pouton et al., Adv Drug Deliv Rev 59:698-717, 2007). CRISPR-Cas9 interacts specifically with both genomic and non-genomic dsDNA (Doudna and Charpentier, Science 346:1258096, 2014), and nuclease-inactive dCas9 has been used in many applications to localize protein and RNA effectors to specific DNA sequences without cleaving the target sequence (Dominguez et al., Nat Rev Mol Cell Biol 17:5-15, 2016). It was tested whether HDR could be boosted by targeting a dCas9-NLS "shuttle sequence" to the ends of an HDR template by coding 20 bp Cas9 target sequences (also referred to as DNA-binding protein target sequence) at the ends of the homology arms. Indeed, these initial experiments with added dCas9-NLS did show improvements in HDR efficiency in primary human T cells (FIGS. 1A and 1B) but needed two distinct RNPs. These data encouraged the search for another method utilizing the same RNP to both cut a specified genomic site and recruit Cas9-NLS to shuttle sequence-modified HDR templates.

Example 3—Effect of DNA-Binding Protein Target Sequence on Genome Targeting Efficiency It was hypothesized that a single catalytically-active Cas9-NLS RNP would suffice for both on-target genomic cutting and "shuttling" if a truncated (16 bp) DNA-binding protein target sequence was added to the HDR template. A truncated DNA-binding protein target sequence would enable Cas9 binding but not cutting (Jiang and Doudna, Annu Rev Biophys 46:505-529, 2017) (FIG. 2A and FIGS. 3A-3D). With the proper sequence orientation, the additional DNA-binding protein target sequence markedly improved the efficiency of knocking-in a reprogrammed TCRα and TCRβ specificity (with a ~1.5 kb DNA insert) at the endogenous TRAC (T-cell receptor a constant) locus (FIG. 2B and FIGS. 3A-3D). This DNA-binding protein target sequence shuttle system improved genome targeting efficiencies across a variety of loci in different primary human T cell types (FIGS. 2C and 2D and FIGS. 4A-4E). HDR templates with the DNA-binding protein target sequence achieved preferential targeting even in direct competition with unmodified dsDNA HDR templates simultaneously delivered to the same cells (FIG. 2E and FIGS. 5A-5E). The DNA-binding protein target sequence shuttle also improved efficiencies of bi-allelic and multiplexed targeting across different loci (FIG. 2F and FIGS. 5A-5E). The full HDR efficiency gains improved on the presence of an NLS in the Cas9 RNP, use of an on-target gRNA, and pre-incubation of the Cas9-NLS RNP with the DNA-binding protein target sequence-modified HDR template (FIG. 2G and FIGS. 6A-6D). Taken together these data demonstrate that coupling the HDR template to Cas9-NLS with addition of the DNA-binding protein target sequence to the HDR template enhances genome targeting efficiency without requiring modification of the protein or gRNA.

Example 4—Cell Viability

Exogenous DNA (including HDR templates) can be cytotoxic at high concentrations (David and Doherty, *Toxicol Sci* 155:315-325, 2017; Roth et al., *Nature* 559:405-409, 2018; Luecke et al., *EMBO Rep* 18:1707-1715, 2017). The effect of the RNP-HDR template interactions on cell viability was studied. Gene targeting using HDR templates with added DNA-binding protein target sequence improved efficiency, but effect on cell viability was also observed (FIG. 2H). Effect on cell viability was observed with an on-target gRNA and pre-incubation of the RNP with HDR template, but did not entirely depend on the presence of a NLS on Cas9 (FIGS. 6A-6D), consistent with possible enhanced cytoplasmic delivery of DNA during electroporation due to the RNP-HDR template interaction.

Example 5—Effect of Anionic Polymer and DNA-Binding Protein Target Sequence

Figure 7A:
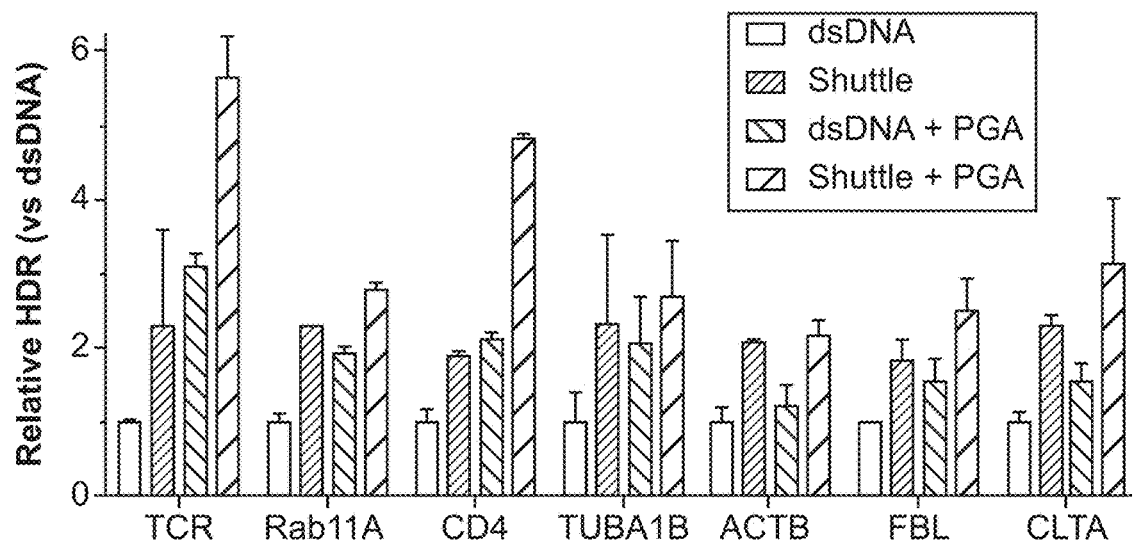
FIGS. 7A-7E: PGA-stabilized Cas9 RNP and tCTS-modified-HDR templates improved knockin gene editing outcomes across a variety of genetic loci and clinically-relevant immune cell types.
Figure 7B:
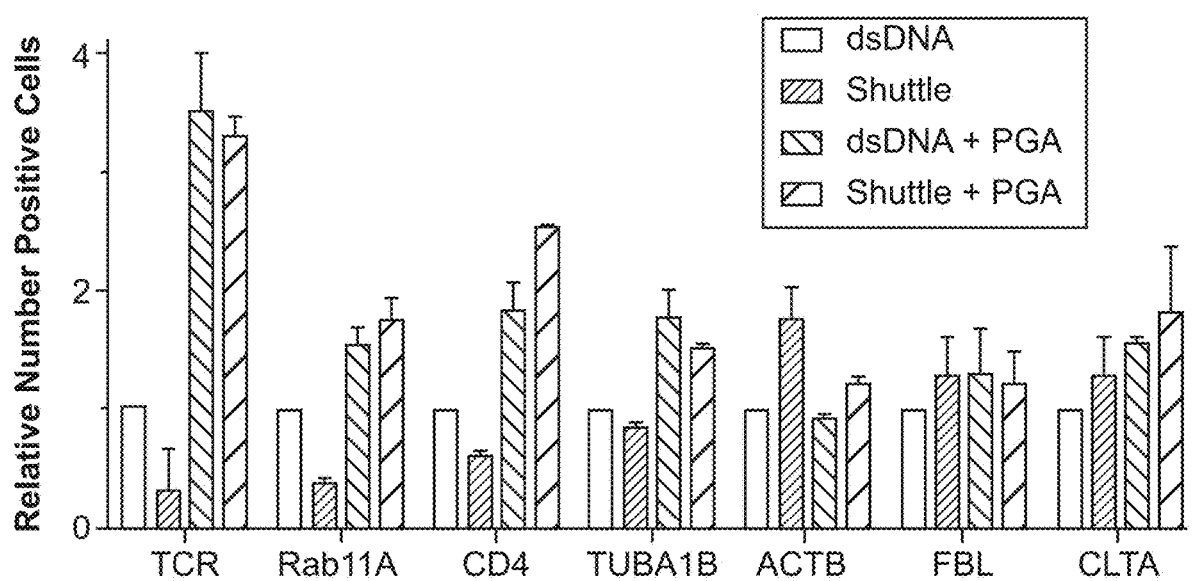
Figure 7C:
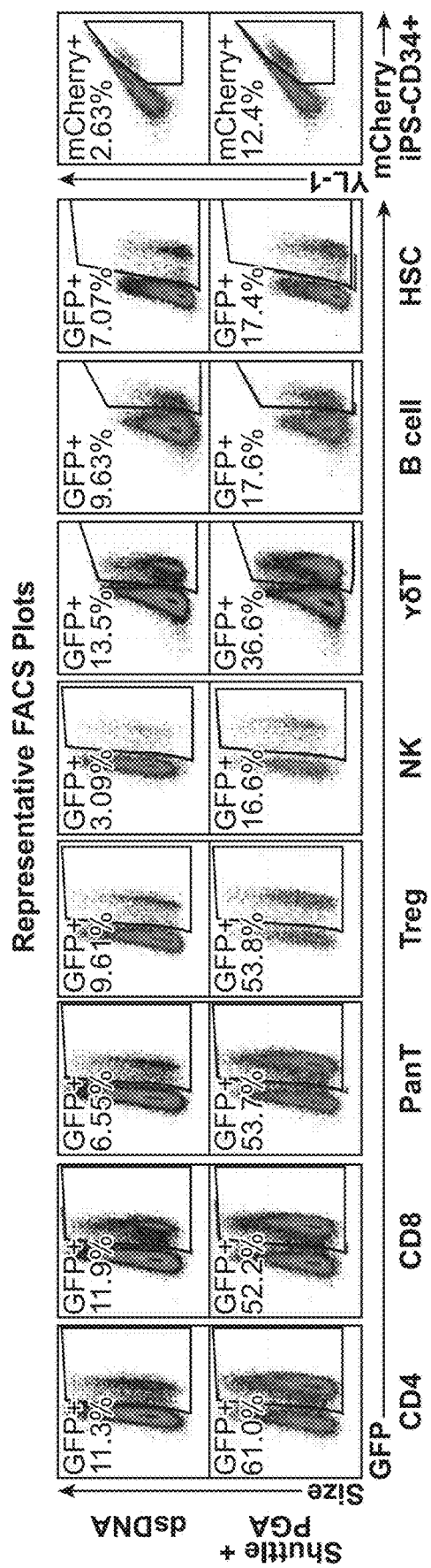
Figure 7D:
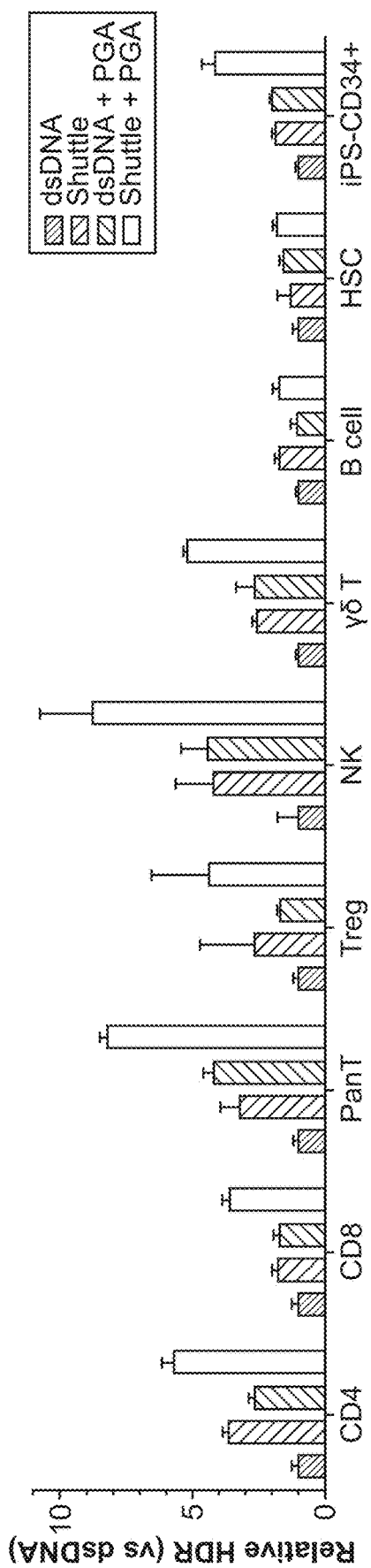
Figure 7E:
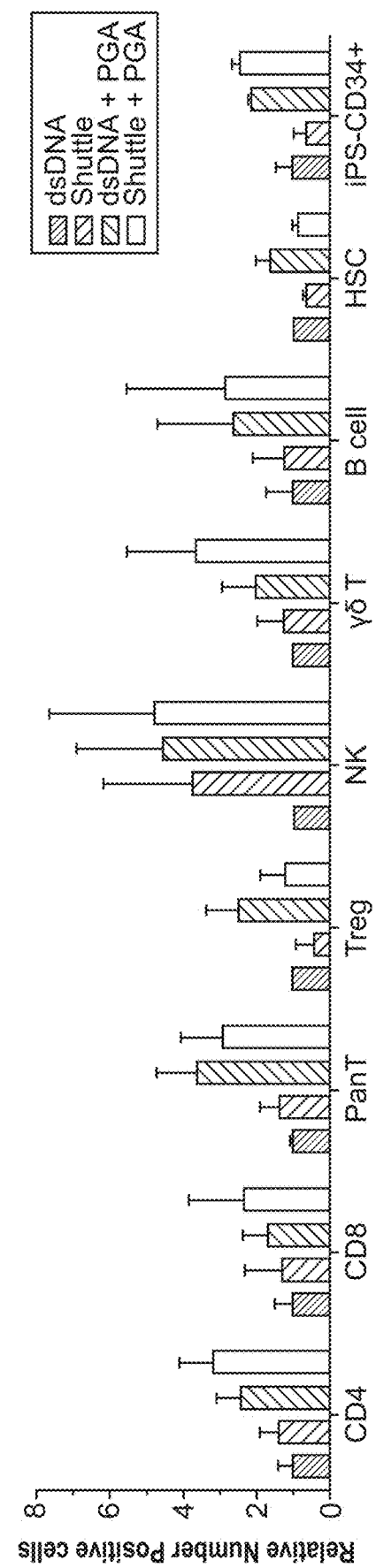
Figure 8A:
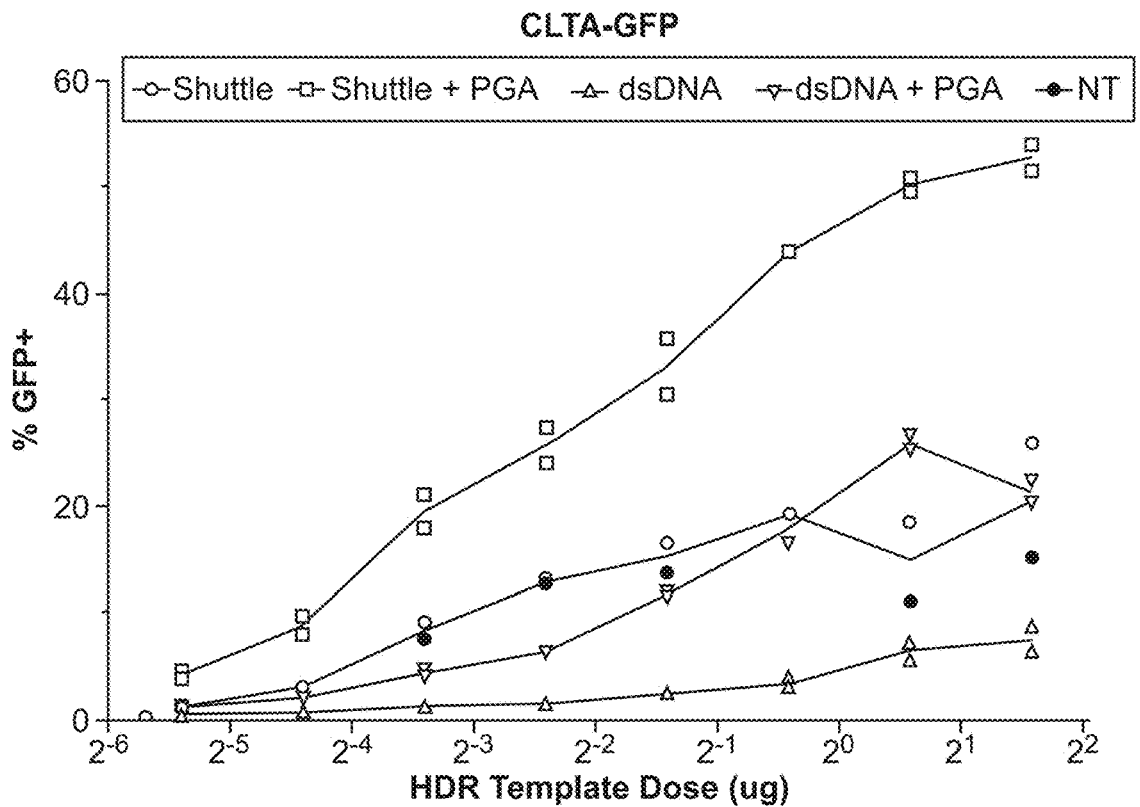
FIGS. 8A and 8B: PGA-stabilized Cas9 RNP nanoparticles improved knock-in. A series of doses of unmodified HDR template or tCTS-modified HDR template targeting a N-terminal fusion of GFP to Clathrin were combined with 50 pmol of regular Cas9 RNP or PGA-stabilized Cas9 RNP then electroporated in primary human bulk (CD3+) T cells.
Figure 8B:
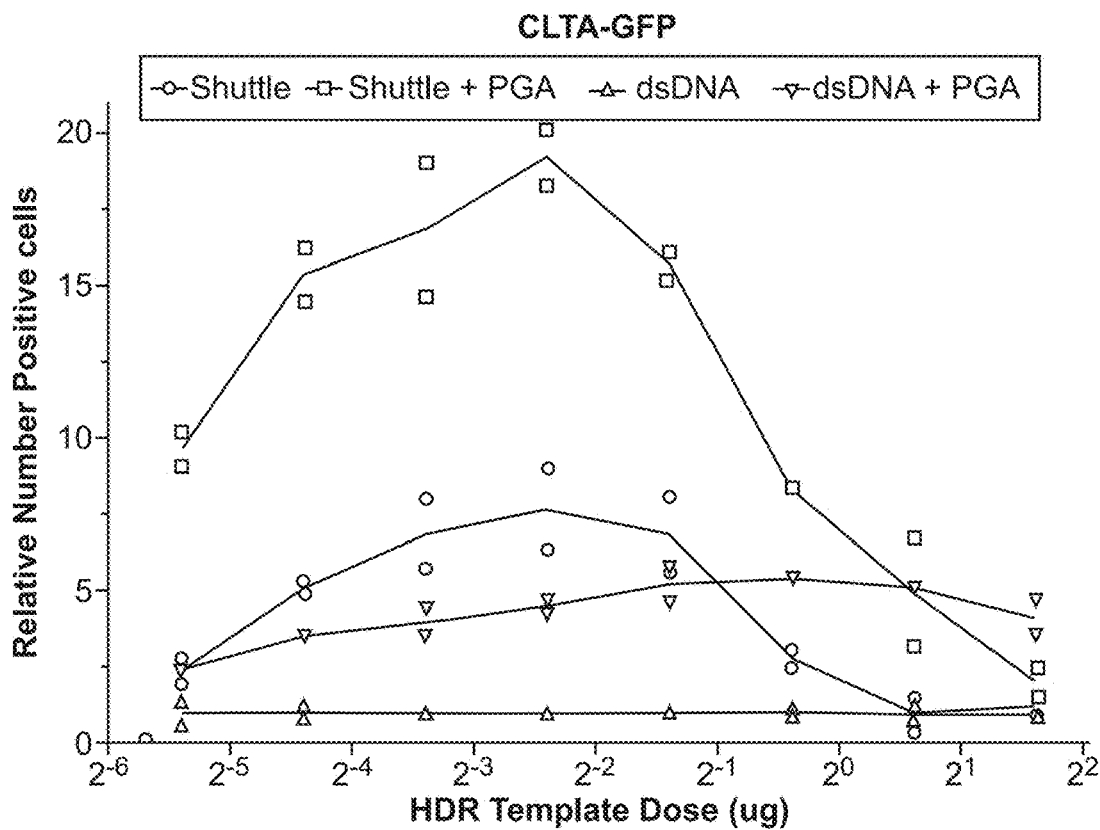
Figure 9:
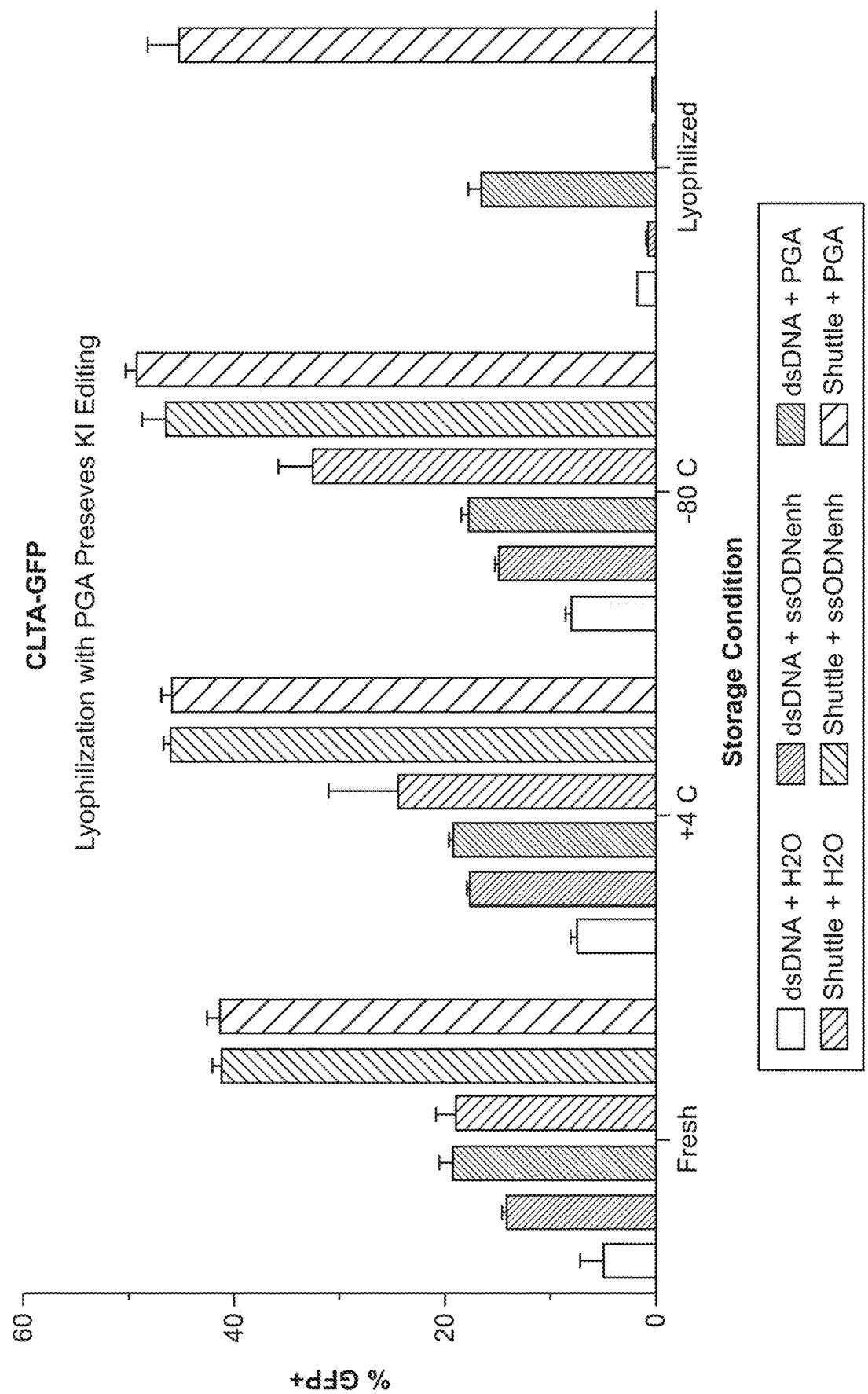
FIG. 9: PGA-stabilized Cas9 RNP nanoparticles complexed with tCTS-modified "shuttle" HDR template can be lyophilized and retain editing efficiency. Cas9 RNPs were prepared at 2:1 ratio gRNA:protein together with extra H2O, PGA, or ssODNenh, then mixed with regular dsDNA HDR template (ds) or tCTS-modified HDR template (tCTS) targeting insertion of an N-terminal fusion of GFP to RAB11A. Samples were incubated at 37° C. to enhance RNP-HDR template interaction, diluted in equal volumes of 50 mM trehalose, frozen in liquid nitrogen, lyophilized overnight, then stored at −80° C. RNP-HDR templates were later reconstituted in water prior to electroporating into primary human bulk (CD3+) T cells. Cas9 RNP-HDR template nanoparticles stabilized with PGA, but not ssODNenh, were protected through lyophilization and reconstitution and retained robust knock-out editing efficiency compared to freshly prepared RNPs. Data shown as the average of three technical replicates for one blood donor; error bars indicate standard deviation.

DNA-binding protein target sequence and anionic polymer in combination could further improve efficiency and viability of non-viral genome targeting. Electroporation of HDR templates with DNA-binding protein target sequence added and PGA-stabilized RNPs markedly enhanced efficiency and viability in primary human T cells across multiple genomic loci (FIG. 7E). Importantly, improved viability from PGA-stabilized RNPs effectively mitigated the dose-dependent toxicity (FIG. 2H) and improved the recovery of viable T cells edited at a variety of endogenous loci (FIG. 7B). Increased efficiency and cell recovery were consistent across human blood donors and was most profound at lower concentrations of HDR template DNA (FIGS. 8A and 8B). The combined DNA-binding protein target sequence-modified HDR template and PGA-stabilized nanoparticle system also retained activity through freeze-thaw cycles and the lyophilization process (FIG. 9).

Encouraged by these results in T cells, the combined system was applied to enable non-viral genome targeting in a wider set of therapeutically relevant primary human hematopoietic cells. Using a Clathrin-GFP fusion template, which was expressed in all tested cell types, improved editing efficiencies with the combined system were consistently observed (FIGS. 7C-7E). Bulk $CD3^+$ T cells, purified $CD4^+$ T cells or $CD8^+$ T cells, and purified $CD127^{low}$ $CD25^+$ $CD4^+$ regulatory T cells (Tregs) all achieved a similarly high knock-in efficiency of over 50% of cells, with 3-8× increase in the percentage of knock-in edited cells at reduced HDR template concentrations (FIGS. 7C and 7D). While standard RNP and unmodified HDR template achieved only minimal knock-in in isolated primary human NK cells or B cells, the combined system resulted in over 15% transgene-positive cells and a 2-5-fold increase in edited cell yield (FIGS. 7C-7E). In Gamma/Delta T cells the combined system exhibited improved editing efficiency from ~5% to ~28%, and 5-6 fold improved edited cell recovery compared to a standard RNP and unmodified HDR template. Finally, the combined system enabled the expression of large transgene insertions in over 15% of human HSPCs without a viral vector, in both mobilized peripheral blood HSPCs and iPS-derived HSPCs (Vo et al., *Nature* 553:506-510, 2018), with a marked viability boost and 2-3× increased yield of edited cells. The combined non-viral system was thus demonstrated to be effective in diverse human hematopoietic cell types.

Together, PGA as a RNP nanoparticle-stabilizing enhancer and the DNA-binding protein target sequence-modified HDR template enabled high percentage editing with improved edited cell yields in a variety of primary immune cell types thus opening the door to highly-efficient non-viral genome editing and adoptive cell therapies beyond T cells. The combined system is a platform to explore gene function and immunoengineering technologies in cell types that had been previously challenging to genome modify. The formation of PGA-stabilized RNP nanoparticles and the utilization of PCR primers to introduce DNA-binding protein target sequence modifications to HDR templates are both methods that can be rapidly adapted to any existing Cas9 RNP-based editing protocol. Notably, marked improvements in large gene targeting to endogenous loci were achieved without further optimizing cell cycle dynamics, small molecule modulation of DNA repair machinery, or specialized chemistries although these complementary strategies could eventually offer additional efficiency gains. Further optimization of polymers or DNA-binding protein target sequence configurations could offer even further improvements. The data demonstrate a technically simple system that greatly enhances the capabilities of Cas9 RNP-mediated non-viral genome targeting in primary human immune cells and has direct translation potential for research, biotechnology, and clinical endeavors.

Example 6—RNP Complexes with Excess Oligodeoxynucleotides

Figure 10A:
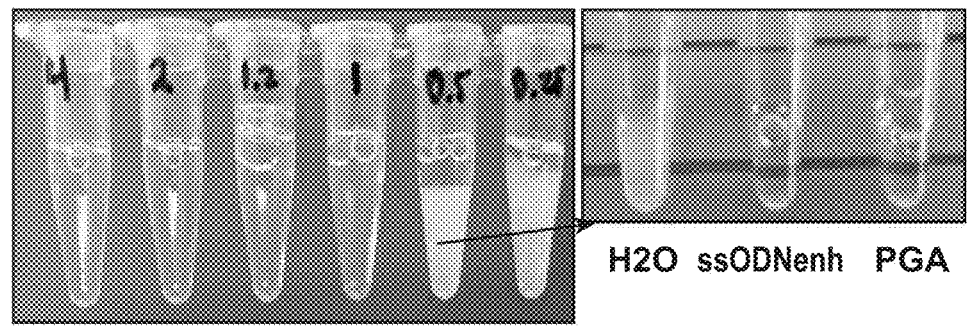
FIG. 10A shows mixtures of Cas9 protein and sgRNA at different sgRNA to Cas9 protein ratio. The addition of a molar excess of a 100-base single strand oligodeoxynucleotide (ssODNenh; which has no sequence homology to mouse or human genes) or PGA to the mixture of Cas9 protein and sgRNA was able to clear the previously opaque solution.
Figure 10B:
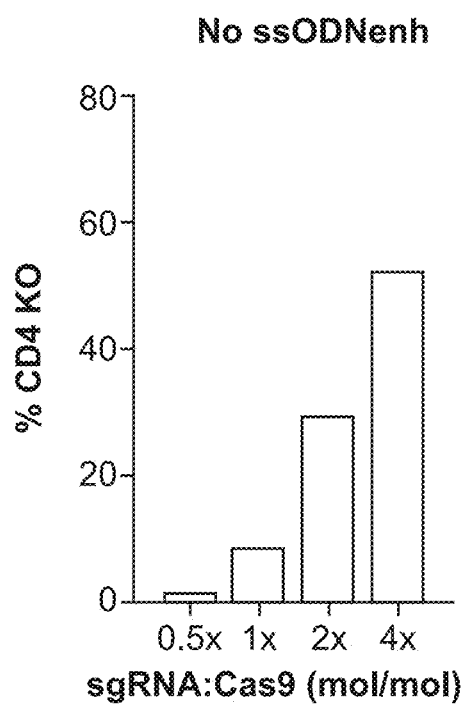
FIG. 10B shows that the addition of excess sgRNA, achieving sgRNA to Cas9 protein ratios of 2:1 and 4:1, greatly improved the editing efficiency in primary human T cells as measured by the knock-out of cell-surface receptors at 3 days.
Figure 10C:
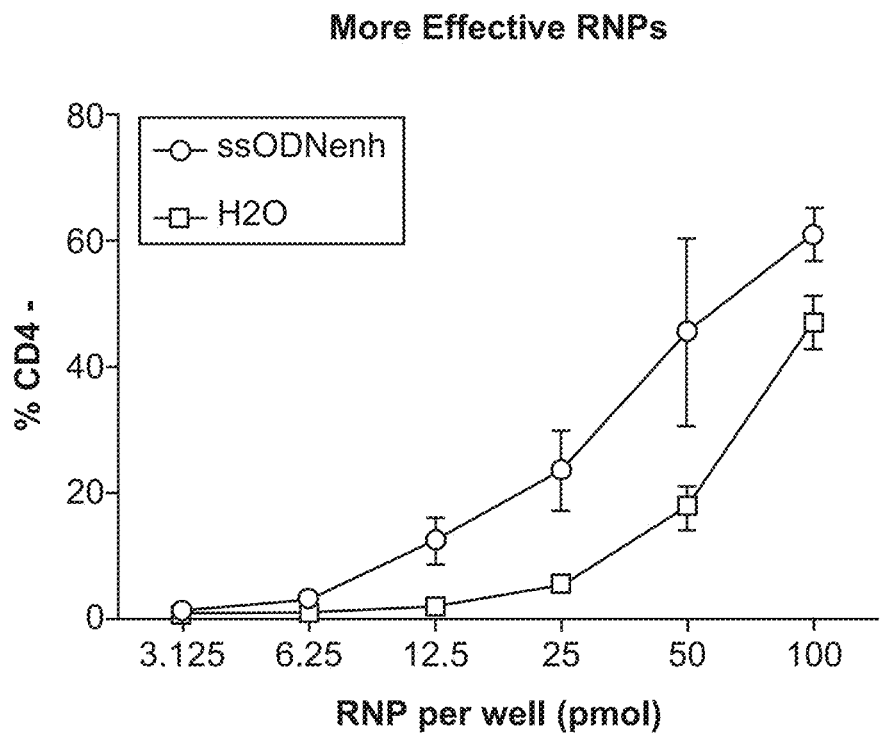
FIG. 10C shows that the addition of ssODNenh to the mixture boosted editing efficiency at any dose of RNP.
Figure 10D:
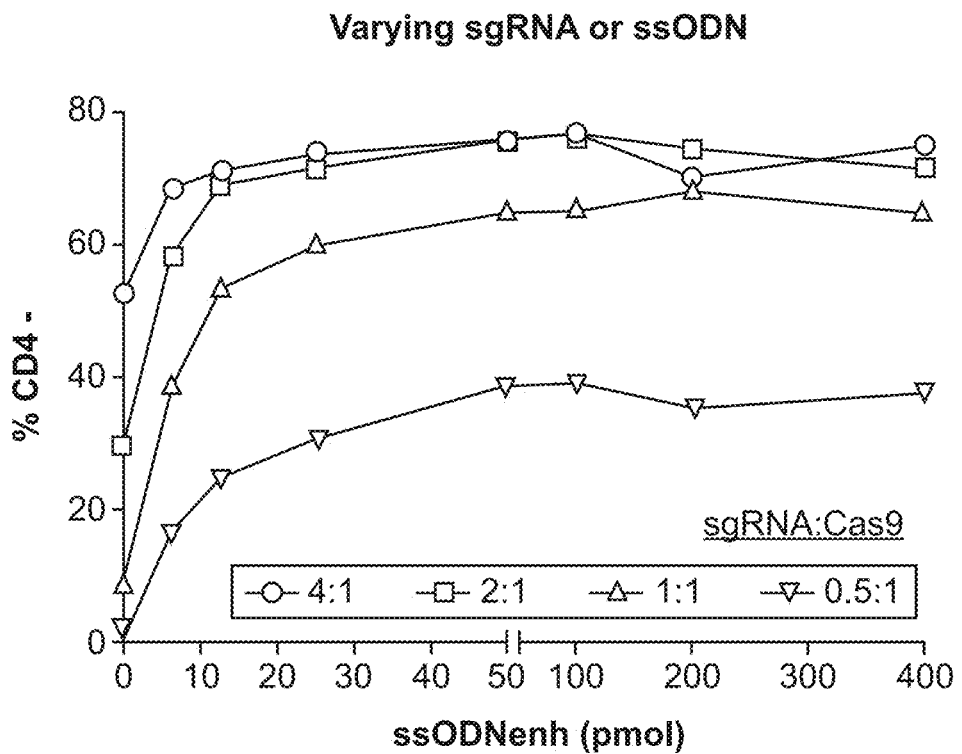
FIG. 10D shows that sgRNA and ssODNenh are both able to boost editing efficiency.

When a purified recombinant Cas9 protein was mixed with sgRNA to form the functional RNP complex with molar excess of Cas9 protein to sgRNA (i.e., sgRNA to Cas9 protein ratio of less than 1.0), the mixture resulted in a milky opaque solution with rapid sedimentation of poorly functional material (FIG. 10A). FIG. 10A shows RNP complexes made with increasing concentrations of sgRNA resulting in 4, 2, 1.2, 1, 0.5, or 0.25 molar ratio of sgRNA to Cas9 protein. At equal molar ratio of sgRNA to Cas9 protein, the solution was temporarily cloudy and sedimented over time. The addition of excess sgRNA, achieving sgRNA to Cas9 protein ratios of 1.2:1, 2:1, and 4:1, greatly improved macroscopic appearance and also the editing efficiency in primary human T cells as measured by the knock-out of cell-surface receptors at 3 days (FIG. 10B). Similarly, the addition of molar excess of a 100-base single strand oligodeoxynucleotide (ssODNenh; which has no sequence homology to mouse or human genes) to the mixture of Cas9 protein and sgRNA having sgRNA to Cas9 protein ratio of 0.5 rapidly cleared the solution and improved the knock-out editing efficiency at any ratio of sgRNA (FIG. 10A). Further, the addition of ssODNenh to the mixture boosted editing efficiency at any dose of RNP complex (FIG. 10C). It was observed that one nucleic acid seemed to effectively be substituted for the other to achieve the same effect (sgRNA and ssODNenh) (FIG. 10D), and the combination of both sgRNA and ssODNenh in excess did not further improve editing.

Example 7—Effect of Anionic Polymers

Figure 18:
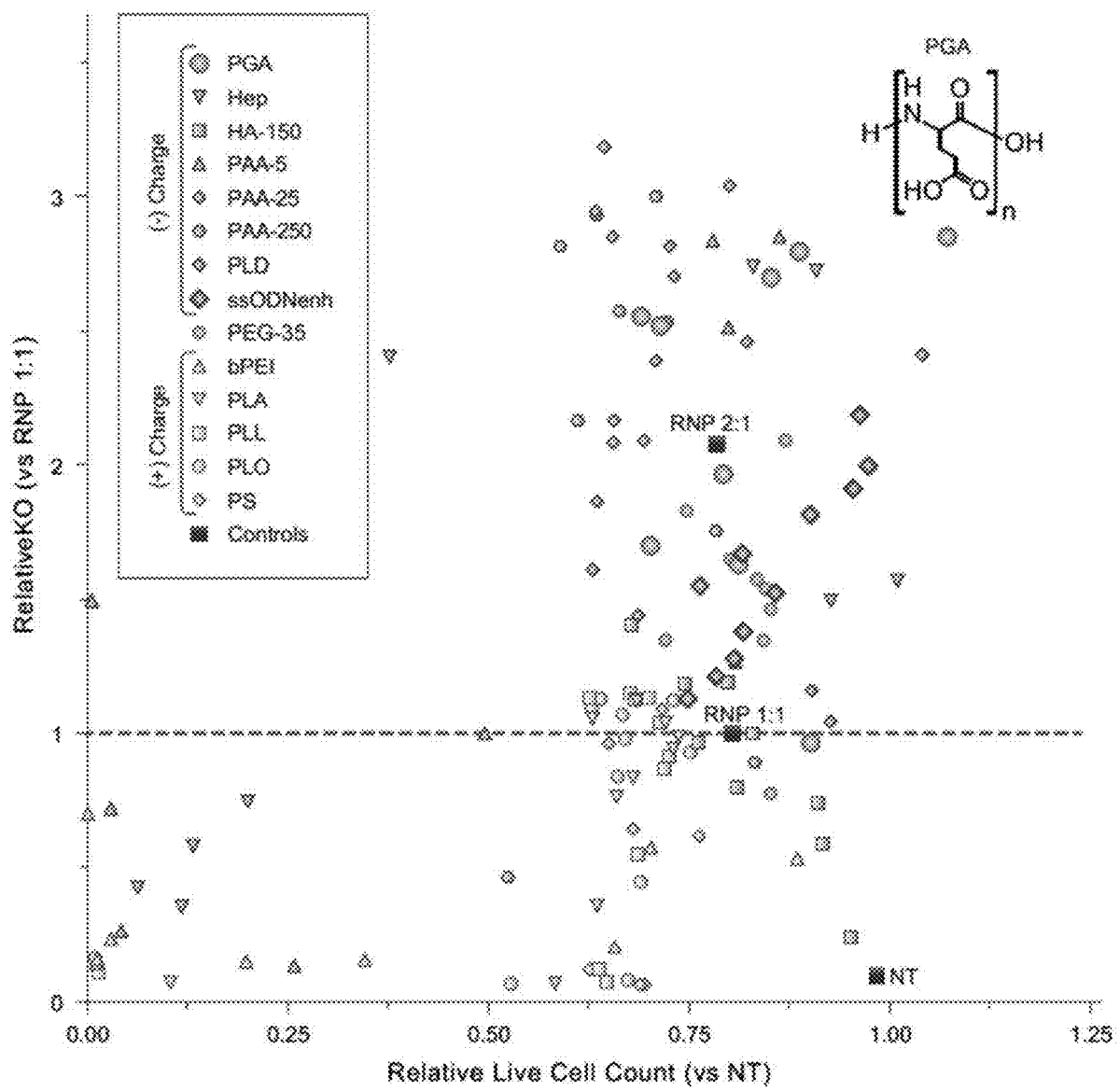
FIG. 18 shows the screening of multiple positively-charged, neutral, and negatively-charged polymers for the ability to enhance CD4 gene knock-out editing.

Various commercially-available water-soluble polymeric materials were added to pre-formed RNP complexes (formulated at a 1:1 sgRNA:Cas9 protein ratio) at various concentrations to test for the ability of the polymers to enhance electroporation-mediated Cas9 knock-out editing efficiency in primary human T cells. FIG. 18 shows the screening of multiple polymers for the ability to enhance CD4 gene knock-out editing. Loss of surface CD4 expression at 3 days assessed by flow cytometry is normalized to unenhanced editing efficiency (RNP 1:1 without any additive) on the y-axis, and the live cell count is normalized to mock non-electroporated (NT) cells on the x-axis. Negatively charged polymers are: poly(L-glutamic acid) (PGA), heparin sulfate (Hep), hyaluronic acid at 150 kDa (HA-150), poly(acrylic acid) at 5 kDa (PAA-5), 25 kDa (PAA-25), or 250 kDa (PAA-250), poly(L-aspartic acid) (PLD), and ssODNenh. Neutral polymer is: poly(ethylene glycol) at 35 kDa (PEG-35), and positively charged polymers are: polyethyleneimine at 25 kDa (PEI), poly(L-arginine) at 15-70 kDa (PLA), poly(L-lysine) at 15-30 kDa (PLL), poly(L-ornithine) at 30-70 kDa (PLO), and protamine sulfate (PS). PGA with chemical structure shown inset above data point that corresponds to 100 mg/mL concentration. Each polymer sample was tested at serial dilutions to avoid potential dose-dependent cytotoxicity falsely masking impact on editing efficiency, and each concentration is depicted as an individual point that is an average for two different blood donors.

Figure 10E:
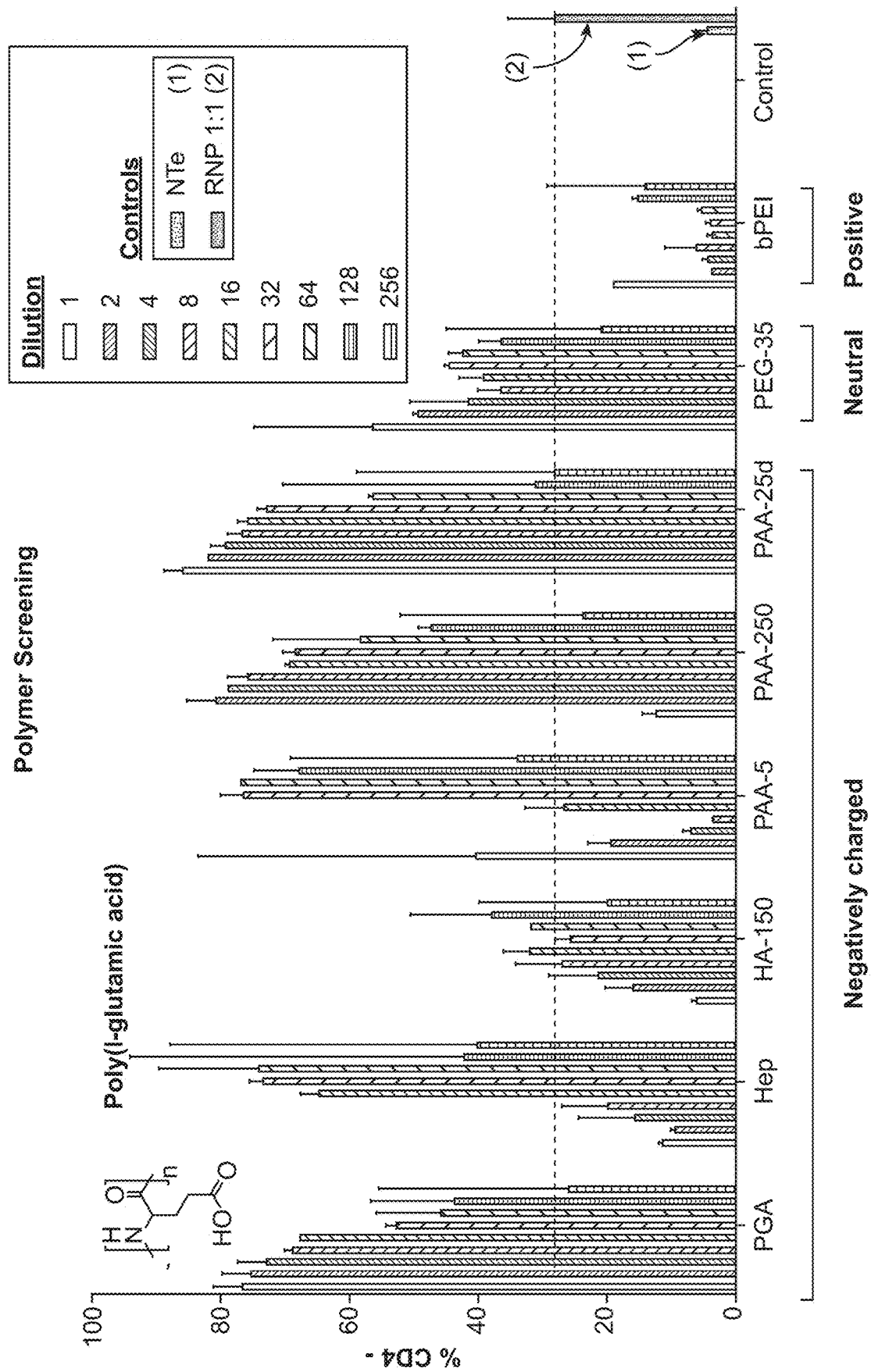
FIGS. 10E and 10F show the test of various commercially-available water-soluble polymeric materials (polyglutamic acid (PGA), hyaluronic acid (HA), poly(acrylic acid) (PAA), polyethylene glycol (PEG), and polyethylenimine (PEI)) for their ability to enhance electroporation-mediated Cas9 knock-out editing efficiency in primary human T cells and the associated toxicity.
Figure 10F:
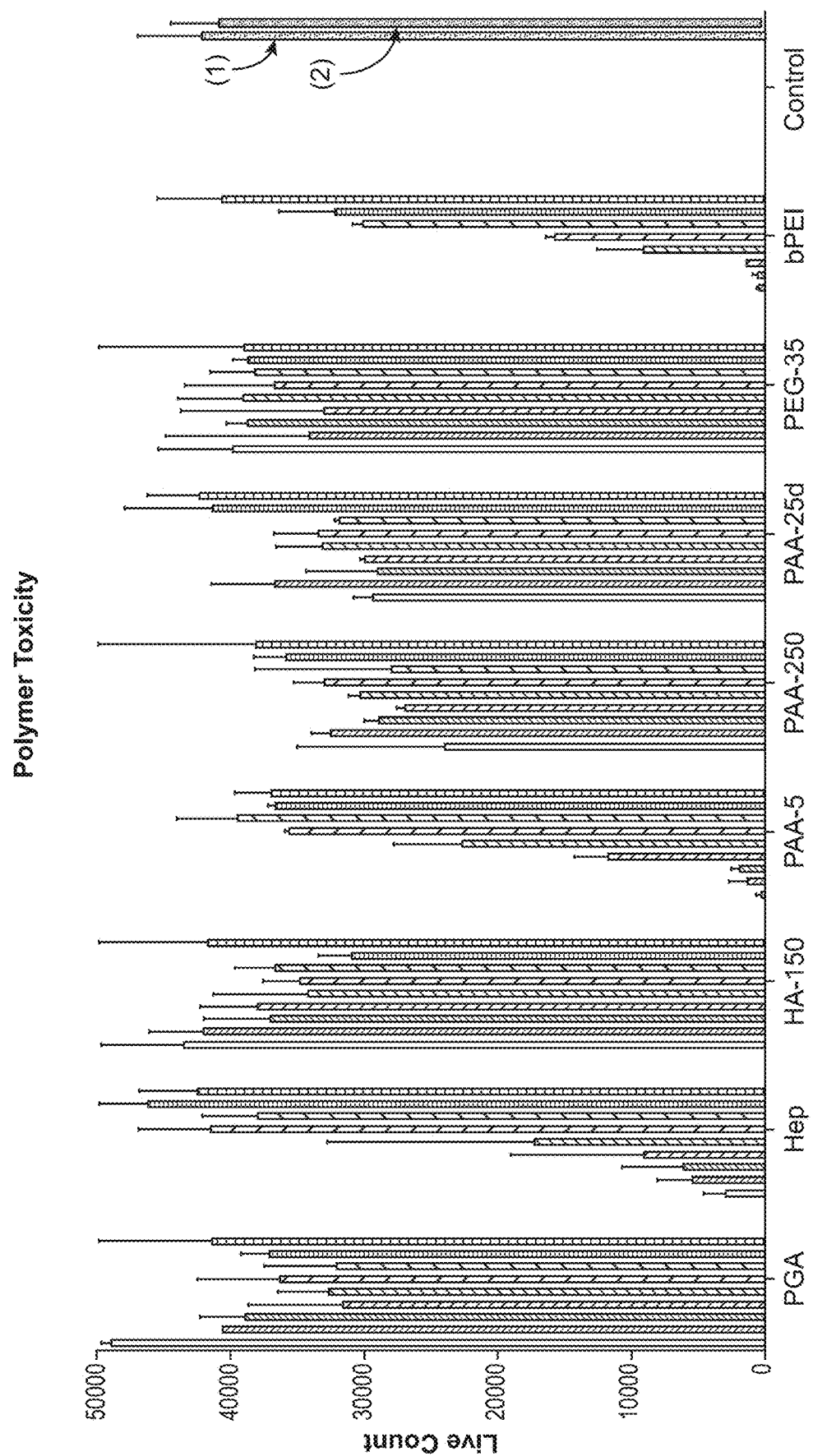

Positively charged (polyethylenimine (PEI)) and neutral (polyethylene glycol (PEG)) polymers either inhibited or did not enhance RNP complex activity (FIG. 10E). However, multiple different anionic polymers (polyglutamic acid (PGA), hyaluronic acid (HA), poly(acrylic acid) (PAA)) were able to significantly enhance editing efficiency in a dose-dependent manner. Polyglutamic acid (PGA) was found to efficiently enhance editing without additional cytotoxicity (FIG. 10F).

Figure 10G:
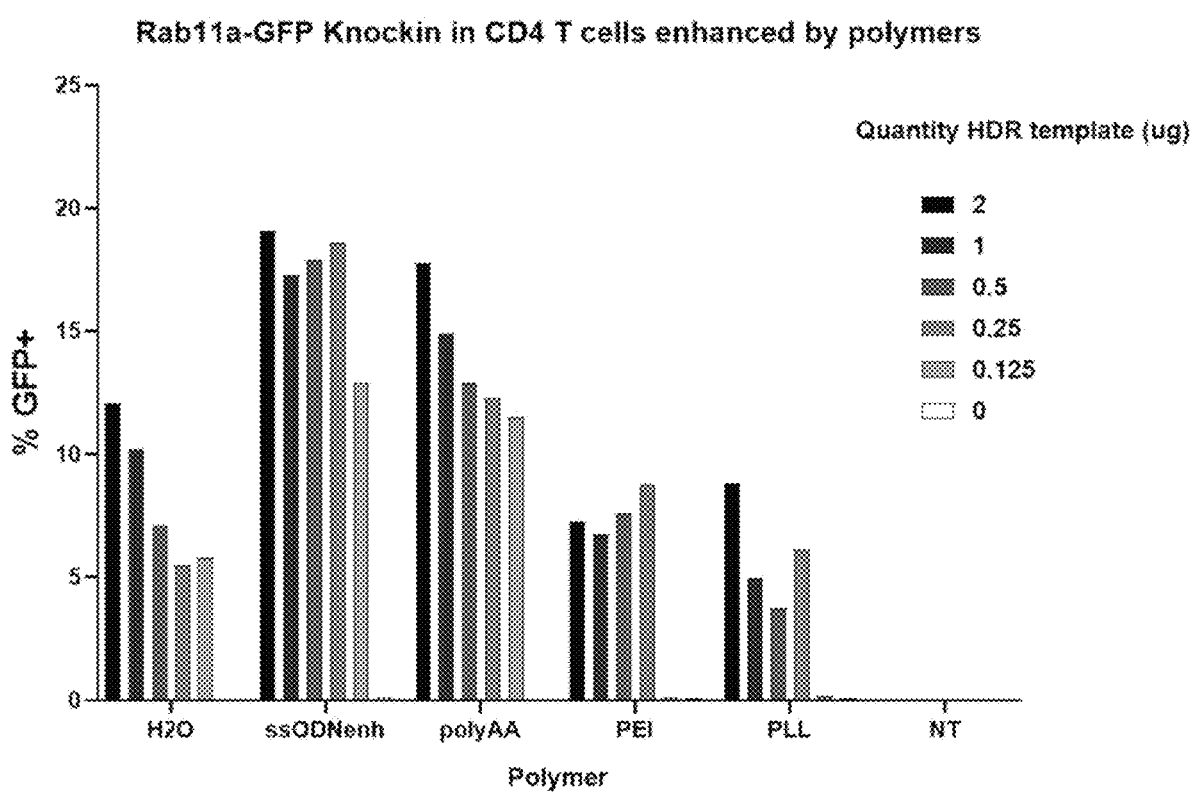
FIG. 10G shows that poly(acrylic acid) (PAA) enhances Rab11a-GFP knock-in in CD4+ T cells.
Figure 10H:
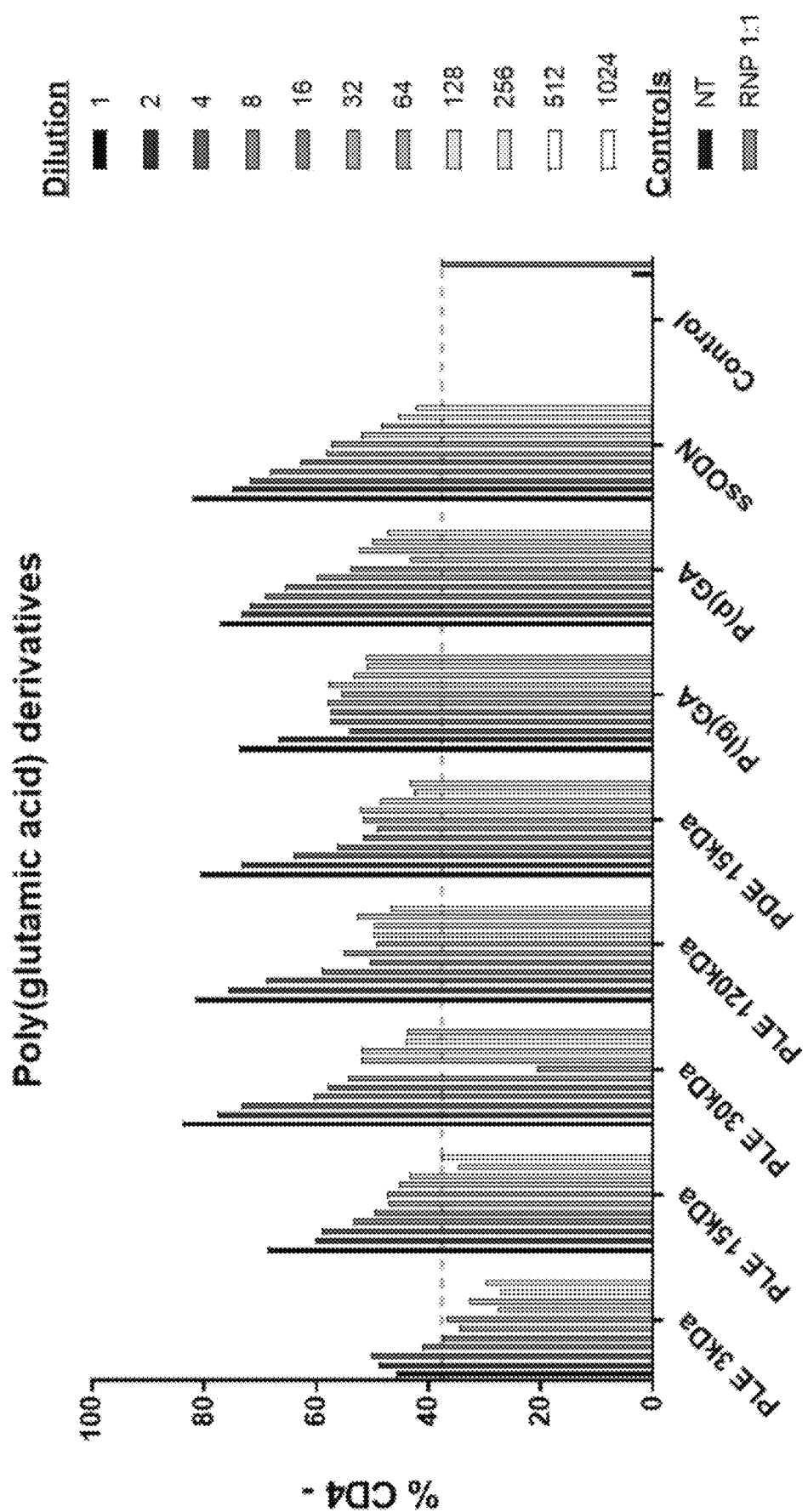
FIG. 10H shows that by testing various monodispersed preparations of PGA, it was observed that the enhancement of RNP-based editing was improved when the anionic non-nucleic acid polymer had a molecular weight of 15 kDa or greater. PLE=monodisperse (indicated MW) poly(L-glutamic acid); PDE=monodisperse (indicated MW) poly(D-glutamic acid); P(lg)GA=polydisperse (varying MW) copolymer of both L- and D-glutamic acid; and P(d)GA=polydisperse (varying MW) poly(D-glutamic) acid.
Figure 10I:
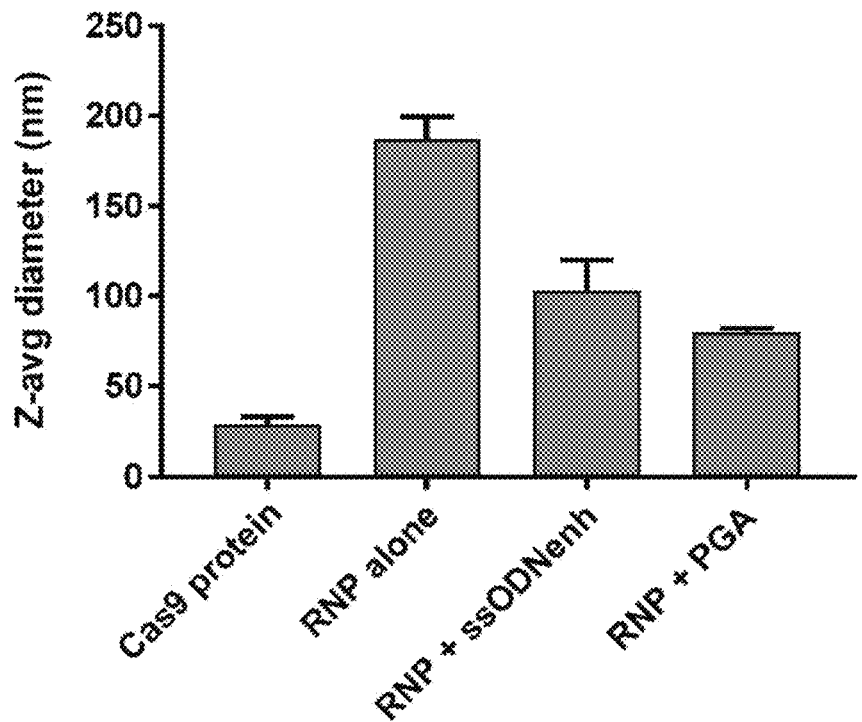
FIG. 10I shows that the addition of excess anionic polymer prevented aggregation into micron-sized particles and improved the size of RNP complex nanoparticles.
Figure 10J:
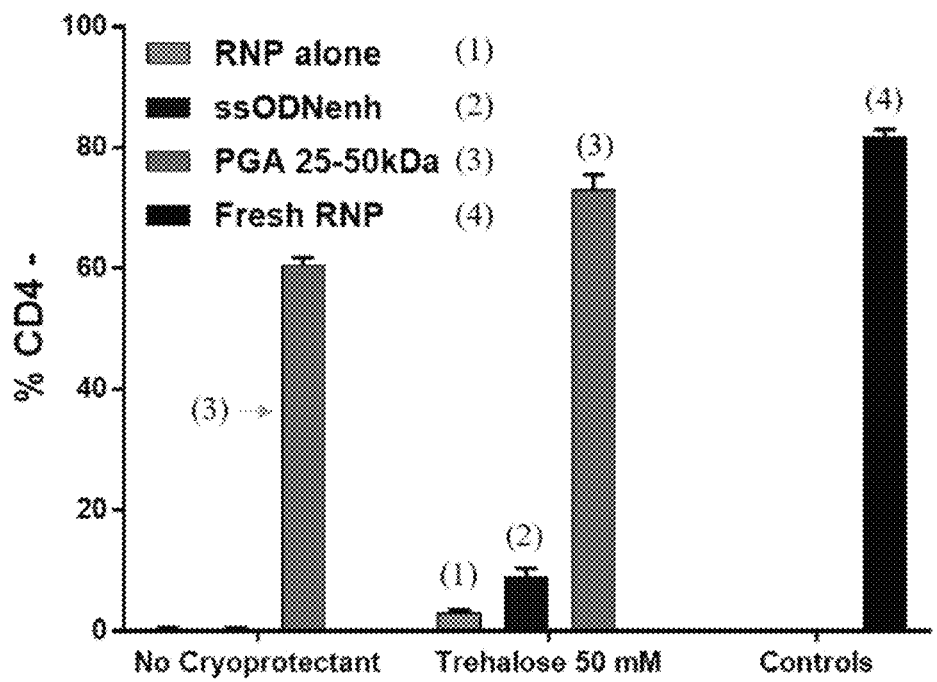
FIG. 10J shows that lyophilization in the presence of a sugar cryoprotectant and PGA (but not ssODNenh) was able to preserve almost all RNP complex editing activity following resuspension and electroporation into primary human T cells.

Poly(acrylic acid) (PAA) also enhanced Rab1la-GFP knock-in in CD4+ T cells (FIG. 10G). By testing various monodispersed preparations of PGA, it was observed that the enhancement of RNP-based editing was improved when the anionic non-nucleic acid polymer had a molecular weight of 15 kDa or greater (FIG. 10H). Other isoforms of PGA had similar enhancement efficiency (FIG. 10H). Finally, a comparison by dynamic light scattering of RNP complex particle sizes as formed in the presence of extra $H_2O$ (control), ssODNenh, or PGA revealed that the addition of excess anionic polymer prevented aggregation into micron-sized particles and improved the size of RNP complex nanoparticles, which exhibited stable peaks in the 20 nm and 90 nm size range (Table 4 and FIG. 10I).

TABLE 4

|  | Zavg | PDI | Peak 1 | Peak 2 |
| --- | --- | --- | --- | --- |
| extra $H_2O$ (control) | 177.5 nm | 0.343 | 217.9 (68.1%) | 62.8 (31.9%) |
| ssODNenh | 90.76 nm | 0.357 | 115.3 (85.9%), | 21.14 (14.1%) |
| PGA | 77.87 nm | 0.317 | 116.4 (87.1%) | 23.21 (12.9%) |

Moreover, mixing PGA with Cas9 protein at the time of RNP complex formation did not appear to inhibit RNP complex efficiency and produced the most consistent results from batch to batch, so subsequent experiments were formulated in this manner Finally, it was observed that Cas9 RNP complexes stabilized by anionic polymers exhibited activity for over 1 week at 4° C. and retained activity after a −20° C. freeze-thaw cycle.

Further, lyophilization of preformed RNP complexes would allow for improved stability, but lyophilization had previously been observed to destroy RNP complex activity. It was observed that lyophilization in the presence of a sugar cryoprotectant and PGA (but not ssODNenh) was able to preserve almost all RNP complex editing activity following resuspension and electroporation into primary human T cells (FIG. 10J).

Example 8—Editing Efficiency

Figure 11A:
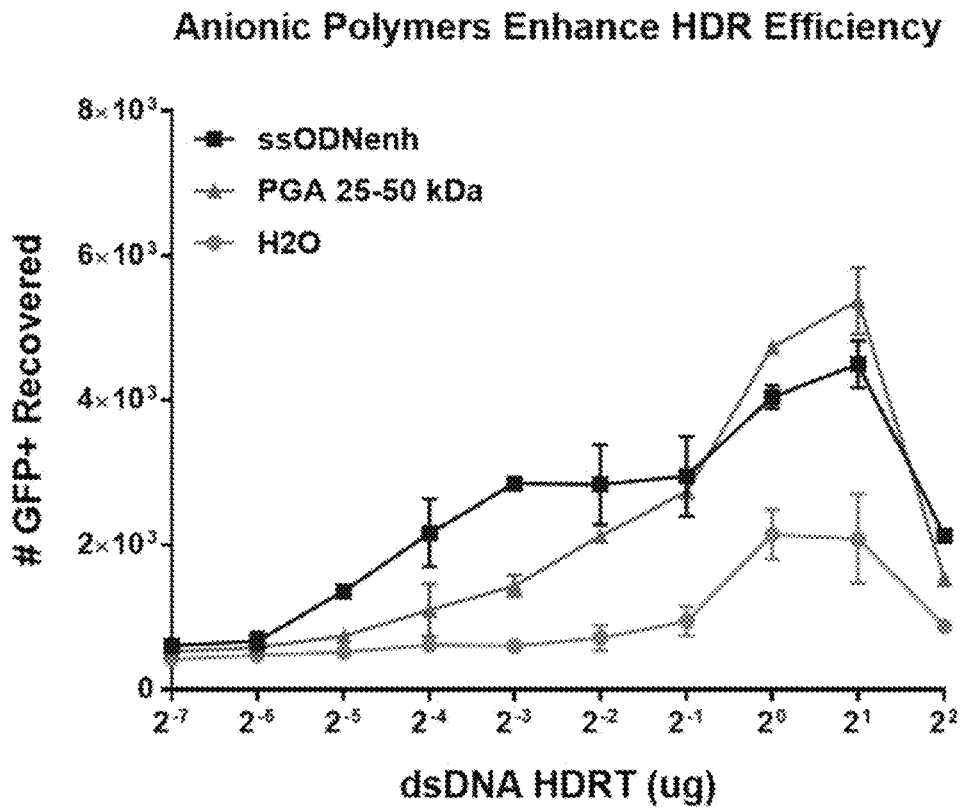
FIGS. 11A-11C show that Cas9 protein and sgRNA RNP complexes co-formulated with the anionic polymer PGA and an HDR template achieved large efficiency gains in primary human T cells, particularly at lower doses of HDR template (FIG. 11A), when compared to RNP complexes without the anionic polymer. These gains were noted as both an increase in the percentage of cells expressing the transgene as well as a decrease in cytotoxicity (FIGS. 11B and 11C).
Figure 11B:
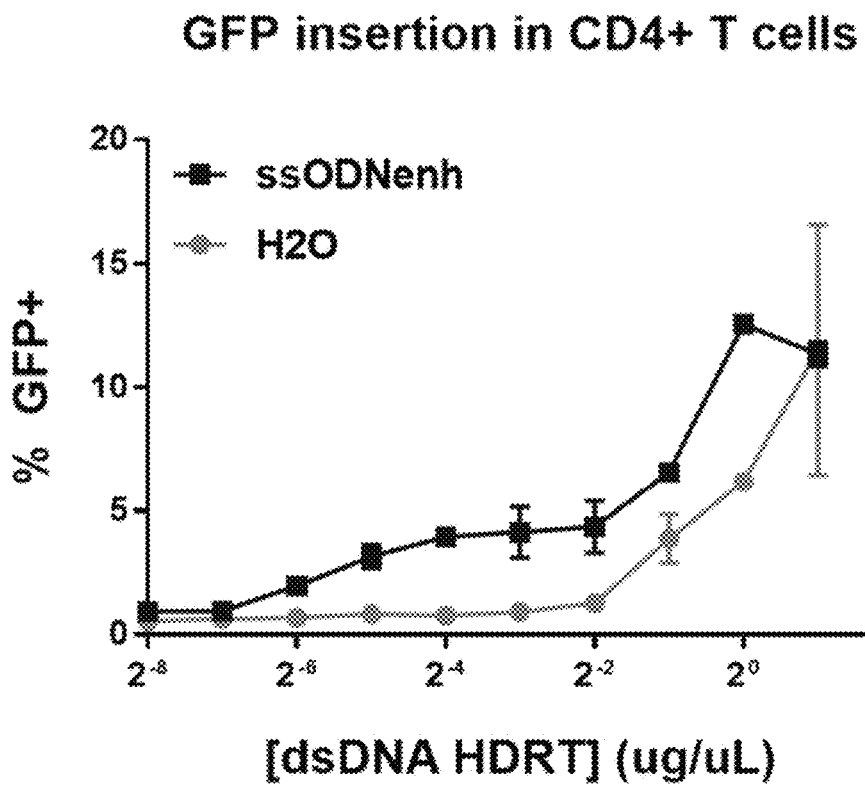
Figure 11C:
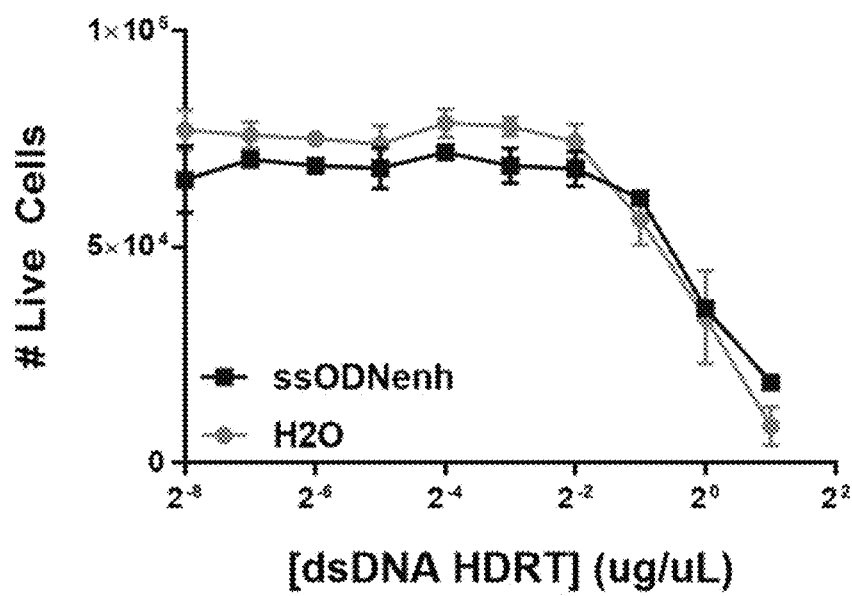

Testing knock-out editing was a rapid and useful method to screen for anionic polymers that have stabilizing abilities. Anionic polymers may be used to improve the efficiency of Cas9-targeted homology directed repair (HDR) to target large transgenes into primary and iPS-derived cells without the need for viral delivery. HDR templates can be easily produced by creating a PCR amplicon encoding the desired gene insertion with flanking sequences of homology to the target gene region. However, dsDNA exhibits dose-dependent cytotoxicity, and current protocols for RNP-based editing generally require fresh preparations of RNP complex reagent for each experiment, which limits scalability and adds complexity that could be a barrier to clinical translations. It was found that RNP complexes co-formulated with an anionic polymer and an HDR template encoding a fusion of GFP and the Rab11 gene revealed large efficiency gains in primary human T cells, particularly at lower doses of HDR template (FIG. 11A), when compared to RNP complexes without the anionic polymer. These gains were noted as both an increase in the percentage of cells expressing the transgene as well as a decrease in cytotoxicity (FIGS. 11B and 11C).

To ensure that polymer-mediated efficiency gains were not unique to the specific system of Cas9 protein and sgRNA used, additional commercially-available components were tested. Both PGA and ssODNenh equally boosted knock-out editing using sgRNA supplied by Dharmacon, IDT, or Synthego. The addition of anionic polymer also boosted both knock-out and knock-in editing efficiency when used in conjunction with the HiFi Cas9 v3 from IDT. Lyophilization of the RNP complex together with an HDR template in the presence of PGA retained some activity.

Example 9—Electroporation

Figure 12:
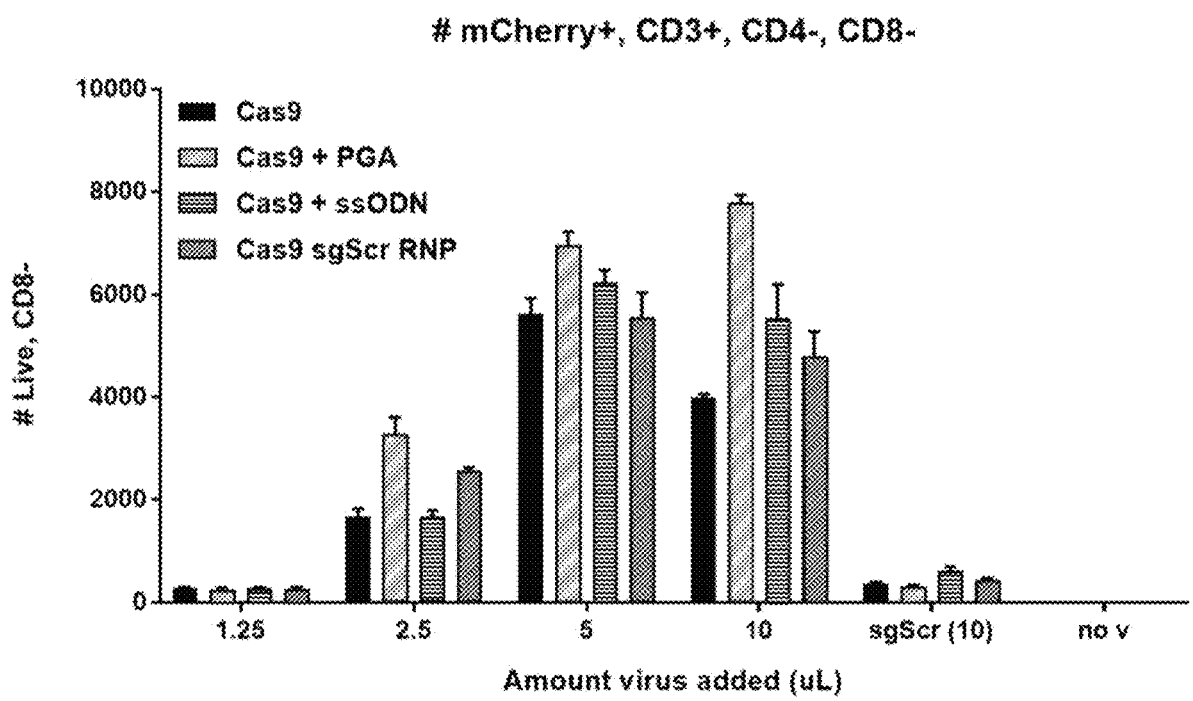
FIG. 12 shows that the anionic polymer PGA was able to enhance electroporation of Cas9 protein and a lentivirus encoding mCherry and sgRNA targeting against CD8 surface receptor. PGA-enhanced electroporation led to a high percentage of edited cells with low cell death.

The anionic polymer also improves delivery of the Cas9 protein itself, even when the protein is not complexed to an sgRNA. Primary human CD8+ T cells were infected with a lentivirus vector that expressed a fluorescent marker (mCherry) as well as an sgRNA targeting knockout of the CD8 gene. Infected cells were then electroporated with: Cas9 protein, Cas9 protein mixed with PGA, Cas9 protein mixed with the ssODNenh, or Cas9 protein formed into an RNP complex with a scrambled sequence. At day 4, mCherry+ cells (i.e., CD8+ cells that were infected with the lentivirus) were assayed for surface expression of CD8. The composition containing Cas9 mixed with PGA exhibited the highest ability to enter the cells-Cas9 formed an RNP complex with the expressed sgRNA in situ, and knocked out surface CD8 expression (FIG. 12).

Example 10—Editing of Natural Killer Cells

Figure 13:
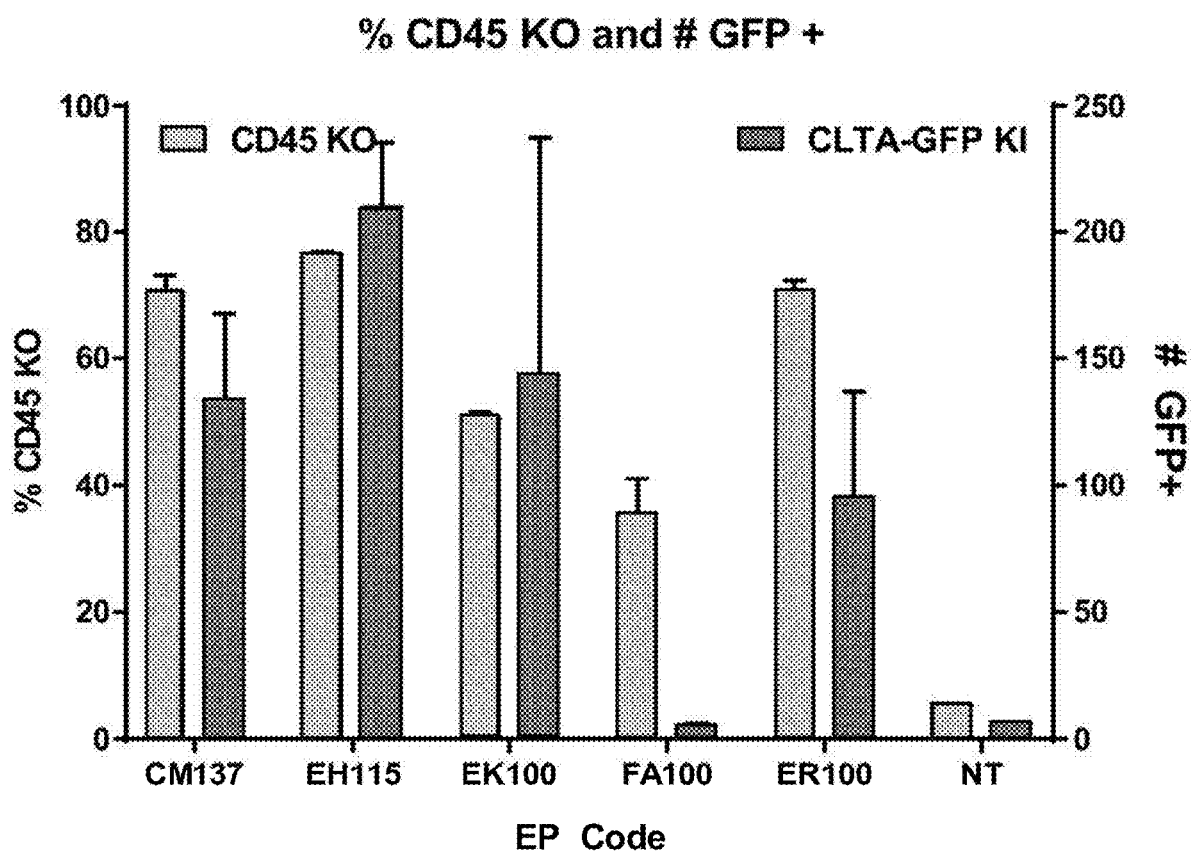
FIG. 13 shows efficient large gene CLTA-GFP knock-ins, as well as CD45 knock-outs, using RNP complexes enhanced with PGA in primary human NK cells.

Natural killer (NK) cells were stimulated for 48 hours prior to editing with Cas9 protein and sgRNA RNP complex targeting CD45 gene for knock-out, or RNP complex targeting clathrin (CLTA gene) together with an HDR template encoding an N-terminal GFP fusion for knock-in. All the RNP complexes were enhanced with the PGA polymer. FIG. 13 shows efficient large gene CLTA-GFP knock-ins, as well as CD45 knock-outs. Each group on the x-axis represents a different electroporation code (proprietary pulse protocols per Lonza, the manufacturer of the 4D Nucleofector electroporation machine).

Figure 14A:
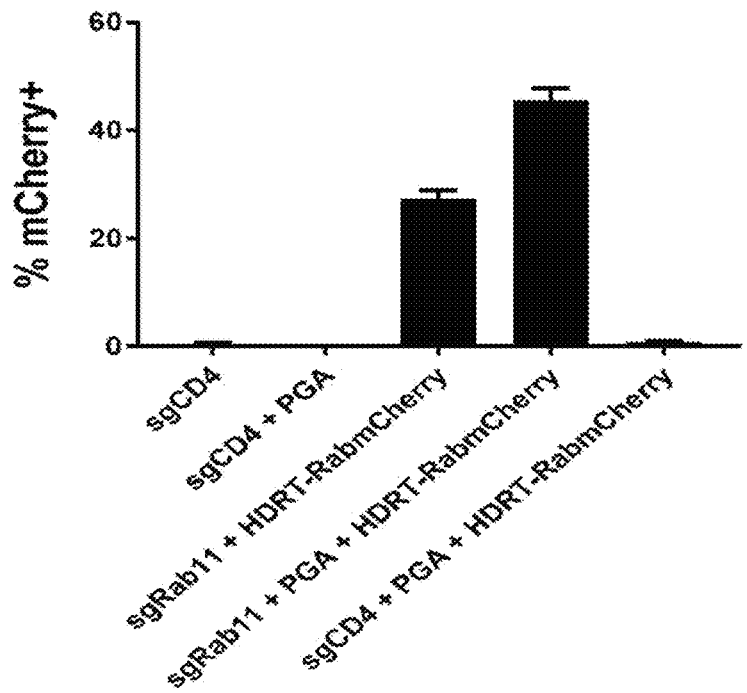
FIGS. 14A and 14B show a high number of cells with high on-target editing efficiency was recovered when the RNP complex with a high-fidelity Cas9 protein was used with the PGA polymer.
Figure 14B:
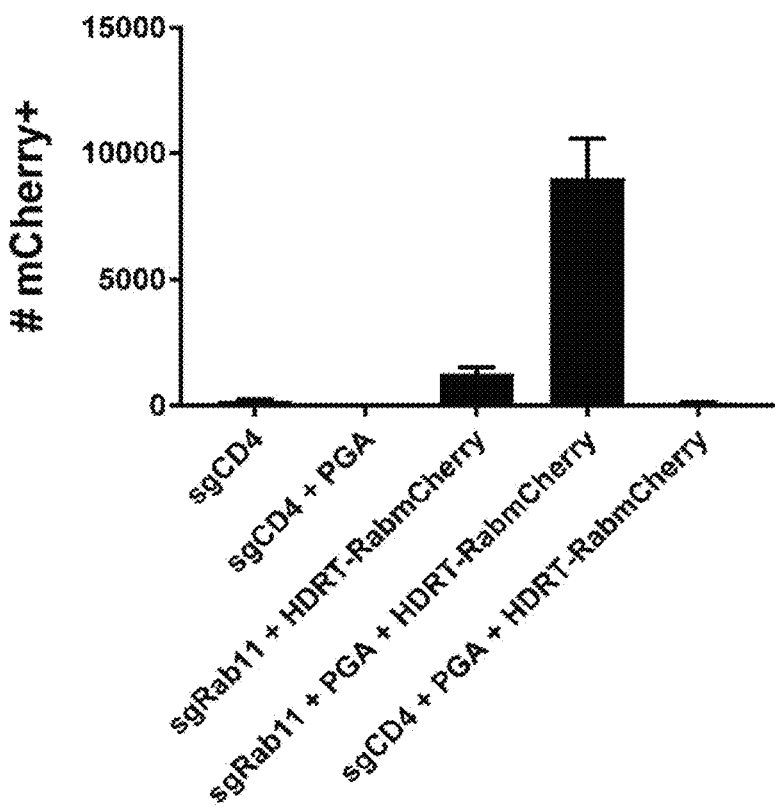

Example 11—Editing with High-Fidelity Cas9 Protein $CD4^+$ T cells were electroporated with RNP complexes with or without PGA. The RNP complexes targeted the CD4 gene (off-target) or the Rab11 gene (on-target). An HDR template to knock-in a fusion of Rab11a and mCherry was also used. High-fidelity Cas9 protein has been reported to have a lower on-target efficiency than regular Cas9 protein. However, in this experiment, a high number of cells with high on-target editing efficiency was recovered when the PGA polymer was used (FIG. 14). No evidence of increased off-target effects was observed with the use of the PGA polymer.

Example 12—Editing of Primary Human $CD4^+$ T Cells

Figure 15:
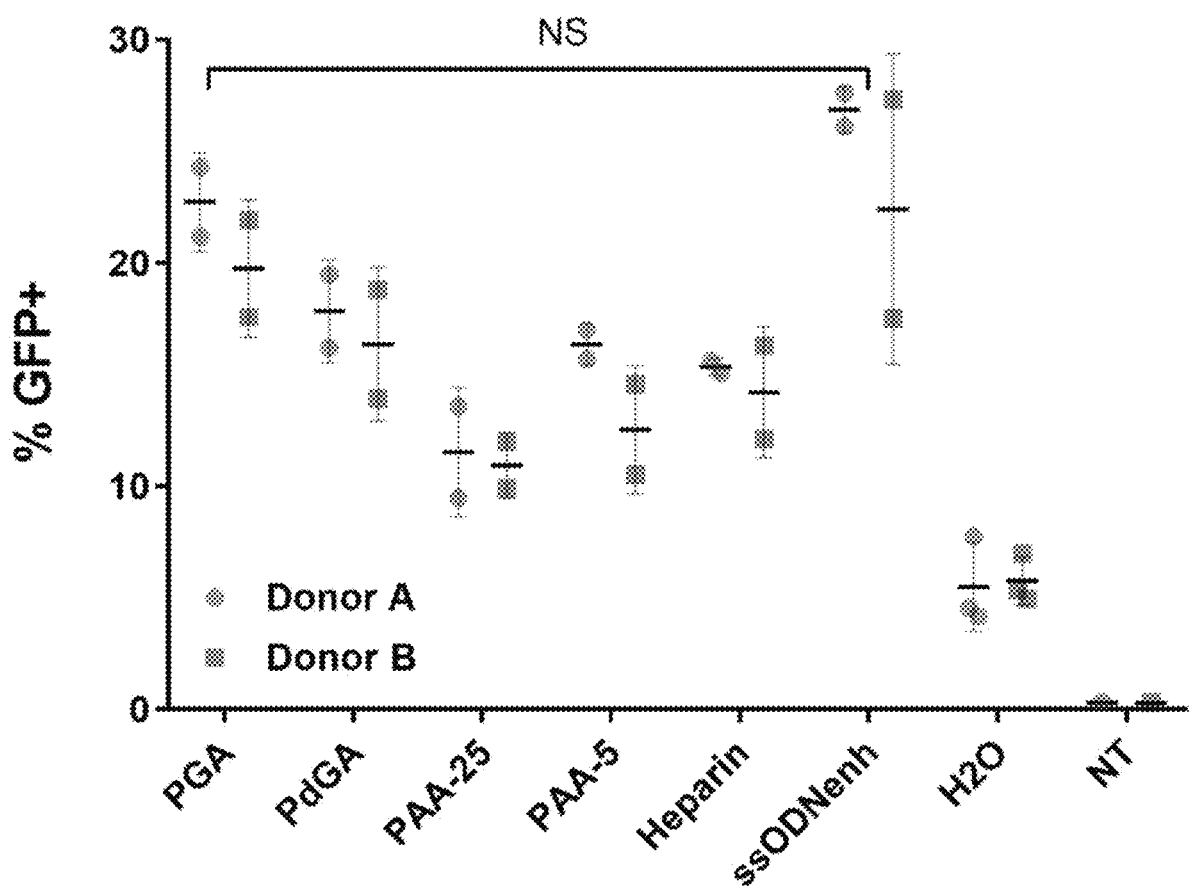
FIG. 15 shows efficient large gene GFP knock-ins in primary human CD4+ T cells.

Primary human $CD4^+$ T cells were isolated from two (anonymized) blood donors, stimulated for 48 hours, then edited with Cas9 protein and sgRNA RNP complex targeting Rab11a together with an HDR template encoding an N-terminal GFP fusion for knock-in. Various anionic polymers (PGA=polyglutamic acid, PdGA=poly(D-glutamic acid), PAA=poly(acrylic acid)) of MW 5 or 25 kDa) were tried in this experiment. It was found that RNP complexes co-formulated with many anionic polymers caused large efficiency gains in primary human $CD4^+$ T cells when compared to RNP complexes without the anionic polymer (FIG. 15).

Example 13—Editing of Hematopoietic Stem Cells

Figure 16A:
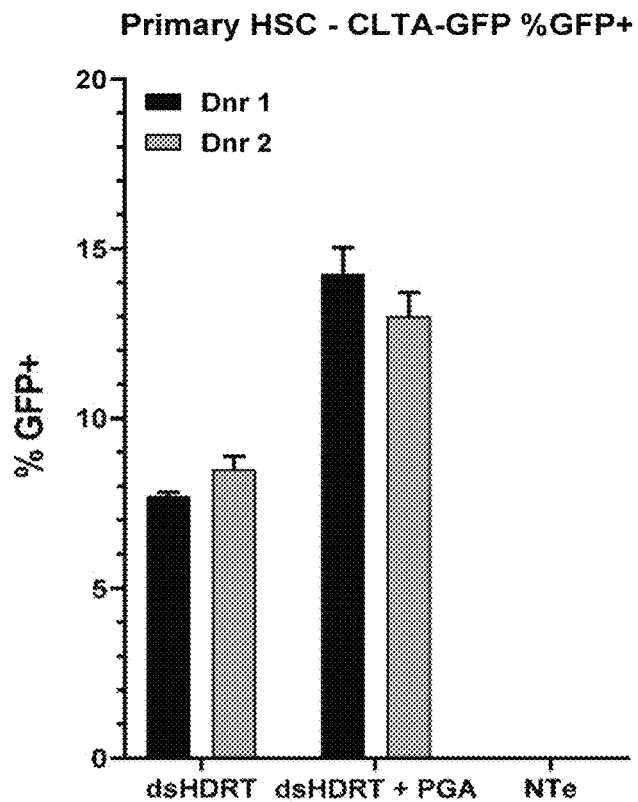
FIGS. 16A and 16B show efficient large gene CLTA-GFP knock-ins in hematopoietic stem cells.
Figure 16B:
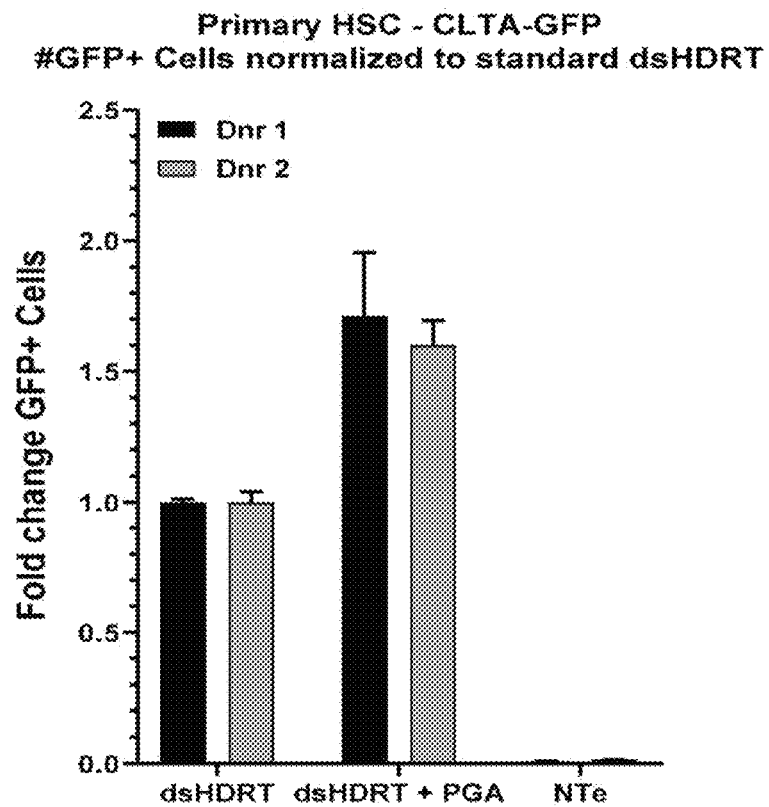

Primary mobilized peripheral blood hematopoietic progenitor stem cells (PB-HSCs) were purchased from a commercial supplier. Cells were grown and stimulated for 48 hours prior to editing with Cas9 protein and sgRNA RNP complex targeting clathrin (CLTA gene) together with an HDR template encoding an N-terminal GFP fusion for knock-in. RNP complexes were as standard (no enhancement) or enhanced with the PGA polymer as shown in FIGS. 16A and 16B. After 4 days, cells were analyzed for GFP expression by flow cytometry. FIG. 16A shows increased efficiency of large gene CLTA-GFP knock-ins due to PGA, presented in terms of GFP percentage of all live cells. FIG. 16B shows increased efficiency and viability of large gene CLTA-GFP knock-ins due to PGA, presented in terms of recovered live GFP cells, normalized to un-enhanced knock-in.

Example 14—Editing of Primary Immune Cells

Figure 17A:
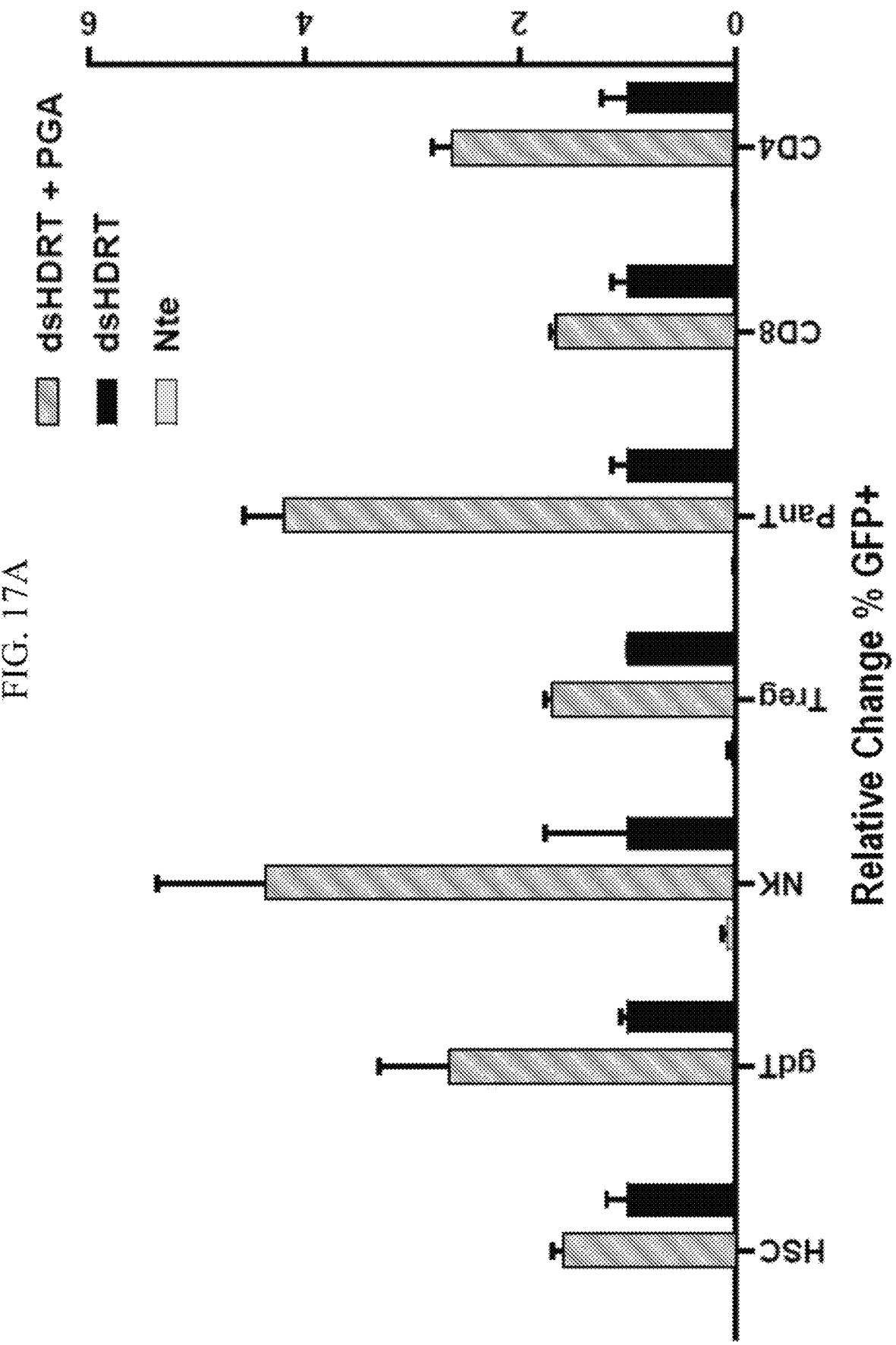
FIGS. 17A and 17B show efficient large gene CLTA-GFP knock-ins in multiple types of primary immune cells.
Figure 17B:
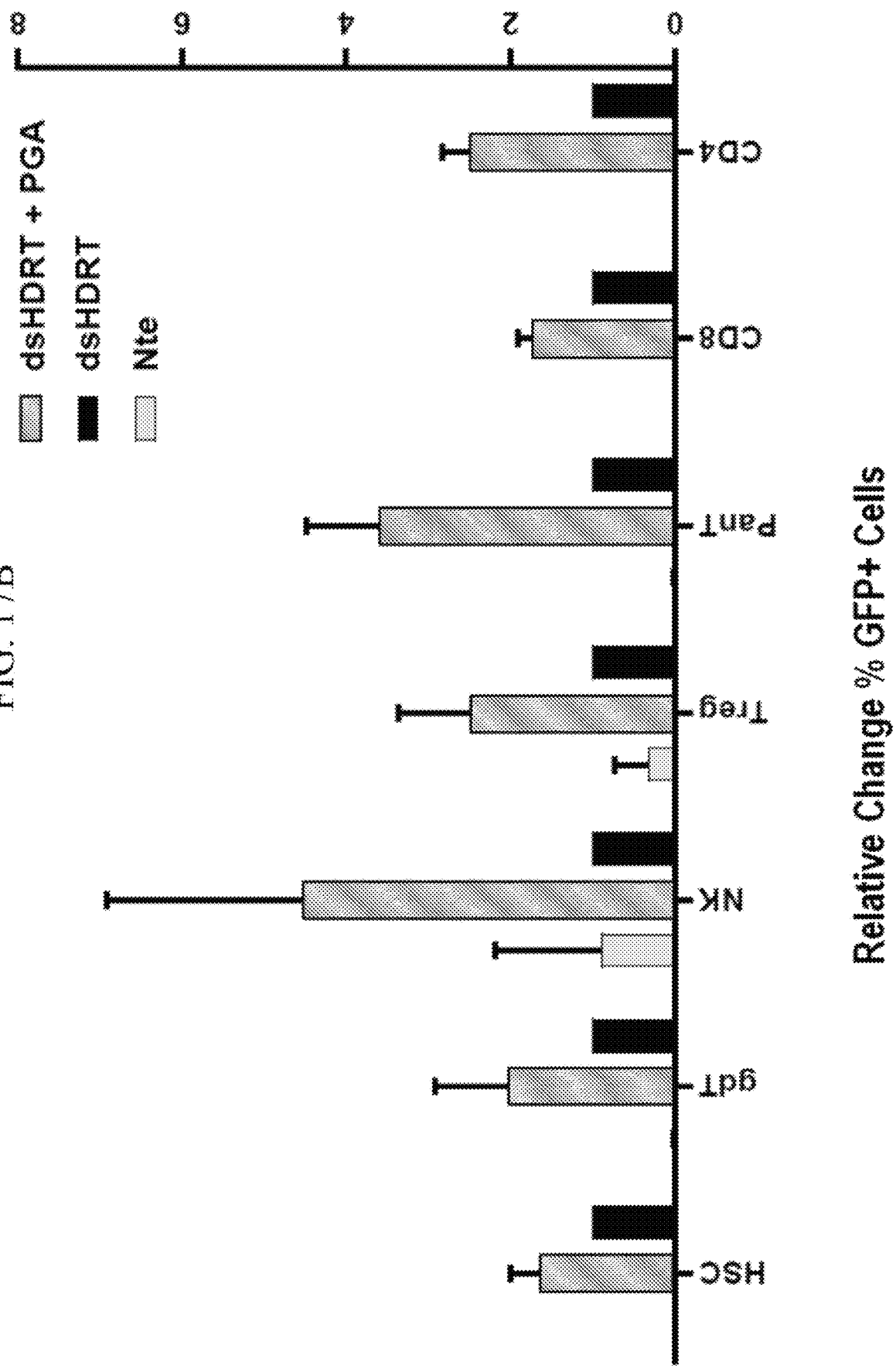

Primary human cells ($CD4^+$ T cells, $CD8^+$ T cells, $CD3^+$ Bulk T cells, $CD56^+$ NK cells, or gamma-delta T cells) were isolated from (anonymized) blood donors (n=2 to 3). Mobilized peripheral blood hematopoietic progenitor stem cells (PB-HSCs) were purchased from a commercial supplier. Cells were grown and stimulated for 48 hours prior to editing with Cas9 protein and sgRNA RNP complex targeting clathrin (CLTA gene) together with an HDR template encoding an N-terminal GFP fusion for knock-in. RNP complexes were as standard (dsHDRT) or enhanced with the PGA polymer (dsHDRT+PGA). After 4 days (6 days for NK cells), cells were analyzed for GFP expression by flow cytometry. FIG. 17A shows increased efficiency of large gene CLTA-GFP knock-ins due to PGA, presented in terms of $GFP^+$ percentage of all live cells normalized to unenhanced control dsHDRT knock-in. FIG. 17B shows increased viability of large gene CLTA-GFP knock-ins due to PGA, in terms of recovered live GFP cells normalized to unenhanced control dsHDRT knock-in. Background $GFP^+$ signal measured from untreated, electroporated cells).

Example 15—Multiple Anionic Polymers Boosted Knock-in Editing Efficiency

Figure 19:
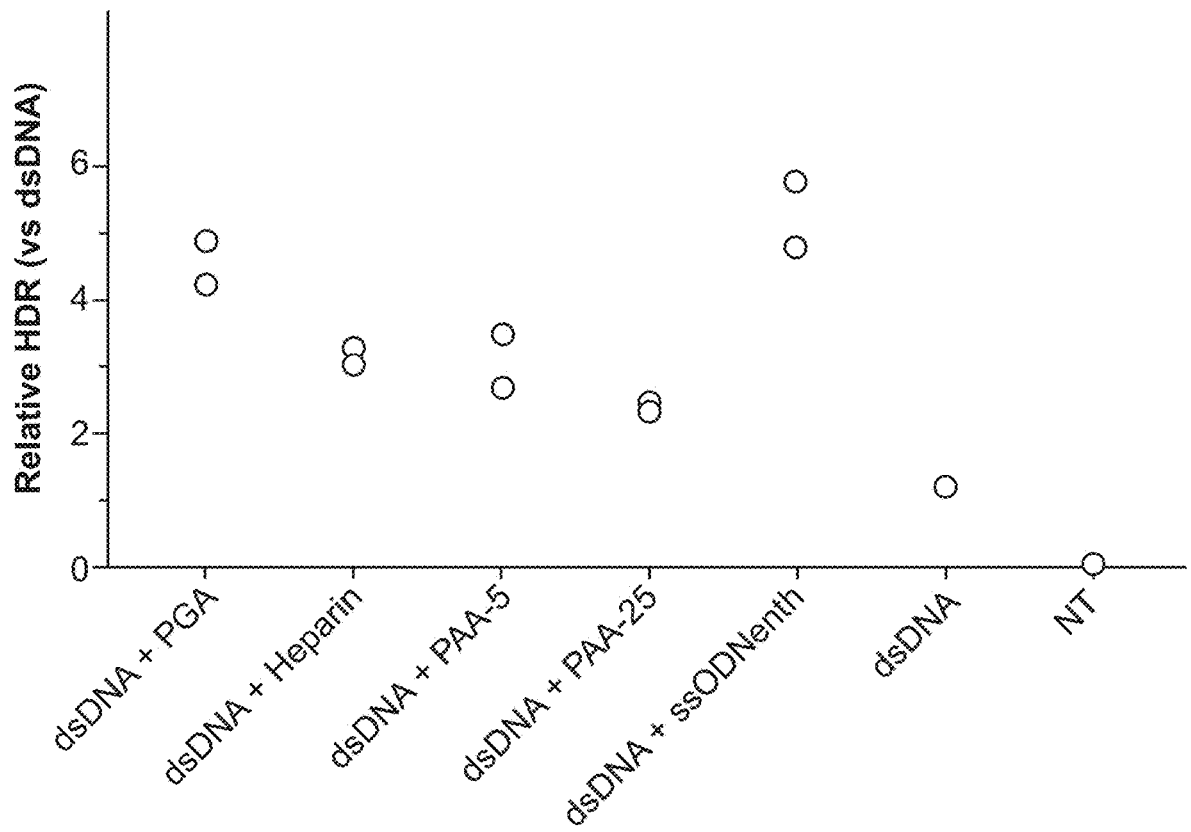
FIGS. 19-21 show the ability of various anionic polymers to boost knock-in editing efficiency.
Figure 20:
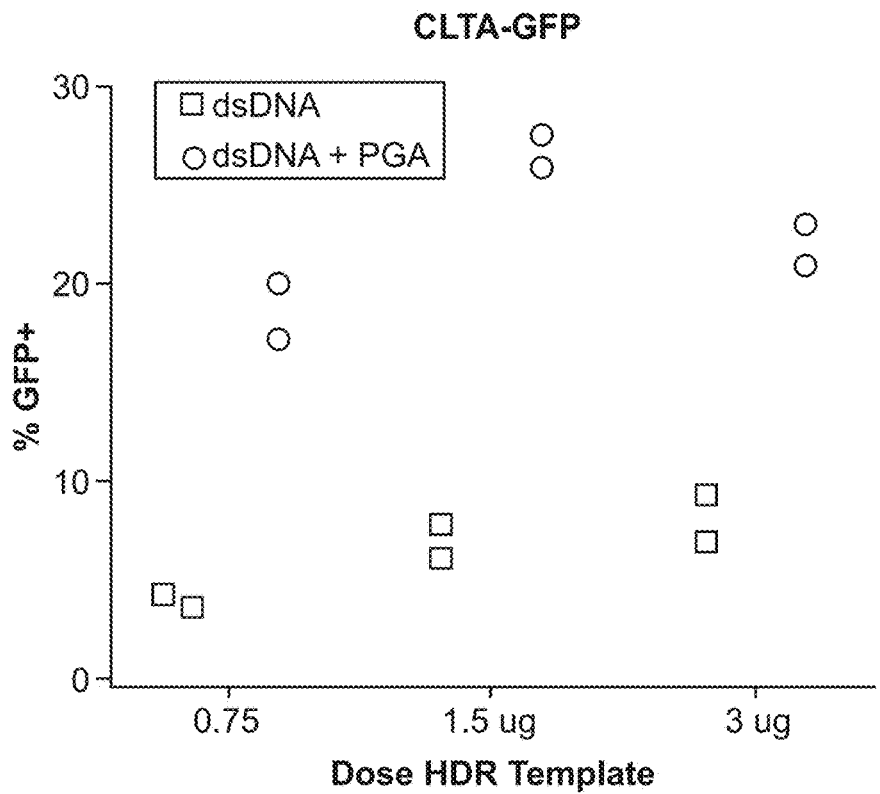
Figure 21:
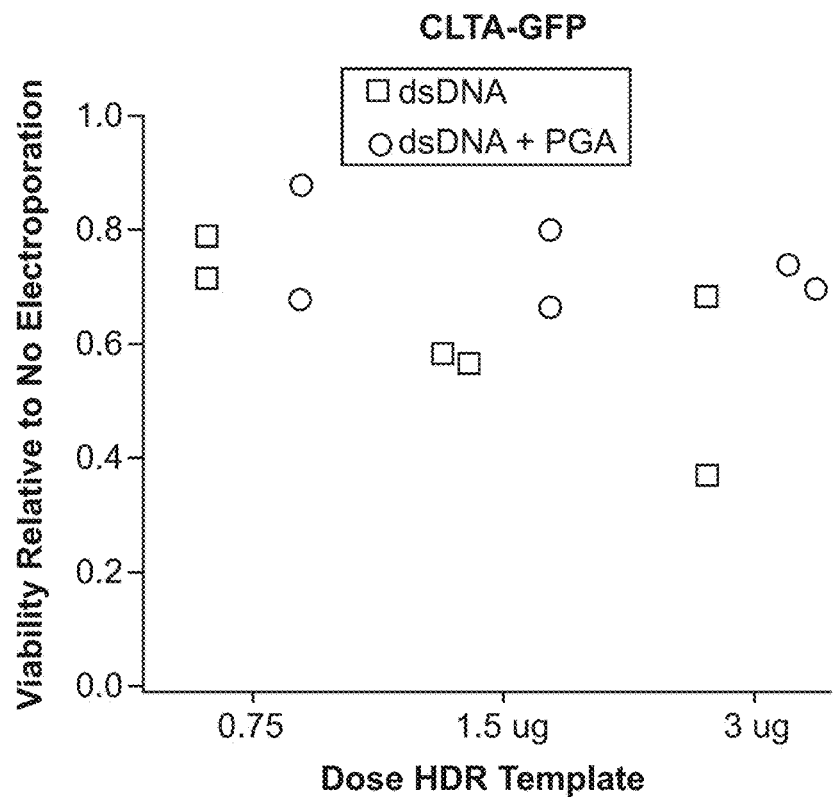

Polymers mixed with Cas9 RNPs prepared at a 2:1 gRNA:protein ratio were further mixed with 1 μg unmodified dsDNA HDR templates (targeting insertion of an N-terminal fusion of GFP to Rab11a), electroporated into $CD4^+$ T cells, and editing efficiency were assessed by flow cytometry at day 3. The relative rates of HDR is displayed compared to unmodified dsDNA HDR template without enhancer. Data shown for each of n=2 biologically independent blood donors (FIG. 19). As further shown in FIGS. 20 and 21, PGA-stabilized Cas9 RNPs prepared at a 2:1 ratio gRNA:protein markedly improved knock-in editing in primary human bulk ($CD3^+$) T cells targeting a C-terminal fusion of GFP to clathrin and improved viability of electroporated cells, especially at higher doses of HDR template (compared to untreated cells). Data shown for each of n=2 biologically independent blood donors.

Figure 22:
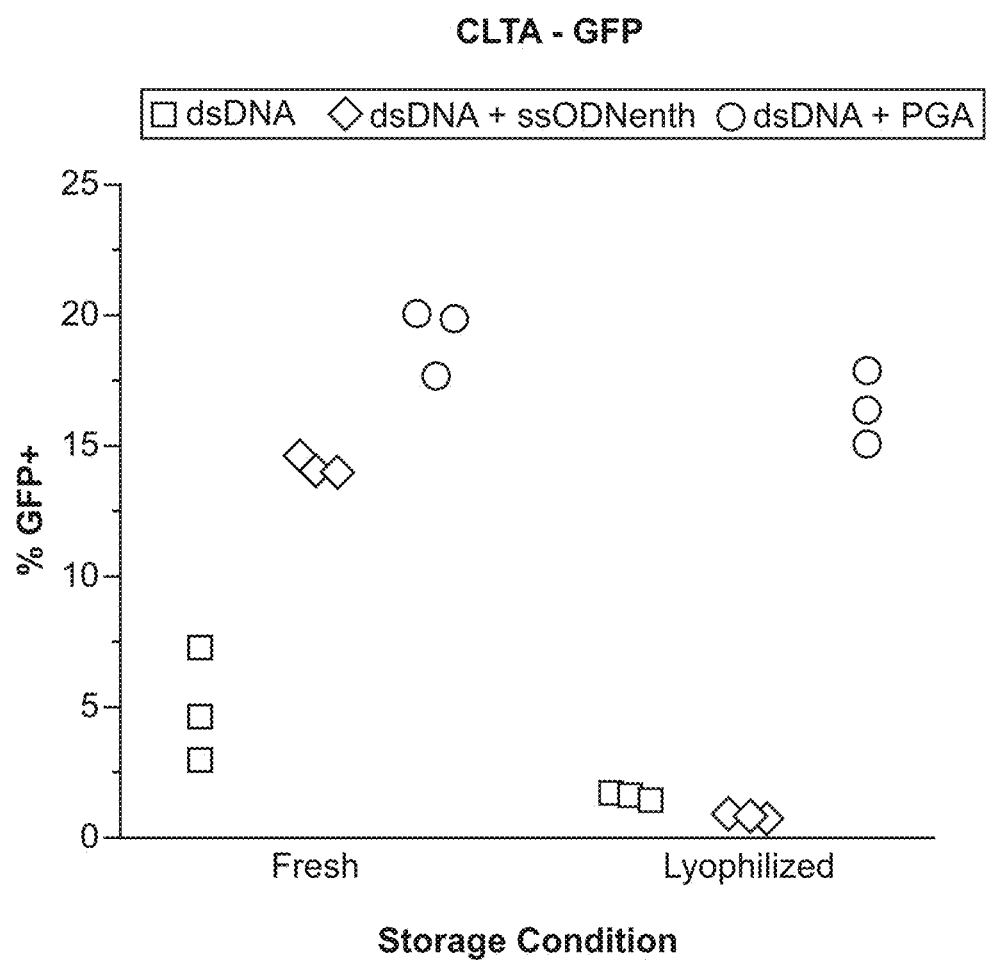
FIG. 22 shows that PGA-stabilized Cas9 nanoparticles retained activity for robust knock-in editing when reconstituted after lyophilization.

Example 16—Efficiency of Reconstituted PGA-Stabilized Cas9 Nanoparticles After Lyophilization Cas9 RNPs prepared at a 2:1 ratio gRNA:protein without or with PGA or ssODNenh were mixed with 1 μg of unmodified dsDNA HDR template targeting an N-terminal fusion of GFP to RAB11A, lyophilized overnight, stored dry at −80° C., then later reconstituted in water prior to electroporating into primary human $CD3^+$ (Pan) T cells. PGA-stabilized Cas9 nanoparticles were protected through lyophilization and reconstitution and retained activity for robust knock-in editing. Three technical replicates shown for n=1 blood donor, representative of two repeated independent experiments (FIG. 22).

Example 17—Poly(glutamic acid) Enhanced Editing at Higher Molecular Weights

Figure 23A:
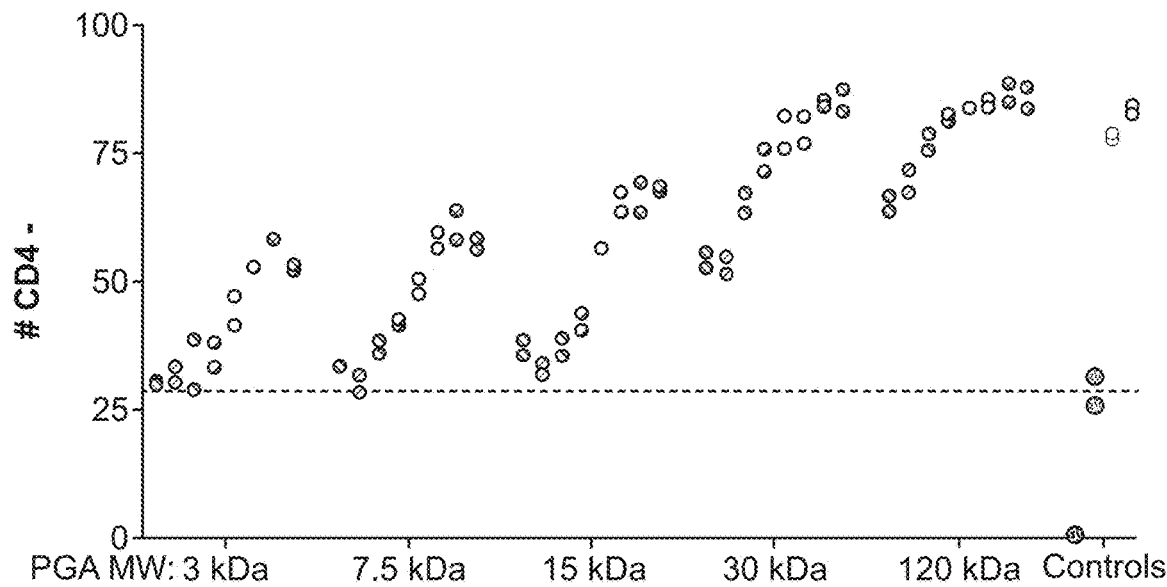
FIGS. 23A and 23B show that PGA enhanced editting at various molecular weights from 3 kD to 120 kD.
Figure 23B:
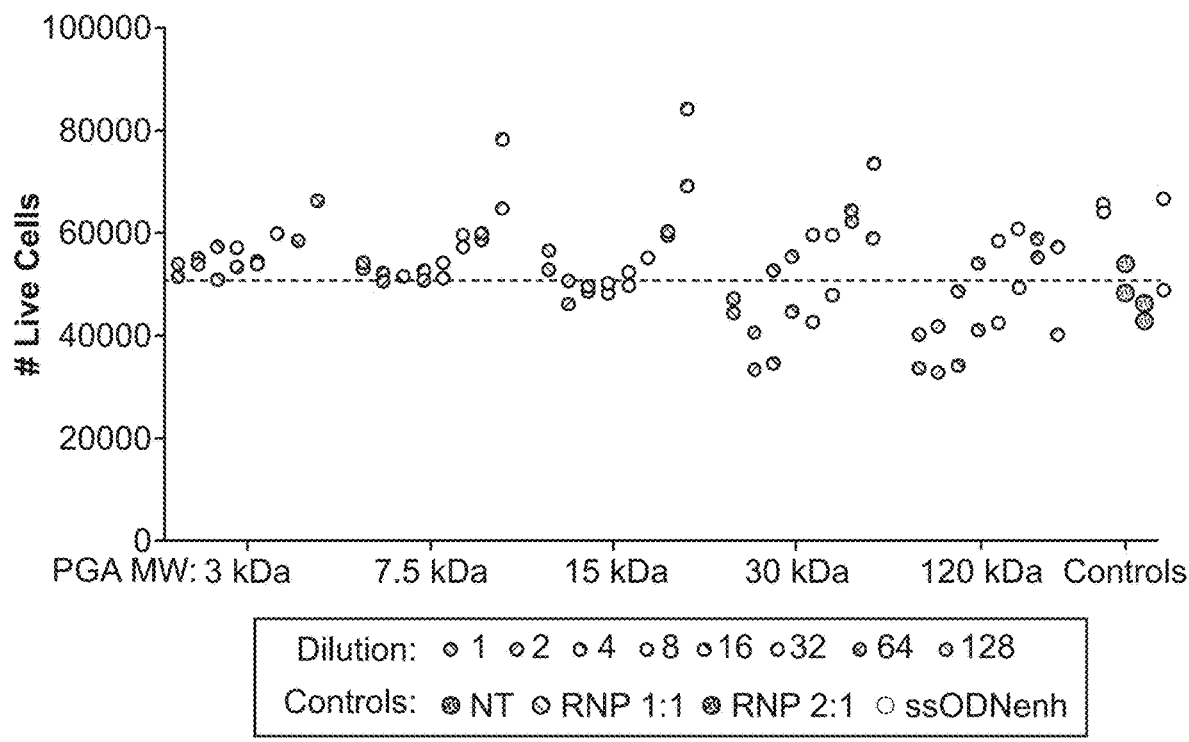

PGA samples with narrowly-defined molecular weight were assessed for the ability to enhance CD4 gene knockout editing. Polymers were reconstituted to 100 mg/mL then serially diluted as indicated, mixed with RNPs formulated at a 1:1 gRNA:protein ratio, and electroporated into primary human CD4+ T cells. FIGS. 23A and 23B show loss of surface CD4 expression and live cell count at 3 days post electroporation were assessed by flow cytometry. Higher molecular weight resulted in improved editing but reduced cell viability at the highest MW. Data shown for each of n=2 biologically independent blood donors.

Figure 24:
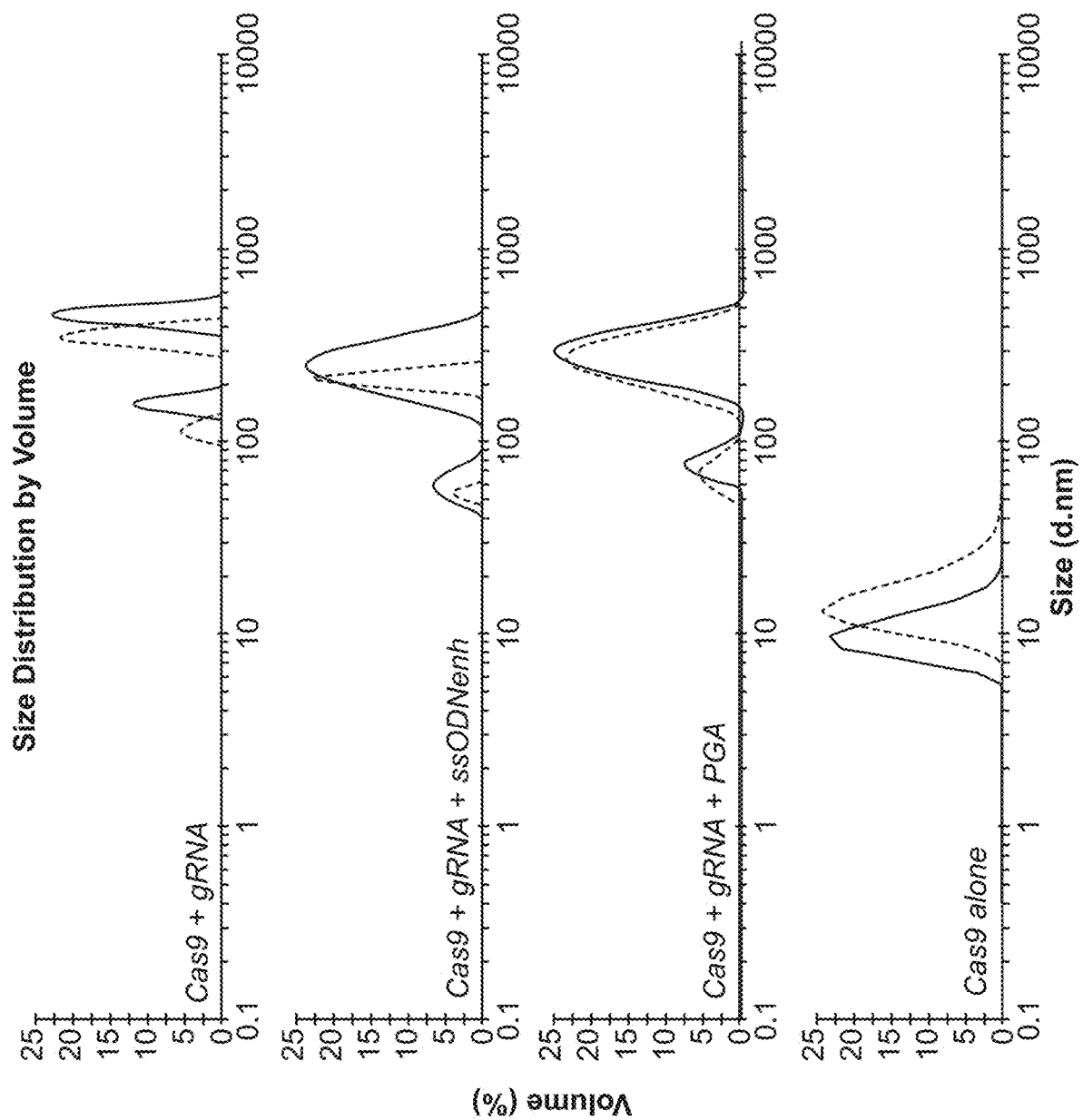
FIG. 24 shows that anionic polymers stabilized and reduced the hydrodynamic size of RNP nanoparticles.

Example 18—Anionic Polymers Stabilized and Reduced the Hydrodynamic Size of RNP Nanoparticles Cas9 RNPs were prepared at a 2:1 gRNA:protein ratio, mixed with PGA or ssODNenh, then assessed for particle size by dynamic light scattering. Size distribution by volume % and a summary table of statistics for each of n=2 independent preparations averaged over ten repeated measurements (PDI=polydispersity index) are shown in FIG. 24.

Example 19—Order of Addition Did Not Affect Editing Efficiency

Figure 25:
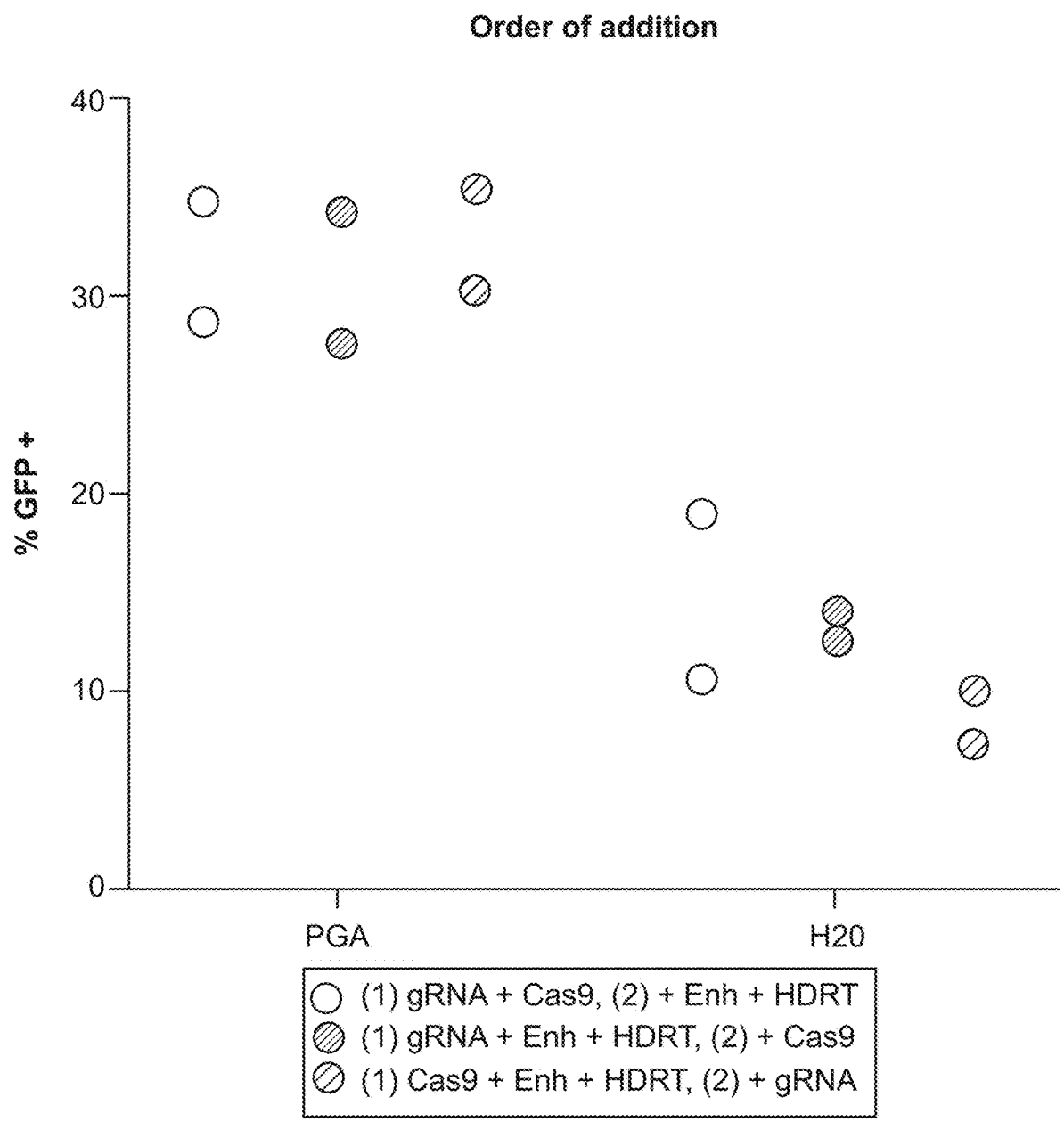
FIG. 25 shows that the order of addition (PGA polymer added after RNP formation, after gRNA formation but prior to adding Cas9, or mixed with the protein prior to adding gRNA) did not affect editing efficiency.

Cas9 RNP were formulated at 2:1 gRNA:protein ratio with regular dsDNA HDR template targeting insertion of an N-terminal fusion of GFP to RAB11A. PGA polymer or water was added after RNP formation, after gRNA formation but prior to adding Cas9, or mixed with the protein prior to adding gRNA. In all three cases, PGA improved editing efficiency but order of addition had no immediately discernable impact. However, we noted improved consistency and workflow when mixing PGA with gRNA first then adding Cas9 protein, and this protocol was adopted for subsequent studies. Data shown for each of n=2 biologically independent blood donors (FIG. 25).

Example 20—PGA Improved Editing Independent of Guide RNA Source

Figure 26A:
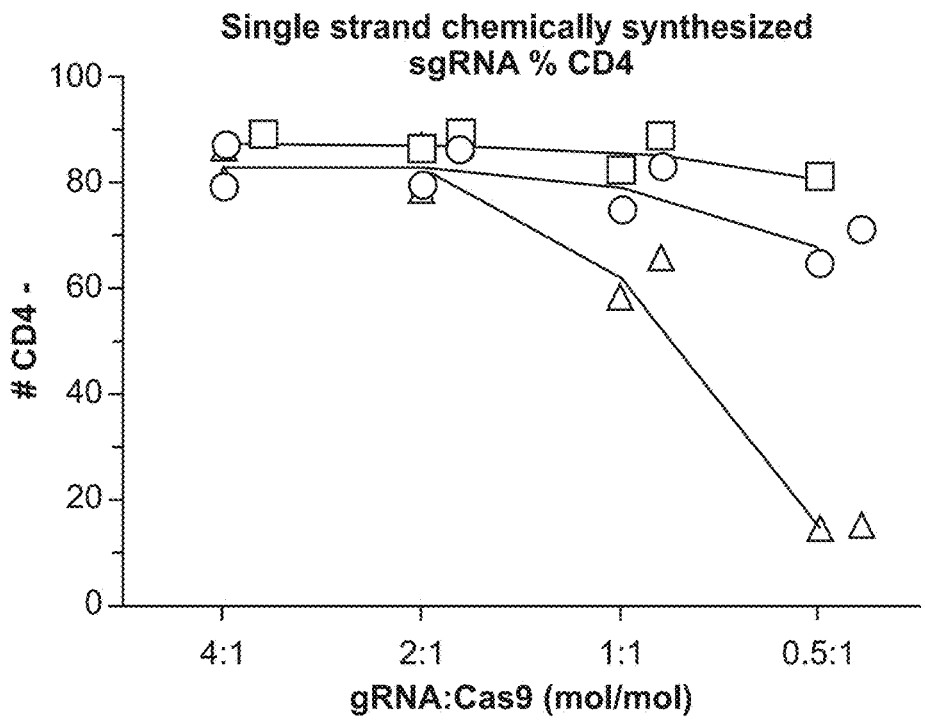
FIGS. 26A-26F show that PGA improved editing independent of gRNA source, e.g., single strand chemically synthesized sgRNA or chemically synthesized duplexed tracrRNA:crRNA gRNA.
Figure 26B:
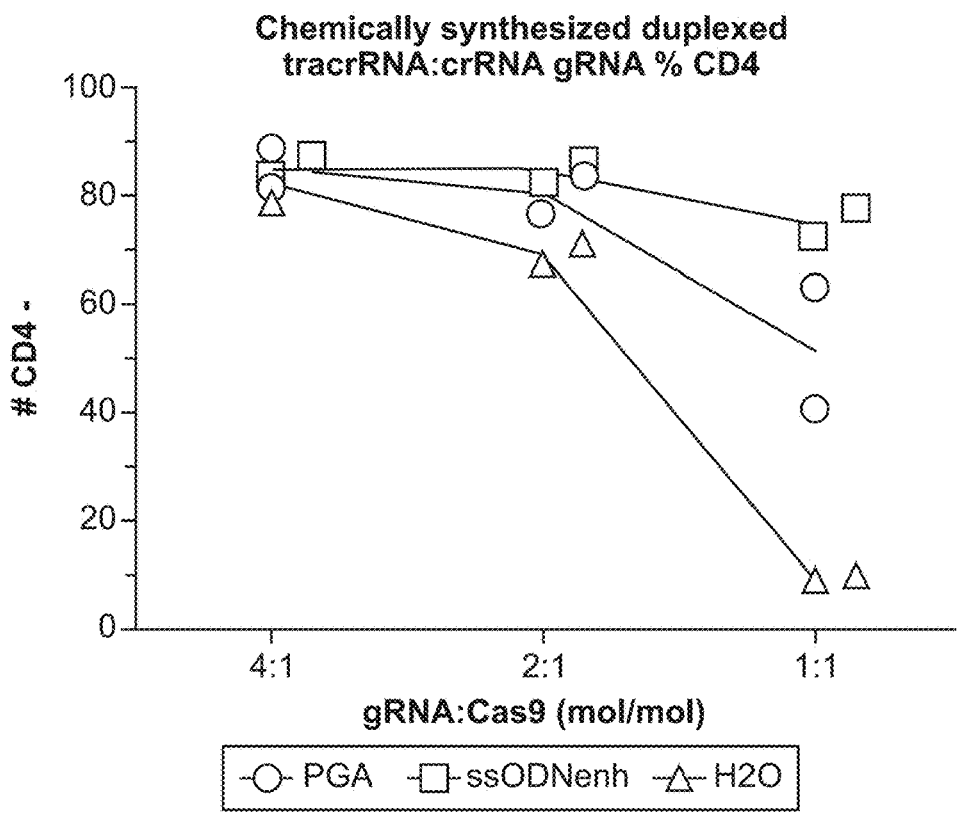
Figure 26C:
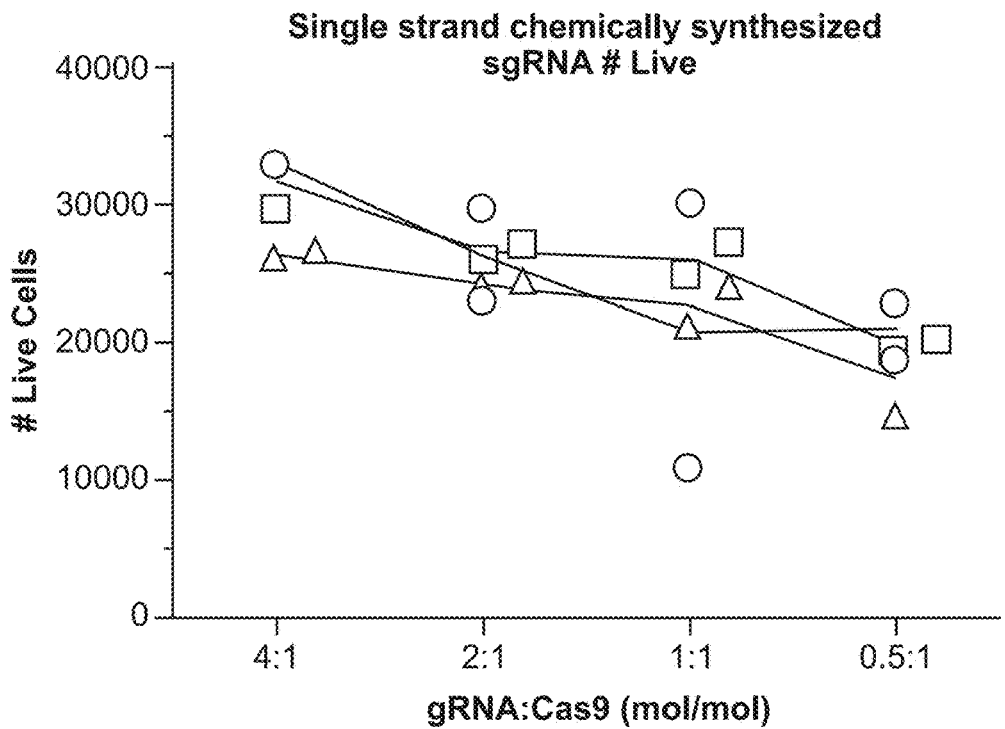
Figure 26D:
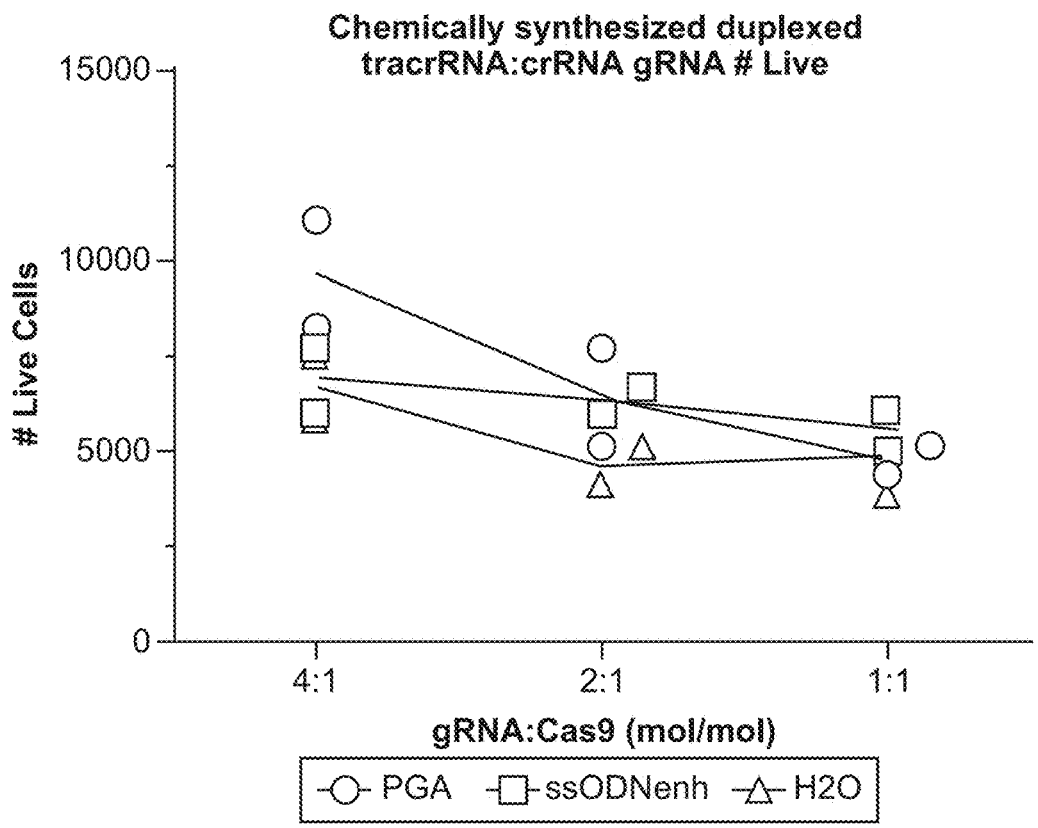
Figure 26E:
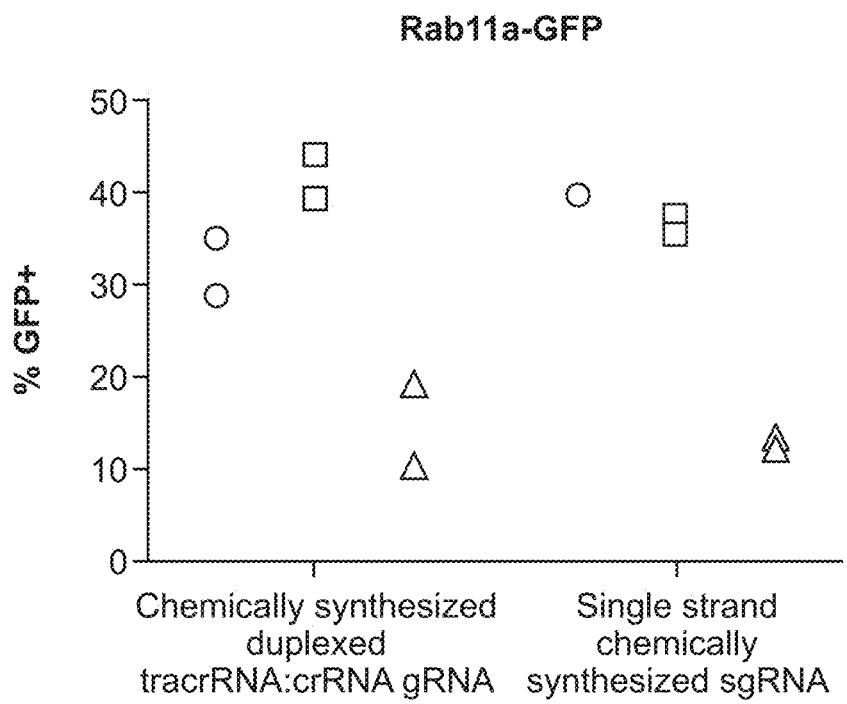
Figure 26F:
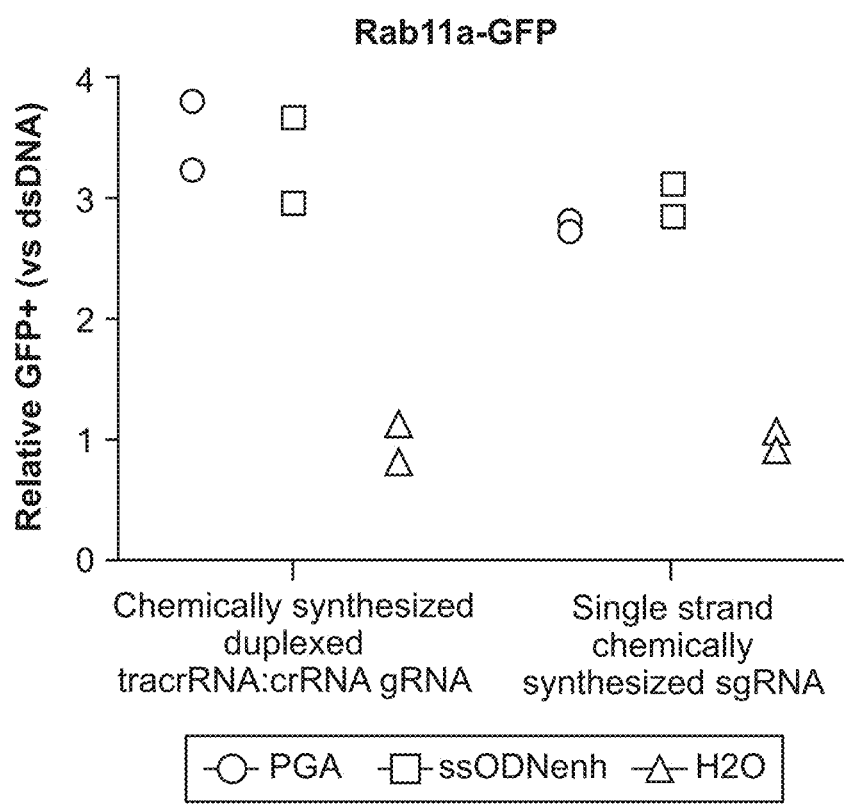

Cas9 RNPs were generated at the indicated RNA:protein ratio plus no enhancer ($H_2O$) or with either PGA or ssOD-Nenh and electroporated into primary human CD4+ T cells. RNPs targeted CD4 gene knock-out (FIGS. 26A-26D), or targeted insertion of an N-terminal fusion of GFP to RAB11A when mixed with 1 µg of dsDNA HDR template (FIGS. 26E and 26F). Loss of surface CD4 expression or GFP positivity and live cell count at 3 days was assessed by flow cytometry. Regardless of guide RNA type either single strand chemically synthesized sgRNA (FIGS. 26A, 26C, and 26E), or chemically synthesized duplexed tracrRNA:crRNA gRNA (FIGS. 26B, 26D, and 26F), the addition or either PGA or ssODNenh improved both knock-out and knock-in editing efficiency assessed by flow cytometry at day 3. Data shown for each of n=2 biologically independent blood donors with a line connecting means (FIGS. 26A-26D).

Example 21—Anionic Polymers Improved Editing Efficiency with Variant Cas9 RNPs

Figure 27A:
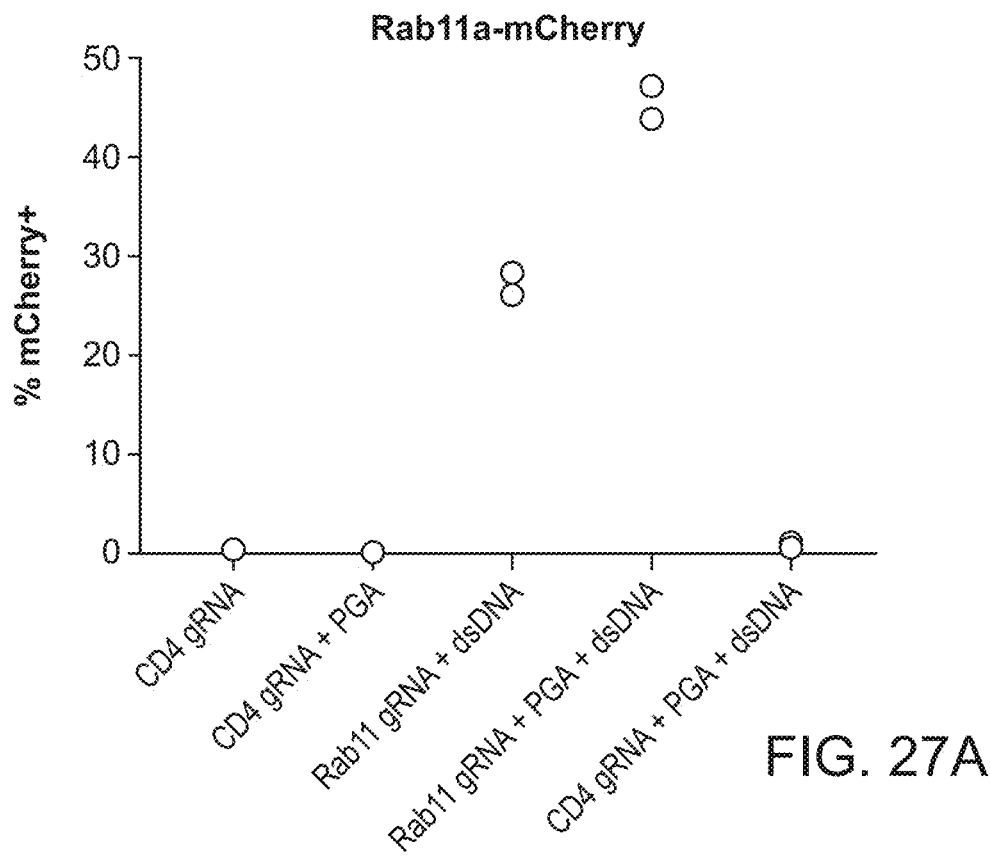
FIGS. 27A-27D show that anionic polymers improved editing efficiency with variant Cas9 RNPs, e.g., HiFi Cas9 and D10a 'nickase' variant Cas9.
Figure 27B:
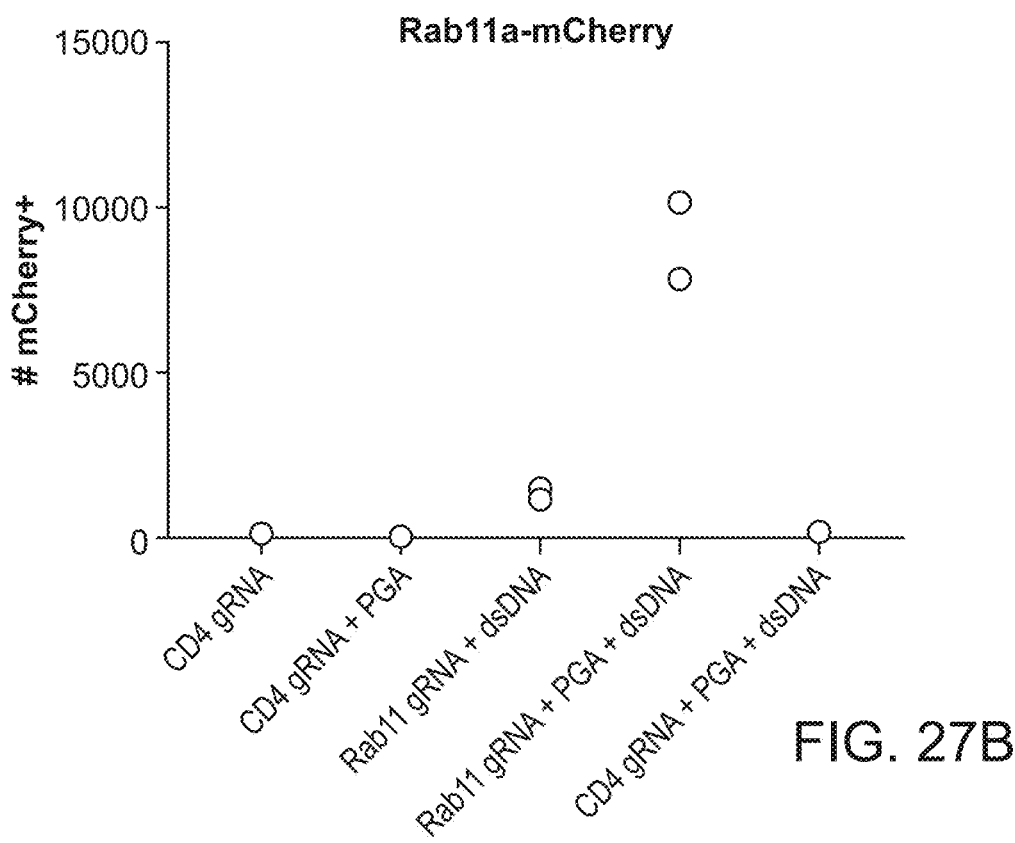

PGA improved editing efficiency with HiFi SpyCas9 (FIGS. 27A- and 27B). A novel Cas9 variant, HiFi Cas9, was recently developed with reduced off-target activity but slightly reduced on-target efficiency. HiFiCas9 RNPs were formulated with a guide RNA targeting either the CD4 gene or RAB11A gene with or without PGA polymer at a 2:1 gRNA:protein ratio and electroporated into primary human bulk ($CD3^{30}$) T cells together with an unmodified dsDNA HDR template for targeted integration of an N-terminal fusion of mCherry to RAB11A. As shown in FIGS. 27A and 27B, mCherry-expressing cells and live cell count were quantified at day 3 by flow cytometry. PGA improved on-target editing efficiency while maintaining minimal detection of mCherry+ cells when using an off-target gRNA. Data shown for each of n=2 biologically independent blood donors.

Figure 27C:
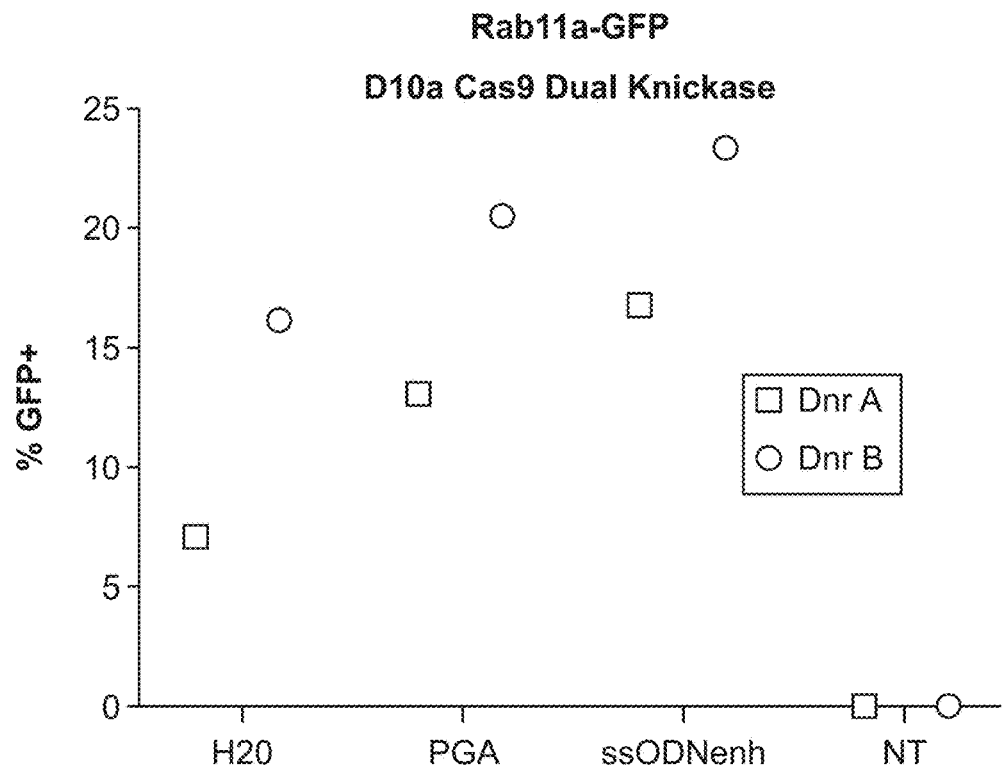
Figure 27D:
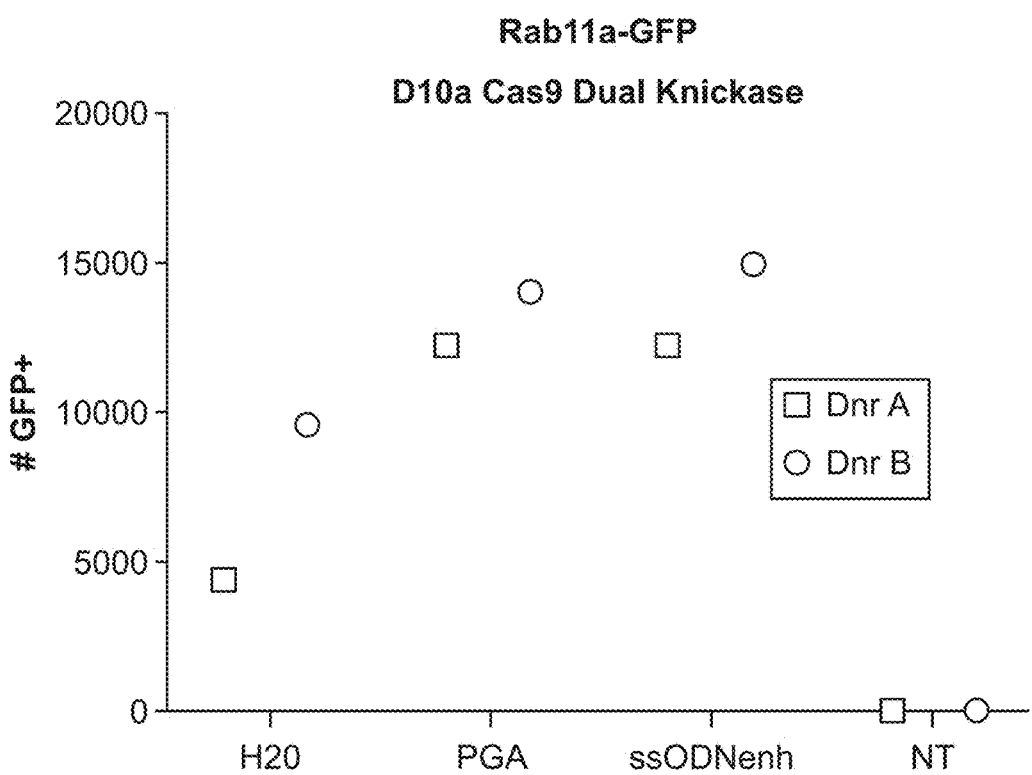

PGA or ssODNenh improved editing efficiency with D10a 'nickase' variant Cas9 RNPs (FIGS. 27C and 27D). A dual nickase approach to induce neighboring opposed single strand breaks has been proposed as a strategy to minimize off-target editing. D10a Cas9 RNPs were formulated with guide RNAs as previously described (Roth et a., Nature 559:405-409, 2018) targeting the RAB11A gene exon 1 with or without polymer at a 2:1 gRNA:protein ratio, and 50 pmol RNP were electroporated into primary human bulk (CD3+) T cells together with 1 µg of regular dsDNA HDR template encoding insertion of an N-terminal fusion of GFP to RAB11A. As shown in FIGS. 27C and 27D, GFP-expressing cells and live cell count were quantified at day 3 by flow cytometry. Data shown for each of n=2 biologically independent blood donors.

Figure 28A:
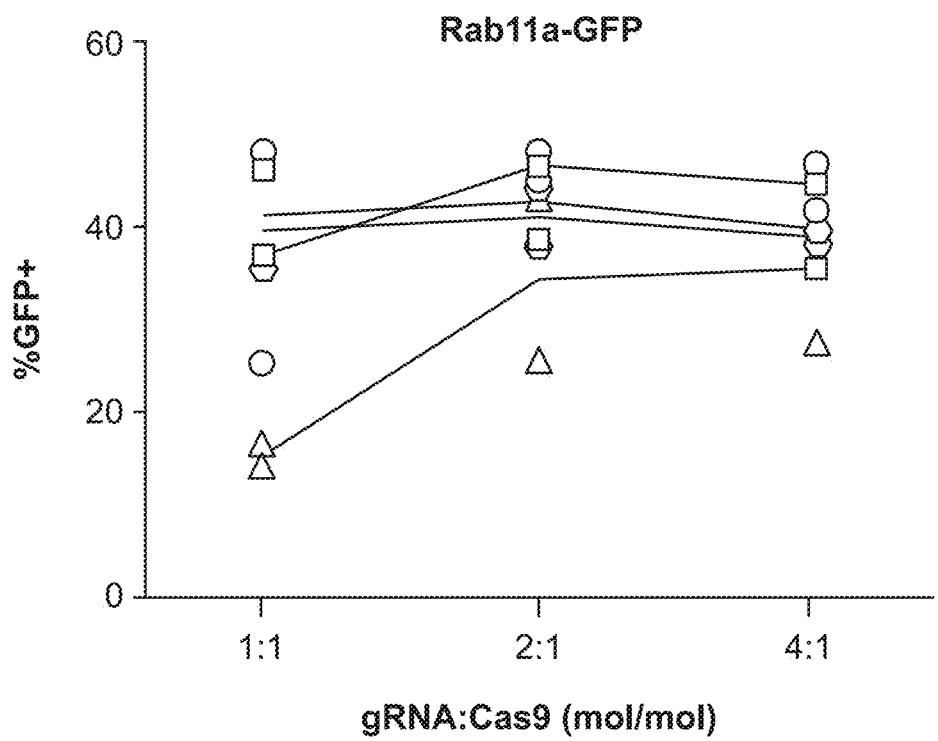
FIGS. 28A-28D show that the further addition of ssOD-Nenh to PGA did not increase knock-in efficiency.
Figure 28B:
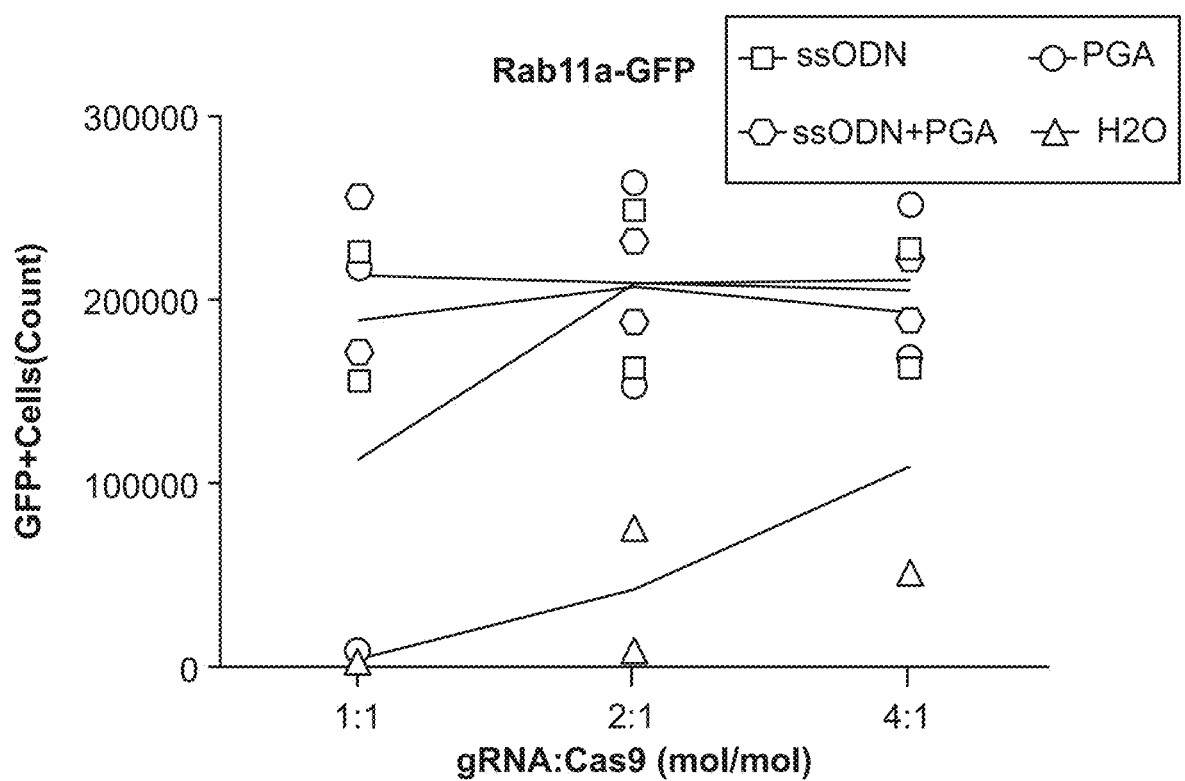
Figure 28C:
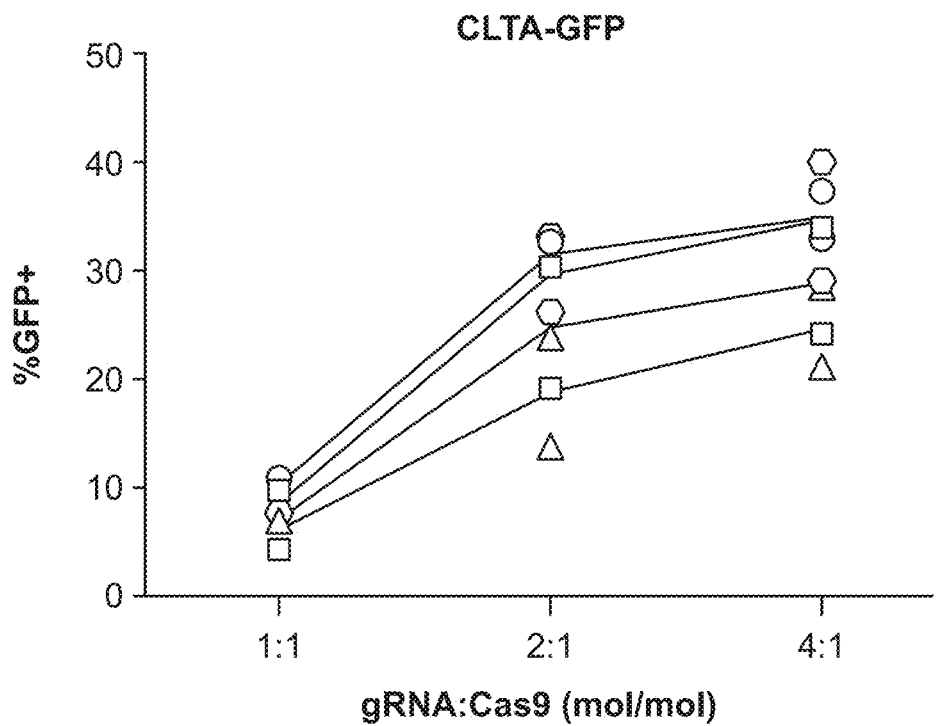
Figure 28D:
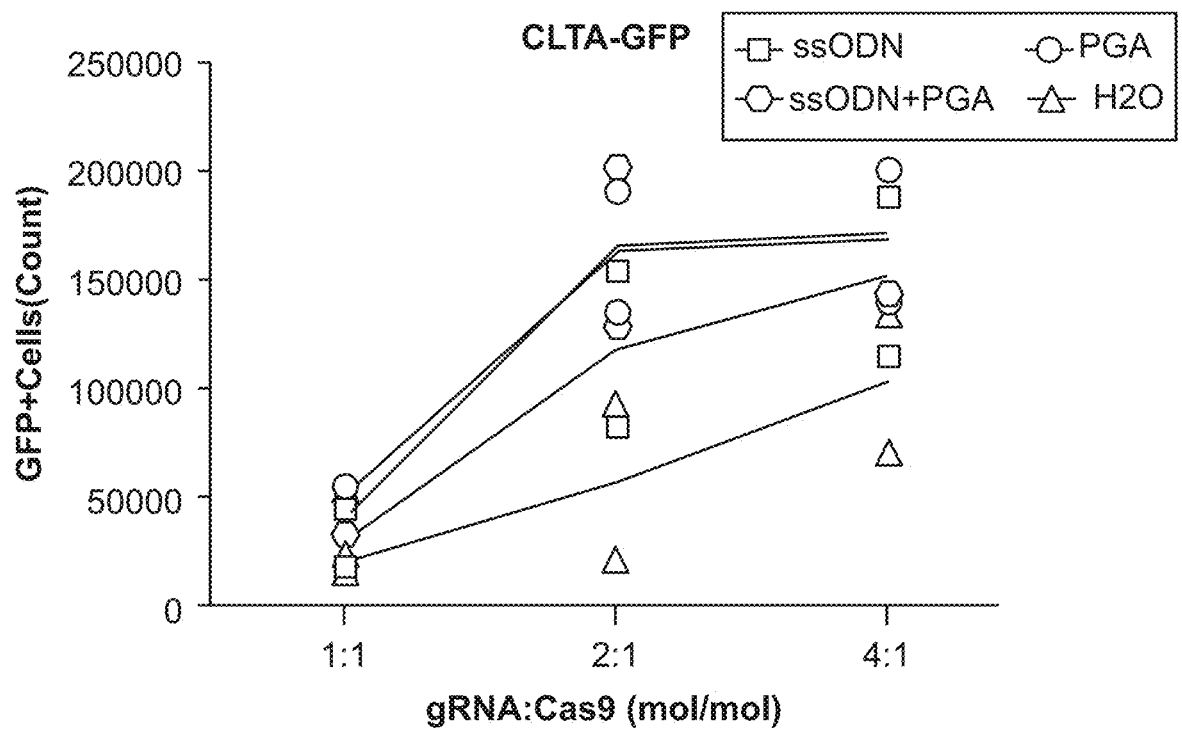

Example 22—Addition of ssODNenh to PGA Did Not Further Increase Knock-in Efficiency at 2:1 or Greater gRNA:Cas9 Ratios Cas9 RNPs were generated at the indicated RNA:protein ratio plus no enhancer ($H_2O$), with either PGA or ssOD-Nenh, or with a combination of PGA and ssODNenh at equivalent total dose, and electroporated into primary human CD3+ Bulk T cells along with 1 tig of a standard dsDNA HDR template targeting insertion of an N-terminal fusion of GFP to RAB11A (FIGS. 28A and 28B) or CLTA (FIGS. 28C and 28D). Expression of GFP positivity and live cell count was assessed by flow cytometry at 4 days. Data shown for each of n=2 biologically independent blood donors with a line connecting means.

Example 23—PGA-Stabilized Cas9 RNP Nanoparticles Could Be Lyophilized with Retained Knock-Out and Knock-In Editing Efficiency Cas9 RNP nanoparticles (with or without HDR template) that are stabilized with PGA, but not ssODNenh, were protected through lyophilization-reconstitution and retained robust knock-out (FIG. 29A) and knock-in (FIG. 29B) editing efficiency compared to freshly prepared RNPs. We hypothesize this is attributable to the capability of polypeptides to crystalize and form powders while long nucleic acids tend to form amorphous viscous solids at lower temperature.

Figure 29A:
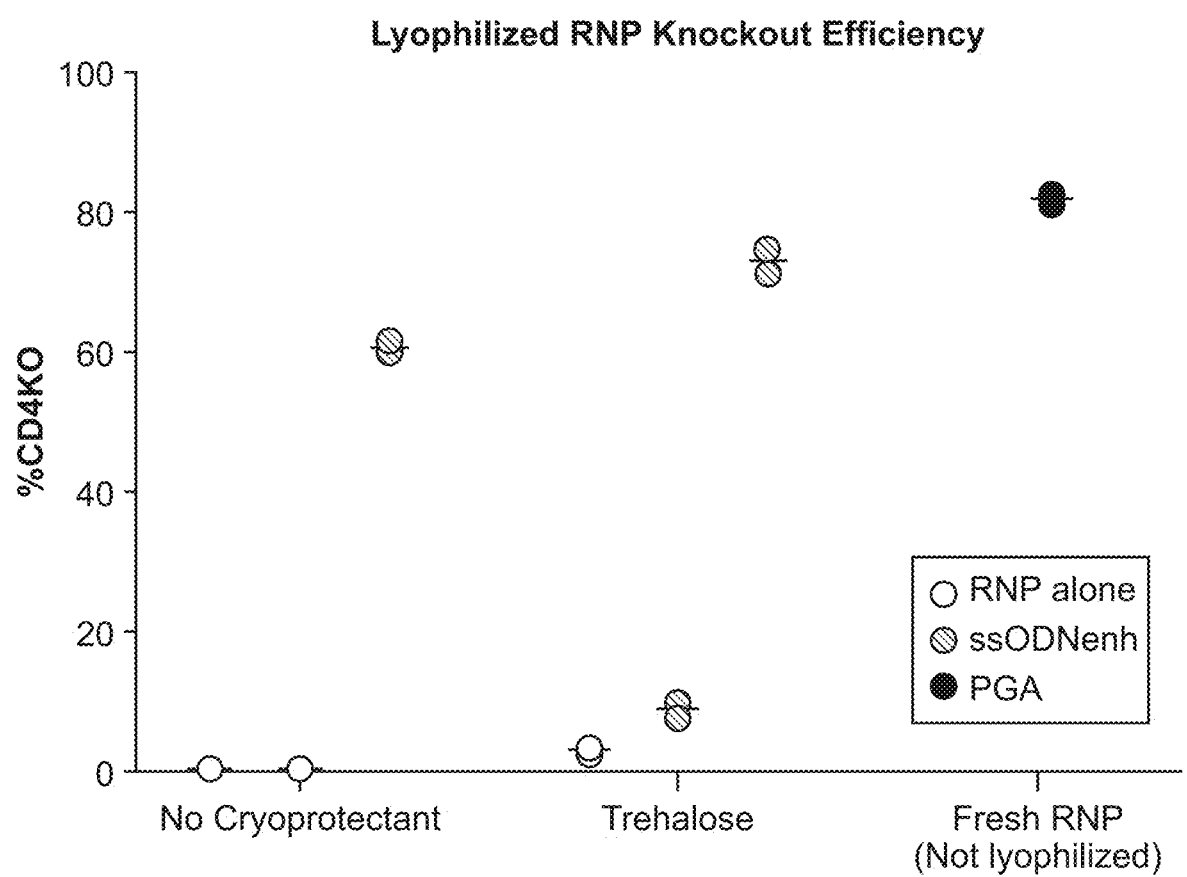
FIGS. 29A and 29B show that PGA-stabilized Cas9 RNP nanoparticles could be lyophilized with retained knock-out and knock-in editing efficiency.

FIG. 29A shows Cas9 RNPs targeting the CD4 gene were prepared at 2:1 ratio of gRNA:protein without or with PGA or ssODNenh then lyophilized with or without Trehalose cryoprotectant. RNPs were later reconstituted in water, and a fresh batch of RNP was made for comparison prior to electroporating into primary human CD4+ T cells. Two technical replicates shown for n=1 blood donor, representative of three repeated independent experiments; center lines indicate mean.

Figure 29B:
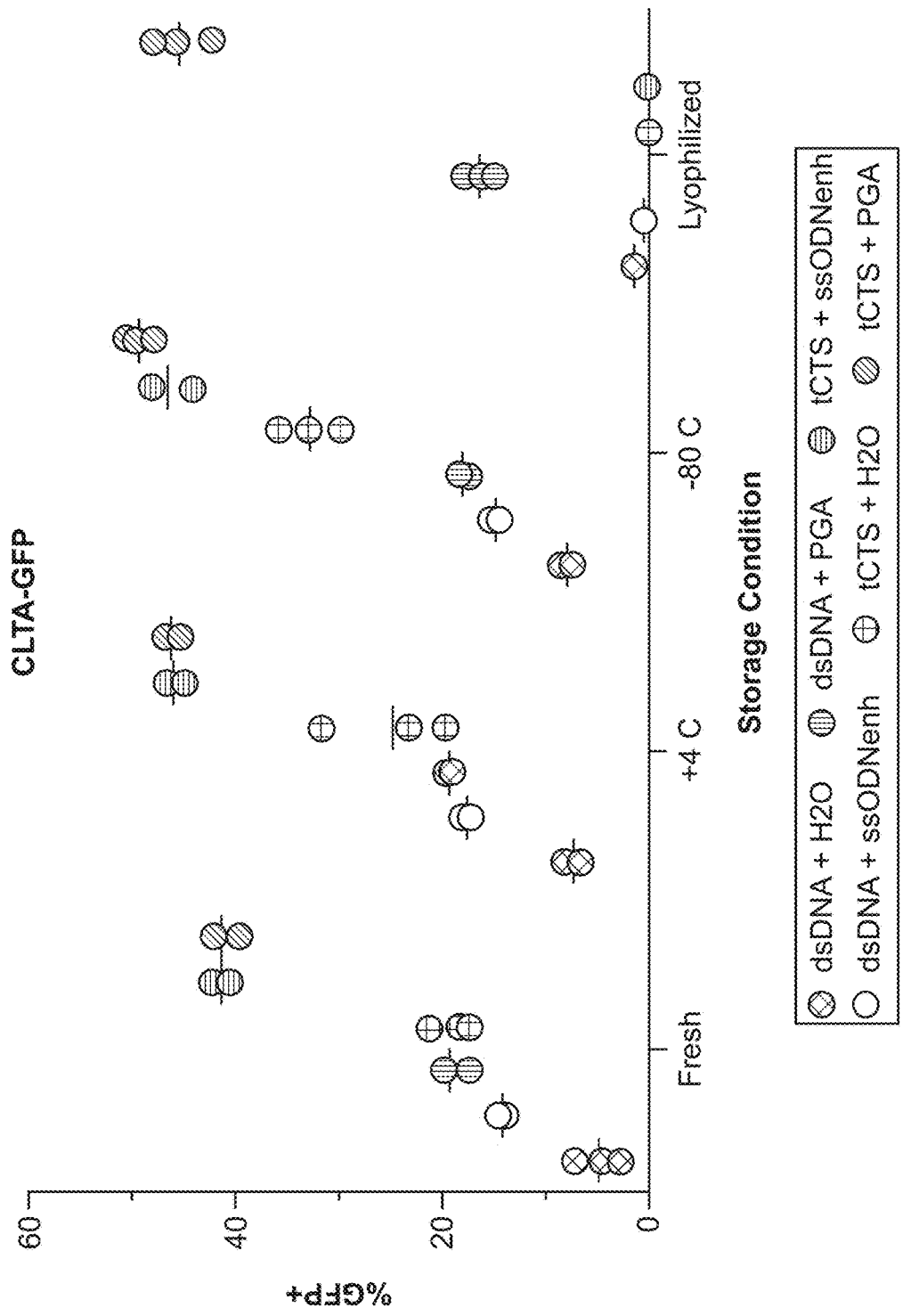

FIG. 29B shows Cas9 RNPs were prepared at 2:1 ratio gRNA:protein together with extra $H_2O$, PGA, or ssODNenh, then mixed with regular dsDNA HDR template (ds) or tCTS-modified HDR template (tCTS) targeting insertion of an N-terminal fusion of GFP to RAB11A. Samples were incubated at 37° C. to enhance RNP-HDR template interaction prior to storage at 4° C. or −80° C. for 2 days or immediate lyophilization. Lyophilized RNP-HDR templates were later reconstituted in water, and a fresh batch of RNP and HDR template were made for comparison prior to electroporating into primary human bulk (CD3+) T cells. Three technical replicates shown for n=1 blood donor, representative of two repeated independent experiments; center lines indicate mean.

Example 24—PGA-Stabilized Cas9 RNP Nanoparticles Improved Knock-In

Figure 30A:
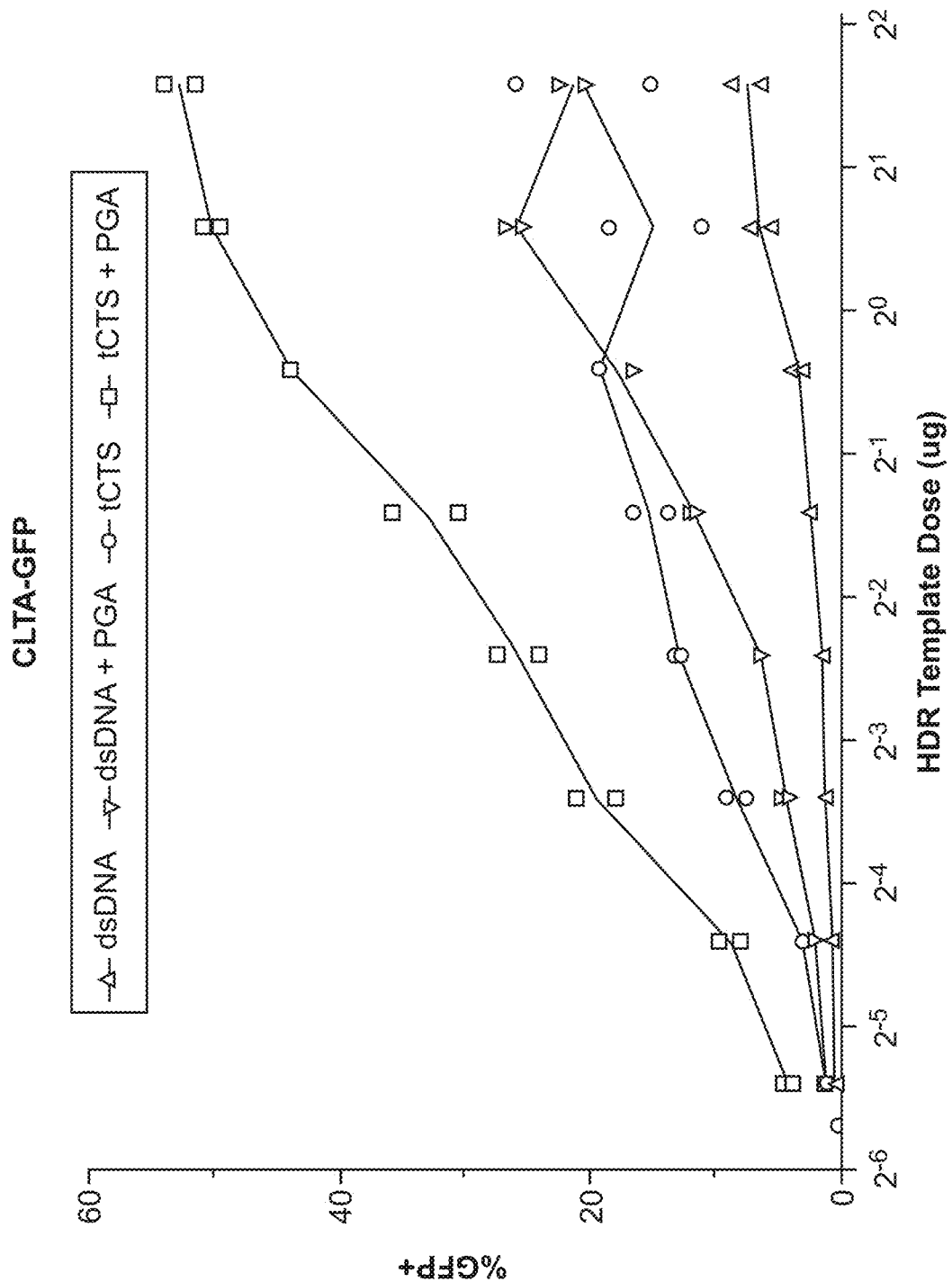
FIGS. 30A-30D show that PGA-stabilized Cas9 RNP nanoparticles improved knock-ins of an N-terminal fusion of GFP to CLTA and a TCR targeting the NY-ESO 1 tumor antigen.
Figure 30B:
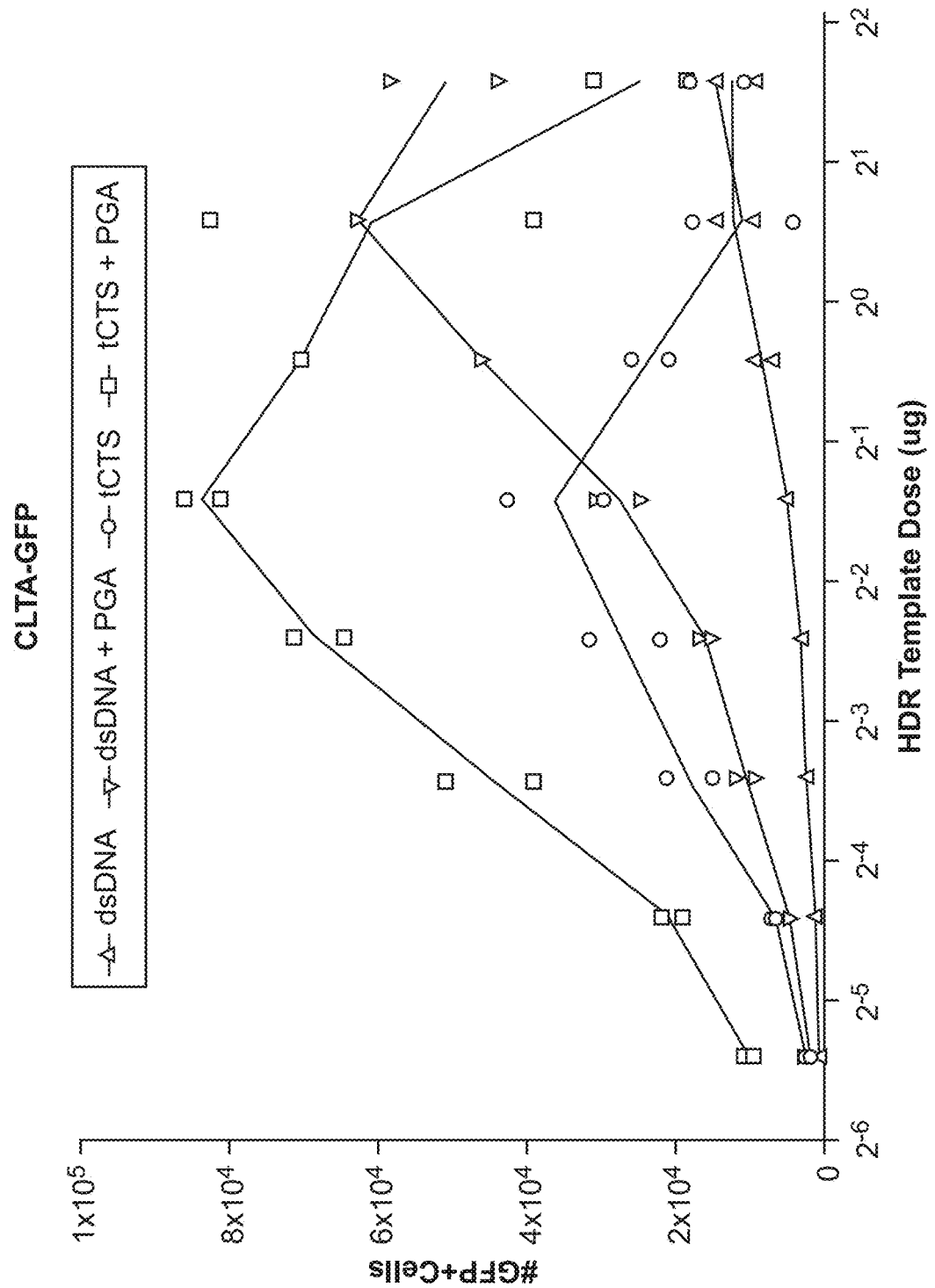
Figure 30C:
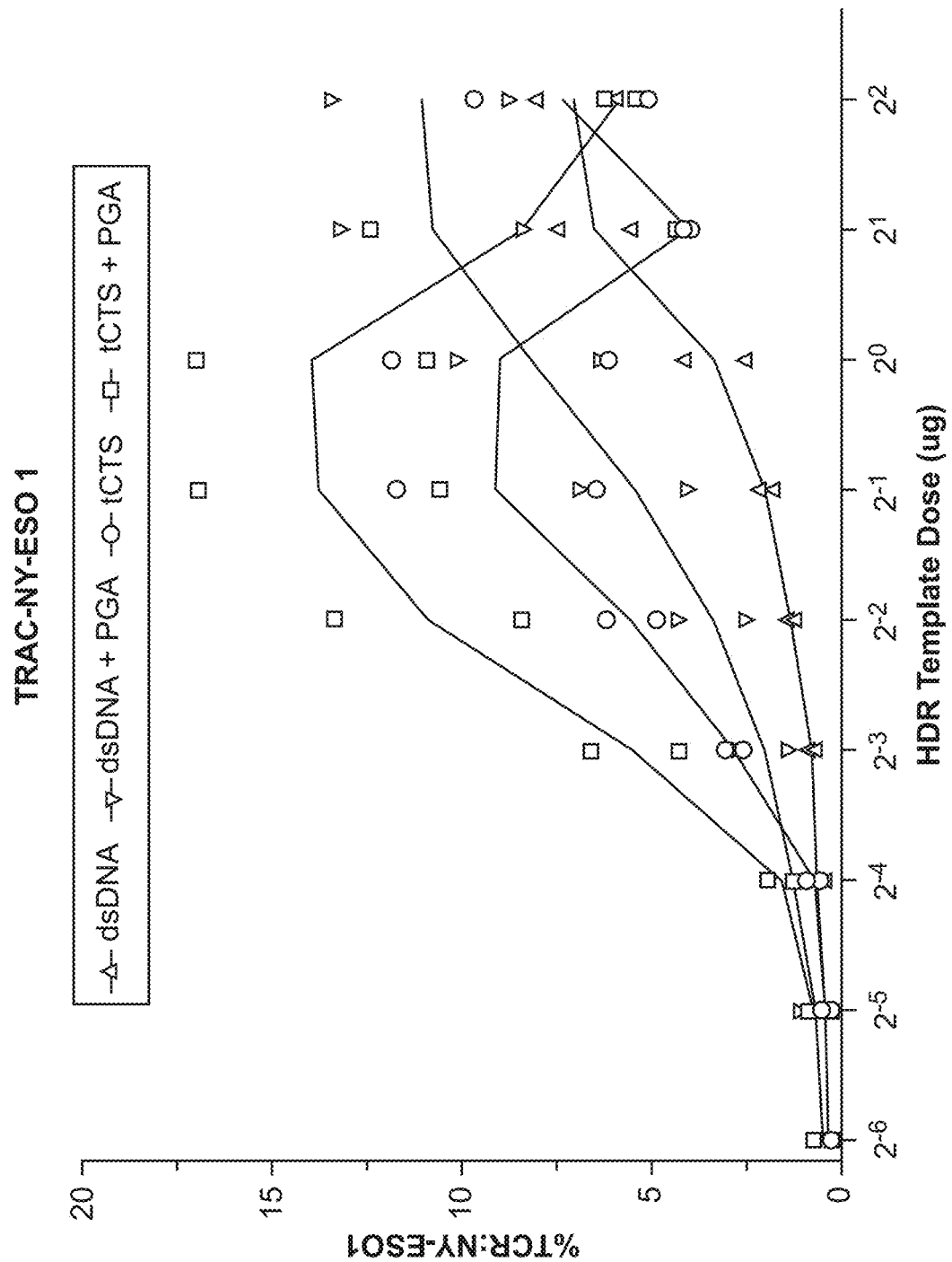
Figure 30D:
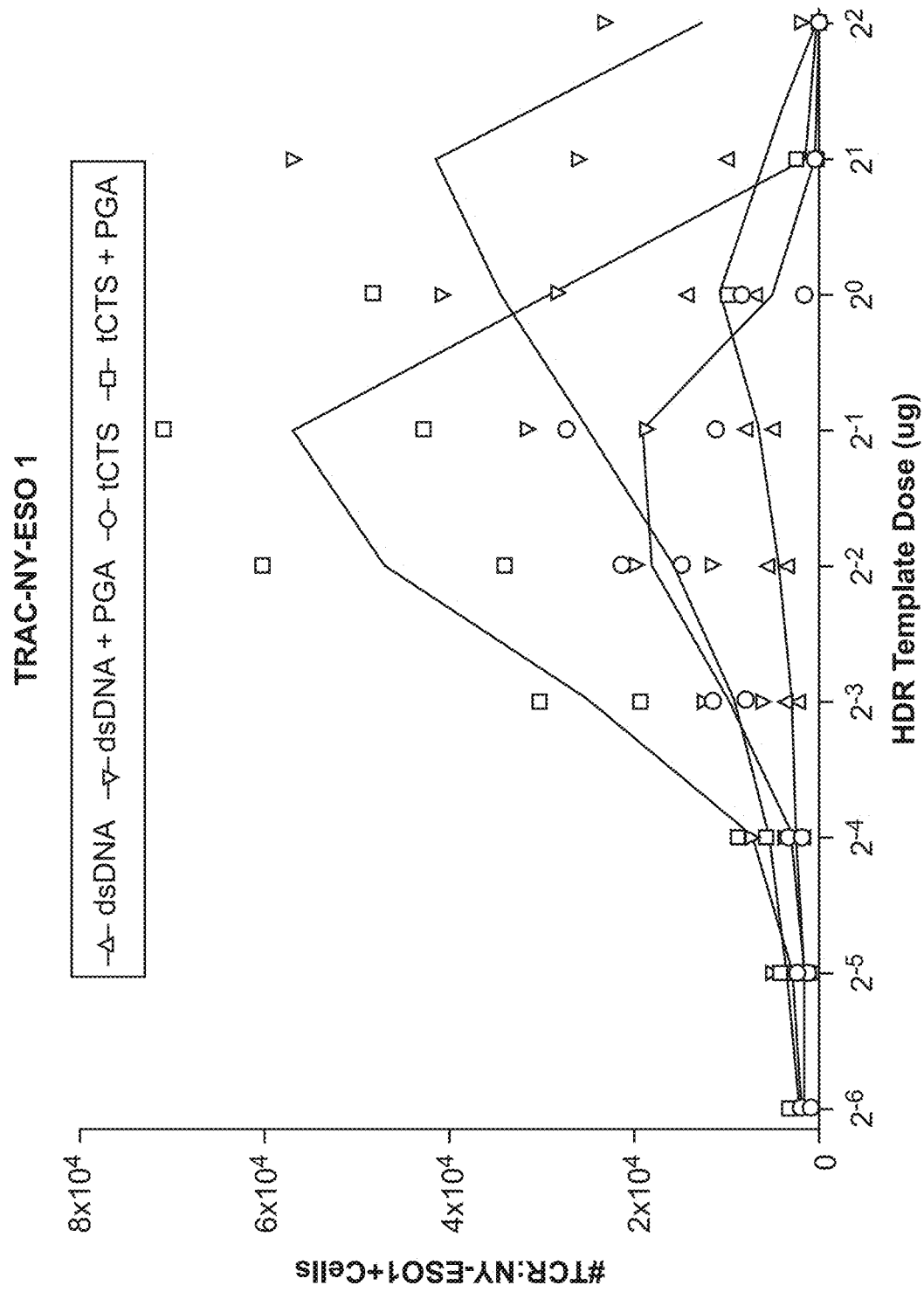

A series of doses of unmodified HDR template or tCTS-modified HDR template were combined with 50 pmol of regular Cas9 RNP or PGA-stabilized Cas9 RNP then electroporated into primary human bulk (CD3+) T cells targeting insertion of an N-terminal fusion of GFP to CLTA (FIGS. 30A and 30B) or replacement of the endogenous T cell receptor with a TCR targeting the NY-ESO 1 tumor antigen (FIGS. 30C and 30D). The fraction of successful knock-in edited cells (FIGS. 30A and 30C) and the knock-in edited cell count yield (FIGS. 30B and 30D) were measured at day 3 (FIGS. 30A and 30B) or day 4 (FIGS. 30C and 30D) by flow cytometry. Data shown for each of n=2 biologically independent blood donors with a line connecting means.

Figure 31A:
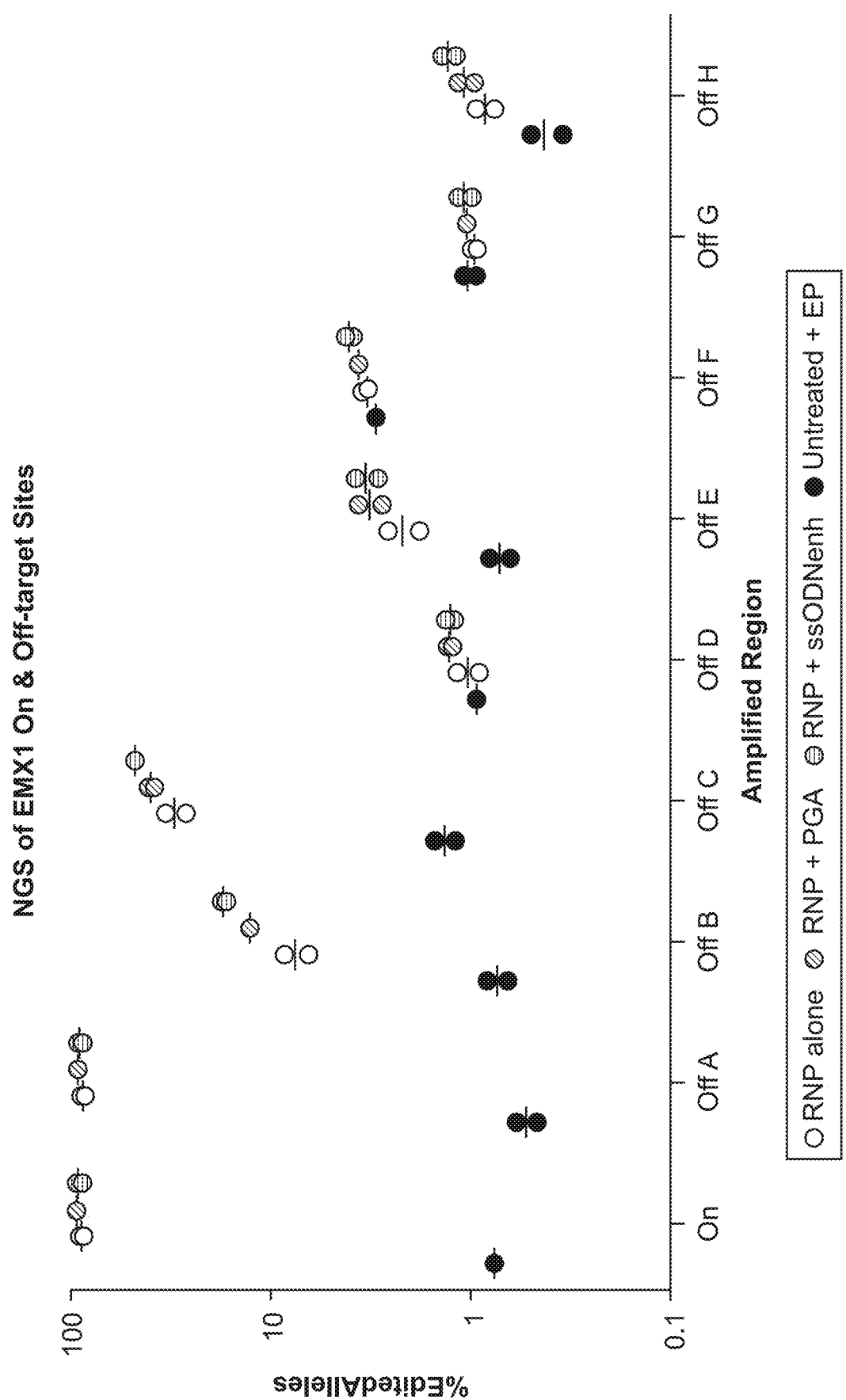
FIGS. 31A-31C show the effects of anionic polymers and tCTS-modified HDR templates on off-target genome modifications.

Example 25—Effects of Anionic Polymers and tCTS-Modified HDR Templates on Off-Target Genome Modifications The anionic polymers PGA or ssODNenh can increase NHEJ editing efficiency, including at off-target sites, as shown in FIG. 31A. CD3+ T cells isolated from two healthy donors were treated with regular, PGA-stabilized, or ssOD-Nenh-stabilized RNPs incorporating a gRNA targeting the EMX1 gene previously identified by CIRCLE-Seq to create multiple off-target double-strand breaks(V akulskas et al., Nat Med 24:1216-1224, 2018; Tsai et al., Nat Methods 14:607-614, 2017). Control cells were electroporated without RNP. On- and off-target genomic regions were PCR-amplified, and editing outcomes were quantified by deep sequencing with reads aligned and indels identified by CRISPresso2 (ignoring substitutions arising from PCR or sequencing errors). Off-target region A is a duplication of the entire gRNA target (with high efficiency editing), while off-target regions B-H have varying amounts of gRNA target homology.

Figure 31B:
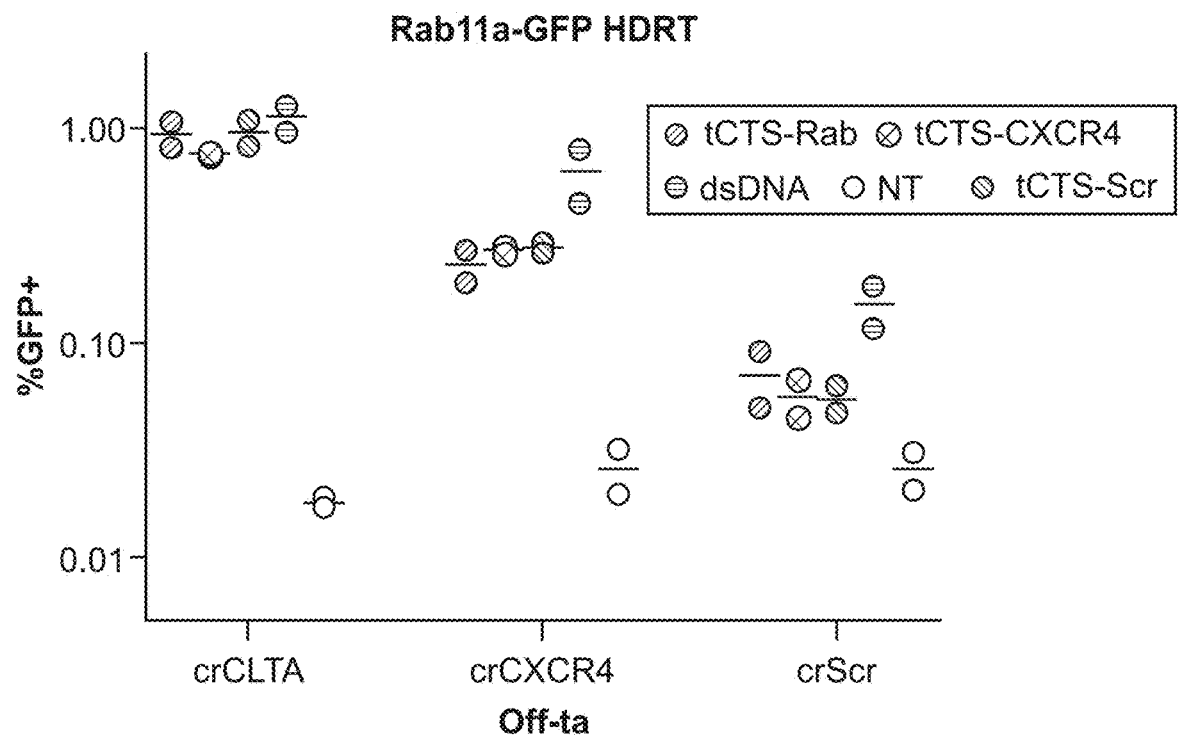
Figure 31C:
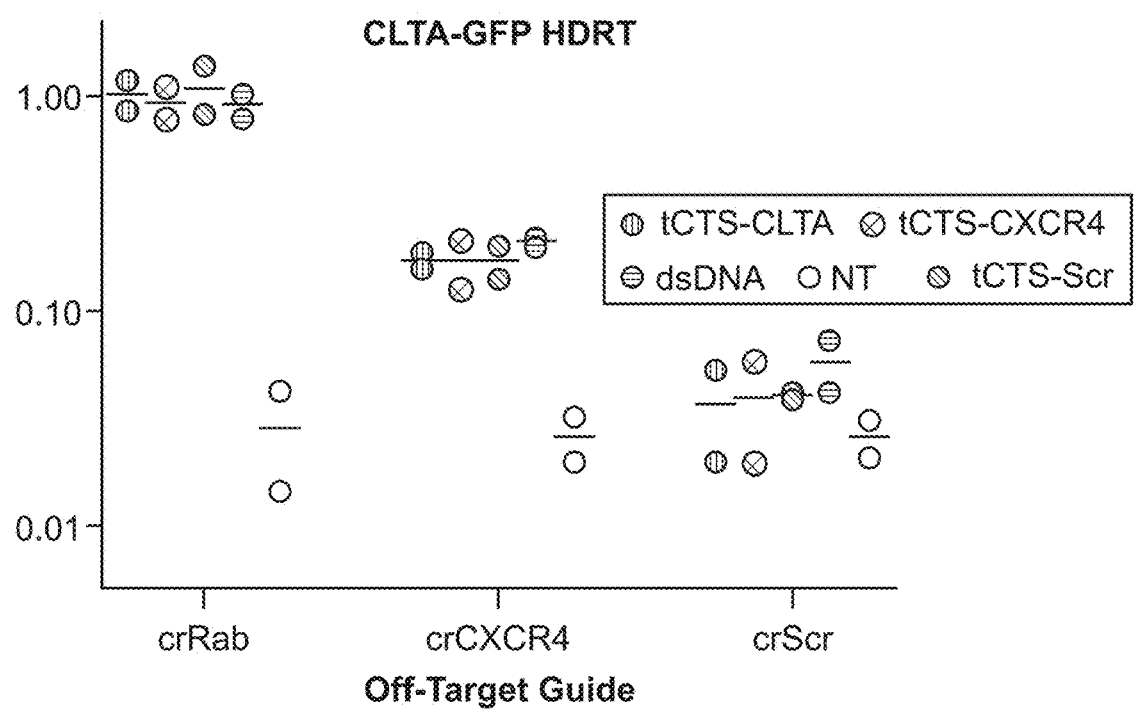

CD3+ T cells were treated with PGA-stabilized off-target gRNA RNPs and tCTS-modified HDR templates designed for targeting insertion of an N-terminal fusion of GFP to (FIG. 31B) RAB11A or CLTA (FIG. 31C). Appending a tCTS designed to bind off-target gRNA sequences (as indicated in the legend) did not exacerbate off-target transgene expression regardless of which off-target gRNA was used (indicated on the x-axis). Transgene expression was measured as percentage of live cells expressing GFP at 4 days post electroporation; NT=background signal from non-treated cells. Data shown for each of n=2 biologically independent blood donors; center lines indicate mean.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

1 Yin, H., Xue, W. & Anderson, D. G. CRISPR-Cas: a tool for cancer research and therapeutics. Nat Rev Clin Oncol, doi:10.1038/s41571-019-0166-8 (2019).

2 Dunbar, C. E. et al. Gene therapy comes of age. Science 359, doi:10.1126/science.aan4672 (2018).

3 Cornu, T. I., Mussolino, C. & Cathomen, T. Refining strategies to translate genome editing to the clinic. Nat Med 23, 415-423, doi:10.1038/nm.4313 (2017).

4 David, R. M. & Doherty, A. T. Viral Vectors: The Road to Reducing Genotoxicity. Toxicol Sci 155, 315-325, doi: 10.1093/toxsci/kfw220 (2017).

5 Roth, T. L. et al. Reprogramming human T cell function and specificity with non-viral genome targeting. Nature 559, 405-409, doi:10.1038/s41586-018-0326-5 (2018).

6 Vo, L. T. et al. Regulation of embryonic haematopoietic multipotency by EZH1. Nature 553, 506-510, doi: 10.1038/nature25435 (2018).

7 Pouton, C. W., Wagstaff, K. M., Roth, D. M., Moseley, G. W. & Jans, D. A. Targeted delivery to the nucleus. Adv Drug Deliv Rev 59, 698-717, doi:10.1016/j.addr.2007.06.010 (2007).

8 Doudna, J. A. & Charpentier, E. Genome editing. The new frontier of genome engineering with CRISPR-Cas9. Science 346, 1258096, doi:10.1126/science.1258096 (2014).

9 Dominguez, A. A., Lim, W. A. & Qi, L. S. Beyond editing: repurposing CRISPR-Cas9 for precision genome regulation and interrogation. Nat Rev Mol Cell Biol 17, 5-15, doi:10.1038/nrm.2015.2 (2016).

10 Jiang, F. & Doudna, J. A. CRISPR-Cas9 Structures and Mechanisms. Annu Rev Biophys 46, 505-529, doi: 10.1146/annurev-biophys-062215-010822 (2017).

11 Luecke, S. et al. cGAS is activated by DNA in a length-dependent manner EMBO Rep 18, 1707-1715, doi:10.15252/embr.201744017 (2017).

12 Richardson, C. D., Ray, G. J., Bray, N. L. & Corn, J. E. Non-homologous DNA increases gene disruption efficiency by altering DNA repair outcomes. Nat Commun 7, 12463, doi:10.1038/ncomms12463 (2016).

13 Bernkop-Schnurch, A. Strategies to overcome the polycation dilemma in drug delivery. Adv Drug Deliv Rev 136-137, 62-72, doi:10.1016/j.addr.2018.07.017 (2018).

14 Vakulskas, C. A. et al. A high-fidelity Cas9 mutant delivered as a ribonucleoprotein complex enables efficient gene editing in human hematopoietic stem and progenitor cells. Nat Med 24, 1216-1224, doi:10.1038/s41591-018-0137-0 (2018).

15 Ran, F. A. et al. Double nicking by RNA-guided CRISPR Cas9 for enhanced genome editing specificity. Cell 154, 1380-1389, doi:10.1016/j.cell.2013.08.021 (2013).

What is claimed is:

1. A composition for modifying a target nucleic acid, comprising:
   (a) a targetable nuclease;
   (b) a DNA-binding protein; and
   (c) a donor template comprising a homology directed repair (HDR) template, two or more protospacer adjacent motifs (PAMs), and two or more DNA-binding protein target sequences.

2. The composition of claim 1, wherein each of the targetable nuclease and the DNA-binding protein is an RNA-guided nuclease.

3. The composition of claim 2, wherein the RNA-guided nuclease is a Cas protein.

4. The composition of claim 1, wherein the composition further comprises a target guide RNA (gRNA) and a donor gRNA; wherein the target gRNA is complementary to the target nucleic acid; and wherein each of the DNA-binding protein target sequences hybridizes to the donor gRNA or a portion thereof.

5. The composition of claim 1, wherein each of the DNA-binding protein target sequences is complementary to an equal length portion of the sequence of the donor gRNA.

6. The composition of claim 1, wherein the DNA-binding protein comprises a transcription activator-like (TAL) effector DNA-binding protein or a zinc finger DNA-binding protein.

7. The composition of claim 1, wherein the targetable nuclease is fused to a nuclear localization signal (NLS) sequence.

8. The composition of claim 1, wherein the DNA-binding protein is fused to an NLS sequence.

9. The composition of claim 1, wherein the targetable nuclease has nuclease activity.

10. The composition of claim 1, wherein the targetable nuclease does not have nuclease activity.

11. A method for modifying a target nucleic acid in a cell, comprising introducing into the cell a composition of claim 1, wherein the HDR template is integrated into the target nucleic acid.

12. The composition of claim 1, wherein a first DNA-binding protein target sequence and a first PAM are located at the 5' terminus of the HDR template and a second DNA-binding protein target sequence and a second PAM are located at the 3' terminus of the HDR template.

13. The composition of claim 12, wherein the first PAM is located at the 5' terminus of the first DNA-binding protein target sequence and the second PAM is located at the 5' terminus of the second DNA-binding protein target sequence.

14. The composition of claim 12, wherein the first PAM is located at the 5' terminus of the first DNA-binding protein target sequence and the second PAM is located at the 3' terminus of the second DNA-binding protein target sequence.

15. The composition of claim 12, wherein the first PAM is located at the 3' terminus of the first DNA-binding protein target sequence and the second PAM is located at the 5' terminus of the second DNA-binding protein target sequence.

16. The composition of claim 12, wherein the first PAM is located at the 3' terminus of the first DNA-binding protein target sequence and the second PAM is located at the 3' terminus of the second DNA-binding protein target sequence.

* * * * *

SEQUENCE LISTING

<160> NUMBER OF SEQ ID NOS: 48

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Val Lys Arg Pro Ala Ala Thr Lys Lys Ala Gly Gln Ala Lys Lys
1               5                   10                  15

Lys Lys Leu Asp
            20

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ala Ala Lys Arg Val Lys Leu Asp
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Lys Ile Lys Arg Pro Val Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Lys Lys Lys Arg Lys Val
1               5

```
<210> SEQ ID NO 6
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggcgggact agtggcccat gtcgtactcg tcgtcgcgga gcaagcggcc actaagacta      60
t                                                                     61

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ttagctctgt ttacgtccca gcgggcatga gagtaacaag agggtgtggt aatattacgg      60
taccgagcac tatcgataca atatgtgtca tacggacacg                           100

<210> SEQ ID NO 8
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ggtagctagg agttccagga ctcagtttcc cctttgagcc tcctttagcg actaaagctt      60
gaagccccac gcatctcgac tctcgcgcac accgcccttg ttgggctcag ggcggggcg     120 ccgcccccgg aagtacttcc ccttaaaggc tggggcctgc cggaaatggc gcagcggcag    180 ggagggggctc ttcacccagt ccggcagttg aagctcggcg ctcgggttac ccctgcagcg   240
acgccccctg gtcccacaga taccactgct gctcccgccc tttcgctcct cggccgcgca    300
atgggcggat cgggtgggac tagtggcagc aagggcgagg agctgttcac cggggtggtg    360
cccatcctgg tcgagctgga cggcgacgta aacggccaca agttcagcgt gcgcggcgag    420
ggcgagggcg atgccaccaa cggcaagctg accctgaagt tcatctgcac caccggcaag    480
ctgcccgtgc cctggcccac cctcgtgacc accctgacct acggcgtgca gtgcttcagc    540
cgctaccccg accacatgaa gcgccacgac ttcttcaagt ccgccatgcc cgaaggctac    600
gtccaggagc gcaccatcag cttcaaggac gacggcacct acaagacccg cgccgaggtg    660
aagttcgagg gcgacaccct ggtgaaccgc atcgagctga agggcatcga cttcaaggag    720
gacggcaaca tcctggggca caagctggag tacaacttca acagccacaa cgtctatatc    780
accgccgaca agcagaagaa cggcatcaag gccaacttca agatccgcca caacgtggag    840
gacggcagcg tgcagctcgc cgaccactac cagcagaaca cccccatcgg cgacggcccc    900
gtgctgctgc ccgacaacca ctacctgagc acccagtccg tgctgagcaa agaccccaac    960
gagaagcgcg atcacatggt cctgctggag ttcgtgaccg ccgccgggat cactctggaacc   1020 ggtgctggaa gtggtacacg cgacgacgag tacgactacc tctttaaagg tgaggccatg    1080
ggctctcgca ctctacacag tcctcgttcg gggacccggg ccactcccgg tggaccctcg    1140
tgccggccac ccctgcactg atataggcct ccctcagccc ttcctttttg tgcggttccg    1200
```

| | |
|---|---|
| tctcctaccc agctcagcct cttctccccc gctcagacag gggtcccat cacatgccgc | 1260 |
| tctctgagcg acctctccat aggccttcgc tggcctcaga gcccctccct gcgtgtcctt | 1320 |
| cccctggcgg actgccttct cccacatcgt | 1350 |

<210> SEQ ID NO 9
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | |
|---|---|
| ggtagctagg agttccagga ctcagtttcc cctttgagcc tcctttagcg actaaagctt | 60 |
| gaagccccac gcatctcgac tctcgcgcac accgcccttg ttgggctcag gggcggggcg | 120 |
| ccgcccccgg aagtacttcc ccttaaaggc tggggcctgc cggaaatggc gcagcggcag | 180 |
| ggagggcctc ttcacccagt ccggcagttg aagctcggcg ctcgggttac ccctgcagcg | 240 |
| acgcccctg gtcccacaga taccactgct gctcccgccc tttcgctcct cggccgcgca | 300 |
| atgggcggat cgggtgggac tagtggcgtg agcaaggggcg aggaggataa catggccatc | 360 |
| atcaaggagt tcatgcgctt caaggtgcac atggagggct ccgtgaacgg ccacgagttc | 420 |
| gagatcgagg gcgagggcga gggccgcccc tacgagggca cccagaccgc caagctgaag | 480 |
| gtgaccaagg gtggcccct gcccttcgcc tgggacatcc tgtcccctca gttcatgtac | 540 |
| ggctccaagg cctacgtgaa gcaccccgcc gacatcccg actacttgaa gctgtccttc | 600 |
| cccgagggct tcaagtggga gcgcgtgatg aacttcgagg acggcggcgt ggtgaccgtg | 660 |
| acccaggact cctccctgca ggacggcgag ttcatctaca aggtgaagct gcgcggcacc | 720 |
| aacttcccct ccgacggccc cgtaatgcag aagaagacca tgggctggga ggcctcctcc | 780 |
| gagcggatgt accccgagga cggcgccctg aagggcgaga tcaagcagag gctgaagctg | 840 |
| aaggacggcg gccactacga cgctgaggtc aagaccacct acaaggccaa gaagcccgtg | 900 |
| cagctgcccg gcgcctacaa cgtcaacatc aagttggaca tcacctccca caacgaggac | 960 |
| tacaccatcg tggaacagta cgaacgcgcc gagggccgcc actccaccgg cggcatggac | 1020 |
| gagctgtaca agggaaccgg tgctggaagt ggtacacgcg acgacgagta cgactacctc | 1080 |
| tttaaaggtg aggccatggg ctctcgcact ctacacagtc ctcgttcggg gacccgggcc | 1140 |
| actcccggtg gaccctcgtg ccggccaccc ctgcactgat ataggcctcc ctcagccctt | 1200 |
| ccttttttgtg cggttccgtc tcctacccag ctcagcctct tctccccgc tcagacaggg | 1260 |
| gtccccatca catgccgctc tctgagcgac ctctccatag gccttcgctg gcctcagagc | 1320 |
| ccctccctgc gtgtccttcc cctggcggac tgccttctcc cacatcgt | 1368 |

<210> SEQ ID NO 10
<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| ctccctatca ggcagcactt ccgcctcccg gggcccgcgc agctcacctc cctcacctcc | 60 |
| cgccctaccc cagtcacgag ttgttttagg gggaccgccc ctccacttgc tgattgggta | 120 |

```
gctcctgaac cattgttgtc ctctgattgg ttgttcccct ttcggctctg caacaccgcc      180
tagaccgacc ggatacacgg gtagggcttc cgctttaccc gtctccctcc tggcgcttgt      240
cctcctctcc cagtcggcac cacagcggtg gctgccgggc gtggtgtcgg tgggtcggtt      300
ggttttttgtc tcaccgttgg tgtccgtgcc gttcagttgc ccgccatggc tggatcgggt      360
gggactagtg gcagcaaggg cgaggagctg ttcaccgggg tggtgcccat cctggtcgag      420
ctggacggcg acgtaaacgg ccacaagttc agcgtgcgcg gcgagggcga gggcgatgcc      480
accaacggca agctgaccct gaagttcatc tgcaccaccg gcaagctgcc cgtgccctgg      540
cccaccctcg tgaccaccct gacctacggc gtgcagtgct tcagccgcta ccccgaccac      600
atgaagcgcc acgacttctt caagtccgcc atgcccgaag gctacgtcca ggagcgcacc      660
atcagcttca aggacgacgg cacctacaag acccgcgccg aggtgaagtt cgagggcgac      720
accctggtga accgcatcga gctgaagggc atcgacttca aggaggacgg caacatcctg      780
gggcacaagc tggagtacaa cttcaacagc cacaacgtct atatcaccgc cgacaagcag      840
aagaacggca tcaaggccaa cttcaagatc cgccacaacg tggaggacgg cagcgtgcag      900
ctcgccgacc actaccagca gaacaccccc atcggcgacg gccccgtgct gctgcccgac      960
aaccactacc tgagcaccca gtccgtgctg agcaaagacc ccaacgagaa gcgcgatcac     1020
atggtcctgc tggagttcgt gaccgccgcc gggatcactg gaaccggtgc tggaagtggt     1080
gagctggatc cgttcggcgc ccctgccggc gccctggcg tcccgcgct ggggaacgga     1140
gtggccggcg ccggcgaaga agacccggct gcggccttct ggcgcagca agagagcgag     1200
attgcgggca tcgagaacga cgaggccttc gccatcctgg acggcggcgc ccccgggccc     1260
cagccgcacg gcgagccgcc gggggtccg ggtgagagtg cgggcgcgtt tggggcgaga     1320
ggacttgtct ggaaactcgg tccacagtgg gtccgagagc ttctgtgtga ctcgtgctcc     1380
ttg                                                                    1383
```

<210> SEQ ID NO 11  
<211> LENGTH: 1401  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 11

```
ctccctatca ggcagcactt ccgcctcccg gggcccgcgc agctcacctc cctcacctcc       60
cgccctaccc cagtcacgag ttgttttagg gggaccgccc ctccacttgc tgattgggta      120
gctcctgaac cattgttgtc ctctgattgg ttgttcccct ttcggctctg caacaccgcc      180
tagaccgacc ggatacacgg gtagggcttc cgctttaccc gtctccctcc tggcgcttgt      240
cctcctctcc cagtcggcac cacagcggtg gctgccgggc gtggtgtcgg tgggtcggtt      300
ggttttttgtc tcaccgttgg tgtccgtgcc gttcagttgc ccgccatggc tggatcgggt      360
gggactagtg gcgtgagcaa gggcgaggag ataacatgg ccatcatcaa ggagttcatg      420
cgcttcaagg tgcacatgga gggctccgtg aacggccacg agttcgagat cgagggcgag      480
ggcgagggcc gccctacga gggcacccag accgccaagc tgaaggtgac caagggtggc      540
ccctgccct cgcctgggga catcctgtcc cctcagttca tgtacggctc caaggcctac      600
gtgaagcacc ccgccgacat ccccgactac ttgaagctgt ccttcccga ggcttcaag      660
tgggagcgcg tgatgaactt cgaggacggc ggcgtggtga ccgtgaccca ggactcctcc      720
```

| | |
|---|---|
| ctgcaggacg gcgagttcat ctacaaggtg aagctgcgcg gcaccaactt ccctccgac | 780 |
| ggccccgtaa tgcagaagaa gaccatgggc tgggaggcct cctccgagcg gatgtacccc | 840 |
| gaggacggcg ccctgaaggg cgagatcaag cagaggctga agctgaagga cggcggccac | 900 |
| tacgacgctg aggtcaagac cacctacaag gccaagaagc ccgtgcagct gcccggcgcc | 960 |
| tacaacgtca acatcaagtt ggacatcacc tcccacaacg aggactacac catcgtggaa | 1020 |
| cagtacgaac gcgccgaggg ccgccactcc accggcggca tggacgagct gtacaaggga | 1080 |
| accggtgctg gaagtggtga gctggatccg ttcgcgccc ctgccggcgc cctggcggt | 1140 |
| cccgcgctgg ggaacggagt ggccggcgcc ggcgaagaag accggctgc ggccttcttg | 1200 |
| gcgcagcaag agagcgagat tgcgggcatc gagaacgacg aggccttcgc catcctggac | 1260 |
| ggcggcgccc ccgggcccca gccgcacggc gagccgccgg ggggtccggg tgagagtgcg | 1320 |
| ggcgcgtttg gggcgagagg acttgtctgg aaactcggtc cacagtgggt ccgagagctt | 1380 |
| ctgtgtgact cgtgctcctt g | 1401 |

<210> SEQ ID NO 12
<211> LENGTH: 1490
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

| | |
|---|---|
| cccggtttag gatgggaagg taacattcat taaaagcaac gtagactata gtgtagctgt | 60 |
| tctcaaaagt agtacatctt agaaaaggat ctttagaaaa gatcgcttta gaaaaggaaa | 120 |
| ttcgttttca gattacgtga gtagcctagg taacacagcc agacctcatc tccacaaaaa | 180 |
| aaatgaaaaa attagccagc ttggtggtct gtgcctgtgg tcccagctgc tccagaggct | 240 |
| gaggtggggg gatgactgga gcctaggctg cagtgagcct agatggcatc actgcactca | 300 |
| agcctgggcg acagacctta tctctaaaaa aataaagatt gcatgagtat tttgttccac | 360 |
| ttgacagtca tcaatagatt ggtttaaatt gtgatatctt ttttacttac cgcaggtgag | 420 |
| caagggcgag gagctgttca ccggggtggt gcccatcctg gtcgagctgg acggcgacgt | 480 |
| aaacggccac aagttcagcg tgtccggcga gggcgagggc gatgccacct acggcaagct | 540 |
| gacccctgaag ttcatctgca ccaccggcaa gctgcccgtg ccctggccca ccctcgtgac | 600 |
| caccctgacc tacggcgtgc agtgcttcag ccgctacccc gaccacatga agcagcacga | 660 |
| cttcttcaag tccgccatgc ccgaaggcta cgtccaggag cgcaccatct tcttcaagga | 720 |
| cgacggcaac tacaagaccc gcgccgaggt gaagttcgag ggcgacaccc tggtgaaccg | 780 |
| catcgagctg aagggcatcg acttcaagga ggacggcaac atcctggggc acaagctgga | 840 |
| gtacaactac aacagccaca acgtctatat catggccgac aagcagaaga acggcatcaa | 900 |
| ggtgaacttc aagatccgcc acaacatcga ggacggcagc gtgcagctcg ccgaccacta | 960 |
| ccagcagaac acccccatcg gcgacggccc cgtgctgctg cccgacaacc actacctgag | 1020 |
| cacccagtcc aagctgagca agacccccaa cgagaagcgc gatcacatgg tcctgctgga | 1080 |
| gttcgtgacc gccgccggga tcactctcgg catggacgag ctgtacaagg aggttcagg | 1140 |
| aggcagcgag tgcatctcca tccacgttgg ccaggctggt gtccagattg caatgcctg | 1200 |
| ctgggagctc tactgcctgg aacacggcat ccagcccgat ggccagatgc aagtgacaa | 1260 |
| gaccattggg ggaggagatg actccttcaa caccttcttc agtgagacgg cgctggcaa | 1320 |

```
gcacgtgccc cgggctgtgt ttgtagactt ggaacccaca gtcattggtg agttgacctc    1380
agtaacctga gatcccagga tgctgggaca ggaggtctgt ccaggggctt ctcttgtcac    1440
tcactcactc cctccgtcct tctctccctc ctccagatga agttcgcact              1490
```

<210> SEQ ID NO 13
<211> LENGTH: 1523
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
ctgggactca aggcgctaac tgcgcgtgcg ttctggggcc cggggtgccg cggcctgggc      60
tggggcgaag gcgggctcgg ccggaagggg tggggtcgcc gcggctcccg ggcgcttgcg     120
cgcacttcct gcccgagccg ctggccgccc gagggtgtgg ccgctgcgtg cgcgcgcgcc     180
gacccggcgc tgtttgaacc gggcggaggc ggggctggcg cccggttggg aggggggttgg   240 ggcctggctt cctgccgcgc gccgcgggga cgcctccgac cagtgtttgc cttttatggt    300
aataacgcgg ccgccccggc ttcctttgtc cccaatctgg gcgcgcgccg cgcccctg      360 gcggcctaag gactcggcgc gccggaagtg gccagggcgg gggcgacctc ggctcacagc    420
gcgcccggct attctcgcaa ctgacaatgg tgagcaaggg cgaggagctg ttcaccgggg    480
tggtgcccat cctggtcgag ctggacggcg acgtaaacgg ccacaagttc agcgtgtccg    540
gcgagggcga gggcgatgcc acctacggca agctgaccct gaagttcatc tgcaccaccg    600
gcaagctgcc cgtgccctgg cccaccctcg tgaccaccct gacctacggc gtgcagtgct    660
tcagccgcta ccccgaccac atgaagcagc acgacttctt caagtccgcc atgcccgaag    720
gctacgtcca ggagcgcacc atcttcttca aggacgacgg caactacaag acccgcgccg    780
aggtgaagtt cgagggcgac accctggtga accgcatcga gctgaagggc atcgacttca    840
aggaggacgg caacatcctg ggcacaagc tggagtacaa ctacaacagc cacaacgtct    900
atatcatggc cgacaagcag aagaacggca tcaaggtgaa cttcaagatc cgccacaaca    960
tcgaggacgg cagcgtgcag ctcgccgacc actaccagca gaacacccccc atcggcgacg   1020 gccccgtgct gctgcccgac aaccactacc tgagcaccca gtccaagctg agcaaagacc    1080
ccaacgagaa gcgcgatcac atggtcctgc tggagttcgt gaccgccgcc gggatcactc    1140
tcggcatgga cgagctgtac aaggccggct ccggtaccga tgatgatatc gcagcgctcg    1200
tcgtcgacaa cggctccggc atgtgcaagg ccggcttcgc gggcgacgat gccccccggg   1260
ccgtcttccc ctccatcgtg gggcgcccca ggcaccaggt aggggagctg gctgggtggg    1320
gcagccccgg gagcgggcgg gaggcaaggg cgctttctct gcacaggagc ctcccggttt    1380
ccggggtggg ggctgcgccc gtgctcaggg cttcttgtcc tttccttccc agggcgtgat    1440
ggtgggcatg ggtcagaagg attcctatgt gggcgacgag gcccagagca agagaggcat    1500 cctcacccctg aagtaccccca tcg                                         1523
```

<210> SEQ ID NO 14
<211> LENGTH: 1478
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gaaaaacagc ccaaagccct gttgtagaca ttagtccttt ctcctcttta ggccaactgc    60
attgactcca cagcctcagc cgaggccgtg tttgcctccg aagtgaaaaa gatgcaacag   120
gagaacatga agccgcagga gcagttgacc cttgagccat atgaaagaga ccatgccgtg   180
gtcgtgggag tgtacaggtg agcagggcc cagcaataca ccaagacaga catctctgtc   240
ccttgcaccc cgagtgccat gatcctgggg accctccttc atcacctatc ttcctctcac   300
aggccacctc ctaaagtgaa gaacaagccc aacagcgccg tggacggcac cgccggcccc   360
ggcgtgagca agggcgagga gctgttcacc ggggtggtgc ccatcctggt cgagctggac   420
ggcgacgtaa acgccacaa gttcagcgtg tccggcgagg gcgagggcga tgccacctac   480
ggcaagctga ccctgaagtt catctgcacc accggcaagc tgcccgtgcc ctggcccacc   540
ctcgtgacca ccctgaccta cggcgtgcag tgcttcagcc gctacccga ccacatgaag   600 cagcacgact tcttcaagtc cgccatgccc gaaggctacg tccaggagcg caccatcttc   660
ttcaaggacg acggcaacta caagacccgc gccgaggtga agttcgaggg cgacaccctg   720
gtgaaccgca tcgagctgaa gggcatcgac ttcaaggagg acggcaacat cctggggcac   780
aagctggagt acaactacaa cagccacaac gtctatatca tggccgacaa gcagaagaac   840
ggcatcaagg tgaacttcaa gatccgccac aacatcgagg acggcagcgt gcagctcgcc   900
gaccactacc agcagaacac ccccatcggc gacggccccg tgctgctgcc cgacaaccac   960
tacctgagca cccagtccaa gctgagcaaa gaccccaacg agaagcgcga tcacatggtc  1020
ctgctggagt tcgtgaccgc cgccgggatc actctcggca tggacgagct gtacaagtaa  1080
tgaagttcag ccctgagcgg attgcgagag atgtgtgttg atactgttgc acgtgtgttt  1140
ttctattaaa agactcatcc gtctcccatg tctgctgctc attcctcccc ttgacctgct  1200
gacacaggga gcacgcaccc ttggtcaatt ttgcggggtt gggtaaattc tcactcggtc  1260
acagagcgca tgctccgttt ctagctgcct ttgcgcagcg gcagcctgga tttcggttct  1320
tgggtgggat tggtagctcg ctgcgcatgc gtgcaggtaa gcggccatct cgcgcaggcg  1380
gagtgtcagt gtgggtcacg tgaggggagc ggagagggag ggatgggggc ggagtccagg  1440
gcgtgggggg gccggtttgt tgtggtcgcc attttgct                          1478
```

<210> SEQ ID NO 15
<211> LENGTH: 1346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
ggagatgggg gctaaagggg tgtggtggag aggatagagg ggtgggaaaa gatggccagg    60
agctagaagg aggcagaagt gggaggatgg agctgaagga gcagcaggcc aggaaaggcc   120
ctgctggaaa gccactggag ctgtgctgcg ctggaaaggc cattggaggt gctagaacgc   180
aaaggggttg cagtggggac agacctgctc cccttcttct ttgttcctgc agccggtttc   240
agaagacatg tagcccccatt ggatcgggtg ggactagtgg cagcaagggc gaggagctgt   300
tcaccggggt ggtgcccatc ctggtcgagc tggacggcga cgtaaacggc cacaagttca   360
gcgtgcgcgc cgagggcgag ggcgatgcca ccaacggcaa gctgaccctg aagttcatct   420
gcaccaccgg caagctgccc gtgccctggc ccacccctcgt gacccctg acctacggcg   480 tgcagtgctt cagccgctac cccgaccaca tgaagcgcca cgacttcttc aagtccgcca   540
```

```
tgcccgaagg ctacgtccag gagcgcacca tcagcttcaa ggacgacggc acctacaaga    600
cccgcgccga ggtgaagttc gagggcgaca ccctggtgaa ccgcatcgag ctgaagggca    660
tcgacttcaa ggaggacggc aacatcctgg ggcacaagct ggagtacaac ttcaacagcc    720
acaacgtcta tatcaccgcc gacaagcaga agaacggcat caaggccaac ttcaagatcc    780
gccacaacgt ggaggacggc agcgtgcagc tcgccgacca ctaccagcag aacacccca    840 tcggcgacgg ccccgtgctg ctgcccgaca ccactacct gagcacccag tccgtgctga    900
gcaaagaccc caacgagaag cgcgatcaca tggtcctgct ggagttcgtg accgccgccg    960
ggatcactgg aaccggtgct ggaagtggtt gaggcacgag gccaggcaga tcccacttgc   1020
agcctcccca ggtgtctgcc ccgcgtttcc tgcctgcgga ccagatgaat gtagcagatc   1080
cccagcctct ggcctcctgt tcgcctcctc tacaatttgc cattgtttct cctgggttag   1140
gccccggctt cactggttga gtgttgctct ctagtttcca gaggcttaat cacaccgtcc   1200
tccacgccat ttccttttcc ttcaagccta gcccttctct cattatttct ctctgaccct   1260
ctccccactg ctcatttgga tcccagggga gtgttcaggg ccagccctgg ctggcatgga   1320
gggtgaggct gggtgtctgg aagcat                                        1346

<210> SEQ ID NO 16
<211> LENGTH: 1508
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
agagtgctag gcagtttcct ggctgaacac gccagcccaa tacttaaaga gagcaactcc     60
tgactccgat agagactgga tggacccaca agggtgacag cccaggcgga ccgatcttcc    120
catcccacat cctccggcgc gatgccaaaa agaggctgac ggcaactggg ccttctgcag    180
agaaagacct ccgcttcact gccccggctg gtcccaaggg tcaggaagat gggggcaggt    240
gccactggcc gcgccatgga cgggccgcgc ctgctgctgt tgctgcttct gggggtgtcc    300
cttggaggtg ccaaggaggc atgccccaca ggcctgtaca cacacagcgg tgagtgctgc    360
aaagcctgca acctgggcga gggtgtggcc cagccttgtg gagccaacca gaccgtgtgt    420
gagccctgcc tggacagcgt gacgttctcc gacgtggtga gcgcgaccga gccgtgcaag    480
ccgtgcaccg agtgcgtggg gctccagagc atgtcggcgc catgcgtgga ggccgacgac    540
gccgtgtgcc gctgcgccta cggctactac caggatgaga cgactgggcg ctgcgaggcg    600
tgccgcgtgt gcgaggcggg ctcgggcctc gtgttctcct gccaggacaa gcagaacacc    660
gtgtgcgagg agtgccccga cggcacgtat tccgacgagg ccaaccacgt ggaccgtgc    720 ctgccctgca ccgtgtgcga ggacaccgag cgccagctcc gcgagtgcac acgctgggcc    780
gacgccgagt gcgaggagat ccctggccgt tggattacac ggtccacacc cccagagggc    840
tcggacagca cagcccccag cacccaggag cctgaggcac ctccagaaca agacctcata    900
gccagcacgg tggcaggtgt ggtgaccaca gtgatgggca gctcccagcc cgtggtgacc    960
cgaggcacca ccgacaacct catccctgtc tattgctcca tcctggctgc tgtggttgtg   1020
ggtcttgtgg cctacatagc cttcaagagg tggaacagcc gcgccaagcg ctcgggttcg   1080
ggtgccacca acttcagcct gctgaagcag gccggcacg tggaggagaa ccccggcccc   1140
atggattcat atctgctgat gtggggactg ctcacgttca tcatggtgcc tggctgccag   1200
```

```
gcaggtaagg gcctgtgggt gcccccggaa ttccgggaag gctgatgggc atccctcttc    1260
ccagccacag aaccagaggg agtccccagg tagatggttc caagaaggga gttgaatctt    1320
gggttccacc tcttgcctgt gacccacggg gacccccagtt tatgcctcac tgttccttgg   1380
tctgtcaaga gagcctgaaa tagcattagg ttctcctgtc cttctcagtc cttgacaatt    1440
aattctggga agaatagtgt ggcatgatat ttgggatatt tggatgttaa cagggtcccg    1500
atgagcag                                                             1508
```

<210> SEQ ID NO 17
<211> LENGTH: 1919
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gtatatgtgc ccacaggagc caagacggta ttttccatcc tcccaaaaca gtagagcttt      60
gacagagatt taagggtgac caagtcaagg aagaggcatg gcatagaacg gtgatgtcgg     120
gggtgggggt tcagaacttc cattatagaa ggtaatgatt tagaggagaa ggtggttgag     180
aatggtgcta gtggtagtga acagatcctt cccaggatct aggtgggctg aggattttttg   240 agtctgtgac actattgtat atccagcttt agtttctgtt taccacctta cagcagcacc    300
taatctccta gaggacttag cccgtgtcac acagcacata tttgccacac cctctgtaaa    360
gccctggttt ataaggttct ttccaccgga agctatgaca gaggaaacgt gtgggtgggg    420
aggggtagtg ggtgagggac ccaggttcct gacacagaca gactacaccc agggaatgaa    480
gagcaagcgc catgggggca ggtgccactg ccgcgccat ggacgggccg cgcctgctgc     540
tgttgctgct tctgggggtg tcccttggag gtgccaagga ggcatgcccc acaggcctgt    600
acacacacag cggtgagtgc tgcaaagcct gcaacctggg cgagggtgtg gcccagcctt    660
gtggagccaa ccagaccgtg tgtgagccct gcctggacag cgtgacgttc tccgacgtgg    720
tgagcgcgac cgagccgtgc aagccgtgca ccgagtgcgt ggggctccag agcatgtcgg    780
cgccatgcgt ggaggccgac gacgccgtgt gccgctgcgc ctacggctac taccaggatg    840
agacgactgg gcgctgcgag gcgtgccgcg tgtgcgaggc gggctcgggc ctcgtgttct    900
cctgccagga caagcagaac accgtgtgcg aggagtgccc cgacggcacg tattccgacg    960
aggccaacca cgtggacccg tgcctgcccc gcaccgtgtg cgaggacacc gagcgccagc   1020
tccgcgagtg cacacgctgg gccgacgccg agtgcgagga gatccctggc cgttggatta   1080
cacggtccac accccagag ggctcggaca gcacagcccc cagcacccag gagcctgagg    1140
cacctccaga acaagacctc atagccagca cggtggcagg tgtggtgacc acagtgatgg    1200
gcagctccca gcccgtggtg acccgaggca ccaccgacaa cctcatcct gtctattgct    1260 ccatcctggc tgctgtggtt gtgggtcttg tggcctacat agccttcaag aggtggaaca    1320
gccgcgccaa gcgctcgggt tcgggtgcca ccaacttcag cctgctgaag caggccggcg    1380
acgtggagga gaaccccggc cccatgttga agccatcgtt gccgtttacc tccctcttat    1440
tcctgcagct gccctgctg ggagtggggc tgaacacgac aattctgacg cccaatggga    1500
atgaagacac cacagctggt gggaaatctg ggactggagg gggctggtga aagggtggc     1560 tgtgggaagg ggccgtacag agatctggtg cctgccactg gccattacaa tcatgtgggc    1620
agaattgaaa agtggagtgg gaagggcaag gggagggtt ccctgcctca cgctacttct    1680
```

```
tctttctttc ttgtttgttt gtttctttct ttcttttgag gcagggtctc actatgttgc    1740
ctaggctggt ctcaaactcc tggcctctag tgatcctcct gcctcagcct ttcaaagcac    1800
caggattaca gacatgagcc accgtgcttg gcctcctcct tctgaccatc atttctcttt    1860
ccctccctgc cttcattttc tccccaatct agatttcttc ctgaccacta tgcccactg     1919

<210> SEQ ID NO 18
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
tttcaggttt ccttgagtgg caggccaggc ctggccgtga acgttcactg aaatcatggc      60
ctcttggcca agattgatag cttgtgcctg tccctgagtc ccagtccatc acgagcagct     120
ggtttctaag atgctatttc ccgtataaag catgagaccg tgacttgcca gccccacaga     180
gccccgccct tgtccatcac tggcatctgg actccagcct gggttggggc aaagagggaa     240
atgagatcat gtcctaaccc tgatcctctt gtcccacaga tatccagaac cctgaccctg     300
cctccggatc cggagagggc aggggatctc tccttacttg tggcgacgtg gaggagaacc     360
ccggccccat gagcatcggc ctcctgtgct gtgcagcctt gtctctcctg tgggcaggtc     420
cagtgaatgc tggtgtcact cagacaccca aattccaggt cctgaagaca ggacagagca     480
tgacactgca gtgtgcccag gatatgaacc atgaatacat gtcctggtat cgacaagacc     540
caggcatggg gctgaggctg attcattact cagttggtgc tggtatcact gaccaaggag     600
aagtccccaa tggctacaat gtctccagat caaccacaga ggatttcccg ctcaggctgc     660
tgtcggctgc tccctcccag acatctgtgt acttctgtgc cagcagttac gtcgggaaca     720
ccggggagct gttttttgga gaaggctcta ggctgaccgt actggaggac ctgaaaaacg     780
tgttcccacc cgaggtcgct gtgtttgagc catcagaagc agagatctcc cacacccaaa     840
aggccacact ggtatgcctg gccacaggct tctaccccga ccacgtggag ctgagctggt     900
gggtgaatgg gaaggaggtg cacagtgggg tcagcacaga cccgcagccc ctcaaggagc     960 agccccgccct caatgactcc agatactgcc tgagcagccg cctgagggtc tcggccacct    1020
tctggcagaa ccccgcaac cacttccgct gtcaagtcca gttctacggg ctctcggaga     1080
atgacgagtg gacccaggat agggccaaac ccgtcaccca gatcgtcagc gccgaggcct    1140
ggggtagagc agactgtggc ttcacctccg agtcttacca gcaagggtc ctgtctgcca     1200 ccatcctcta tgagatcttg ctagggaagg ccaccttgta tgccgtgctg gtcagtgccc    1260
tcgtgctgat ggctatggtc aagagaaagg attccagagg ccgggccaag cggtccggat    1320
ccggagccac caacttcagc ctgctgaagc aggccggcga cgtggaggag aaccccggcc    1380
ccatggagac cctcttgggc ctgcttatcc tttggctgca gctgcaatgg gtgagcagca     1440
aacaggaggt gacgcagatt cctgcagctc tgagtgtccc agaaggagaa aacttggttc     1500
tcaactgcag tttcactgat agcgctattt acaacctcca gtggtttagg caggaccctg    1560
ggaaaggtct cacatctctg ttgcttattc agtcaagtca gagagagcaa acaagtggaa    1620
gacttaatgc ctcgctggat aaaatcatcag gacgtagtac tttatacatt gcagcttctc   1680
agcctggtga ctcagccacc tacctctgtg ctgtgaggcc cctgtacgga ggaagctaca    1740
tacctacatt tggaagagga accagccta ttgttcatcc gtatatccag aaccctgacc     1800
```

```
ctgcggtgta ccagctgaga gactctaaat ccagtgacaa gtctgtctgc ctattcaccg    1860
attttgattc tcaaacaaat gtgtcacaaa gtaaggattc tgatgtgtat atcacagaca    1920
aaactgtgct agacatgagg tctatggact tcaagagcaa cagtgctgtg gcctggagca    1980
acaaatctga ctttgcatgt gcaaacgcct tcaacaacag cattattcca gaagacacct    2040
tcttccccag cccaggtaag ggcagctttg gtgccttcgc aggctgtttc cttgcttcag    2100
gaatggcca                                                            2109
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggtagtcgta ctcgtcgtcg                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaacggatcc agctcagcca                                                  20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tggagatgca ctcacgctgc                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgcggcgata tcatcatcca                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acttcagttc ttcaccttgg                                                  20
```

```
<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctggcctcgt gcctcaaatg                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgagcagtcc ccacatcagc                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tggtaatgat ggcttcaaca                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agagtctctc agctggtaca                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggttcttgac taccgtaatt                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaagcgtgat gacaaagagg                                                    20

<210> SEQ ID NO 30
```

```
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggactagtg gcccatgtcg tactcgtcgt cgcggagcaa gcggccacta agactat        57

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggactagtg gccttgggat ccagctcagc cacggctccc tatcaggcag cacttcc        57

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gggactagtg gcacctgatg cactcacgct gccggcccgg tttaggatgg gaaggta        57

<210> SEQ ID NO 33
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gggactagtg gcgcgcgcga tatcatcatc cacggctggg actcaaggcg ctaact         56

<210> SEQ ID NO 34
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gggactagtg gctgaacagt tcttcacctt ggcgggaaaa acagcccaaa gccctgt        57

<210> SEQ ID NO 35
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gggactagtg gcgacccctc gtgcctcaaa tgcggctaaa ggggtgtggt ggagagg        57

<210> SEQ ID NO 36
<211> LENGTH: 57
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gggactagtg gcactccagt ccccacatca gccggagagt gctaggcagt ttcctgg      57

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gggactagtg gctcccatgt gaatggtaat gacgggtata tgtgcccaca ggagcca      57

<210> SEQ ID NO 38
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggcgggact agtggctctc tctctcagct ggtacacggt ttcaggtttc cttgagtggc      60
a                                                                      61

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acttccagca ccccatgtcg tactcgtcgt cgcggcgtag aacccgggga aaggaat      57

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acttccagca cccttgggat ccagctcagc cacggcaagg agcacgagtc acacaga      57

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acttccagca ccacctgatg cactcacgct gccggagtgc gaacttcatc tggagga      57

<210> SEQ ID NO 42
```

```
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acttccagca ccgcgcgcga tatcatcatc cacggcgatg gggtacttca gggtgag         57

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acttccagca cctgaacagt tcttcacctt ggcggagcaa aatggcgacc acaacaa         57

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acttccagca ccgacccctc gtgcctcaaa tgcggggaaa aggaaatggc gtggagg         57

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acttccagca ccactccagt ccccacatca gccggctgct catcgggacc ctgttaa         57

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acttccagca cctcccatgt gaatggtaat gacggcagtg gcatagtgg tcaggaa          57

<210> SEQ ID NO 47
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caccacttcc agcacctctc tctctcagct ggtacacggt ggccattcct gaagcaagga      60
a                                                                      61
```

```
<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Leu Leu Met Trp Ile Thr Gln Val
1               5
```